US008680241B2

(12) United States Patent
Naparstek et al.

(10) Patent No.: US 8,680,241 B2
(45) Date of Patent: Mar. 25, 2014

(54) HUMANIZED ANTIBODIES SPECIFIC FOR HSP65-DERIVED PEPTIDE-6 METHODS AND USES THEREOF

(75) Inventors: Yaakov Naparstek, Jerusalem (IL); Shira Yair, Jerusalem (IL)

(73) Assignee: Protab Ltd., Jerusalem (IL)

(*) Notice: Subject to any disclaimer, the term of this patent is extended or adjusted under 35 U.S.C. 154(b) by 0 days.

(21) Appl. No.: 13/392,548

(22) PCT Filed: Sep. 6, 2010

(86) PCT No.: PCT/IL2010/000731

§ 371 (c)(1), (2), (4) Date: Feb. 27, 2012

(87) PCT Pub. No.: WO2011/027349

PCT Pub. Date: Mar. 10, 2011

(65) Prior Publication Data

US 2012/0156201 A1 Jun. 21, 2012

Related U.S. Application Data

(60) Provisional application No. 61/240,218, filed on Sep. 6, 2009.

(51) Int. Cl.

*C07K 16/00* (2006.01)
*C12P 21/08* (2006.01)
*A61K 39/395* (2006.01)
*A61K 39/00* (2006.01)
*C07H 21/04* (2006.01)

(52) U.S. Cl.

USPC .................. 530/387.1; 530/387.3; 424/130.1; 424/133.1; 536/23.53

(58) Field of Classification Search

None

See application file for complete search history.

(56) References Cited

U.S. PATENT DOCUMENTS

| | | | |
|---|---|---|---|
| 7,488,476 | B2 | 2/2009 | Naparstek |
| 2005/0123535 | A1 | 6/2005 | Naparstek et al. |
| 2007/0048325 | A1 | 3/2007 | Van Epps |
| 2008/0019979 | A1 | 1/2008 | Wang-Johanning |
| 2009/0202556 | A1 | 8/2009 | Ohta |

FOREIGN PATENT DOCUMENTS

| | | |
|---|---|---|
| WO | 2006008246 | 1/2006 |
| WO | 2006082406 | 8/2006 |
| WO | 2007099341 | 9/2007 |
| WO | 2009064854 | 5/2009 |
| WO | 2010/113148 A1 | 10/2010 |

OTHER PUBLICATIONS

Amagai, Mo, J. Dermatol. Sci., 1999, 20:92-102.*
Tan et al., Cutis, 2006, 77:161-165.*
Janeway et al., Immunobiology, third edition, 1997, p. 11.*
Brand et al., "Immunopathogenesis of Collagen Arthritis"; Springer Semin Immunopathol (2003) 25:3-18.
Stark et al.; "Ig heavy chain V region—mouse" Genbank Direct Submission Accession 536328; Jun. 20, 2000 (1 page).
Epstein et al., "The SCID-hu Myeloma Model"; Methods in Molecular Medicine, vol. 113: 183-90 (2005).
Holoshitz, J. et al. "Lines of T Lymphocytes Induce or Vaccinate Against Autoimmune Arthritis"; Science 219:56-58 (1983).
Johnson et al., "Kabat Database and its applications: future directions" Nucleic Acids Research, 29: 205-206 (2001).
Moudgil, K. et al.; "Diversification of T Cell Responses to Carboxy-terminal Determinants within the 65-kD Heat-shock Protein is Involved in Regulation of Autoimmune Arthritis", J. Exp. Med. 185:1307-1316 (1997).
Ulmansky et al.; "Immunoglobulins from rats that are resistant to adjuvant arthritis suppress the disease in arthritis-susceptible rats"; Eur. J. Immunol. 25:952-957 (1995).
Ulmansky et al.; "Resistance to Adjuvant Arthritis is due to Protective Antibodies Against Heat Shock Protein Surface Epitopes and the Induction of IL-10 Secretion"; J. Immunol. 168: 6463-6469 (2002).
Vanderkerken et al; "The 5T2MM Murine Model of Multiple Myeloma"; Methods Mol. Med. 113:191-205 (2005).
www.bioinf.org uk/abs/simkab.html—(3 pages) based exclusively on the specification's disclosure this document or a version thereof was publicly available prior to Sep. 6, 2009 but this document was published on Oct. 15, 2012 and the document confirms it was last modified on Jul. 9, 2012.
www.prf.or.ip—(2 pages) based exclusively on the specification's disclosure this document or a version thereof was publicly available prior to Sep. 6, 2009 but this document was published on Oct. 15, 2012 and the document confirms it was last modified on Sep. 26, 2012.
Myers et al.; "Collagen-Induced Arthritis, An Animal Model of Autoimmunity"; Life Sciences 61(19): 1861-1878 (1997).
Lider, O. et al.; "Therapeutic vaccination against adjuvant arthritis using autoimmune T cells treated with hydrostatic pressure"; Proc. Natl. Acad. Sci. 84:4577-4580 (1987).
Prakken et al; "Heat shcok protein 60 and adjuvant arthritis: a model for T cell regulation in human arthritis" Springer Semin Immunopathol (2003) 25:47-63.
Ulmansky et al., "Resistance to Adjuvant Arthritis Is Due to Protective Antibodies Against Heat Shock Protein Surface Epitopes and the Induction of IL-10 Secretion" The Journal of Immunology, 2002, 7 pages.
Naperstek et al. "Treatment of autoimmune arthritis by protective antibodies against a heat shock protein surface epitope that induce IL-10 secretion", Ann Rheum Dis 2006, 65 (Suppl II): 134, 1 page.

* cited by examiner

*Primary Examiner* — Hong Sang

(74) *Attorney, Agent, or Firm* — Browdy and Neimark, PLLC

(57) ABSTRACT

The present invention relates to humanized antibodies that specifically bind a polypeptide comprising peptide-6 as denoted by SEQ ID NO. 15, that is an HSP65 derived peptide. More specifically, the invention relates to humanized anti-peptide-6 antibodies, compositions, methods and uses thereof for the treatment of immune-related disorders, specifically, inflammatory disorders such as arthritis, IBD, psoriasis, diabetes and MS. The invention further provides combined compositions and kit combining the humanized antibodies of the invention and at least one anti-inflammatory agent, as well as uses of the humanized antibodies in diagnostic kits and methods.

21 Claims, 40 Drawing Sheets

M. Heav. Ch. Seq.

```
                                                                                           CDR1
       10        20        30        40        50        60        70        80        90       100
CAGGTTACTCTGAAAGAGTCTGGCCCTGGGATATTGCAGCCCTCCCAGACCCTCAGTCTGACTTGTTCTTTCTCTGGGTTTTCACTGAGCACTTCTAATA
 Q  V  T  L  K  E  S  G  P  G  I  L  Q  P  S  Q  T  L  S  L  T  C  S  F  S  G  F  S  L  S  T  S  N
                         10                                      20                             30
                                                                                      CDR2
      110       120       130       140       150       160       170       180       190       200
TGGGTGTAGGCTGGATTCGTCAGCCTTCAGGGAAGGGTCTGGAGTGGCTGTTACACATTTTGTGGAATGATAGTAAGTACTATAACCCAGCCCTGAAGAG
M  G  V  G  W  I  R  Q  P  S  G  K  G  L  E  W  L  L  H  I  L  W  N  D  S  K  Y  Y  N  P  A  L  K  S
  35  A  B              40                                     50                                  60

      210       220       230       240       250       260       270       280       290       300
CCGGCTCACAATCTCCAAGGATACCTACAACAACCAGGTATTCCTCAAGATCGCCAATGTGGACACTGCAGATACTGCCACATACTACTGTGCTCGAATG
  R  L  T  I  S  K  D  T  Y  N  N  Q  V  F  L  K  I  A  N  V  D  T  A  D  T  A  T  Y  Y  C  A  R  M
           70                                  80    82  A  B  C                          90
                   CDR3
      310       320       330       340
GGGGGCTACTATGGTAACTATGGGTACTATGCTATGGACTACTGGGGTCAAGGAACCTCAGTCACCGTCTCCTCA  SEQ ID No. 3
 G  G  Y  Y  G  N  Y  G  Y  Y  A  M  D  Y  W  G  Q  G  T  S  V  T  V  S  S  SEQ ID No. 1
           100  A  B  C  D  E  F  G                                110
```

Fig. 1A

M. Ligh. Ch. Seq.

```
                                                                              CDR1
      10        20        30        40        50        60        70        80        90       100
CAAATTGTTCTCACCCAGTCTCCAGCAATCATGTCTGCATCTCTAGGGGAACGGGTCACCATGACCTGCACTGCCAGCTCAAGTGTAAGTTCCAGTTACT
 Q  I  V  L  T  Q  S  P  A  I  M  S  A  S  L  G  E  R  V  T  M  T  C  T  A  S  S  S  V  S  S  S  Y
                            10                                     20                          30 A

                                                    CDR2
     110       120       130       140       150       160       170       180       190       200
TGCACTGGTACCAGCAGAAGCCAGGATCCTCCCCCAAACTCTGGATTTATAGCACATCCAACCTGGCTTCTGGAGTCCCAGCTCGCTTCAGTGGCAGTGG
 L  H  W  Y  Q  Q  K  P  G  S  S  P  K  L  W  I  Y  S  T  S  N  L  A  S  G  V  P  A  R  F  S  G  S  G
                      40                                  50                          60

                                                                             CDR3
     210       220       230       240       250       260       270       280       290       300
GTCTGGGACCTCTTACTCTCTCACAATCAGCAGCATGGAGGCTGAAGATGCTGCCACTTATTACTGCCACCAGTATCATCGTTCCCCACCCACGTTCGGC
 S  G  T  S  Y  S  L  T  I  S  S  M  E  A  E  D  A  A  T  Y  Y  C  H  Q  Y  H  R  S  P  P  T  F  G
          70                                      80                     90

     310
TCGGGGACAAAGTTGGAAATAAAA SEQ ID No. 4
 S  G  T  K  L  E  I  K  SEQ ID No. 2
100                106 A
```

Fig. 1B

VH1: SEQ ID No.20

```
1.    QVTLKESGPAIVKPTQTLTLTCSFSGFSLSTSNMGVGWIRQPSGKGLEWLLHILWNDSK
2.    ----------I----------CS--GFSLSTSNMGVG-----S------LLHILWNDSK
      QVTLKESGPAI                                 GKGLEWLL
3.               VKPTQTLTLTCSFSGFSLSTS     WIRQPSGKGLEW  HILWNDSK
                                      NMGVGWIRQP

1.    YYNPALKSRLTISKDTYKNQVVLTMTNMDPVDTATYYCARMGGYYGNYGYYAMDYWGQGTSVTVSS
2.    YYNPALKS--------Y-------------------C--MGGYYGNYGYYAMDY-----S-----
              RLTISKDT                         GYYGNYGY
3.                 TYKNQVVLTMTNMDPVDTAT              YAMDYWGQGT
      YYNPALKSR                     YYCARMGGYY         WGQGTSVTVSS
```

VH2: SEQ ID No.21

```
1.    QVTLKESGPALVKPTQTLTLTCSFSGFSLSTSNMGVGWIRQPAGKGLEWLL
2.    ---------------------CS--GFSLSTSNMGVG------------LL
      QVTLKESGPALVKPTQTLTLTC                      GKGLEWLL
3.               VKPTQTLTLTCSFSGFSLSTS     WIRQPAGKGLEW
                                      NMGVGWIRQP

1.    HILWNDSKYYNPALKSRLTISKDTYKNQVVLTMTNMDPVDTATYYCARMGGYYGNYGYYAMDYWGQGTLVTVSS
2.    HILWNDSKYYNPALKS--------Y-------------------C--MGGYYGNYGYYAMDY-----------
                            TYKNQVVLTMTNMDPVDTAT              YAMDYWGQGTLVTVSS
3.    HILWNDSK        RLTISKDT                      YYCARMGGYY
              YYNPALKSR                                 GYYGNYGY
```

Fig. 4

VH3: SEQ ID No.22

```
1.    QVTLKESGPALVKPTQTLTLTCSFSGFSLSTSNMGVGWIRQPAGKGLEWLLHILWNDSK
2.    -------------------CS--GFSLSTSNMGVG-----------LLHILWNDSK
      QVTLKESGPALVKPTQTLTLTC                       GKGLEWLL
3.              VKPTQTLTLTCSFSGFSLSTS      WIRQPAGKGLEW  HILWNDSK
                                      NMGVGWIRQP

1.    YYNPALKSRLTISKDTSKNQVVLTMTNMDPVDTATYYCARMGGYYGNYGYYAMDYWGQGTLVTVSS
2.    YYNPALKS--------------------------C--MGGYYGNYGYYAMDY----------
             RLTISKDTSKNQVVLTMTNMDPVDTAT        YGNYGY
3.    YYNPALKSR                         YYCARMGGYY     YAMDYWGQGTLVTVSS
```

VH4: SEQ ID No.23

```
1.    QVTLKESGPALVKPTQTLTLTCSFSGFSLSTSNMGVGWIRQPAGKGLEWLAHILWNDSK
2.    -------------------CS--GFSLSTSNMGVG-----------L-HILWNDSK
      QVTLKESGPALVKPTQTLTLTC                       GKGLEWLA
                VKPTQTLTLTCSFSGFSLSTS      WIRQPAGKGLEW  HILWNDSK
3.                                   NMGVGWIRQP

1.    YYNPALKSRLTISKDTSKNQVVLTMTNMDPVDTATYYCARMGGYYGNYGYYAMDYWGQGTLVTVSS
2.    YYNPALKS--------------------------C--MGGYYGNYGYYAMDY----------
      YYNPALKSR                                        YAMDYWGQGTLVTVSS
3.           RLTISKDTSKNQVVLTMTNMDPVDTAT        YGNYGY
                                        YYCARMGGYY
```

Fig. 4 (cont.1)

```
VK1: SEQ ID No.24
1.  QIVLTQSPAILSLSPGERATMSCTASSSVSSSYLHWYQQKPGKAPKLWIYSTSNLASGVPSRFSGSGSGT
2.  Q-------I----------M-CTASSSVSSSYLH-----------W--STSNLAS-----------
    QIVLTQSPA      GERATMSCTAS       YLHWYQQKPGKAPKL        LASGVPSRFSGSGSGT
3.           AILSLSPGERAT       SSVSSSYL            PKLWIYS
                                                         IYSTSNL

1.  DYTLTISSLQAEDFATYYCHQYHRSPPTFGQGTKLEIK
2.  -Y-------A------CHQYHRSPPT---------
    DYTLTISSLQ EDFATYYCHQYHR
3.            QAEDFATYYCHQ   SPPTFGQGTKLEIK

VK2: SEQ ID No.25
1.  QIVLTQSPATLSLSPGERATMSCTASSSVSSSYLHWYQQKPGKAPKLWIYSTSNLASGVPSRFSGSGSGT
2.  Q---------------M-CTASSSVSSSYLH----------W--STSNLAS-----------
    QIVLTQSPA      GERATMSCTAS       YLHWYQQKPGKAPKL        LASGVPSRFSGSGSGT
3.           ATLSLSPGERAT       SSVSSSYL            PKLWIYS

                                                         IYSTSNL

1.  DYTLTISSLQPEDFATYYCHQYHRSPPTFGQGTKLEIK
2.  -Y-------------CHQYHRSPPT---------
3.  DYTLTISSLQPEDFATYYC      SPPTFGQGTKLEIK
              PEDFATYYCHQYHR

VK3: SEQ ID No.26
1.  QIVLTQSPATLSLSPGERATLSCTASSSVSSSYLHWYQQKPGKAPKLWIYSTSNLASGVPSRFSGSGSGT
2.  Q-----------------CTASSSVSSSYLH----------W--STSNLAS-----------
    QIVLTQSPA                SSVSSSYL                IYSTSNL
3.           ATLSLSPGERATLSCTAS       YLHWYQQKPGKAPKL        LASGVPSRFSGSGSGT

                                                    PKLWIYS

1.  DYTLTISSLQPEDFATYYCHQYHRSPPTFGQGTKLEIK
2.  -Y-------------CHQYHRSPPT---------
    DYTLTISSLQPEDFATYYC
```

Fig. 4 (cont.2)

VH Var. 1

```
                                                                                                CDR1
        10        20        30        40        50        60        70        80        90       100
CAGGTTACTCTGAAAGAGTCTGGCCCTGCCATAGTGAAGCCCACCCAGACCCTCACCCTGACTTGTTCTTTCTCTGGGTTTTCACTGAGCACTTCTAATA
 Q  V  T  L  K  E  S  G  P  A  I  V  K  P  T  Q  T  L  T  L  T  C  S  F  S  G  F  S  L  S  T  S  N
                            10                            20                            30
                                                                                  CDR2
       110       120       130       140       150       160       170       180       190       200
TGGGTGTAGGCTGGATTCGTCAGCCTTCAGGGAAGGGTCTGGAGTGGCTGTTACACATTTTGTGGAATGATAGTAAGTACTATAACCCAGCCCTGAAGAG
M  G  V  G  W  I  R  Q  P  S  G  K  G  L  E  W  L  L  H  I  L  W  N  D  S  K  Y  Y  N  P  A  L  K  S
  35  A  B             40                            50                            60

       210       220       230       240       250       260       270       280       290       300
CCGGCTCACAATCTCCAAGGATACCTACAAGAACCAGGTAGTGCTCACCATGACCAATATGGACCCTGTGGATACTGCCACATACTACTGTGCTCGAATG
  R  L  T  I  S  K  D  T  Y  K  N  Q  V  V  L  T  M  T  N  M  D  P  V  D  T  A  T  Y  Y  C  A  R  M
              70                            80    82  A  B  C                         90
                CDR3
       310       320       330       340       350       360       370
GGGGGCTACTATGGTAACTATGGGTACTATGCTATGGACTACTGGGGTCAAGGAACCTCAGTCACCGTCTCCTCA SEQ ID No. 27
 G  G  Y  Y  G  N  Y  G  Y  Y  A  M  D  Y  W  G  Q  G  T  S  V  T  V  S  S  SEQ ID No. 20
             100  A  B  C  D  E  F  G                        110
```

Fig. 6A

VH Var. 2

```
                                                                                                CDR1
       10        20        30        40        50        60        70        80        90       100
CAGGTTACTCTGAAAGAGTCTGGCCCTGCCCTGGTGAAGCCCACCCAGACCCTCACCCTGACTTGTTCTTTCTCTGGGTTTTCACTGAGCACTTCTAATA
 Q  V  T  L  K  E  S  G  P  A  L  V  K  P  T  Q  T  L  T  L  T  C  S  F  S  G  F  S  L  S  T  S  N
                            10                            20                            30

                                                                                  CDR2
      110       120       130       140       150       160       170       180       190       200
TGGGTGTAGGCTGGATTCGTCAGCCTGCCGGGAAGGGTCTGGAGTGGCTGTTACACATTTTGTGGAATGATAGTAAGTACTATAACCCAGCCCTGAAGAG
M  G  V  G  W  I  R  Q  P  A  G  K  G  L  E  W  L  L  H  I  L  W  N  D  S  K  Y  Y  N  P  A  L  K  S
  35  A  B                 40                           50                            60

      210       220       230       240       250       260       270       280       290       300
CCGGCTCACAATCTCCAAGGATACCTACAAGAACCAGGTAGTGCTCACCATGACCAATATGGACCCTGTGGATACTGCCACATACTACTGTGCTCGAATG
 R  L  T  I  S  K  D  T  Y  K  N  Q  V  V  L  T  M  T  N  M  D  P  V  D  T  A  T  Y  Y  C  A  R  M
             70                            80    82  A  B  C                          90

                CDR3
      310       320       330       340       350       360       370
GGGGGCTACTATGGTAACTATGGGTACTATGCTATGGACTACTGGGGTCAAGGAACCCTGGTCACCGTCTCCTCA  SEQ ID No. 28
 G  G  Y  Y  G  N  Y  G  Y  Y  A  M  D  Y  W  G  Q  G  T  L  V  T  V  S  S   SEQ ID No. 21
            100  A  B  C  D  E  F  G                           110
```

Fig. 6B

VH Var. 3

```
                                                                                                      CDR1
        10        20        30        40        50        60        70        80        90       100
CAGGTTACTCTGAAAGAGTCTGGCCCTGCCCTGGTGAAGCCCACCCAGACCCTCACCCTGACTTGTTCTTTCTCTGGGTTTTCACTGAGCACTTCTAATA
 Q  V  T  L  K  E  S  G  P  A  L  V  K  P  T  Q  T  L  T  L  T  C  S  F  S  G  F  S  L  S  T  S  N
                          10                                      20                             30
                                                                                      CDR2
       110       120       130       140       150       160       170       180       190       200
TGGGTGTAGGCTGGATTCGTCAGCCTGCCGGGAAGGGTCTGGAGTGGCTGTTACACATTTTGTGGAATGATAGTAAGTACTATAACCCAGCCCTGAAGAG
 M  G  V  G  W  I  R  Q  P  A  G  K  G  L  E  W  L  L  H  I  L  W  N  D  S  K  Y  Y  N  P  A  L  K  S
  35 A  B              40                                50                             60
       210       220       230       240       250       260       270       280       290       300
CCGGCTCACAATCTCCAAGGATACCTCCAAGAACCAGGTAGTGCTCACCATGACCAATATGGACCCTGTGGATACTGCCACATACTACTGTGCTCGAATG
  R  L  T  I  S  K  D  T  S  K  N  Q  V  V  L  T  M  T  N  M  D  P  V  D  T  A  T  Y  Y  C  A  R  M
              70                             80    82 A  B  C                       90
                 CDR3
       310       320       330       340       350       360       370
GGGGGCTACTATGGTAACTATGGGTACTATGCTATGGACTACTGGGGTCAAGGAACCCTGGTCACCGTCTCCTCA  SEQ ID No. 29
 G  G  Y  Y  G  N  Y  G  Y  Y  A  M  D  Y  W  G  Q  G  T  L  V  T  V  S  S   SEQ ID No. 22
           100 A  B  C  D  E  F  G                             110
```

Fig. 6C

VH Var. 4

```
                                                                                          CDR1
        10        20        30        40        50        60        70        80        90       100
CAGGTTACTCTGAAAGAGTCTGGCCCTGCCCTGGTGAAGCCCACCCAGACCCTCACCCTGACTTGTTCTTTCTCTGGGTTTTCACTGAGCACTTCTAATA
 Q  V  T  L  K  E  S  G  P  A  L  V  K  P  T  Q  T  L  T  L  T  C  S  F  S  G  F  S  L  S  T  S  N
                            10                                     20                                   30
                                                                                   CDR2
       110       120       130       140       150       160       170       180       190       200
TGGGTGTAGGCTGGATTCGTCAGCCTGCCGGGAAGGGTCTGGAGTGGCTGGCCCACATTTTGTGGAATGATAGTAAGTACTATAACCCAGCCCTGAAGAG
M  G  V  G  W  I  R  Q  P  A  G  K  G  L  E  W  L  A  H  I  L  W  N  D  S  K  Y  Y  N  P  A  L  K  S
  35  A  B              40                             50                       60

       210       220       230       240       250       260       270       280       290       300
CCGGCTCACAATCTCCAAGGATACCTCCAAGAACCAGGTAGTGCTCACCATGACCAATATGGACCCTGTGGATACTGCCACATACTACTGTGCTCGAATG
  R  L  T  I  S  K  D  T  S  K  N  Q  V  V  L  T  M  T  N  M  D  P  V  D  T  A  T  Y  Y  C  A  R  M
         70                             80  82  A  B  C                         90
            CDR3
       310       320       330       340       350       360       370
GGGGGCTACTATGGTAACTATGGGTACTATGCTATGGACTACTGGGGTCAAGGAACCCTGGTCACCGTCTCCTCA SEQ ID No. 30
 G  G  Y  Y  G  N  Y  G  Y  Y  A  M  D  Y  W  G  Q  G  T  L  V  T  V  S  S  SEQ ID No. 23
           100  A  B  C  D  E  F  G                         110
```

Fig. 6D

VK Var. 1

```
                                                                                  CDR1
       10        20        30        40        50        60        70        80        90       100
CAAATTGTTCTCACCCAGTCTCCAGCAATCCTGTCTCTGTCTCCAGGGGAACGGGCCACCATGAGCTGCACTGCCAGCTCAAGTGTAAGTTCCAGTTACT
 Q  I  V  L  T  Q  S  P  A  I  L  S  L  S  P  G  E  R  A  T  M  S  C  T  A  S  S  S  V  S  S  S  Y
                            10                            20                 27 A        30
                                                        CDR2
      110       120       130       140       150       160       170       180       190       200
TGCACTGGTACCAGCAGAAGCCAGGAAAGGCCCCCAAACTCTGGATTTATAGCACATCCAACCTGGCTTCTGGAGTCCCATCTCGCTTCAGTGGCAGTGG
 L  H  W  Y  Q  Q  K  P  G  K  A  P  K  L  W  I  Y  S  T  S  N  L  A  S  G  V  P  S  R  F  S  G  S  G
                      40                                  50                      60
                                                                                   CDR3
      210       220       230       240       250       260       270       280       290       300
GTCTGGGACCGATTACACCCTCACAATCAGCAGCCTGCAGGCTGAAGATTTCGCCACTTATTACTGCCACCAGTATCATCGTTCCCCACCCACGTTCGGC
  S  G  T  D  Y  T  L  T  I  S  S  L  Q  A  E  D  F  A  T  Y  Y  C  H  Q  Y  H  R  S  P  P  T  F  G
         70                            80                          90

      310       320
CAGGGGACAAAGTTGGAAATAAAA  SEQ ID No. 31
 Q  G  T  K  L  E  I  K   SEQ ID No. 24
100                106 A
```

Fig. 6E

VK Var. 2

```
                                                                                         CDR1
       10        20        30        40        50        60        70        80        90       100
CAAATTGTTCTCACCCAGTCTCCAGCAACCCTGTCTCTGTCTCCAGGGGAACGGGCCACCATGAGCTGCACTGCCAGCTCAAGTGTAAGTTCCAGTTACT
 Q  I  V  L  T  Q  S  P  A  T  L  S  L  S  P  G  E  R  A  T  M  S  C  T  A  S  S  S  V  S  S  S  Y
                            10                        20                     27 A        30
                                                               CDR2
      110       120       130       140       150       160       170       180       190       200
TGCACTGGTACCAGCAGAAGCCAGGAAAGGCCCCCAAACTCTGGATTTATAGCACATCCAACCTGGCTTCTGGAGTCCCATCTCGCTTCAGTGGCAGTGG
 L  H  W  Y  Q  Q  K  P  G  K  A  P  K  L  W  I  Y  S  T  S  N  L  A  S  G  V  P  S  R  F  S  G  S  G
                       40                          50                          60
                                                                                  CDR3
      210       220       230       240       250       260       270       280       290       300
GTCTGGGACCGATTACACCCTCACAATCAGCAGCCTGCAGCCTGAAGATTTCGCCACTTATTACTGCCACCAGTATCATCGTTCCCCACCCACGTTCGGC
 S  G  T  D  Y  T  L  T  I  S  S  L  Q  P  E  D  F  A  T  Y  Y  C  H  Q  Y  H  R  S  P  P  T  F  G
          70                          80                          90

      310       320
CAGGGGACAAAGTTGGAAATAAAA   SEQ ID No. 32
 Q  G  T  K  L  E  I  K    SEQ ID No. 25
100              106  A
```

Fig. 6F

VK Var. 3

CDR1

CAAATTGTTCTCACCCAGTCTCCAGCAACCCTGTCTCTGTCTCCAGGGGAACGGGCCACCCTGAGCTGCACTGCCAGCTCAAGTGTAAGTTCCAGTTACT

Q I V L T Q S P A T L S L S P G E R A T L S C T A S S S V S S S Y 10 20 27 A 30

CDR2

TGCACTGGTACCAGCAGAAGCCAGGAAAGGCCCCCAAACTCTGGATTTATAGCACATCCAACCTGGCTTCTGGAGTCCCATCTCGCTTCAGTGGCAGTGG

L H W Y Q Q K P G K A P K L W I Y S T S N L A S G V P S R F S G S G 40 50 60

CDR3

GTCTGGGACCGATTACACCCTCACAATCAGCAGCCTGCAGCCTGAAGATTTCGCCACTTATTACTGCCACCAGTATCATCGTTCCCCACCCACGTTCGGC

S G T D Y T L T I S S L Q P E D F A T Y Y C H Q Y H R S P P T F G 70 80 90

CAGGGGACAAAGTTGGAAATAAAA SEQ ID No. 33

Q G T K L E I K SEQ ID No. 26

Rituximab

Chim. M-H α Pept. 6

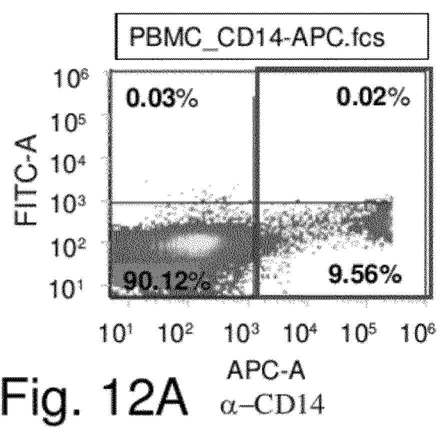
Fig. 12A α–CD14
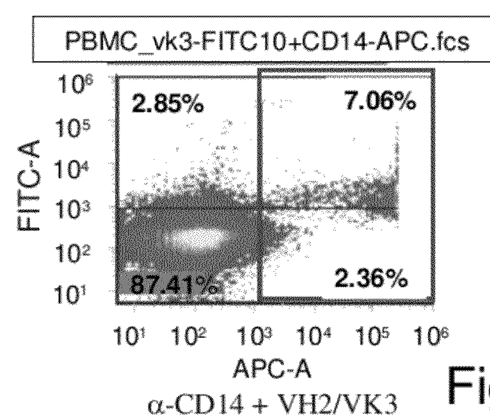
α-CD14 + VH2/VK3 Fig. 12B
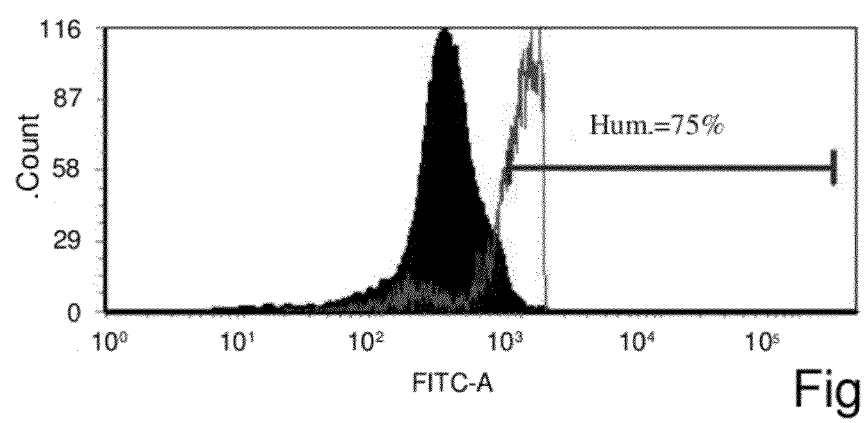
Fig. 12C Cont. (TBS)

Hum. VH2/VK3

HUMANIZED ANTIBODIES SPECIFIC FOR HSP65-DERIVED PEPTIDE-6 METHODS AND USES THEREOF

REFERENCE TO CO-PENDING APPLICATIONS

Priority is claimed as a 371 of international application number PCT/IL2010/000731, filed on Sep. 6, 2010; which claims priority to U.S. Provisional Patent application No. 61/240,218, filed on Sep. 6, 2009.

FIELD OF THE INVENTION

The present invention relates to humanized anti-HSP65 derived peptide, specifically, peptide-6 antibodies and any antigen-binding fragments thereof. More specifically, the invention relates to humanized anti-peptide-6 antibodies, compositions, methods and uses thereof for the treatment of immune-related disorders.

BACKGROUND OF THE INVENTION

All publications mentioned throughout this application are fully incorporated herein by reference, including all references cited therein.

The 65-kDa heat shock protein (HSP65) of the *Mycobacterium tuberculosis* (MT) plays a significant role in the pathogenesis of autoimmune arthritis. Its effect is well exemplified in the experimental model of adjuvant arthritis (AA). AA can be induced in susceptible, inbred strains of rats such as Lewis or Wistar, by intracutaneous inoculation of heat killed mycobacteria suspended in Freund's adjuvant. AA can be passively transferred by a T-cell clone reactive to residues 180-188 of the HSP65 [Holoshitz, J. et al. Science 219:56-58 (1983)].

Evidence has been reported that protection from disease may be due to cellular responses to HSP65 [Lider, O. et al. Proc. Natl. Acad. Sci. 84:4577-4580 (1987); Moudgil, K. et al. J. Exp. Med. 185:1307-1316 (1997)], suggesting that this protein contains different epitopes which participate in both pathogenesis and acquisition of resistance. The inventors have previously shown that resistance to AA can also be conferred by antibodies against HSP65 and can be passively transferred by intravenous infusion of immunoglobulins from arthritis-resistant strains to arthritis-susceptible rats [Ulmansky, R. and Naparstek, Y. Eur. J. Immunol. 25:952-957 (1995)]. Further analysis defined the epitope specificity of the anti-HSP protective antibodies to amino-acid residues 31-46, designated as peptide-6 (also denoted by SEQ ID NO. 15) [Ulmansky, R. and Naparstek, Y. J. Immunol. 168: 6463-6469 (2002)]. Vaccination of Lewis rats with this peptide resulted in the production of antibodies against the whole molecule as well as resistance to disease induction.

The inventors have previously shown that polyclonal antibodies directed against peptide-6 stimulate Interleukin-10 (IL-10) production by peripheral blood mononuclear cells (PBMCs) [Ulmansky (2002) ibid.]. The anti-inflammatory cytokine IL-10 plays an important role in innate immunity mostly due to its inhibitory effects, which allow suppression of inflammatory responses. Monoclonal anti-peptide-6 antibodies generated by the inventors were shown to retain this protective effect by binding to PBMCs and stimulating IL-10 secretion from the cells.

The inventors have further shown that antibodies directed against peptide-6 interact not only with peptide-6, but moreover, they apparently cross react directly with a surface ligand on macrophages, and this interaction is the key to comprehension of the mechanism of action of these antibodies. Following binding of the anti-peptide-6 antibodies to macrophages, there is activation of a signal transduction pathway that leads to an increase in production and secretion of cytokines, specifically IL-10. As an anti-inflammatory cytokine, IL-10 attenuates and inhibits inflammatory processes, thereby leading to amelioration and treatment of an inflammatory disorder. This tilts the balance between pro-inflammatory Th1 cytokines, such as tumor necrosis factor alpha (TNF-alpha), and anti-inflammatory Th2 cytokines, such as IL-10. Modulation of the Th1/Th2 balance towards a Th2 anti-inflammatory response using the anti-peptide-6 antibodies is therefore applicable in the treatment of inflammatory disorders.

However, the administration of rodent antibodies or antibody fragments has had drawbacks that limit their applicability in humans due, in part, to immunogenicity of the antibodies or fragments thereof. To overcome the undesirable properties of rodent antibodies, humanized antibodies have been developed by replacing the framework regions, excluding the antigen-binding site, with regions of a human antibody. A method frequently used for preparing such humanized antibodies is based on selection of a gene encoding a human antibody showing the closest sequence similarity to the mouse antibody and replacing only the complementarity determining region (CDR) of the human antibody with that of the mouse antibody by way of a CDR grafting method. The humanized antibody has the advantage of reducing the in vivo immune response. However, when only the CDR is grafted on the human antibody, its selectivity and reactivity are often compromised.

Moreover, although the techniques of humanization have provided antibodies which are generally well tolerated when administered to man and generally have less immunogenicity than non-human monoclonal antibodies. Several antibodies generated by these techniques have been shown to elicit immunogenicity in patients even where the genetic origins of such antibodies are human. Such induction of immunogenicity is likely to result from the presence, within the antibody variable region, of tracts of non-self amino acid sequences which, in some cases, can create T cell epitopes which induce T cell responses resulting in immunogenicity.

The potential use of anti-peptide-6 antibodies as immunomodulating agents requires production of a humanized antibody having reduced antigenic potential. There is therefore a need to produce highly specific humanized anti-peptide-6 antibodies having a high primarily sequences of human origin and avoiding the creation of sequences which might induce T cell responses.

It is therefore an object of the invention to provide such humanized anti-peptide-6 antibodies for modulating the Th1/Th2 balance in a subject suffering from an immune-related disorder.

These and other objects of the invention will become apparent as the description proceeds.

SUMMARY OF THE INVENTION

According to a first aspect, the invention relates to a humanized antibody or any antigen-binding fragment thereof that specifically binds a polypeptide comprising SEQ ID NO: 15. It should be noted that the polypeptide of SEQ ID NO. 15, known as peptide-6, is derived from HSP65.

According to one embodiment, the humanized antibody of the invention comprises:

(a) a heavy chain variable region which comprises Cys at position H22, Ser at H23, Gly at H26, Phe at H27, Ser at H28, Leu at H29, Ser at H30, Thr at H31, Ser at H32, Asn at H33, Met at H34, Gly at H35, Val at H35A, Gly at H35B, Leu at H48, His at H50, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and optionally, at least one of Leu at H49, Tyr at H74, Ile at H11, Ser at H41 and Ser at H108; and (b) a light chain variable region which comprises Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Trp at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and optionally at least one of Met at L21, Ile at L10 and Ala at L80. It should be appreciated that all indicated positions are determined according to the Kabat numbering system.

Another aspect of the invention relates to a composition comprising as an active ingredient an effective amount of at least one isolated and purified humanized antibody according to the invention.

The invention further provides a pharmaceutical composition for preventing, treating, ameliorating or inhibiting an immune-related disorder. The pharmaceutical composition of the invention comprises as an active ingredient a therapeutically effective amount of at least one isolated and purified humanized antibody of the invention.

In another aspect the invention provides a composition and method for increasing the expression and levels of IL-10 (Interleukin-10) in a subject in need thereof, specifically, a subject suffering from an immune-related disorder.

A further aspect of the invention provides a method for preventing, treating, ameliorating or inhibiting the treatment or amelioration of an immune-related disorder. The method of the invention comprises the step of administering to a subject in need thereof a therapeutically effective amount of at least one isolated and purified humanized antibody according to the invention or of a composition comprising the same as the active ingredient.

According to one embodiment, the method of the invention may be particularly applicable for treating and ameliorating immune-related disorders such as autoimmune or inflammatory disorders.

Still further, the invention provides a combined composition comprising at least one isolated and purified humanized antibody according to the invention and at least one anti-inflammatory agent. In certain embodiments, such anti-inflammatory agent may be selected from a group consisting of Methylprednisone (MPS), anti-TNF agents, etanercept (ENBREL®), infliximab REMICADE®), adalimumab (HUMIRA®), certolizumab pegol (CIMZIA®), anti-IL-6 agents, tocilizumab (ACTEMRA®), anti-IL-1-receptor agents, kineret (ANAKINRA®), CTLA-4-Ig, abatacept (ORENCIA®), anti-CD20 agents, rituximab (MabThera; RITUXAN®), methotrexate, any corticosteroid derivatives, and any other anti-inflammatory agent that induces an anti-inflammatory response through any signaling pathway. More specifically, the additional anti-inflammatory agent may induce a pathway that is different than the pathways induced by anti-peptide 6 antibodies, for example, any pathway involved in IL-10 induction. Said combined composition may optionally further comprise a pharmaceutically acceptable carrier, excipient or diluent.

A further aspect of the invention relates to a kit for achieving a therapeutic effect in a subject suffering from an immune-related disorder comprising:

(i) at least one isolated and purified humanized antibody according to the invention or any antigen-binding fragment thereof or a pharmaceutically acceptable derivative thereof and a pharmaceutically acceptable carrier or diluent, optionally, in a first unit dosage form;

(ii) at least one anti-inflammatory agent and a pharmaceutically acceptable carrier or diluent, optionally, in a second unit dosage form; and (iii) container means for containing said first and second dosage forms.

In certain embodiments, the anti-inflammatory agent comprised within the kit of the invention may be selected from a group consisting of Methylprednisone (MPS), anti-TNF agents, etanercept (ENBREL®), infliximab (REMICADE®), adalimumab (HUMIRA®), certolizumab pegol (CIMZIA®), anti-IL-6 agents, tocilizumab (ACTEMRA®), anti-IL-1-receptor agents, kineret (ANAKINRA®), CTLA-4-Ig, abatacept (ORENCIA®), anti-CD20 agents, rituximab (MabThera; RITUXAN®), methotrexate, any corticosteroid derivatives, and any other anti-inflammatory agent that induces an anti-inflammatory response through any signaling pathway.

A further aspect of the invention relates to a host cell line transformed or transfected with an expression vector encoding the humanized antibody of the invention. More specifically, the host cell line of the invention express a humanized antibody having a heavy chain variable region comprising an amino acid sequence as denoted by SEQ ID NO: 21 and a light chain variable region comprising an amino acid sequence as denoted by SEQ ID NO: 26.

In yet another aspect, the invention provides a chimeric monoclonal antibody that specifically binds a polypeptide comprising SEQ ID NO: 15 or to any polypeptide comprising the same, wherein said antibody comprises a human immunoglobulin constant region and a murine immunoglobulin variable region.

Other aspects of the invention will become apparent by the hand of the following figures.

BRIEF DESCRIPTION OF THE FIGURES

FIG. 1A-1B: Amino acid and nucleic acid sequences of the chimeric mouse-human anti-peptide-6 antibody Figure shows the amino acid sequences and the nucleic acid sequences of the variable domain of the chimeric mouse-human antibody.

FIG. 1A. shows the amino acid sequence (SEQ ID NO. 1) and the encoding nucleic acid sequence (SEQ ID NO. 3) of the mouse antibody heavy chain variable region.

FIG. 1B. shows the amino acid sequence (SEQ ID NO. 2) and the encoding nucleic acid sequence (SEQ ID NO. 4) of the mouse antibody light chain variable region. CDR definitions and protein sequence numbering according to Kabat. CDR nucleotide and protein sequences are underlined.

Abbreviations: M. Heav.Ch. Seq. (mouse heavy chain sequence); M. Ligh.Ch. Seq. (mouse light chain sequence), SEQ ID NO. (sequence identification number).

Figure 2:
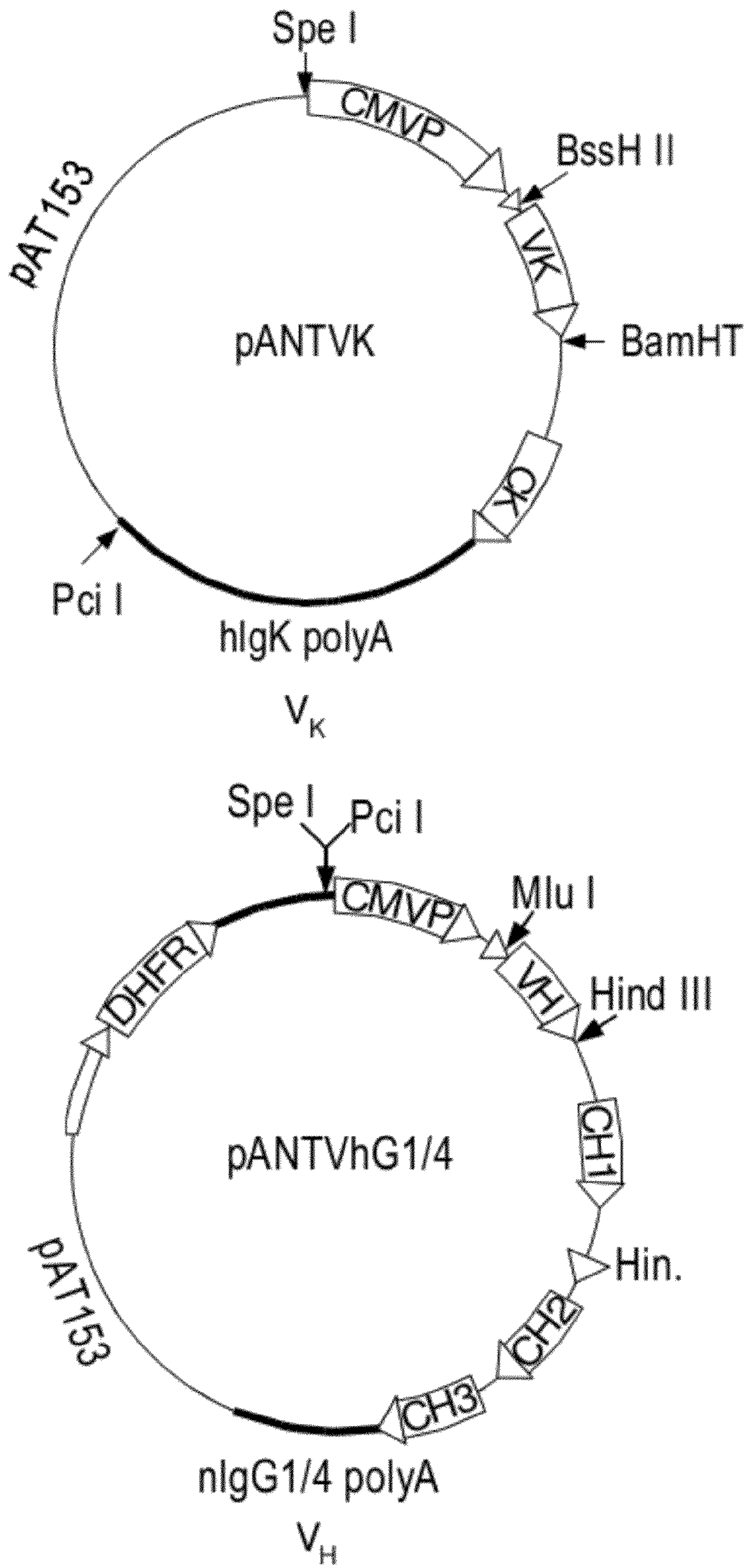

FIG. 2: Diagrams of pANTVK, the VK and pANTVhG1/4, the VH expression vectors Figure shows diagrams of the VK and VH expression vectors showing key genetic elements and restriction enzyme sites. Elements for propagation in bacteria (including ColE1 replicon and ampicillin resistance gene) are not shown.

Abbreviations: Hin. (hinge).

Figure 3A:
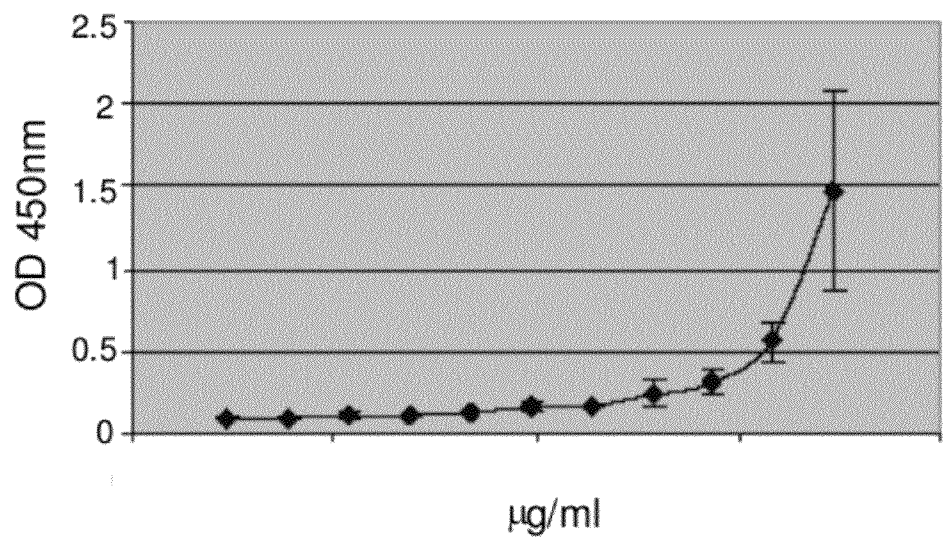
Figure 3B:
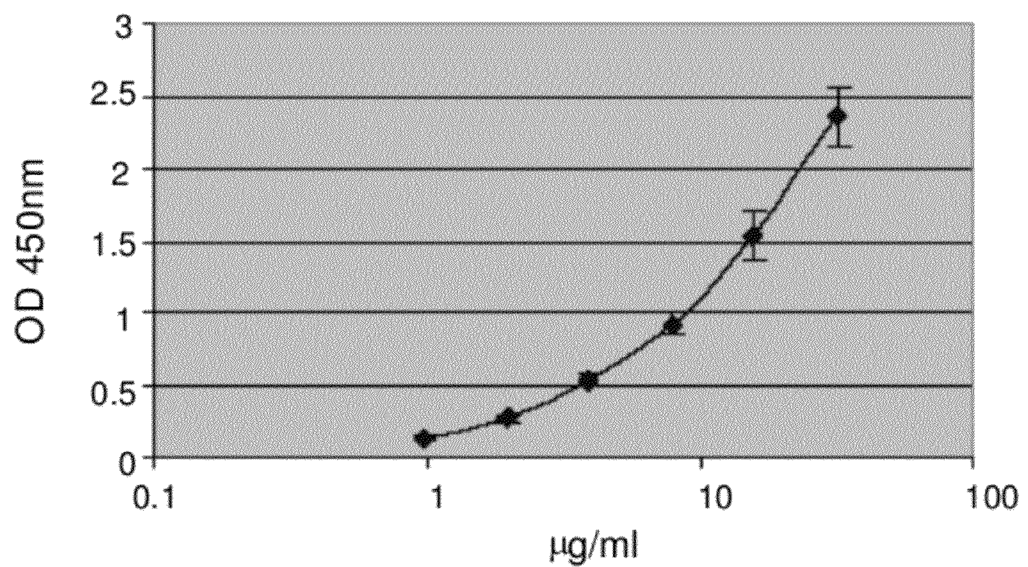

FIG. 3A-3B: Chimeric anti-peptide-6 antibodies binding curves to peptide-6

FIGS. 3A-3B show binding curves for mouse-IgM (3A) and chimeric mouse-human IgG1 (3B) to peptide-6 antigen coated at 10 μg/ml.

Abbreviations: OD (optical density).

FIG. 4: Composite antibody sequence and aligned segments and constraining amino acids Figure shows the amino acid sequence of the humanized variant heavy (VH1-4) and light (VK1-3) chains (Line 1), the constraining residue map (Line 2) and sequence segments used in the assembly of the Composite Human sequences (Line 3) (Line 3 in the figure is composed of lines 3, 4, 5 that represent the different segments as denoted by SEQ ID NO. 12-14, 16-19 and 34-59, 96 and 97) of the different variants.

Abbreviations: VH (variable heavy chain), VK (variable light chain), SEQ ID NO. (Sequence identification number).

Figure 5:
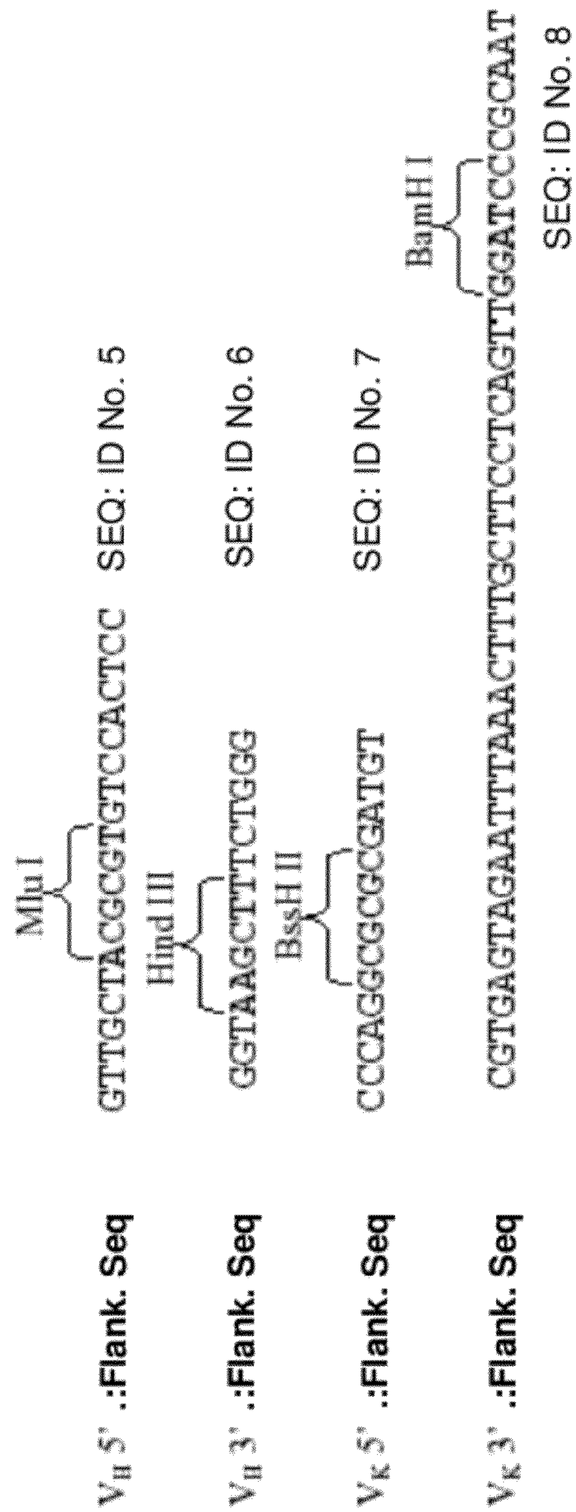

FIG. 5: Flanking sequences used in the cloning of synthesized Composite Human Antibody™ VII and VK genes into expression vectors Figure shows the flanking sequences (SEQ ID NO. 5, 6, 7 and 8) used in the cloning of synthesized Composite Human Antibody™ VH and VK genes into expression vectors.

Abbreviations: Flank. Seq. (flanking sequence), SEQ ID NO. (sequence identification number), VH (variable heavy chain), VK (variable light chain).

FIG. 6A-6G: Amino acid and nucleic acid sequences of the different humanized antibodies variants FIGS. 6A-6D. show the variable heavy chain nucleotide and deduced amino acid sequences of variants VH1-4, having the amino acid sequences of SEQ ID NO. 20, 21, 22 and 23, and the nucleic acid sequences of SEQ ID NO. 27, 28, 29 and 30, respectively.

FIGS. 6E-6G. show the variable light chain nucleotide and deduced amino acid sequences of variants VK1-3, having the amino acid sequences of SEQ ID NO. 24, 25 and 26, and the nucleic acid sequences of SEQ ID NO. 31, 32 and 33, respectively.

CDR definitions and protein sequence numbering according to Kabat. CDR nucleotide and protein sequences are underlined. Amino acids changed from the original hybridoma sequence are highlighted in bold.

Abbreviations: Var. (variant), CDR (Complementarity Determining Region), VH (variable heavy chain), VK (variable light chain), SEQ ID NO. (sequence identification number).

Figure 7A:
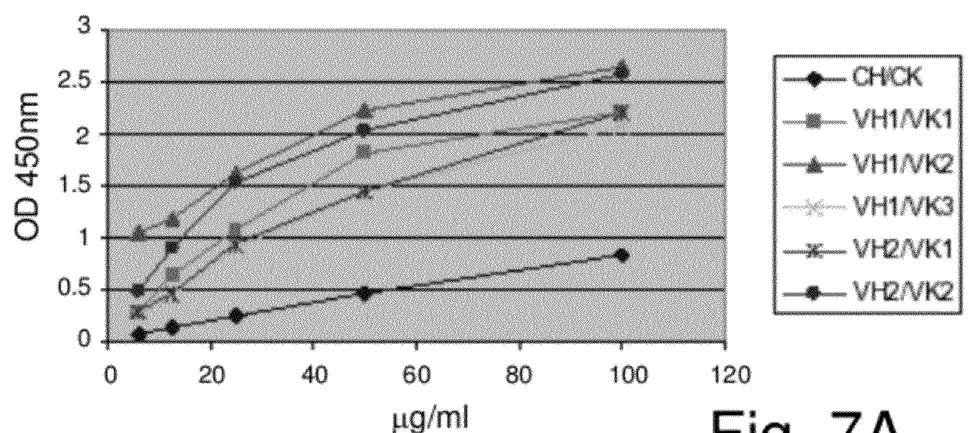
Figure 7B:
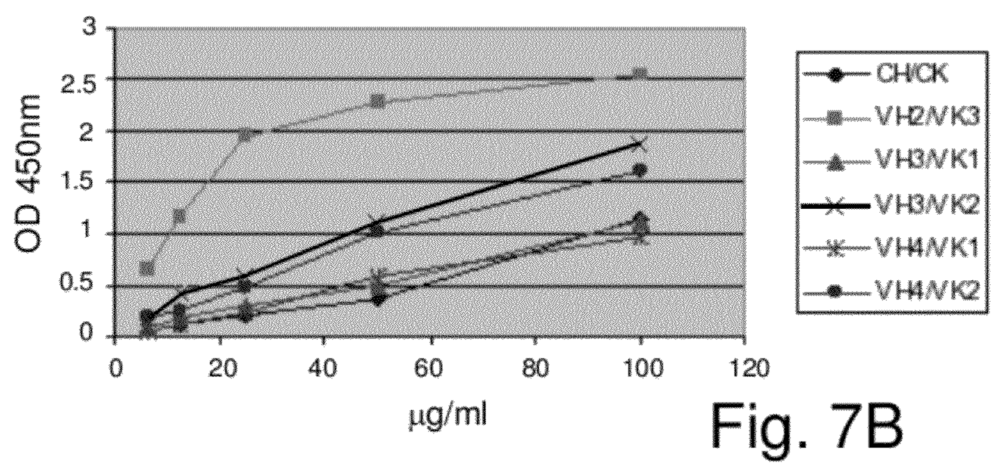
Figure 7C:
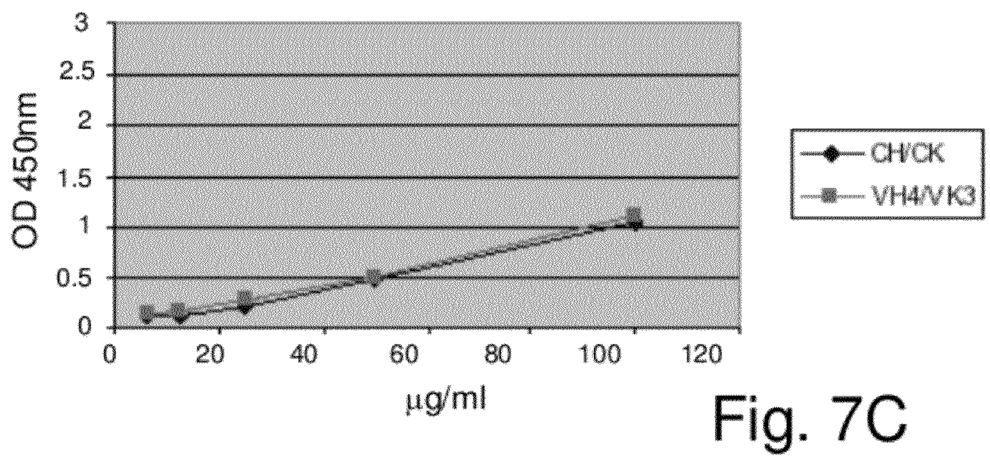

FIG. 7A-7C: Binding of composite human antibodies to peptide-6

The binding of the purified Composite Human Antibodies variants to peptide-6 was tested by ELISA. Antibody variants were diluted from 100 μg/ml to 6.125 μg/ml and bound to a peptide-6 coated NuncMaxiSorp 96 well plate. Binding was detected via anti-human IgG kappa HRP and TMB substrate. Absorbance was measured at 450 nm.

Abbreviations: VH (variable heavy chain), VK (variable light chain), CH/CK chimeric mouse antibody, OD (optical density).

Figure 8:
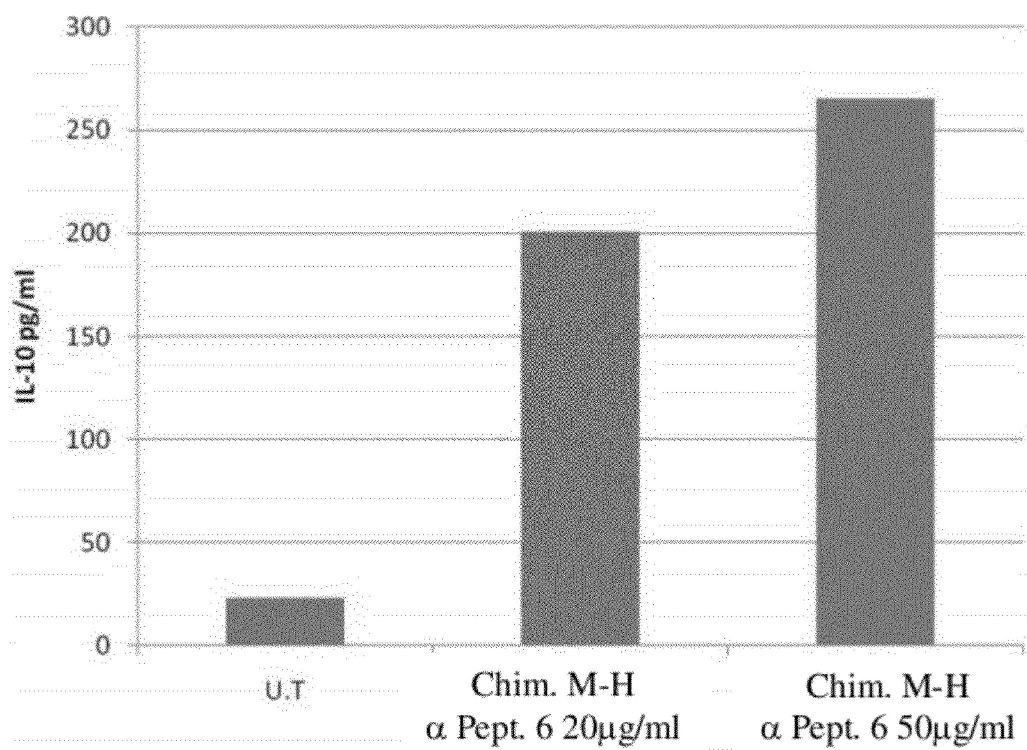

FIG. 8: Chimeric anti-peptide-6 antibody stimulates IL-10 secretion from human macrophages Histogram shows IL-10 secretion of human PBMC that were incubated with varying doses of the chimeric mouse-human anti-peptide-6 antibody for 48 hours. Untreated cells served as a control. The supernatant was collected and assayed with an IL-10 ELISA detection kit (R&D systems).

Abbreviations: Chim. M-H a-pept. 6 (chimeric mouse anti-human peptide-6), α (anti), U.T. (untreated).

Figure 9:
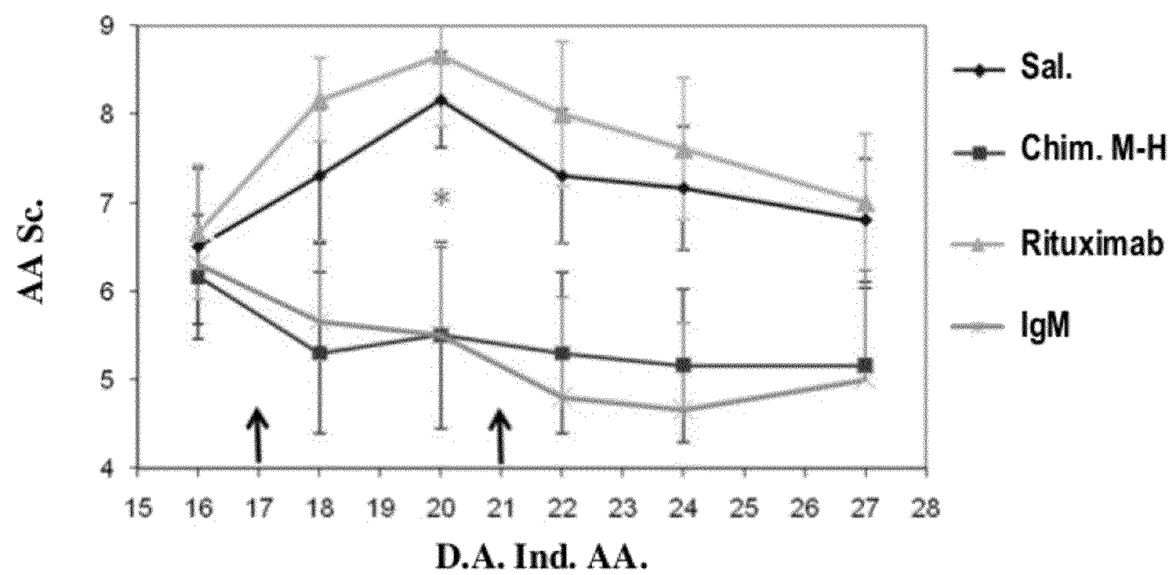

FIG. 9: Chimeric anti-peptide-6 antibody suppresses the severity of established AA Figure shows arthritis score of different experimental groups of animals treated with the mouse IgM and the chimeric mouse-human IgG1 anti-peptide-6 antibodies, a control chimeric Rituximab antibody and Saline. Arthritis score is the mean of 6-7 animals. *$p<0.05$ compared to Saline treated rats on day 20.

Abbreviations: D.A. Ind. AA. (days after induction of arthritis); Sal. (saline); Chim. M-H (chimeric mouse anti human); AA Sc. (arthritis score).

Figure 10A:
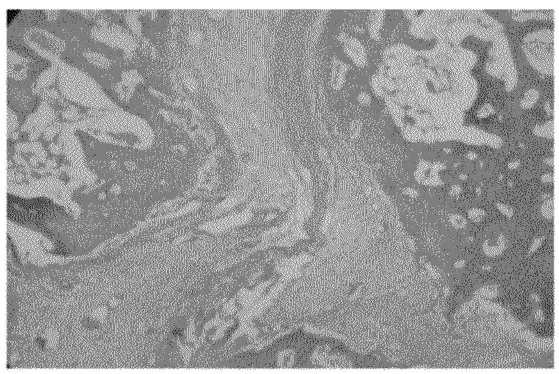
Figure 10B:
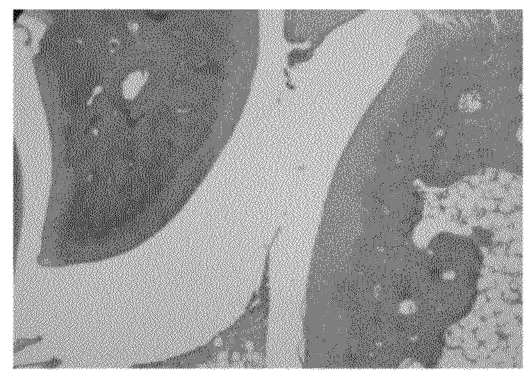

FIG. 10A-10B: Chimeric anti-peptide-6 antibody suppresses the severity of established AA Figure depicts the pathology findings of joints from rats treated with the chimeric mouse-human anti-peptide-6 antibody (FIG. 10B) compared to rats treated with the control antibody Rituximab (FIG. 10A).

Abbreviations: Chim. M-H Pept 6 (chimeric mouse anti human peptide-6).

Figure 11:
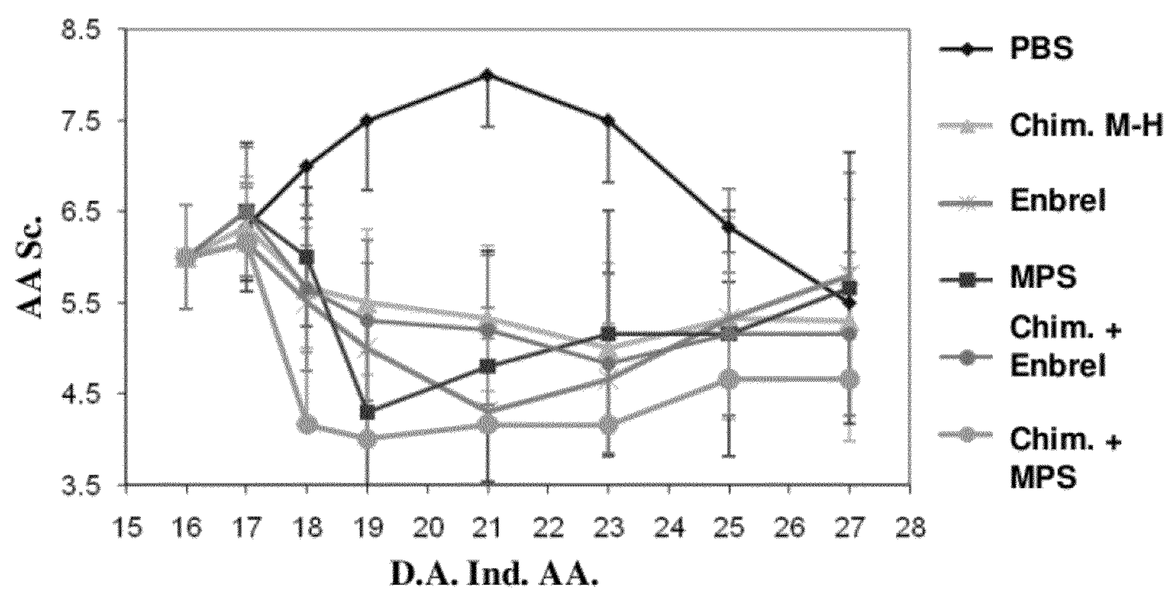

FIG. 11: The effects of chimeric anti-peptide-6 antibody, MPS & ENBREL® on established AA Figure shows arthritis score of different experimental groups of animals treated with the chimeric mouse-human IgG1 anti-peptide-6 antibody, methylprednisone (MPS) or ENBREL®, and combinations thereof with the chimeric mouse-human antibody. Arthritis score is the mean of 6 animals. $p<0.05$, $p<0.02$, $p<0.05$ comparing the chimeric anti-peptide-6 antibody, ENBREL® or MPS, respectively to PBS on day 21. $p<0.05$ comparing MPS to PBS on day 19. $P<0.02$ and $p<0.05$ comparing the chimeric anti-peptide-6 antibody ENBREL® to PBS on days 21 and 23 respectively. $p<0.02$, $p<0.02$, $p<0.01$ and $p<0.05$ comparing the chimeric anti-peptide-6 antibody+MPS to PBS on days 18, 19, 21 and 23 respectively.

Abbreviations: D.A. Ind. AA. (days after induction of arthritis); Chim. M-H (chimeric mouse anti human); Chim. (chimeric); AA. Sc. (arthritis score).

FIG. 12A-12C: Humanized anti-peptide-6 antibody binds to human macrophages (CD14+ cells)

Human PBMC were stained with an anti-CD14 antibody (APC conjugated) alone or double stained with the humanized VH2/VK3 anti-peptide-6 antibody (FITC conjugated; 10 μg). The cells were then analyzed by FACS for the binding of the antibodies.

FIGS. 12A, 12B depict density plots of the anti-CD14 stained cells (A) and cells stained with the anti-CD14+ humanized antibodies (B).

FIG. 12C depicts a histogram plot of the stained cells.

Abbreviations: Hum. (humanized); Cou. (count); α (anti), VH (variable heavy chain), VK (variable light chain).

Figure 13:
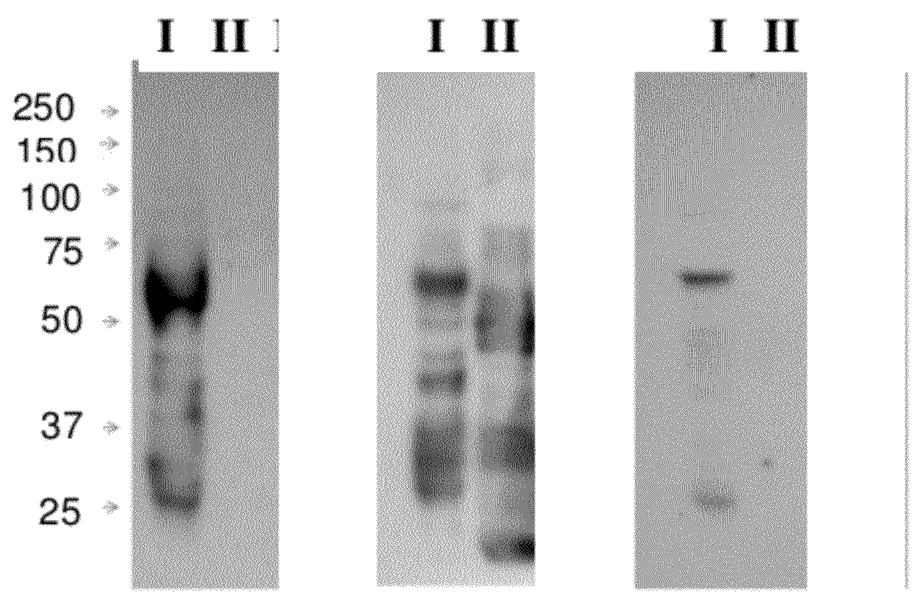

FIG. 13: Humanized anti-peptide-6 antibody binds over-expressed His-CAP1, but not His-CREBP Commercial mouse anti human CAP1, commercial mouse anti His-tag and Humanized anti-peptide-6 VH2/VK3 variant, were used for Western blot analysis of over-expressed and purified His-CAP1 (I) and His-CREB (II).

Abbreviations: α Hum. CAP1 (anti-human CAP1 antibody); α His (anti-his tag antibody); Hum. α-pep. 6. (humanized anti-peptide-6 antibody, the VH2/VK3 variant).

Figure 14:
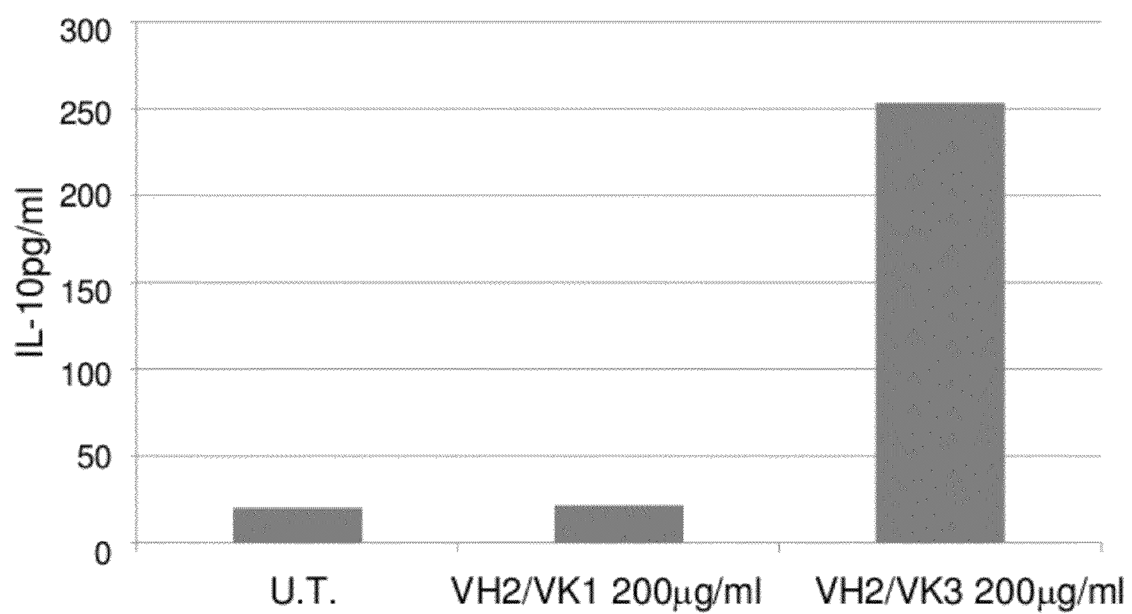

FIG. 14: Humanized anti-peptide-6 antibody induces IL-10 secretion from human macrophages Histogram shows IL-10 secretion of human PBMC that were incubated with two variants of the humanized anti-peptide-6 antibodies, the VH2/VK1 and VH2/VK3, for 48 hours. Untreated cells served as a control. The supernatant was collected and assayed with an IL-10 ELISA detection kit (R&D systems).

Abbreviations: U.T. (untreated), VH (variable heavy chain), VK (variable light chain).

Figure 15A:
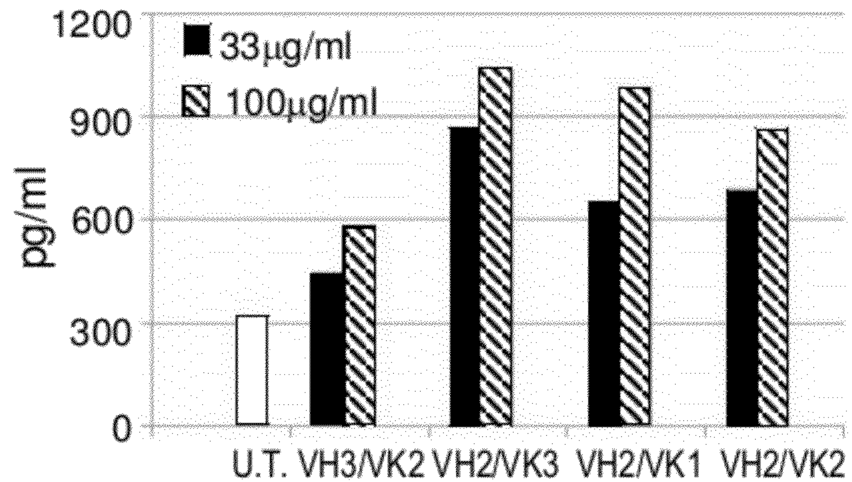
Figure 15B:
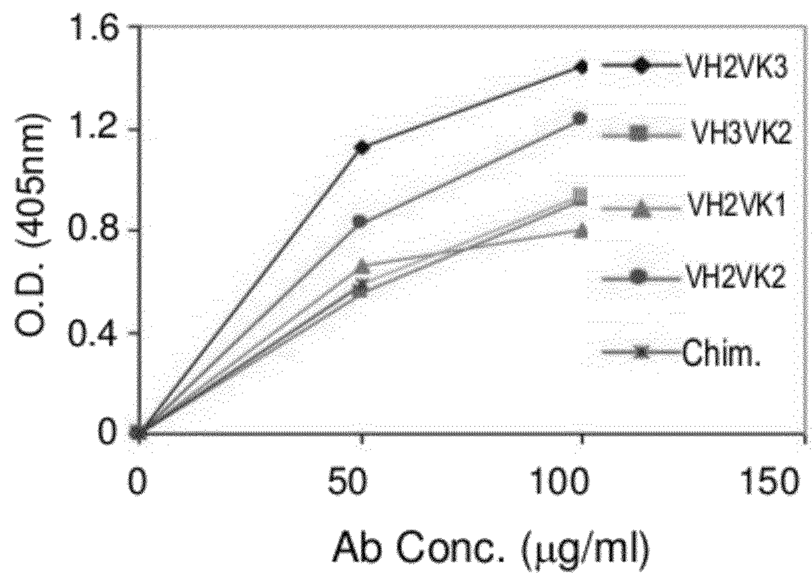

FIG. 15A-15B: Binding of composite human antibodies to peptide-6 and IL-10 induction are not directly correlated FIG. 15A: PBMC IL-10 induction capacities of either 33 μg/ml or 100 μg/ml different VH and VK humanized antibody variants.

FIG. 15B: Peptide-6 affinities for VH3/VK2, VH2/VK3, VH2/VK1 and VH2/VK2.

Abbreviations: Chim. (chimera); O.D. (optical density); Ab. Conc. (antibody concentration), U.T. (untreated), VH (variable heavy chain), VK (variable light chain).

Figure 16A:
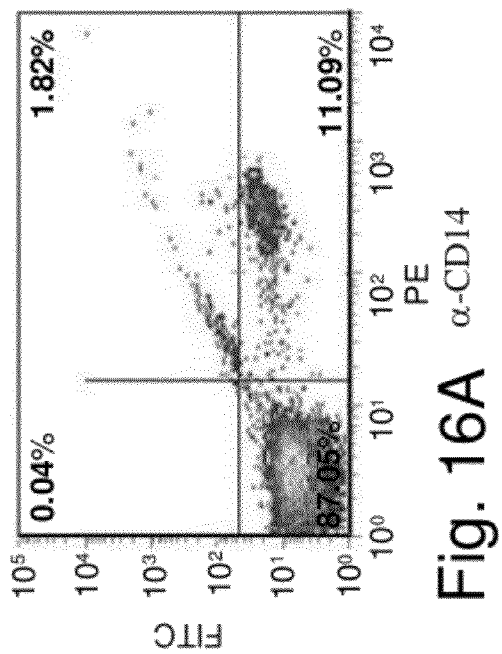
Figure 16B:
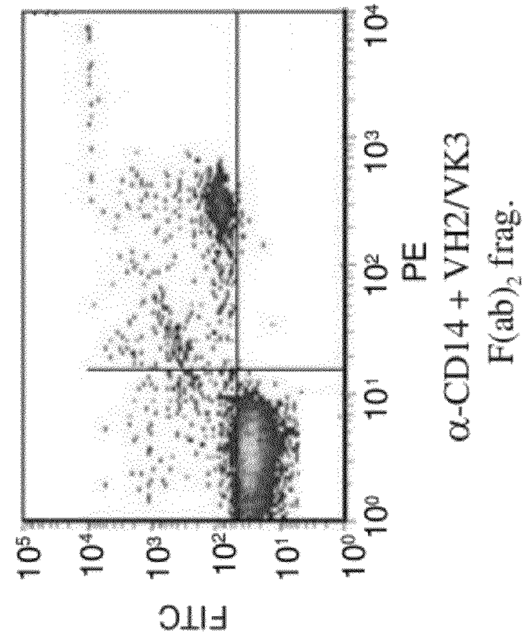
Figure 16C:
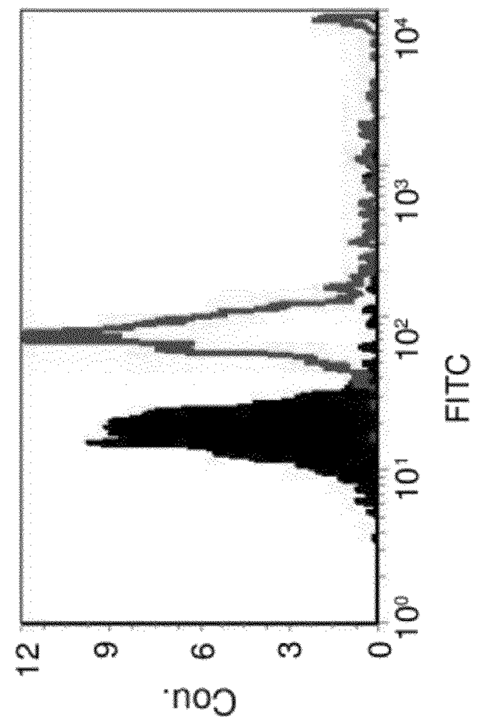

FIG. 16A-16C: Humanized anti-peptide-6 $F(ab)_2$ fragment binds to human macrophages Human PBMC were stained with an anti-CD14 antibody (PE conjugated) alone or double stained with $F(ab)_2$ fragment of the humanized VH2/VK3 anti-peptide-6 antibody (FITC conjugated; 10 μg) fragment of the humanized VH2/VK3 anti-peptide-6 antibody (FITC conjugatees.

FIGS. 16A, 16B depict density plots of the anti-CD14 stained cells (A) and cells stained with the anti-CD 14+ $F(ab)_2$ fragment of the humanized antibodies (B). FIG. 16C depicts a histogram plot of the stained cells.

Abbreviations: Frag. (fragment); Cou. (count); α (anti), VH (variable heavy chain), VK (variable light chain).

Figure 17:
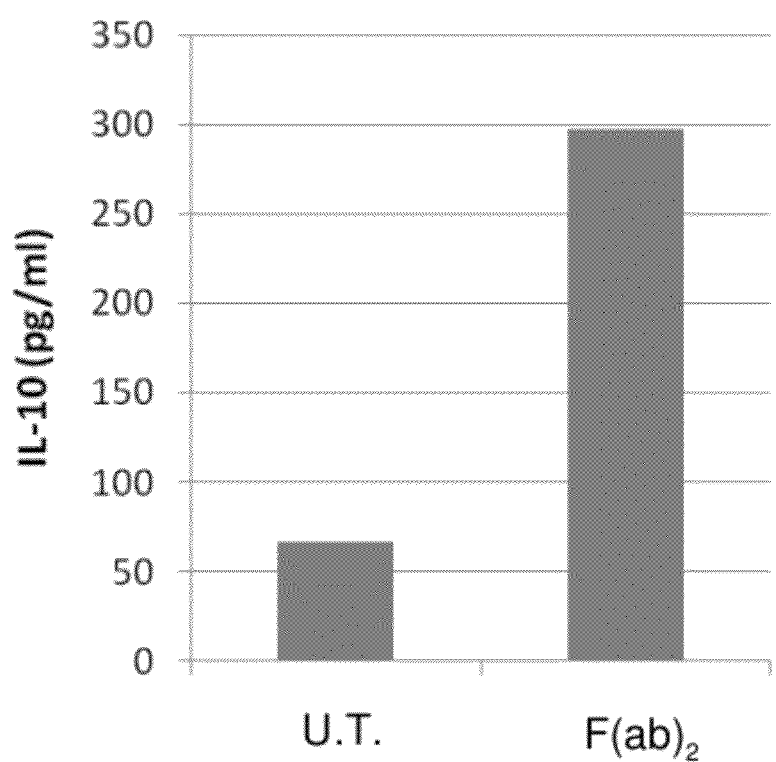

FIG. 17: Humanized anti-peptide-6 $F(ab)_2$ fragment induces IL-10 secretion from human macrophages Histogram shows IL-10 secretion of human PBMC that were incubated with the $F(ab)_2$ fragment of the humanized anti-peptide-6 VH2/VK3 variant, for 48 hours. Untreated cells served as a control. The supernatant was collected and assayed with an IL-10 ELISA detection kit (R&D systems).

Abbreviations: U.T. (untreated).

Figure 18:
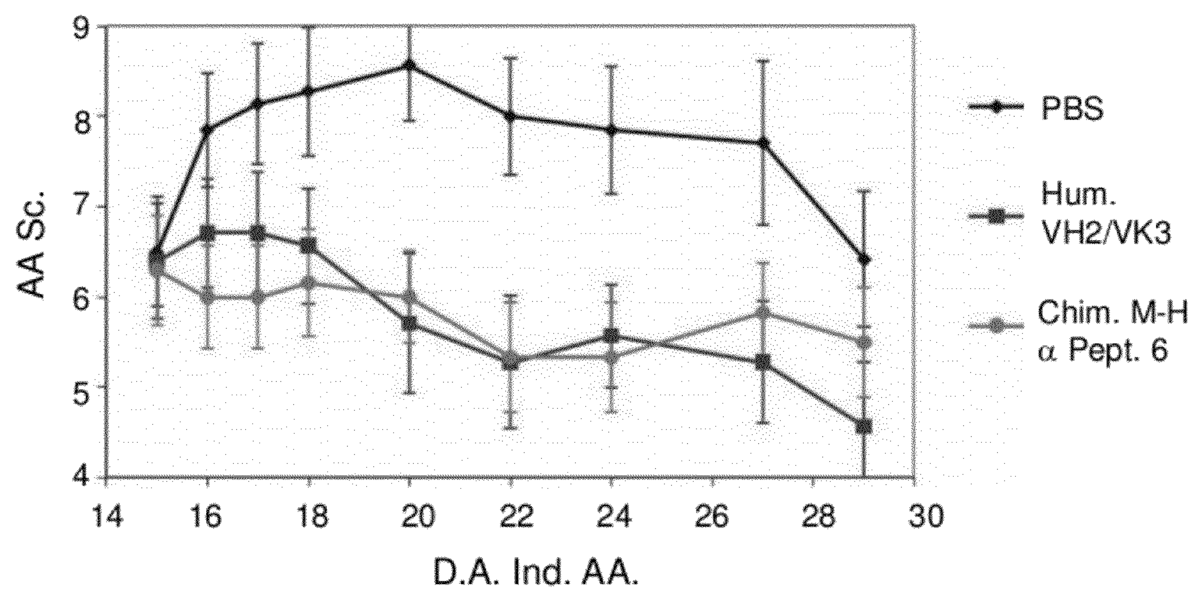

FIG. 18: Humanized anti-peptide-6 antibody suppresses the severity of established AA Figure shows arthritis score of animals treated with the mouse-human chimeric IgG1 anti-peptide-6 antibody, the humanized anti-peptide-6 variant VH2/VK3 or PBS as control.

Arthritis score is the mean of 6-7 animals. *$P<0.02$ comparing the humanized anti-peptide-6 antibody to PBS on days 20 and 22, and $P<0.05$ on day 24. *$P<0.01$ comparing the chimeric anti-peptide-6 antibody to PBS on days 20 and 22, and $P<0.02$ on day 24, and $P<0.05$ on day 18.

Abbreviations: D.A. Ind. AA. (days after induction of arthritis); Chim. M-H α Pept. 6 (chimeric mouse anti human peptide-6); Hum. (humanized); AA. Sc. (arthritis score).

Figure 19:
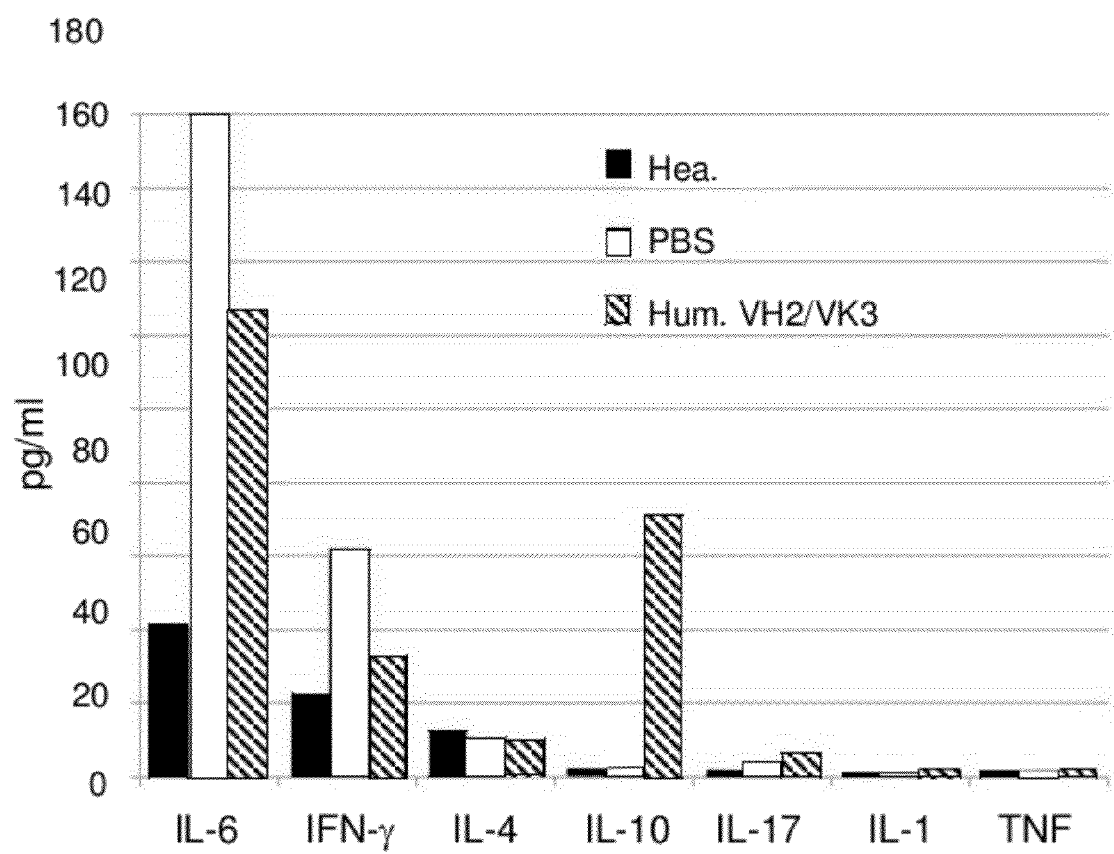

FIG. 19: The effect of humanized anti-peptide-6 antibody on various cytokines in AA Histogram shows levels of the following cytokines: IL-6, IFN-γ, IL-4, IL-10, IL-17, IL-1 and TNF-α, in the serum of rats with established AA. Animals were treated with the humanized anti-peptide-6 VH2/VK3 variant or with PBS. Serum of healthy, non-arthritic animals served as a control. Results are the mean±SE of 2 rats per group for all cytokines, except IL-17, IL-1 and TNF-α where the results represent 1 rat per group.

Abbreviations: Health. (healthy); Hum. (humanized); IFNγ (interferon gamma), VH (variable heavy chain), VK (variable light chain).

Figure 20:
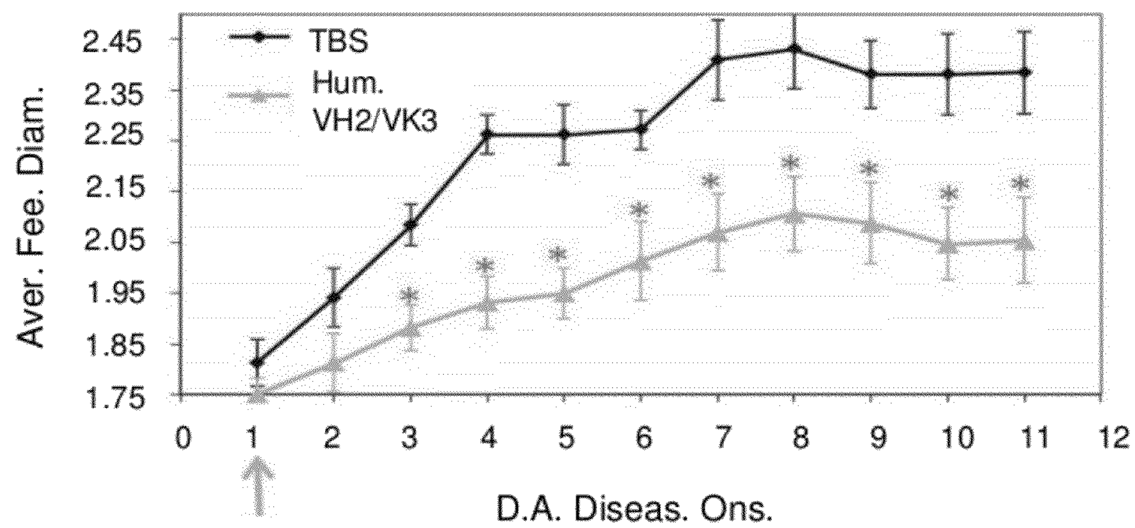

FIG. 20: Humanized anti-peptide-6 antibody suppresses the severity of established Collagen-Induced Arthritis (CIA)

Figure shows arthritis score of animals treated with the humanized VH2/VK3 anti-peptide-6 antibody, in comparison to TBS treated animals.

Arthritis was evaluated by measuring feet diameter and is the average of 8 mice per group. *$p<0.05$ compared to TBS treated mice.

Abbreviations: Hum. (humanized); D.A. Diseas. Ons. (days after disease onset); Aver. Fee. Diam. (average feet diameter), VH (variable heavy chain), VK (variable light chain).

Figure 21:
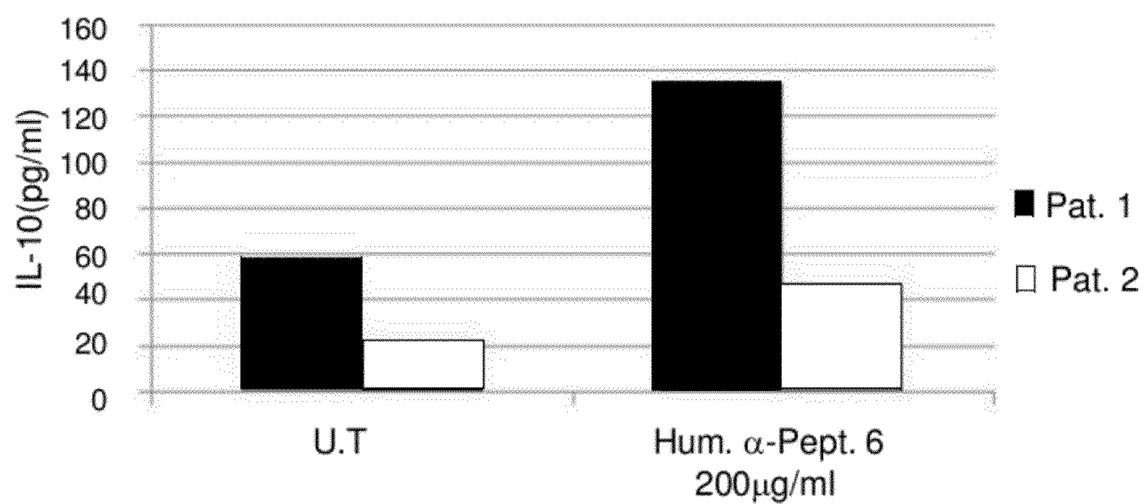

FIG. 21: Humanized anti-peptide-6 antibody induces IL-10 secretion from rheumatoid arthritis patients PBMC IL-10 levels in culture supernatant of PBMC collected from two RA patients after 48 hours incubation with or without the VH2/VK3 anti-peptide-6 humanized antibody.

Abbreviations: U.T. (untreated); Pat. (patient), hum. α-pep-6 (the VH2/VK3 anti-peptide-6 humanized antibody).

Figure 22:
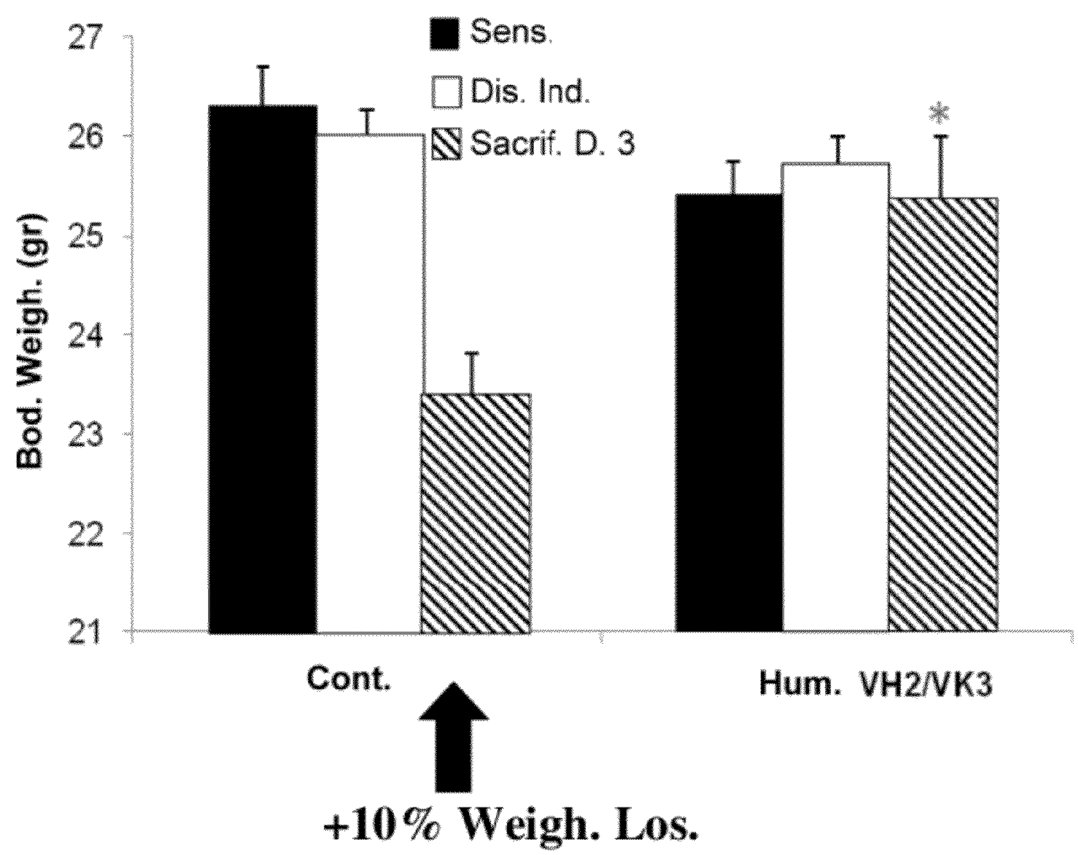

FIG. 22: Humanized anti-peptide-6 antibody ameliorates TNBS Colitis, a model for Inflammatory Bowel Disease (IBD)

Histogram shows body weight (gr) measured in TBNS-colitis model with animals treated with the humanized VH2/VK3 antibody variant, in comparison to control animals (10 animals in each group). *$p<0.05$ compared to control mice.

Abbreviations: Bod. Weigh. Gr. (body weight in grams); Weigh. Los (weight loss); Sens. (at time of sensitization); Dis. Ind. (at time of disease induction); Sacrif. D. 3 (at sacrifice (day 3)); Hum. (humanized); Cont. (control), VH (variable heavy chain), VK (variable light chain).

Figure 23A:
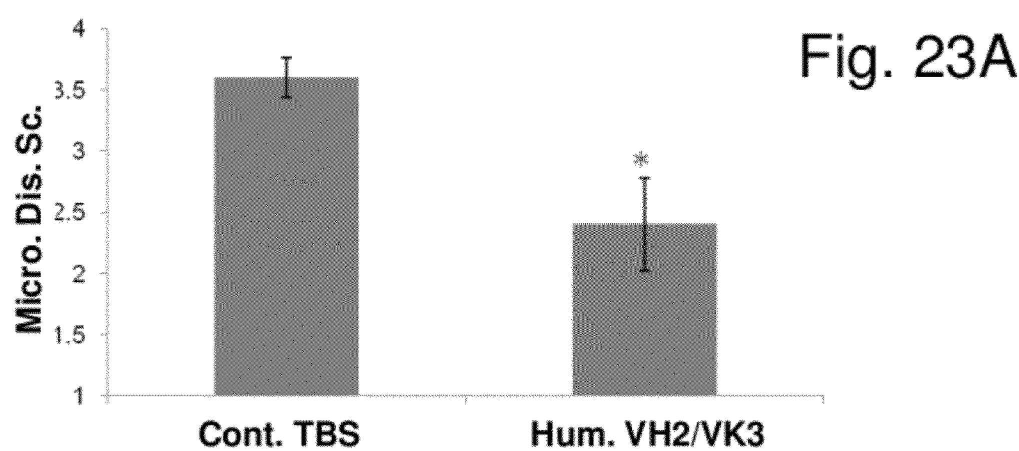
Figure 23B:
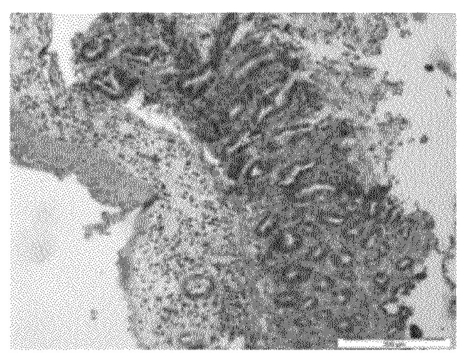
Figure 23C:
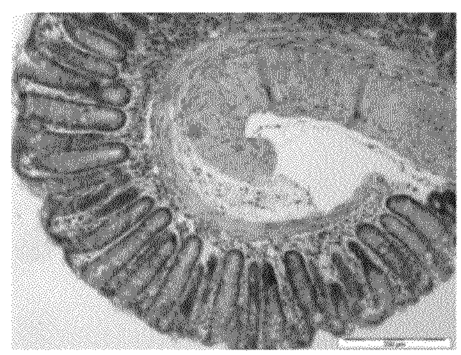

FIG. 23A-23C: Humanized anti-peptide-6 antibody ameliorates TNBS Colitis, a model for IBD FIG. 23A. shows histogram indicating the microscopic disease score of TNBS-colitis animals treated with the humanized VH2/VK3 antibody variant as compared to control (10 animals in each group).

FIGS. 23B-23C. show histological section taken from treated (C) and control (B) animals (magnification ×100). *$p<0.05$ compared to control mice.

Abbreviations: Micro. Dis. Sc. (microscopic disease score); Hum. (humanized); Cont. (control), VH (variable heavy chain), VK (variable light chain).

Figure 24:
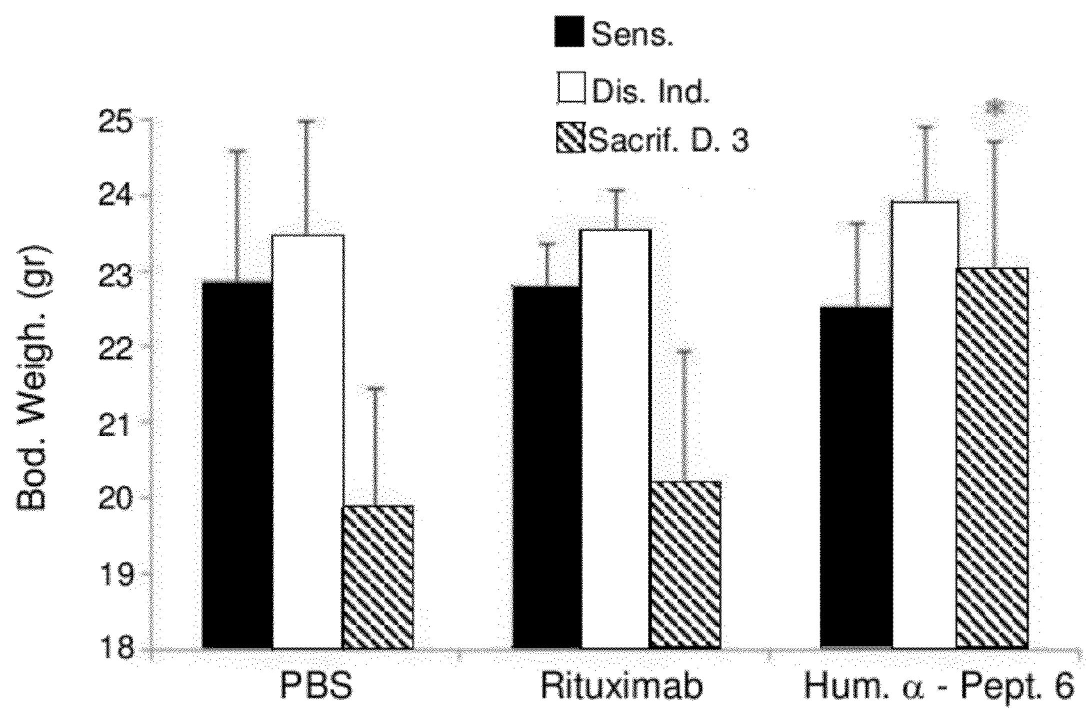

FIG. 24: Humanized anti-peptide-6 antibody suppresses body weight loss in TNBS-Colitis IBD model Comparison of body weight between mice challenged with intrarectal TNBS administration and treated with the humanized anti-peptide-6 antibody (VH2/VK3), Rituximab or PBS at Day −7 (sensitization), Day 0 (disease induction) and Day 3 (sacrifice), 10 mice were used in each group. *$p<0.05$ compared to control mice.

Abbreviations: Bod. Wei. (body weight); Sens. (sensitization); Dis. Ind. D. 3 (disease induction (day 3)); Sacrif. (sacrifice), Hum. α-pep-6 (humanized anti-peptide-6 antibody, VH2/VK3 variant).

Figure 25:
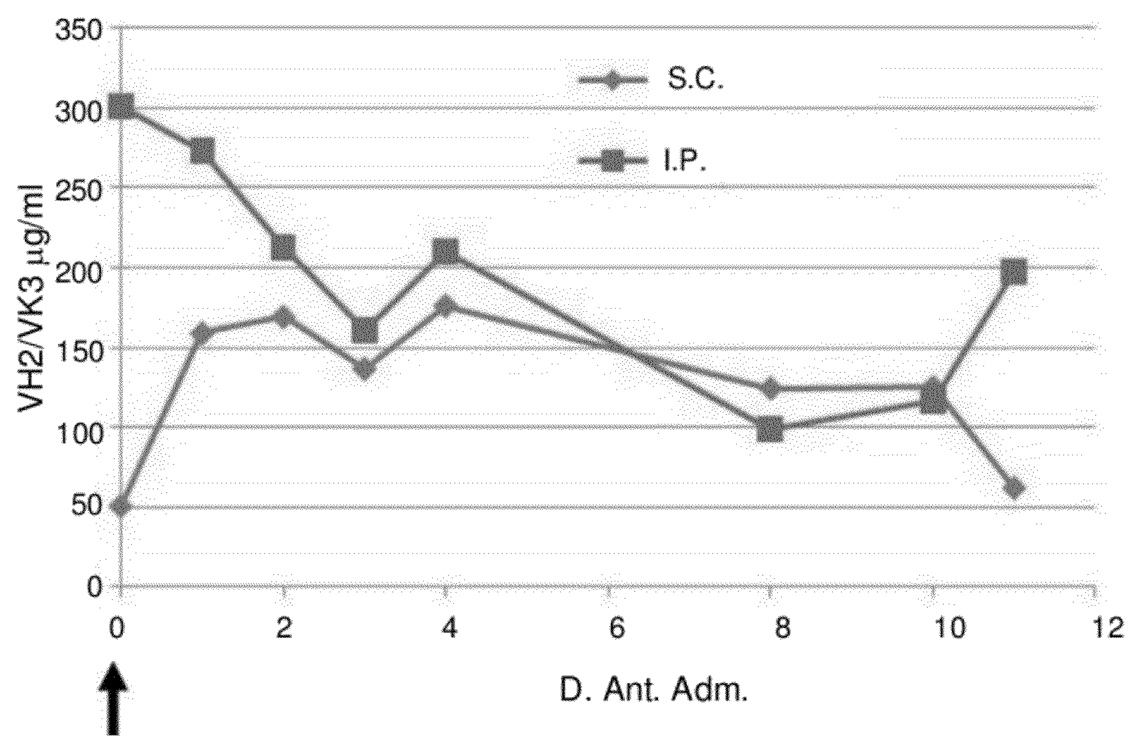

FIG. 25: Pharmacokinetic profile of the humanized anti-peptide-6 antibody

A plot of the mouse serum humanized anti-peptide-6 antibody (humanized anti-peptide-6 antibody, VH2/VK3 variant) levels during an 11-day period after either i.p. or s.c. administration of 20 mg/Kg of the humanized anti-peptide-6 antibody.

Abbreviations: S.C. (subcutaneous); I.P. (intraperitoneal); D. Ant. Adm. (days from antibody administration).

Figure 26:
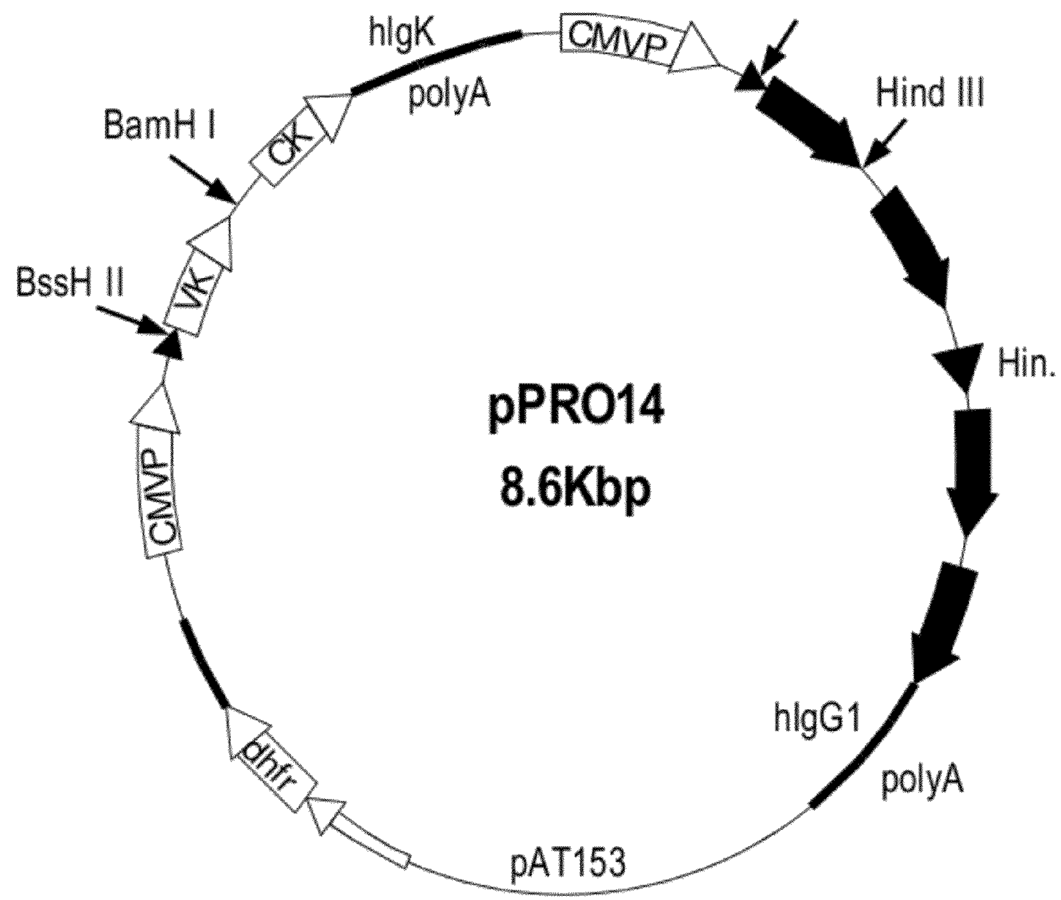

FIG. 26: Map of the bicistronic pPRO14 expression vector

Elements needed for human IgG expression and for selection in eukaryotic cells are shown (not to scale). VH region is PRO01 heavy chain variant 2 and VK region is PRO01 light chain variant 3. Details of elements for prokaryotic propagation and selection are not shown.

Abbreviations: Hin. (hinge).

Figure 27A:
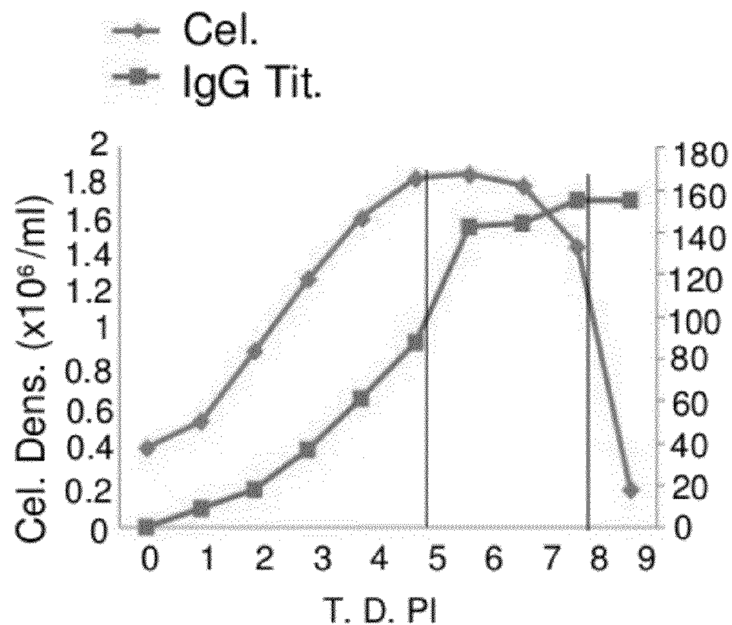
Figure 27B:
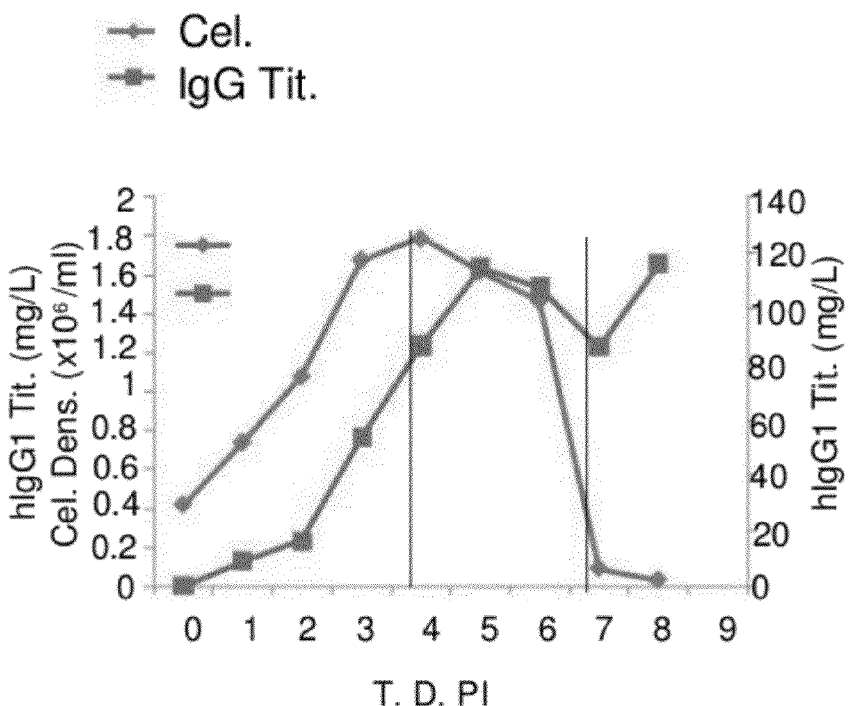

FIG. 27A-27B: Cell line PRO01-SF-14-524-AJ productivity and growth

Analysis of cell line PRO01-SF-14-524-AJ productivity and growth characteristics over a ten generation period. SPR (specific productivity rate) cultures were set up ten generations apart, as 70 ml cultures in 250 ml shake flasks and samples were taken for cell count, cell viability and IgG titre daily. (FIG. 27A) SPR#1, (FIG. 27B) SPR#2. Dotted lines indicate time window for calculation of peak SPR.

Abbreviations: Cel. Dens. (cell density); Cel. Cou. (cell count); Tit. (titre); T. D. PI (time in days post inoculation).

Figure 28A:
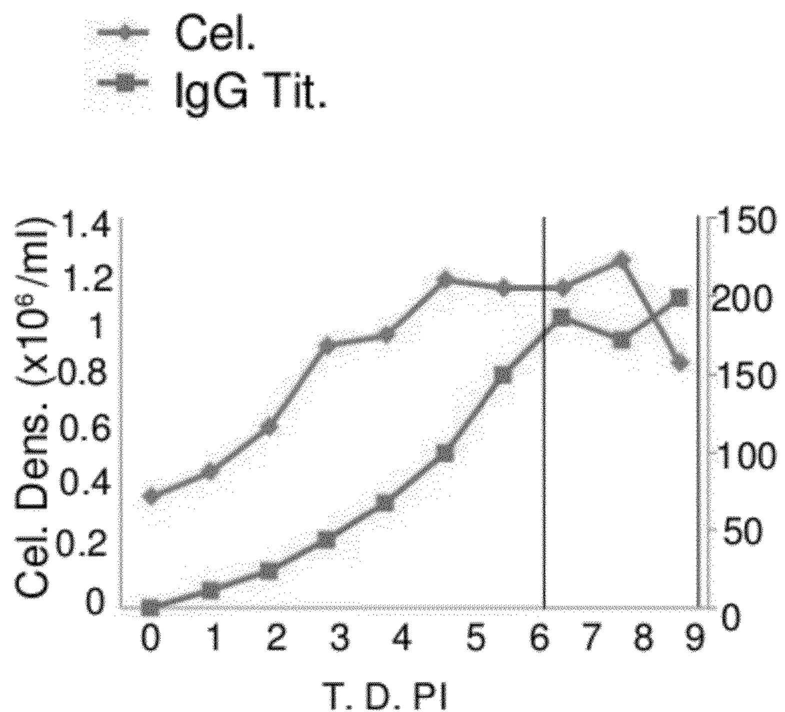
Figure 28B:
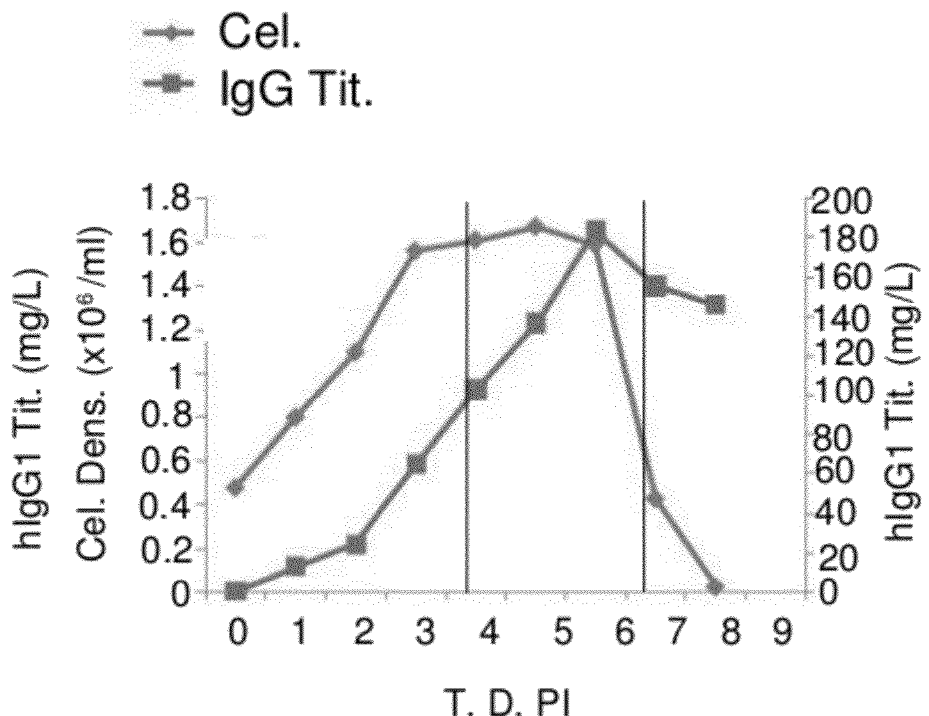

FIG. 28A-28B: Cell line PRO01-SF-14-524-AO productivity and growth

Analysis of cell line PRO01-SF-14-524-AO productivity and growth characteristics over a ten generation period. SPR cultures were set up ten generations apart, as 70 ml cultures in 250 ml shake flasks and samples were taken for cell count, cell viability and IgG titre daily. (FIG. 28A) SPR#1, (FIG. 28B) SPR#2. Dotted lines indicate time window for calculation of peak SPR.

Abbreviations: Cel. Dens. (cell density); Cel. Cou. (cell count); Tit. (titre); T. D. PI (time in days post inoculation).

Figure 29A:
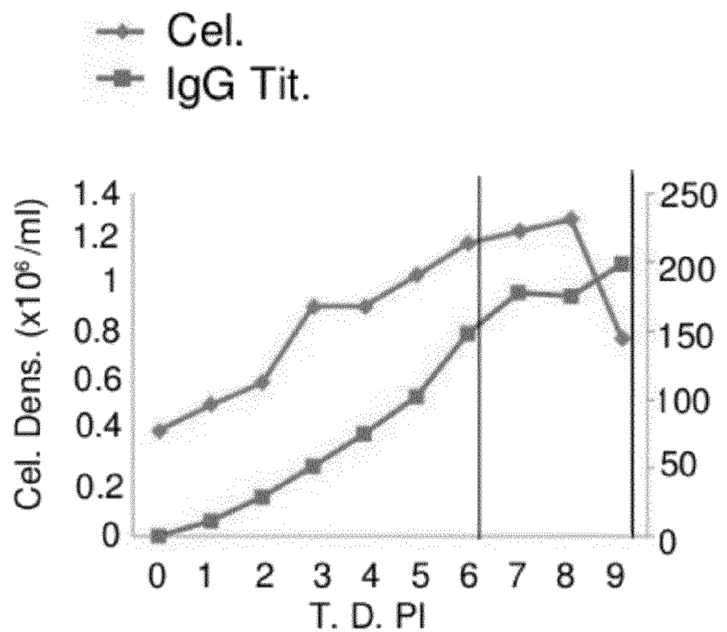
Figure 29B:
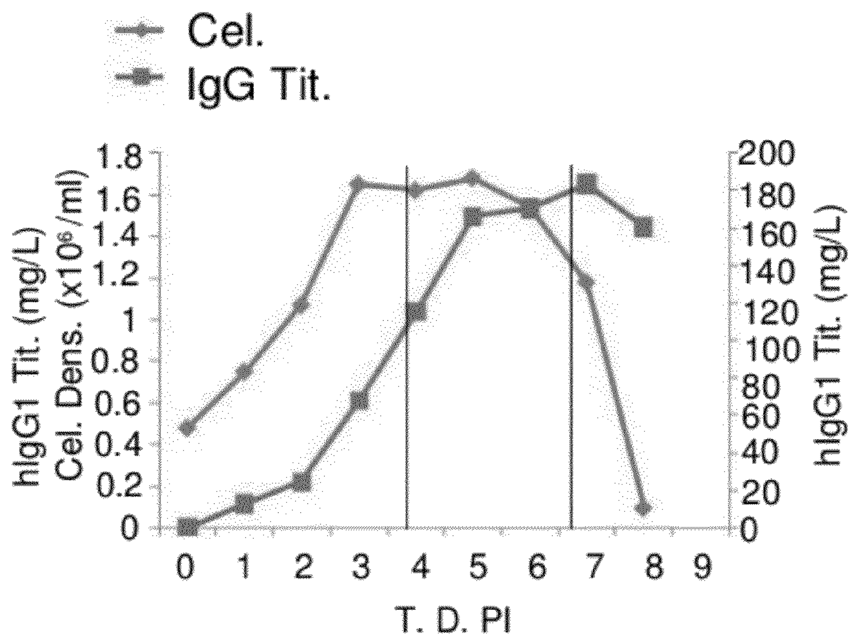

FIG. 29A-29B: Cell line PRO01-SF-14-524-AZ productivity and growth

Analysis of cell line PRO01-SF-14-524-AZ productivity and growth characteristics over a ten generation period. SPR cultures were set up ten generations apart, as 70 ml cultures in 250 ml shake flasks and samples were taken for cell count, cell viability and IgG titre daily. (FIG. 29A) SPR#1, (FIG. 29B) SPR#2. Dotted lines indicate time window for calculation of peak SPR.

Abbreviations: Cel. Dens. (cell density); Cel. Cou. (cell count); Tit. (titre); T. D. PI (time in days post inoculation).

Figure 30A:
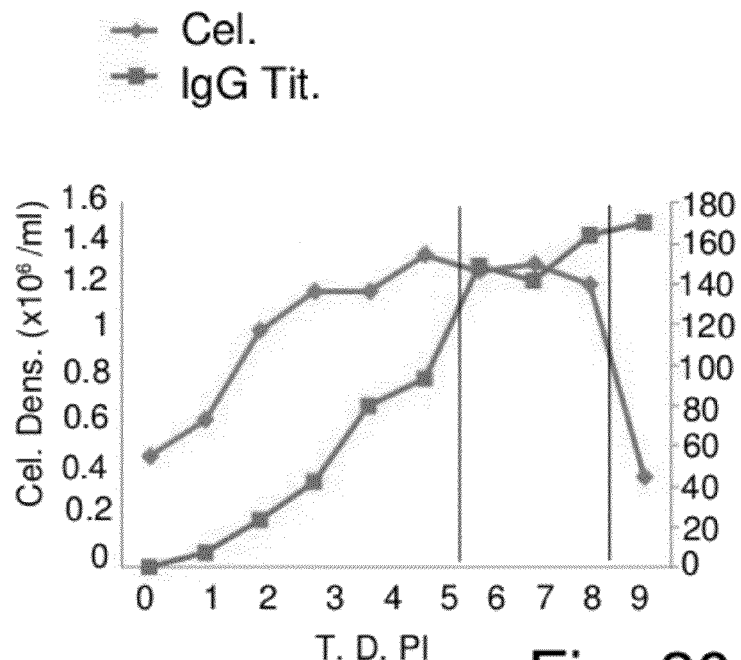
Figure 30B:
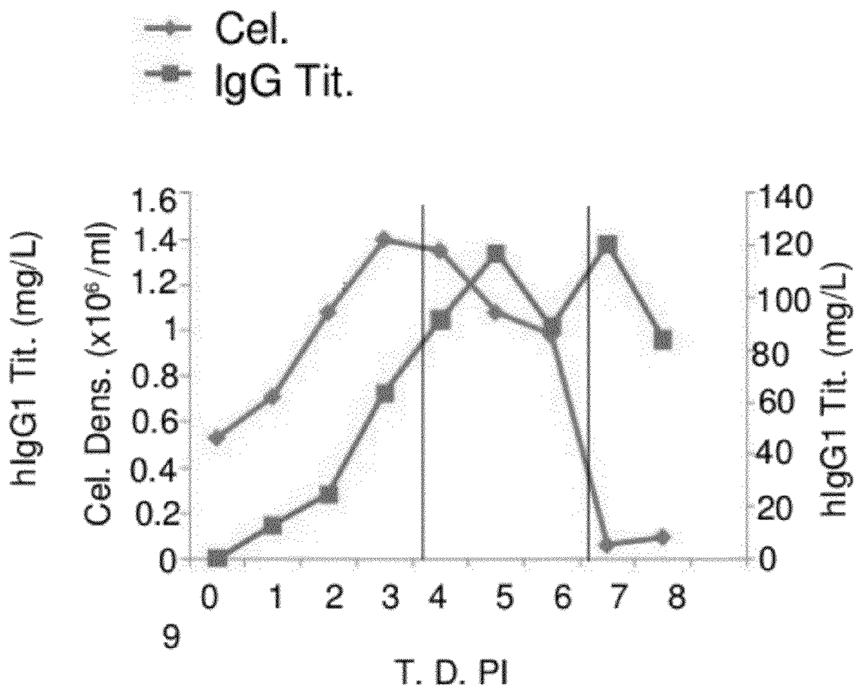

FIG. 30A-30B: Cell line PRO01-SF-14-524-BE productivity and growth

Analysis of cell line PRO01-SF-14-524-BE productivity and growth characteristics over a ten generation period. SPR cultures were set up ten generations apart, as 70 ml cultures in 250 ml shake flasks and samples were taken for cell count, cell viability and IgG titre daily. (FIG. 30A) SPR#1, (FIG. 30B) SPR#2. Dotted lines indicate time window for calculation of peak SPR.

Abbreviations: Cel. Dens. (cell density); Cel. Cou. (cell count); Tit. (titre); T. D. PI (time in days post inoculation).

Figure 31:
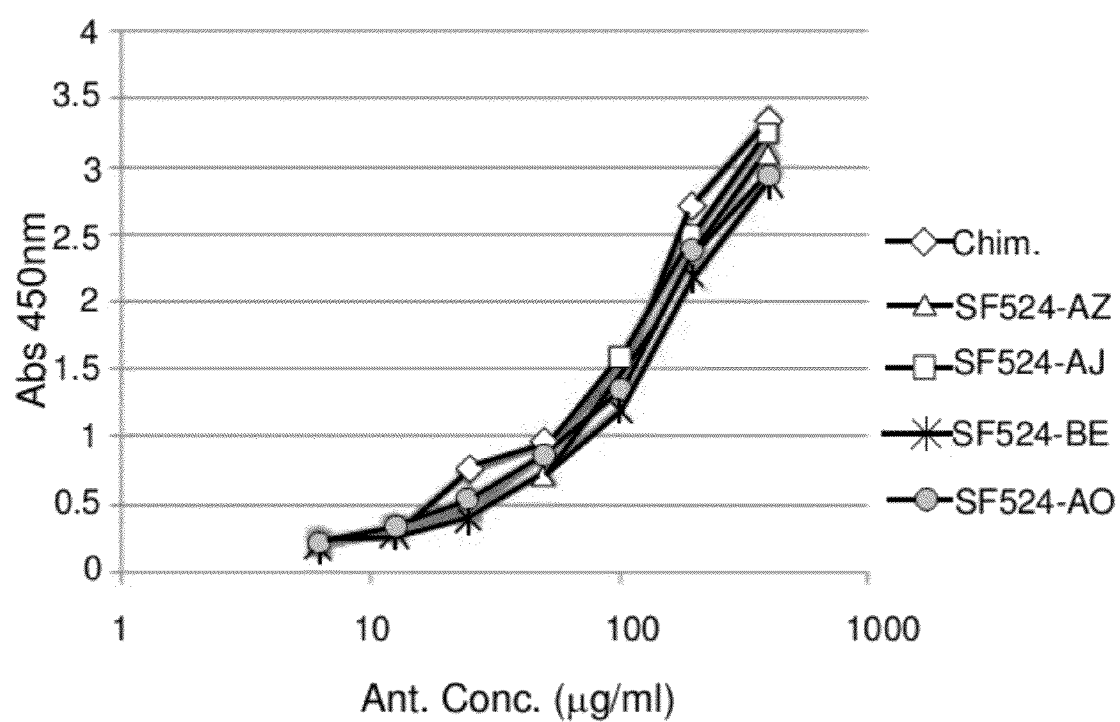

FIG. 31: Binding of antibodies from the different cell lines

Binding of antibodies purified from the supernatants of cell lines PRO01-SF-14-524-AJ, PRO01-SF-14-524-AO, PRO01-SF-14-524-AZ and PRO01-SF-14-524-BE. A dilution series of each antibody was incubated in a microtitre plate pre-coated with 10 μg/ml Peptide-6. Binding was detected with HRP labelled mouse anti-human kappa light chains and TMB.

Abbreviations: Chim. (chimeric); Ant. Conc. (antibody concentration), Abs (absorbance).

DETAILED DESCRIPTION OF THE INVENTION

Abbreviations:

BSA—Bovine serum albumin

CDR—Complementarity Determining. Region of an antibody variable region (numbered CDR1-3 for each of the heavy and light chains, as defined by Kabat).

Ec(0.1%) The absorbance of a 1 mg/ml solution of protein

ED50—The concentration of a test substance that gives 50% of the maximum observable effect.

ELISA—Enzyme linked immunosorbent assay

FR—Framework region—scaffold region of a variable domain supporting the CDRs

IgG—Immunoglobulin G mAb Monoclonal antibody

MHC Major histocompatibility complex

OD280 nm—Optical density measured at 280 nm.

PBS Phosphate-buffered saline

TMB 3,3',5,5'-tetramethylbenzidine

PCR Polymerase chain reaction

V-region Variable region of an antibody chain

The present invention provides humanized antibodies that specifically recognize and bind a polypeptide comprising the amino acid sequence of SEQ ID NO. 15. It should be noted that the polypeptide of SEQ ID NO. 15 known as peptide-6, is derived from HSP65. As demonstrated herein later, exemplified humanized antibodies of the invention were created by combining segments of amino acid sequence from a range of other human antibody variable regions. In a first step, a library of different variable region genes was generated, cloned into an expression vector and subsequently screened to recover members of the library with desirable properties such as binding to peptide-6 (SEQ ID NO. 15).

These segments were selected as containing "constraining" amino acid residues involved in epitope recognition, that are also present in the reference mouse antibody used by the invention.

More particularly, the library of VH and VL sequences is designed by selecting segments of VH and VL sequence from known human V region sequences such as those available in the Kabat antibody database, the NCBI database and from protein databases, such as UniProt and PRF/SBQDB. In addition, these can be supplemented by collection of human VH and VL sequences by direct sequencing of amplified VH and VL mRNA of human source from one or more individual segments. Various combinations of sequence segments were considered for design of VH and VL genes.

It will be understood to those skilled in the art that, in addition to methods described above, there will be other methods for creating and testing the humanized antibodies of the invention and for optimizing the properties of such antibodies. The antibodies of the present invention are new and, as a result of the totally human origin of the V regions, should be less immunogenic in humans than other antibodies containing non-human sequences. Additional optional features of humanized antibodies of the invention, namely the avoidance of T cell epitopes, may also contribute to lower immunogenicity. It will be understood that antibody segments and their combinations creating a combined human antibody might be selected to meet a range of criteria including the optional avoidance of T cell epitopes. For example, segments of human protein sequence and combinations thereof can be selected for avoidance of B cell epitopes and other epitopes such as MHC class I-restricted epitopes, for avoidance of amino acid sequences which might be deleterious to expression of the humanized antibody, for avoidance of sequences which might direct inappropriate modification of humanized antibodies such as N-glycosylation, for inclusion of certain functions such as helper T cell epitopes and/or B cell epitopes (for example, in vaccine applications), for subsequent conjugation to other moieties, and for a range of other criteria. It should be noted that "T-cell epitopes" as used herein are antigenic determinants recognized and bound by the T-cell receptor. Epitopes recognized by the T-cell receptor are often located in the inner, unexposed side of the antigen, and become accessible to the T-cell receptors after proteolytic processing of the antigen. MHC-restricted antigen recognition, or MHC restriction, refers to the fact that a given T cell will recognize a peptide antigen only when it is bound to a particular MHC molecule. Normally, as T cells are stimulated only in the presence of self-MHC molecules, antigen is recognized only as peptides bound to self-MHC molecules.

In one embodiment, the heavy and light chain variable regions of the anti-peptide-6 humanized antibody or antigen binding fragment thereof are derived entirely from one or more human antibodies, as described in WO2006/08246. In another embodiment, the variable regions are composed of segments of amino acid sequence from one or more human antibodies. In yet another embodiment the human segments are two or more amino acids in length. In one embodiment, the human segments are 100 or fewer amino acids in length. In further embodiments, the human segments are 50 or fewer, 40 or fewer, 30 or fewer, 20 or fewer, 15 or fewer, 10 or fewer, 9 or fewer, 8 or fewer, 7 or fewer, 6 or fewer, 5 or fewer, 4 or fewer, or 3 or fewer amino acids in length. Examples for such segments are demonstrated by FIG. 4.

Thus, according to a first aspect, the invention relates to an isolated and purified humanized antibody or any antigen-binding fragment thereof that specifically binds a polypeptide comprising SEQ ID NO: 15.

According to one embodiment, the humanized antibody of the invention comprises:

(a) a heavy chain variable region which comprises Cys at position H22, Ser at H23, Gly at H26, Phe at H27, Ser at H28, Leu at H29, Ser at H30, Thr at H31, Ser at 1132, Asn at H33, Met at H34, Gly at H35, Val at H35A, Gly at H35B, Leu at H48, His at H50, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and optionally, at least one of Leu at H49, Tyr at H74, Ile at H11, Ser at H41 and Ser at H108; and (b) a light chain variable region which comprises Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Trp at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and optionally at least one of Met at L21, Ile at L10 and Ala at L80.

It should be appreciated that all indicated positions are determined according to the Kabat numbering system.

It should be noted that according to certain embodiments, the constraining amino acid residues, specifically, residues Ser at L27, Ser at L27A, Val at L28, Ser at L29, Ser at L30, Ser at L31 of the light chain variable region, may be numbered according to the numbering shown in FIG. 1B, as follows: Ser at L27, Ser at L28, Val at L29, Ser at L30, Ser at L30A.

It should be further noted that the amino acid residues indicated above were identified by the present invention as "constraining" amino acids that are involved in the recognition of the epitope, peptide-6 (SEQ ID NO. 15). These residues are also present in the corresponding reference mouse antibody having a heavy chain variable region as denoted by SEQ ID NO. 1 and a light chain variable region as denoted by SEQ ID NO. 2. Therefore, according to one embodiment the heavy chain variable region of the humanized antibody of the invention comprises at least 30% identity to SEQ ID NO. 1 and the light chain variable region comprise at least 25% identity to SEQ ID NO 2 of the mouse reference variable regions.

The skilled artisan will recognize that the position numbers of the heavy and light chains are designated in accordance with common numbering schemes, e.g., the Kabat and Chothia numbering scheme. The Chothia number scheme is identical to the Kabat scheme, but places the insertions in CDR-L1 and CDR-H1 at structurally different positions. Unless otherwise indicated, the Kabat numbering scheme is used herein in reference to the sequence positions. The position of an amino acid residue in a particular $V_H$ or $V_L$ sequence does not refer to the number of amino acids in a particular sequence, but rather refers to the position as designated with reference to a numbering scheme.

The positions of the CDR's and hence the positions of the framework regions of the human heavy chain and light chains are determined using definitions that are standard in the field. For example, the following four definitions are commonly used. The Kabat definition is based on sequence variability and is the most commonly used. The Chothia definition is based on the location of the structural loop regions. The AbM definition is a compromise between the two used by Oxford Molecular's AbM antibody modeling software. The contact definition has been recently introduced and is based on an analysis of the available complex crystal structures.

For example, the framework of a light chain of the invention typically comprises residues 1-23, 35-49, 57-88, and 98-109 (or 98 through the C-terminal residue, e.g., 98-108) using Kabat numbering. As appreciated by one of skill in the art, these numbers may not refer to the number of amino acids in the $V_H$ or $V_L$ sequence, but the positions of the residues using the Kabat numbering system (or other numbering system).

The term "antibody" refers to a polypeptide encoded by an immunoglobulin gene or functional fragments thereof that specifically bind and recognize an antigen (i.e., antigen binding fragments, as defined below). The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. More specifically, the variable region is subdivided into hypervariable and framework (FR) regions. Hypervariable regions have a high ratio of different amino acids in a given position, relative to the most common amino acid in that position. Within light and heavy chains, three hypervariable regions exist. Four FR regions which have more stable amino acids sequences separate the hypervariable regions. The hypervariable regions directly contact a portion of the antigen's surface. For this reason, hypervariable regions are herein referred to as "complementarity determining regions", or "CDRs". The FR regions form a beta-sheet structure which serves as a scaffold to hold the hypervariable regions in position to contact antigen.

From N-terminal to C-terminal, both light and heavy chains comprise the domains FR1, CDR1, FR2, CDR2, FR3, CDR3 and FR4. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. The numbering of the light and heavy chain variable regions described herein is in accordance with Kabat [see, e.g., Johnson et al., (2001) "Kabat Database and its applications: future directions" *Nucleic Acids Research,* 29: 205-206; and the Kabat Database of Sequences of Proteins of Immunological Interest, Feb. 22, 2002 Dataset] unless otherwise indicated.

A "framework" of a $V_H$ or $V_L$ chain refers to the framework regions of the chain. The term as applied to each chain encompasses all of the framework regions.

A "humanized antibody" as used herein refers to an antibody that comprises a reference antibody binding specificity, i.e., the CDR regions that are substantially identical to those of the reference antibody, typically a mouse monoclonal antibody. More specifically, according to the present invention, the reference antibody may be a monoclonal mouse anti-peptide-6 antibody having heavy and light chains variable regions of SEQ ID NO. 1 and 2, respectively. A "humanized antibody" as used herein binds to the same epitope as the reference antibody and typically has at least 25% of the binding affinity. An exemplary assay for binding affinity is described in Example 2 (FIG. 7). Methods to determine whether the antibody binds to the same epitope are well known in the art, see, e.g., Harlow & Lane, Using Antibodies, A Laboratory Manual, Cold Spring Harbor Laboratory Press, 1999, which discloses techniques for epitope mapping or alternatively, competition experiments, to determine whether an antibody binds to the same epitope as the reference antibody.

As indicated herein above, according to certain embodiments, the invention provides a humanized anti-peptide-6 antibody and any antigen binding fragment thereof. The term "an antigen-binding fragment" refers to any portion of an antibody that retains binding to the antigen. Examples of antibody functional fragments include, but are not limited to, complete antibody molecules, antibody fragments, such as Fv, single chain Fv (scFv), complementarity determining regions (CDRs), $V_L$ (light chain variable region), $V_H$ (heavy chain variable region), Fab, $F(ab)_2$, and any combination of those or any other functional portion of an immunoglobulin peptide capable of binding to target antigen. As appreciated by one of skill in the art, various antibody fragments can be obtained by a variety of methods, for example, digestion of an intact antibody with an enzyme, such as pepsin, or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries. The term antibody also includes bivalent molecules, diabodies, triabodies, and tetrabodies.

References to "$V_H$" or a "VH" refer to the variable region of an immunoglobulin heavy chain, including an Fv, scFv, a disulfilde-stabilized Fv (dsFv) or Fab. References to "$V_L$" or a "VL" refer to the variable region of an immunoglobulin light chain, including of an Fv, scFv, dsFv or Fab.

More specifically, the phrase "single chain Fv" or "scFv" refers to an antibody in which the variable domains of the heavy chain and of the light chain of a traditional two chain antibody have been joined to form one chain. Typically, a linker peptide is inserted between the two chains to allow for the stabilization of the variable domains without interfering with the proper folding and creation of an active binding site. A single chain humanized antibody of the invention, e.g., humanized anti-peptide-6 antibody, may bind as a monomer. Other exemplary single chain antibodies may form diabodies, triabodies, and tetrabodies.

Still further, the humanized antibodies of the invention, e.g., humanized peptide-6 antibody may also form one component of a "reconstituted" antibody or antibody fragment, e.g., a Fab, a Fab' monomer, a $F(ab)_2$ dimer, or a whole immunoglobulin molecule. It should be noted that the humanized antibody of the present invention may further comprise a human Fc region.

According to certain embodiments, the invention provides a humanized antibody that specifically recognizes the polypeptide of SEQ ID NO. 15 (peptide-6), or any sequence comprising said peptide-6, for example, the sequence of SEQ ID NO. 98. In certain embodiments, the humanized antibody of the invention may also recognize a sequence comprising a fragment of SEQ ID NO. 15. A non-limiting example for such fragment is denoted by SEQ ID NO. 101 (designated as peptide-7).

It should be therefore noted that the term "binding specificity", "specifically binds to an antigen", "specifically immuno-reactive with", "specifically directed against" or "specifically recognizes", when referring to an epitope, refers to a binding reaction which is determinative of the presence of the epitope in a heterogeneous population of proteins and other biologics. Thus, under designated immunoassay conditions, the specified antibodies bind to a particular epitope at least two times the background and more typically more than 10 to 100 times background. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

As indicated above, in certain embodiments, the invention provides isolated and purified humanized antibodies. As used herein, "isolated" or "substantially purified", in the context of an antibody or nucleic acid molecule encoding an antibody, means the antibody or nucleic acid has been removed from its natural milieu or has been altered from its natural state. As such "isolated" does not necessarily reflect the extent to which the antibody or nucleic acid molecule has been purified. However, it will be understood that an antibody or nucleic acid molecule that has been purified to some degree is "isolated". If the antibody or nucleic acid molecule does not exist in a natural milieu, i.e. it does not exist in nature, the molecule is "isolated" regardless of where it is present. By way of example, a humanized antibody that does not naturally exist in humans is "isolated" even when it is present in humans.

Furthermore, the term "isolated" or "substantially purified", when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

As shown by FIG. 4 and Table 3, the variable regions of the humanized antibodies of the invention are composed of different segments derived from different human antibodies combined to create the heavy and light chains variable regions of the antibody of the invention. Thus, in certain embodiments, the heavy and the light variable regions of said humanized antibody are composed of at least two or more segments of at least two or more human antibodies, creating a humanized antibody that is completely composed of segments of a human origin. It should be noted that the segments are neither whole CDRs nor framework regions.

In the context of the present invention, the term "segments" refers to a contiguous amino acid sequence found within an antibody molecule, such segments ranging in size from 2 to 125 amino acids long, preferably ranging from 2 to 31 amino acids long where such segments are neither whole CDRs nor whole framework regions. As illustrated by FIG. 4, the humanized antibodies of the present invention will typically combine two or more segments of amino acid sequence from different human antibodies within the variable regions of the humanized antibody. In particular, the present invention relates to humanized antibody heavy and light chain variable regions (VH and VL respectively) where each VH and VL is composed entirely of segments of sequence from two or more human antibody variable regions and where typically each combined VH and VL includes segments of human variable region sequence positions corresponding to their positions in the source human antibody VHs and VLs, for example amino acids 1 to 10 in the combined VH sequence will derive from amino acids 1 to 10 in a human antibody. Alternatively, segments of human VH or VL sequence in the humanized antibody of the invention may be positioned at any sequence location irrespective of the sequence position in the source human antibody VH or VL. The source human antibody VHs and VLs will be any existing human antibody variable (V) region amino acid sequence, for example as provided in databases of human monoclonal antibody V region sequences, and may include sequences from affinity-matured antibodies with V region somatic mutations and other variations differing from germ-line, sequences from germ-line V regions, sequences from artificially constructed antibody V regions created from segments of sequence from antibodies of the species such as antibodies with a set of fixed V region frameworks but with variable CDRs, sequences selected from human antibody libraries such as phage display libraries, and sequences of human antibodies derived from transgenic animals expressing genes encoding human antibodies or antibody fragments.

More specifically, as shown by FIG. 4 and Table 3, according to one embodiment, the heavy chain variable region of the humanized antibody of the invention may comprise:

a) Framework region 1 (FR1) comprising the amino acid sequence of the segments of SEQ ID NO. 12 and SEQ ID NO. 13 or any part thereof; or the segments of SEQ ID NO. 40 and SEQ ID NO. 13 or any part thereof;
b) Complementarity Determining Region 1 (CDR1) comprising the amino acid sequence of the segments of SEQ ID NO. 13 or any part thereof, and SEQ ID NO. 14 or any part thereof;
c) FR2 comprising the amino acid sequence of the segments of SEQ ID NO. 16, SEQ ID NO. 14 and SEQ ID NO. 17 or any part thereof or the segments of SEQ ID NO. 41, SEQ ID NO. 14 and SEQ ID NO. 17 or the segments of SEQ ID NO. 41, SEQ ID NO. 14 and SEQ ID NO. 44;
d) CDR2 comprising the amino acid sequence of the segments of SEQ ID NO. 18 and SEQ ID NO. 19 or any part thereof;
e) FR3 comprising the amino acid sequence of the segments of SEQ ID NO. 34, SEQ ID NO. 19, SEQ ID NO. 35 and SEQ ID NO. 36 or any part thereof or the segments of SEQ ID NO. 43, SEQ ID NO. 19 and SEQ ID NO. 36 or any part thereof;
f) CDR3 comprising the amino acid sequence of the segments of SEQ ID NO. 36 or any part thereof, SEQ ID NO. 37 and SEQ ID NO. 38 or any part thereof or the segments of SEQ ID NO. 36 or any part thereof, SEQ ID NO. 37 and SEQ ID NO. 42 or any part thereof, or the segments of SEQ ID NO. 36 or any part thereof, SEQ ID NO. 96 and SEQ ID NO. 42 or any part thereof; and
g) FR4 comprising the amino acid sequence of the segments of SEQ ID NO. 38 or any part thereof and SEQ ID NO: 39 or the segment of SEQ ID NO. 42 or any part thereof;

It should be noted that the heavy chain variable region comprises a substitution in at least one position selected from a group consisting of H10, H11, H12, H13, H15, H19, H41, H49, H74, H75, H79, H81, H82, H82A, H82C, H84, H85 and H108 wherein the positions are determined according to the Kabat numbering system.

According to another embodiment, the light chain variable region of said composite antibody shown in FIG. 4 and Table 3 comprises:

a) FR1 comprising the amino acid sequence of the segments of SEQ ID NO. 45, SEQ ID NO. 46 and SEQ ID NO. 47 or any part thereof or the segments of SEQ ID NO. 45, SEQ ID NO. 57 and SEQ ID NO. 47 or any part thereof or the segments of SEQ ID NO. 45 and SEQ ID NO. 97 or any part thereof;
b) CDR1 comprising the amino acid sequence of the segments of SEQ ID NO. 47 or any part thereof, SEQ ID NO. 48 and SEQ ID NO. 49 or any part thereof, or the segments of SEQ ID NO. 97 or any part thereof, SEQ ID NO. 48 and SEQ ID NO. 49 or any part thereof;
c) FR2 comprising the amino acid sequence of the segments of SEQ ID NO. 49 or any part thereof, SEQ ID NO. 50 or any part thereof and SEQ ID NO. 51 or any part thereof;
d) CDR2 comprising the amino acid sequence of the segments of SEQ ID NO. 50 or any part thereof, SEQ ID NO. 51 or any part thereof and SEQ ID NO. 52 or any part thereof;
e) FR3 comprising the amino acid sequence of the segments of SEQ ID NO. 52 or any part thereof, SEQ ID NO. 53 or any part thereof, SEQ ID NO. 54 or any part thereof and SEQ ID NO. 55 or any part thereof or the segments of SEQ ID NO. 52 or any part thereof, SEQ ID NO. 58 or any part thereof and SEQ ID NO. 59 or any part thereof;
f) CDR3 comprising the amino acid sequence of the segments of SEQ ID NO. 54 or any part thereof, SEQ ID NO. 55 or any part thereof and SEQ ID NO. 56 or any part thereof or the segments of SEQ ID NO. 58 or any part thereof, SEQ ID NO. 59 or any part thereof and SEQ ID NO. 56 or any part thereof; and
g) FR4 comprising the amino acid sequence of the segment of SEQ ID NO. 56 or any part thereof. According to another embodiment, the light chain variable region may comprise a substitution in at least one position selected from a group consisting of L10, L11, L13, L15, L19, L21, L22, L42, L43, L60, L70, L72, L78, L79, L80, L83 and L100 wherein the positions are determined according to the Kabat numbering system.

It should be appreciated that according to certain embodiments, the humanized antibodies of the invention are constructed by combining multiple human VH and VL sequence segments disclosed by Table 3, in combinations which limit or avoid human T cell epitopes in the final humanized antibody V regions. Elimination of T cell epitopes reduces the immunogenicity of the combined humanized antibody.

Human T cell epitopes in this respect are amino acid sequences which can bind to human MHC class II molecules and, through presentation to CD4 T cells, induce a helper T cell response. Human VH and VL sequence segments and combinations of segments can be chosen which limit or avoid T cell epitopes in the final humanized antibody. This can be achieved by use of segments which do not contain T cell epitopes, such as from human germ-line sequences, and by joining of adjacent segments to create a new sequence which does not contain T cell epitopes, for example by creation of a non-MHC binding sequence at the junction of two segments, by creation of another human germ-line sequence, or by creation of a sequence which does not induce a helper T cell response despite a non-germ-line sequence.

Thus, according to one embodiment, both the heavy and the light chain variable regions of the humanized antibody of the invention are devoid of human T cell epitopes. More specifically, about 70%, to 99%, 75% to 99%, 80% to 99%, 85% to 99%, specifically, 90 to 99%, more specifically, 91%, 92%, 93%, 94%, 95%, 96%, 97%, 98% or 99% of all possible T cell epitopes were removed when all human segments were combined to create the final humanized antibodies of the invention.

The term "immunogenicity" refers to the ability of an antibody or antigen binding fragment to elicit an immune response (humoral or cellular) when administered to a recipient and includes, for example, the HAMA (Human anti mouse antibody) response. A HAMA response is initiated when T-cells from a subject mount an immune response to the administered antibody. The T-cells then recruit B-cells to generate specific "anti-antibody" antibodies.

As indicated above, the humanized antibody of the invention comprises a humanized heavy chain and a humanized light chain. Both the heavy and light chain variable regions are composed of combined segments of human origin. According to one specific embodiment, the humanized light chain comprises three complementarity determining regions (CDR1, CDR2 and CDR3) having amino acid sequences that are substantially identical at least in about 60% to 95% to the corresponding complementarity determining regions of the reference mouse anti-peptide-6 antibody. According to one specific embodiment, the reference mouse anti-peptide-6 antibody has variable heavy and light chains comprising the amino acid sequences of SEQ ID NO. 1 and 2, respectively.

In yet another specific embodiment, the humanized antibody of the invention comprises a heavy chain variable region comprising a CDR1, a CDR2, and a CDR3 as shown in SEQ ID NO: 1 and a light chain variable region comprising a CDR1, a CDR2, and a CDR3 as shown in SEQ ID NO: 2, of the reference mouse variable regions.

Thus, in a specific embodiment, the humanized antibody of the invention may comprise:

(a) a heavy chain variable region which is at least about 70% identical to SEQ ID NO. 1 of the reference mouse antibody; and (b) a light chain variable region which is at least about 70% identical to SEQ ID NO. 2 of the reference mouse antibody. More specifically, the heavy and light variable regions of the humanized antibody of the invention may be about 70% to 85% identical to the reference mouse heavy and light chain variable regions of SEQ ID NO. 1 and 2, respectively. More particularly, such amino acid sequence identity may be of at least 70%, 71%, 72%, 73%, 74%, 75%, 76%, 77%, 78%, 79%, 80%, 81%, 82%, 83%, 84% or 85%.

The terms "identical", "substantial identity", "substantial homology" or percent "identity", in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., amino acid sequence SEQ ID NO:1 or 2), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical". This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

Still further, the humanized antibody of the invention may comprise a heavy chain variable region which is at least about 30% to 70% identical to the reference mouse heavy chain variable region of SEQ ID NO. 1, more specifically, at least about 40%, 50%, 60%, 65% or 70% identical to the reference mouse heavy chain variable region of SEQ ID NO. 1. In one specific embodiment, the humanized antibody of the invention may comprise a heavy chain variable region which is at least about 70% identical to the reference mouse heavy chain variable region of SEQ ID NO. 1, having a substitution in at least one position selected from a group consisting of H10, H11, H12, H13, H15, H19, H41, H49, H74, H75, H79, H81, H82, H82A, H82C, H84, H85 and H108. The light chain variable region of the humanized antibody of the invention may be at least about 70% identical to the reference mouse heavy chain variable region of SEQ ID NO. 2 and comprises a substitution in at least one position selected from a group consisting of L10, L11, L13, L15, L19, L21, L22, L42, L43, L60, L70, L72, L78, L79, L80, L83 and L100. As indicated herein before, all indicated positions are determined according to the Kabat numbering system.

In one embodiment, the heavy and light chains variable region of the anti-peptide-6 humanized antibody or antigen binding fragment thereof have 18 or fewer amino acid substitutions in comparison to the mouse reference or parent antibody that binds peptide-6 (SEQ ID NO. 15), or any peptide comprising the amino acid sequence of SEQ ID NO. 15, for example, the peptide of SEQ ID NO. 98, or a peptide comprising a fragment of SEQ ID NO. 15, for example, the sequence as denoted by SEQ ID NO. 101. In another embodiment, the heavy and light chains variable regions of the anti-peptide-6 humanized antibody have 17 or fewer, 16 or fewer, 15 or fewer, 14 or fewer, 13 or fewer, 12 or fewer, 11 or fewer, 10 or fewer, 9 or fewer, 8 or fewer, or 7 or fewer amino acid substitutions in the indicated positions in comparison to the reference mouse anti-peptide-6 antibody. In one embodiment, the heavy or light chains variable regions have at least 2, at least 3, at least 4, at least 5, at least 6, at least 7, at least 8, at least 9, at least 10, at least 11, at least 12, or at least 13 amino acid substitutions, specifically in the positions indicated above, in comparison to the reference mouse anti-peptide-6 antibody that has a heavy and light chain variable regions of SEQ ID NO. 1 and 2, respectively.

With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

According to one particular embodiment, the humanized antibody of the invention comprises:

(a) a heavy chain variable region as shown in SEQ ID NO: 1, except that H10 is Ala, H11 is Ile or Leu, H12 is Val, H13 is Lys, H15 is Thr, H19 is Thr, H41 is Ser or Ala, H49 is Leu or Ala, H74 is Tyr or Ser, H75 is Lys, H79 is Val, H81 is Thr, H82 is Met, H82A is Thr, H82C is Met, H84 is Pro, H85 is Val and H108 is Ser or Leu; and
(b) a light chain variable region as shown in SEQ ID NO: 2, except that L10 is Ile or Thr, L11 is Leu, L13 is Leu, L15 is Pro, L19 is Ala, L21 is Met or Leu, L22 is Ser, L42 is Lys, L43 is Ala, L60 is Ser, L70 is Asp, L72 is Thr, L78 is Leu, L79 is Gln, L80 is Ala or Pro, L83 is Phe and L100 is Gln. The positions are determined according to the Kabat numbering system.

More specifically, the invention provides a humanized antibody comprising:

(a) a heavy chain variable region comprising the amino acid sequence of any one of SEQ ID NO. 21, 22, 23 and 20, or any variant thereof. Such variant may comprise a substitution in at least one position selected from a group consisting of H10, H11, H12, H13, H15, H19, H41, H49, H74, H75, H79, H81, H82, H82A, H82C, H84, H85 and H108; and
(b) a light chain variable region comprising the amino acid sequence of any one of SEQ ID NO. 26, 24 and 25, or any variant thereof. Such variant may comprise a substitution in at least one position selected from a group consisting of L10, L11, L13, L15, L19, L21, L22, L42, L43, L60, L70, L72, L78, L79, L80, L83 and L100 (according to the Kabat numbering system).

Variants of the humanized antibodies of the invention may have at least 80% sequence similarity, often at least 85% sequence similarity, 90% sequence similarity, or at least 95%, 96%, 97%, 98%, or 99% sequence similarity at the amino acid level, with the protein of interest, such as the various variants of the humanized anti-peptide-6 antibodies of the invention.

As noted above, the term "variants" can be applied to both amino acid and nucleic acid sequences. With respect to particular nucleic acid sequences, conservatively modified variants are preferred. These variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

It should be appreciated that the amino acids are selected for substitution based on their possible influence on CDR conformation and/or binding to the peptide-6 antigen. Investigation of such possible influences is by modeling, examination of the characteristics of the amino acids at particular locations, or empirical observation of the effects of substitution or mutagenesis of particular amino acids.

Usually the CDR regions in humanized antibodies are substantially identical, and more usually, identical to the corresponding CDR regions in the mouse reference antibody. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

In one particular embodiment, the invention relates to a humanized antibody having a heavy chain variable region selected from the group consisting of SEQ ID NO: 21, SEQ ID NO: 22, SEQ ID NO: 23 and SEQ ID NO: 20. According to another specific embodiment, the light chain variable region of such humanized antibody may be selected from the group consisting of SEQ ID NO: 26, SEQ ID NO: 24 and SEQ ID NO: 25.

In various embodiments, the humanized anti-peptide-6 antibody presented herein includes a variable heavy chain region having an amino acid sequence of SEQ ID NOs: 21, 22, 23 and 20, or an amino acid sequence having 60% or greater, having 70% or greater, having 80% or greater, having 85% or greater, having 90% or greater, 95% or greater, 98% or greater, or 99% or greater sequence identity to SEQ ID NOs:

21, 22, 23 and 20. In some embodiments where the antibody includes a heavy chain variable region having an amino acid sequence having 90% or greater, 95% or greater, 98% or greater, or 99% or greater sequence identity to SEQ ID NOs: 21, 22, 23 and 20, one or more or all of the amino acid differences are conservative substitutions.

In some embodiments, an anti-peptide-6 antibody presented herein includes a light chain variable region amino acid sequence of SEQ ID NOs: 26, 24 and 25, or an amino acid sequence having 60% or greater, having 70% or greater, having 80% or greater, having 85% or greater, 90% or greater, 95% or greater, 98% or greater or 99% or greater sequence identity to SEQ ID NOs: 26, 24 and 25. In some embodiments where the antibody includes a light chain variable region having an amino acid sequence having 90% or greater, 95% or greater, 98% or greater, or 99% or greater sequence identity to SEQ ID NOs: 26, 24 and 25, one or more or all of the amino acid differences are conservative substitutions. Of course, any possible combination of such heavy chain and light chain amino acid sequences are contemplated herein.

Accordingly, in one embodiment, the invention provides a humanized antibody having the heavy chain variable region of SEQ ID NO: 21 and a light chain variable region that may be selected from the group consisting of SEQ ID NO: 26, SEQ ID NO: 24 and SEQ ID NO: 25.

According to one specific embodiment, the humanized antibody of the invention has a heavy chain variable region of SEQ ID NO: 21 and a light chain variable region of SEQ ID NO: 26. Such humanized antibody variant is designated VH2/VK3.

In another specific embodiment, the humanized antibody of the invention comprises a heavy chain variable region of SEQ ID NO: 21 and a light chain variable region of SEQ ID NO: 25. Such humanized antibody is designated VH2/VK2.

In another specific embodiment, the humanized antibody of the invention comprises a heavy chain variable region of SEQ ID NO: 21 and a light chain variable region of SEQ ID NO: 24. Such variant is designated VH2/VK1.

In another embodiment, the invention provides a humanized antibody having the heavy chain variable region of SEQ ID NO: 22 and a light chain variable region that may be selected from the group consisting of SEQ ID NO: 24, SEQ ID NO: 25 and SEQ ID NO: 26.

According to one specific embodiment, the humanized antibody of the invention may comprise a heavy chain variable region of SEQ ID NO: 22 and a light chain variable region of SEQ ID NO: 25. Such humanized antibody variant is designated VH3/VK2.

Other embodiments of the invention provide humanized antibodies having a heavy chain variable region of SEQ ID NO: 22 and a light chain variable region of SEQ ID NO: 24 (VH3/VK1), a heavy chain variable region of SEQ ID NO: 22 and a light chain variable region of SEQ ID NO: 26 (VH3/VK3), a heavy chain variable region of SEQ ID NO: 23 and a light chain variable region of SEQ ID NO: 24 (VH4/VK1), a heavy chain variable region of SEQ ID NO: 23 and a light chain variable region of SEQ ID NO: 25 (VH4/VK2), a heavy chain variable region of SEQ ID NO: 23 and a light chain variable region of SEQ ID NO: 26 (VH4/VK3), a heavy chain variable region of SEQ ID NO: 20 and a light chain variable region of SEQ ID NO: 24 (VH1/VK1), a heavy chain variable region of SEQ ID NO: 20 and a light chain variable region of SEQ ID NO: 25 (VH1/VK2) and a heavy chain variable region of SEQ ID NO: 20 and a light chain variable region of SEQ ID NO: 26 (VH1/VK3).

As disclosed earlier herein, according to specific embodiments, the humanized antibody of the invention is particularly suited for induction of IL-10 when comprising a heavy chain variable region as shown in SEQ ID NO: 1, except that H10 is Ala, H11 is Ile or Leu, H12 is Val, H13 is Lys, H15 is Thr, H19 is Thr, H41 is Ser or Ala, H49 is Leu or Ala, H74 is Tyr or Ser, H75 is Lys, H79 is Val, H81 is Thr, H82 is Met, H82A is Thr, H82C is Met, H84 is Pro, H85 is Val and H108 is Ser or Leu, as demonstrated by any of the heavy chain variants H2, H3, H4 and H1 as denoted by SEQ ID NO. 21, 22, 23 and 20, respectively, and a light chain variable region as shown in SEQ ID NO: 2, except that L10 is Ile or Thr, L11 is Leu, L13 is Leu, L15 is Pro, L19 is Ala, L21 is Met or Leu, L22 is Ser, L42 is Lys, L43 is Ala, L60 is Ser, L70 is Asp, L72 is Thr, L78 is Leu, L79 is Gln, L80 is Ala or Pro, L83 is Phe and L100 is Gln; as demonstrated by any of the light chain variants K3, K2 and K1 as denoted by SEQ ID NO. 26, 25 and 24, respectively.

It should be noted that the positions are determined according to the Kabat numbering system.

As shown by the following Examples and particularly the comparative FIGS. 7, 14 and 15, each and every one of these substitutions is important and may contribute to the binding affinity of the different variants to peptide-6, or may be reflected by the ability of the different variants to induce IL-10 expression.

More specifically, as shown by FIG. 7, variants that were composed of VH2 heavy chain showed the best binding affinity to peptide-6, whereas the VH1 variants showed the lowest binding affinity. Therefore, according to certain embodiment, preferred substitution of residue H11 may be Leu, as shown in variant VH2. In yet another embodiment, a preferred substitution of residue H41 is Ala, a preferred H74 substitution may be Tyr and a preferred H108 substitution may be Leu, as in variant VH1. FIG. 15B shows that variant VH2/VK3 exhibits the best affinity, whereas variant VH3/VK2 shows much reduces affinity. Substitution of residue H74 to Tyr in H2 as compared to Ser in H3, seems to be important. The various combinations with the different light chains may also contribute to the differential binding affinity, for example, variant VH2/VK3 exhibits better binding affinity compared to VH2/VK2. The only difference between the light chains of both variants is substitution in L21 to Met in the VK2 containing variant, as compared to L21 Leu in the preferred variant VK3. Combination of VH2/VK1 showed the lowest affinity, and may therefore indicate that preferred combination of substitutions in the light chain may be L10 Thr, L21 Leu and L80 Pro.

As shown by FIG. 15, the binding of the different variants to peptide-6 and IL-10 induction are not directly correlated. Therefore, different combinations of substitutions in the heavy and the light chain may be reflected in different ability of the variants to induce IL-10 expression. For Example, as shown by FIGS. 15A and B, the VH2/VK3 variant exhibits the best IL-10 induction. When comparing the different heavy chains, the VH2 containing variant is better then the VH3 variant. The only difference between both is Tyr residue in position H74 in the VH2 variant as compared to H74 Ser in variant VH3. It should be noted that in IL-10 induction, too, the combination with different VK variants is also reflected functionally. For example, the VH2/VK3 variant showed significantly higher induction of IL-10 when compared to variant VH2/VK2. The only difference between both variants is the light chain that differs in one residue. Leu in position L21 in the VK3 variant as compared to Met in the less effective VK2 containing variant. These results indicate that even one substitution may have a significant functional effect.

Therefore, in certain particular embodiments, it should be noted that H11 may be substituted with any one of Ile and Leu, for binding peptide-6 preferably Leu, and for inducing IL-10 expression preferably Leu; H41 may be any one of Ser and Ala, for binding peptide-6 preferably Ala and for inducing IL-10 expression preferably Ala; H49 may be any one of Leu and Ala, for binding peptide-6 preferably Leu and for inducing IL-10 expression preferably Leu; H74 may be any one of Tyr and Ser, for binding peptide-6 preferably Tyr and for inducing IL-10 expression preferably Tyr; H108 may be any one of Leu and Ser, for binding peptide-6 preferably Leu and for inducing IL-10 expression preferably Leu; L10 may be substituted with any one of Ile and Thr, for binding peptide-6 preferably Thr, and for inducing IL-10 expression preferably Thr; L21 may be substituted with any one of Met and Leu, for binding peptide-6 preferably Leu, and for inducing IL-10 expression preferably Leu; L80 may be substituted with any one of Pro and Ala, for binding peptide-6 preferably Pro, and for inducing IL-10 expression preferably Pro.

All combinations of the abovementioned substitutions are also contemplated, comprising a substituted heavy chain comprising H11 Leu, H41 Ala, H49 Ala, H74 Ser and H108 Leu, and a substituted light chain comprising L10 Thr, L21 Leu and L80 Pro; a substituted heavy chain comprising H11 Leu, H41 Ala, H49 Ala, H74 Ser and H108 Leu, and a substituted light chain comprising L10 Thr, L21 Met and L80 Pro; a substituted heavy chain comprising H11 Leu, H41 Ala, H49 Ala, H74 Ser and H108 Leu, and a substituted light chain comprising L10 Ile, L21 Met and L80 Ala; a substituted heavy chain comprising H11 Leu, H41 Ala, H49 Leu, H74 Tyr and H108 Leu, and a substituted light chain comprising L10 Thr, L21 Leu and L80 Pro; a substituted heavy chain comprising H11 Leu, H41 Ala, H49 Leu, H74 Tyr and H108 Leu, and a substituted light chain comprising L10 Thr, L21 Met and L80 Pro; a substituted heavy chain comprising H11 Leu, H41 Ala, H49 Leu, H74 Tyr and H108 Leu, and a substituted light chain comprising L10 Ile, L21 Met and L80 Ala; a substituted heavy chain comprising H11 Ile, H41 Ser, H49 Leu, H74 Tyr and H108 Ser, and a substituted light chain comprising L10 Thr, L21 Leu and L80 Pro; a substituted heavy chain comprising H11 Ile, H41 Ser, H49 Leu, H74 Tyr and H108 Ser, and a substituted light chain comprising L10 Thr, L21 Met and L80 Pro; a substituted heavy chain comprising H11 Ile, H41 Ser, H49 Leu, H74 Tyr and H108 Ser, and a substituted light chain comprising L10 Ile, L21 Met and L80 Ala; a substituted heavy chain comprising H11 Leu, H41 Ala, H49 Leu, H74 Ser and H108 Leu, and a substituted light chain comprising L10 Thr, L21 Met and L80 Pro; a substituted heavy chain comprising H11 Leu, H41 Ala, H49 Leu, H74 Ser and H108 Leu, and a substituted light chain comprising L10 Ile, L21 Met and L80 Ala and, most preferably, a substituted heavy chain comprising H11 Leu, H41 Ala, H49 Leu, H74 Ser and H108 Leu, and a substituted light chain comprising L10 Thr, L21 Leu and L80 Pro.

It should not be overlooked that partial substitutions, wherein some of the above-mentioned substitutions occur and some do not, are also contemplated.

It should be appreciated that the humanized antibodies of the invention include antibodies having all types of constant regions, including IgM, IgG, IgD, IgA and IgE, and any isotype, including IgG1, IgG2, IgG3 and IgG4. The humanized antibody may comprise sequences from more than one class or isotype. According to a specific embodiment, the antibody of the invention is of the IgG-1 isotype.

According to certain embodiments, the humanized antibodies of the invention may exhibit a specific binding affinity for their respective antigen (peptide-6 or any amino acid sequence comprising said peptide, for example, the peptide of SEQ ID NO. 98) of at least $10^5$, $10^6$, $10^7$, $10^8$, $10^9$, or $10^{10}$ $M^{-1}$. Often the upper and lower limits of binding affinity of the humanized antibodies are within a factor of three or five or ten of that of the reference mouse antibody from which they were derived.

The heavy and light chain regions of the invention are typically obtained using recombinant DNA technology. The recombinant DNA methodologies that are commonly employed to perform this are well known to those of skill in the art. Typically, nucleic acid sequences encoding the different segments comprised within the combined humanized antibody of the invention are generated by PCR, for example by overlap extension. In this technique, the segment sequences are typically joined by incorporating the desired sequences into oligonucleotides and creating a series of products using PCR that comprise the desired segment sequences. The products may then be joined, typically using additional PCR reactions, in the proper orientation to create the $V_H$ and $V_L$ chains. The $V_L$ and $V_H$ DNA sequences may be ligated together, either directly or through a DNA sequence encoding a peptide linker, using techniques well known to those of skill in the art. These techniques include PCR as well as techniques such as in vitro ligation. The $V_L$ and $V_H$ sequences may be linked in either orientation.

One of skill will appreciate that, utilizing the sequence information provided for the variable regions, nucleic acids encoding these sequences are obtained using any number of additional methods well known to those of skill in the art. Thus, DNA encoding the Fv regions is prepared by any suitable method, including, for example, other amplification techniques such as ligase chain reaction (LCR), transcription amplification and self-sustained sequence replication, or cloning and restriction of appropriate sequences. This may be converted into double stranded DNA by hybridization with a complementary sequence or by polymerization with a DNA polymerase using the single strand as a template. While it is possible to chemically synthesize an entire single chain Fv region, it is preferable to synthesize a number of shorter sequences (about 100 to 150 bases) that are typically later spliced together, for example using overlap extension PCR.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

The $V_H$ and $V_L$ domains of an antibody of the invention may be directly linked or may be separated by a linker, e.g. to stabilize the variable antibody domains of the light chain and heavy chain, respectively. Suitable linkers are well known to those of skill in the art and include the well known GlyGlyGlyGlySer linker or a variant thereof.

To obtain high level expression of a cloned gene or nucleic acid, such as those cDNAs encoding the humanized antibodies, e.g., a humanized anti-peptide-6 antibody, of the invention or an Fab fragment thereof, one typically sub-clones a nucleic acid encoding the antibody into an expression vector that contains an appropriate promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing protein are available in, e.g., *E. coli, Bacillus* sp., and *Salmonella*. Kits for such expression systems are commercially available. Eukaryotic expression systems for mammalian cells, yeast, and insect cells are well known in the art and are also commercially available.

Often, in order to express a protein, for example, the VH or VK variants of the invention at high levels in a cell, codon preference for the expression system is considered in constructing the nucleic acid sequence to be expressed. Thus, a nucleic acid from one organism, e.g., a human or mouse may be engineered to accommodate the codon preference of the expression system.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein to be expressed and signals required for efficient polyadenylation of the transcript, ribosome binding sites, and translation termination. The nucleic acid sequence encoding a protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences. Such commonly used promoters are for example the CMV promoter as shown in the vectors of FIG. 2, beta-lactamase (penicillinase) and lactose (lac) promoter systems, the tryptophan (trp) promoter system, the tac promoter and the lambda-derived $P_L$ promoter and N-gene ribosome binding site. The particular promoter system is not critical to the invention, any available promoter that functions in prokaryotes can be used.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include vectors allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a GPCR-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of protein, specifically, the different humanized anti-peptide-6 antibody variants of the invention, which are then purified using standard techniques.

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. It is only necessary that the particular genetic engineering procedure used be capable of successfully introducing at least one gene into the host cell capable of expressing a polypeptide of the invention.

After the expression vector is introduced into the cells, the transfected cells are cultured under conditions favoring expression of the protein, which is recovered from the culture using standard techniques identified below.

One of skill would recognize that modifications can be made to a nucleic acid encoding the humanized antibody variants of the present invention without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

Once expressed, the humanized antibodies of the present invention can be purified according to standard procedures of the art, including ammonium sulfate precipitation, affinity columns, column chromatography, and the like. Substantially pure compositions of at least about 90 to 95% homogeneity are preferred, and 98 to 99% or more homogeneity is most preferred for pharmaceutical uses. Once purified, partially or to homogeneity as desired, if to be used therapeutically, the polypeptides should be substantially free of endotoxin.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

In addition to recombinant methods, the antibodies of the invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence.

In addition, the techniques used to screen antibodies in order to identify a desirable antibody may influence the properties of the antibody obtained. A variety of different techniques are available for testing antibody/antigen interactions to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, dot blots, ELIspot, immunoprecipitation assays and immunohistochemistry.

It should be further understood that the present application also provides and therefore encompasses polynucleotide sequences encoding heavy and light chain framework regions and CDRs of antibodies described herein as well as expression vectors for their efficient expression in mammalian cells. More specifically, the present invention encompasses nucleic acid sequences encoding the variable heavy and light chains variants of the invention, specifically, VH1-4 and VK1-3, as denoted by any one of SEQ ID NO. 21, 22, 23, 20, 26, 24 and 25. In one particular embodiment, such nucleic acid sequences may comprise the sequences as denoted by any one of 28, 29, 30, 27, 33, 31 and 32, respectively. The invention further provides nucleic acid constructs and expression vectors comprising at least one of said nucleic acid sequences and any combination thereof, as well as host cells transformed or transfected with said constructs, expression at least one of said VH and VK variants.

The terms "Nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). As appreciate by one of skill in the art, the complement of a nucleic acid sequence can readily be determined from the sequence of the other strand. Thus, any particular nucleic acid sequence set forth herein also discloses the complementary strand.

"Polypeptide", "peptide" and "protein" are used interchangeably herein to refer to a polymer of amino acid residues. The terms apply to naturally occurring amino acid polymers, as well as, amino acid polymers in which one or more amino acid residue is an artificial chemical mimetic of a corresponding naturally occurring amino acid.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

It should be appreciated that in certain aspects, the present application provides the hybridoma cell lines, as well as the monoclonal humanized antibodies produced by these hybridoma cell lines. The cell lines disclosed have uses other than for the production of the monoclonal antibodies. For example, the cell lines can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-peptide-6 humanized antibody, which can be isolated and expressed.

Still further, for diagnostic or therapeutic uses described herein after, the antibodies of the present invention may optionally be covalently or non-covalently linked to a detectable label or to an additional therapeutic agent. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^{3}H$, $^{125}I$, $^{35}S$, $^{14}C$, or $^{32}P$), enzymes (e.g., horseradish peroxidase, alkaline phosphatase and others commonly used in an ELISA and competitive ELISA and other similar methods known in the art) and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Another aspect of the invention relates to a composition comprising as an active ingredient an effective amount of at least one isolated and purified humanized antibody that specifically binds a polypeptide comprising SEQ ID NO: 15, the humanized antibody comprising:

(a) a heavy chain variable region which comprises Cys at position H22, Ser at H23, Gly at H26, Phe at H27, Ser at H28, Leu at H29, Ser at H30, Thr at H31, Ser at H32, Asn at H33, Met at H34, Gly at H35, Val at H35A, Gly at H35B, Leu at H48, His at H50, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and optionally, at least one of Leu at H49, Tyr at H74, Ile at H11, Ser at H41 and Ser at H108; and (b) a light chain variable region which comprises Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Tip at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and optionally at least one of Met at L21, Ile at L10 and Ala at L80; wherein the positions are determined according to the Rabat numbering system. According to certain embodiments the composition of the invention may optionally further comprises a pharmaceutically acceptable carrier, excipient or diluent.

According to one embodiment, the composition of the invention may comprise as an active ingredient at least one of any of the humanized antibodies descried by the invention, or any combinations or fragments thereof. In one particular embodiment, the composition of the invention may comprise at least one humanized antibody having a heavy chain variable region of SEQ ID NO: 21 and a light chain variable region of SEQ ID NO: 26 (VH2/VK3).

In another specific embodiment, the composition of the invention may comprise at least one humanized antibody having a heavy chain variable region of SEQ ID NO: 21 and a light chain variable region of SEQ ID NO: 24 (VH2/VK1).

In another specific embodiment, the composition of the invention may comprise at east one humanized antibody having a heavy chain variable region of SEQ ID NO: 21 and a light chain variable region of SEQ ID NO: 25 (VH2/VK2).

According to another specific embodiment, the composition of the invention may comprise at least one humanized antibody having a heavy chain variable region of SEQ ID NO: 22 and a light chain variable region of SEQ ID NO: 25 (VH3/VK2).

Other specific embodiments of the invention provide compositions comprising at least one of: a humanized antibody having a heavy chain variable region of SEQ ID NO: 22 and a light chain variable region of SEQ ID NO: 24 (VH3/VK1), a humanized antibody having a heavy chain variable region of SEQ ID NO: 22 and a light chain variable region of SEQ ID NO: 26 (VH3/VK3), a humanized antibody having a heavy chain variable region of SEQ ID NO: 23 and a light chain variable region of SEQ ID NO: 24 (VH4/VK1), a humanized antibody having a heavy chain variable region of SEQ ID NO: 23 and a light chain variable region of SEQ ID NO: 25 (VH4/VK2), a humanized antibody having a heavy chain variable region of SEQ ID NO: 23 and a light chain variable region of SEQ ID NO: 26 (VH4/VK3), a humanized antibody having a heavy chain variable region of SEQ ID NO: 20 and a light chain variable region of SEQ ID NO: 24 (VH1/VK1), a humanized antibody having a heavy chain variable region of SEQ ID NO: 20 and a light chain variable region of SEQ ID NO: 25 (VH1/VK2) and a humanized antibody having a heavy chain variable region of SEQ ID NO: 20 and a light chain variable region of SEQ ID NO: 26 (VH1/VK3).

The invention further provides a pharmaceutical composition for preventing, treating, ameliorating or inhibiting an immune-related disorder. The pharmaceutical composition of the invention comprises as an active ingredient a therapeutically effective amount of at least one isolated and purified humanized antibody that specifically binds a polypeptide comprising SEQ ID NO: 15, or any amino acid sequence comprising the same, for example, SEQ ID NO. 98. According to one embodiment the composition of the invention comprises a humanized antibody comprising:

(a) a heavy chain variable region which comprises Cys at position H22, Ser at H23, Gly at H26, Phe at H27, Ser at H28, Leu at H29, Ser at H30, Thr at H31, Ser at H32, Asn at H33, Met at H34, Gly at H35, Val at H35A, Gly at H35B, Leu at H48, His at H50, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and optionally, at least one of Leu at H49, Tyr at H74, Ile at H11, Ser at H41 and Ser at H108; and (b) a light chain variable region which comprises Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Trp at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and optionally at least one of Met at L21, Ile at L10 and Ala at L80. All positions are determined according to the Kabat numbering system. It should be further noted that the composition of the invention may optionally further comprises a pharmaceutically acceptable carrier, excipient or diluent.

According to one specific embodiment, the pharmaceutical composition of the invention may comprise as an active ingredient at least one of any of the humanized antibodies described by the invention or any combinations thereof.

In one specific embodiment, the pharmaceutical composition of the invention comprises at least one humanized antibody having a heavy chain variable region of SEQ ID NO. 21 and a light chain variable region of SEQ ID NO. 26 (VH2/VK3), or any combinations or mixtures thereof.

The results presented by the present invention clearly demonstrate the therapeutic potential of the antibodies of the invention on immune-related disorders. Thus, according to another embodiment, the pharmaceutical composition of the invention may be specifically suitable for treating an immune-related disorder, for example, an autoimmune or inflammatory disorder.

As indicated above, the following Examples 10-13 clearly demonstrate, using two different animal models, the applicability of the humanized antibodies of the invention for treating established inflammatory arthritis. More specifically, Lewis rats treated for AA induction and subsequently with the anti-peptide-6 humanized antibody of the invention (specifically the VH2/VK3 variant) showed a significant reduction in arthritis. Similarly, treatment of DBA/1 mice, induced to develop collagen-induced arthritis (CIA), with the anti-peptide-6 humanized antibody reduced arthritis severity. The invention further demonstrated an ex vivo induction of IL-10 in PBMC collected from rheumatoid arthritis (RA) patients, as well is in PBMC from healthy individuals. Thus, in specific embodiments, the humanized antibodies of the invention induce the secretion of IL-10 from PBMCs of patients suffering from immune-related disorders, e.g. arthritis, IBD, colitis, Crohn's disease and diabetes. For instance, as shown by Example 13, the humanized antibodies of the invention induced the secretion of IL-10 in PBMCs collected from rheumatoid arthritis patients. Thus, according to specific embodiments, the humanized antibodies of the invention induce an at least a 1.1-fold increase, at least a 1.2-fold increase, at least a 1.3-fold increase, at least a 1.4-fold increase, at least a 1.5-fold increase, at least a 1.6-fold increase, at least a 1.7-fold increase, at least a 1.8-fold increase, at least a 1.9-fold increase, or, preferably, at least 2-fold increase in PBMC IL-10 secretion as compared to untreated PBMCs. Moreover, as shown by the Examples, treatment of established arthritis with the antibodies of the invention may reduce disease score by at least 5%, at least 10%, at least 15%, at least 20%, at least 25%, at least 30%, at least 40%, at least 50% or even by at least 55 or 60% or more as compared to the disease score in an untreated control.

Furthermore, as indicated by Berent, J. et al., [Berent, J. et al., Springer Semin. Immunopathol. 25: 7-63 (2003)], adjuvant arthritis (AA) is a well established animal model for rheumatoid arthritis (RA), juvenile idiopathic arthritis (JIA) and septic arthritis. Moreover, different publications [Myers et al. Life Sciences 61(19): 1861-1878 (1997) and Brand et al. Springer Semin Immunopathol (2003) 25:3-18 (2003), respectively], clearly indicate that collagen induced arthritis (CIA) is also an established model for RA as well as to other autoimmunity, rheumatic diseases and inflammation.

It should be appreciated that there are different forms of arthritis that may be generally grouped into two main categories, inflammatory arthritis, and degenerative arthritis, each with different causes. Therefore, according to one specific embodiment, the pharmaceutical compositions of the invention may be specifically intended for the treatment and/or amelioration of an inflammatory disorder, for example, an inflammatory arthritis.

Inflammatory arthritis is characterized by synovitis, bone erosions, osteopenia, soft-tissue swelling, and uniform joint space narrowing. More specifically, the hallmarks of joint inflammation are synovitis and erosion of bone. The latter will initially appear as a focal discontinuity of the thin, white, subchondral bone plate. Normally, this subchondral bone plate can be seen even in cases of severe osteopenia, whereas its discontinuity indicates erosion. Although it is true that periarticular osteopenia and focal subchondral osteopenia can appear prior to true bone erosion, it is the presence of bone erosion that indicates definite joint inflammation. As the bone erosion enlarges, osseous destruction extends into the trabeculae within the medullary space. One important feature of inflammatory arthritis relates to the concept of marginal bone erosion. This term is given to bone erosion that is located at the margins of an inflamed synovial joint. This specific location represents that portion of the joint that is intraarticular but not covered by hyaline cartilage. Therefore, early joint inflammation will produce marginal erosions prior to erosions of the subchondral bone plate beneath the articular surface. When looking for bone erosions, multiple views of a joint are essential to profile the various bone surfaces. A second important characteristic of an inflammatory joint process is uniform joint space narrowing. This occurs because destruction of the articular cartilage is uniform throughout the intraarticular space. A third finding of inflammatory joint disease is soft-tissue swelling.

It should be appreciated that inflammatory arthritis may be further divided into several subgroups, and therefore, the compositions, as well as the methods, combined compositions and kits of the invention described herein after, may be applicable for treating every inflammatory arthritis condition of the different subgroups.

More specifically, involvement of a single joint is indicative of a Septic arthritis. The cause of septic arthritis is usually related to hematogenous seeding owing to staphylococcal or streptococcal microorganisms. The radiographic features of a septic joint encompass those of any inflammatory arthritis, namely, periarticular osteopenia, uniform joint space narrowing, soft-tissue swelling, and bone erosions. Not all findings may be present simultaneously, and, acutely, bone erosions may not be evident. Thus, according to one embodiment, the compositions and methods of the invention may be used for the treatment and/or amelioration of septic arthritis.

A systemic arthritis, in contrast, is characterized by involvement multiple joints, and includes two main categories, rheumatoid arthritis and seronegative spondyloarthropathy.

According to one embodiment, the compositions as well as methods, combined compositions and kits of the invention may be used for the treatment and/or amelioration of rheumatoid arthritis. Rheumatoid arthritis (RA) is a chronic, systemic autoimmune disorder that most commonly causes inflammation and tissue damage in joints (arthritis) and tendon sheaths, together with anemia. It can also produce diffuse inflammation in the lungs, pericardium, pleura, and the sclera of the eye, and also nodular lesions, most common in subcutaneous tissue. It can be a disabling and painful condition, which can lead to substantial loss of functioning and mobility. Serologic markers such as rheumatoid factor and antibodies to cyclic citrullinated peptide are important indicators of rheumatoid arthritis. The radiographic features of rheumatoid arthritis are those of joint inflammation and include particular osteopenia, uniform joint space loss, bone erosions, and soft-tissue swelling. Because of the chronic nature of the inflammation, additional findings such as joint subluxation and subchondral cysts may also be evident.

The seronegative spondyloarthropathy category includes psoriatic arthritis, reactive arthritis, and ankylosing spondylitis, and is characterized by signs of inflammation, multiple joint involvement, and distal involvement in the hands and feet with added features of bone proliferation. Thus, according to one embodiment, the compositions and methods of the invention may be used for the treatment and/or amelioration of any condition of the seronegative spondyloarthropathy category.

More specifically, according to one embodiment, the compositions and methods of the invention may be used for preventing, treating, ameliorating or inhibiting psoriatic arthritis. Psoriatic arthritis is a chronic disease characterized by inflammation of the skin (psoriasis) and joints (arthritis). Nearly 306,000 people in the USA suffer from psoriatic arthritis and additional 308,000 people are believed to suffer from the disease in the five leading markets in Europe. Psoriasis and arthritis often appear separately. In fact, the skin disease precedes the arthritis in nearly 80% of patients. The arthritis may precede the psoriasis in up to 15% of patients.

Psoriasis, one of the characteristics of psoriatic arthritis, is a common skin condition that features patchy, raised, red areas of skin inflammation with scaling. Psoriasis often affects the tips of the elbows and knees, the scalp, the navel, and the area surrounding the genitals or anus. Approximately 10% of patients who have psoriasis also develop an associated inflammation of their joints. Usually, the more severe the skin symptoms are, the greater the likelihood a person will develop psoriatic arthritis. The cause of psoriatic arthritis is unknown, it may have a combination of genetic, environmental, and immune causes.

Males and females are equally likely to suffer from psoriasis. For psoriatic arthritis, males are more likely to have the spondylitic form (in which the spine is affected), and females are more likely to have the rheumatoid form (in which many joints may be involved). Psoriatic arthritis usually develops in people aged 35-55 years. However, it can develop in people of almost any age. Psoriatic arthritis shares many features with several other arthritic conditions, such as ankylosing spondylitis, reactive arthritis, and arthritis associated with Crohn's disease and ulcerative colitis. All of these conditions can cause inflammation in the spine and joints, in the eyes, skin, mouth, and various organs.

According to another embodiment, the compositions, as well as methods, combined compositions and kits of the invention may be used for preventing, treating, ameliorating or inhibiting ankylosing spondylitis. Ankylosing spondylitis (AS, previously known as Bechterew's disease, Bechterew syndrome, Marie Strümpell disease and a form of spondyloarthritis), is usually a chronic and progressive form of arthritis, caused due to inflammation of multiple joints, characteristically the spinal facet joints and the sacroiliac joints at the base of the spine. While ankylosing spondylitis tends to affect these joints and the soft tissues around the spine, other joints may also be affected, as well as tissues surrounding the joints (entheses, where tendons and ligaments attach to bone). Ankylosing spondylitis may also involve areas of the body other than the joints, such as the eyes, heart, and lungs.

This disorder frequently results in bony ankylosis (or fusion), hence the term ankylosing, which is derived from the Greek word ankylos, meaning stiffening of a joint. Spondylos means vertebra (or spine) and refers to inflammation of one or more vertebrae.

The disease is estimated to affect approximately 0.1-0.2% of the general population. Ankylosing spondylitis primarily affects young males. Males are four to ten times more likely to have ankylosing spondylitis than females. Most people with the disease develop it at age 15-35 years, with an average age of 26 years at onset.

Although the exact cause is unknown, ankylosing spondylitis is believed to be due to the combination of a genetic influence and a triggering environmental factor. Approximately 90-95% of patients with ankylosing spondylitis have the tissue antigen Human Leukocyte Antigen B27 (HLA-B27), compared to 7% in the general population. People with ankylosing spondylitis often have a family history of the disease.

In yet another embodiment, the compositions, as well as methods, combined compositions and kits of the invention may be used for preventing, treating, ameliorating or inhibiting reactive arthritis (ReA). Reactive arthritis, another type of seronegative spondyloarthropathy, is an autoimmune condition that develops in response to an infection in another part of the body. Coming into contact with bacteria and developing an infection can trigger reactive arthritis. It has symptoms similar to various other conditions collectively known as "arthritis," such as rheumatism. It is caused by another infection and is thus "reactive", i.e., dependent on the other condition. The "trigger" infection has often been cured or is in remission in chronic cases, thus making determination of the initial cause difficult.

The symptoms of reactive arthritis very often include a combination of three seemingly unlinked symptoms, an inflammatory arthritis of large joints, inflammation of the eyes (conjunctivitis and uveitis), and urethritis. It should be indicated that ReA is also known as Reiter's syndrome, after German physician Hans Reiter, it is also known as arthritis urethritica, venereal arthritis and polyarteritis enterica.

It should be appreciated that there are many other forms of inflammatory arthritis, including juvenile idiopathic arthritis, gout and pseudo gout, as well as arthritis associated with colitis or psoriasis. It should be therefore appreciated that the compositions, as well as methods, combined compositions and kits of the present invention are also applicable for these conditions as well.

Therefore, according to another embodiment, the compositions and methods of the invention may be used for preventing, treating, ameliorating or inhibiting juvenile idiopathic arthritis (JIA). JIA, is the most common form of persistent arthritis in children. (juvenile in this context refers to an onset before age 16, idiopathic refers to a condition with no defined cause, and arthritis is the inflammation of the synovium of a joint). JIA is a subset of arthritis seen in childhood, which may be transient and self-limited or chronic. It differs significantly from arthritis commonly seen in adults (rheumatoid arthritis), and other types of arthritis that can present in childhood which are chronic conditions (e.g. psoriatic arthritis and ankylosing spondylitis).

According to another embodiment, the compositions, as well as methods, combined compositions and kits of the invention may be used for the treatment and/or amelioration of gout. Gout (metabolic arthritis) is a disease created by a buildup of uric acid. In this condition, crystals of monosodium urate or uric acid are deposited on the articular cartilage of joints, tendons and surrounding tissues. These crystals cause inflammation and pain, both severe. If untreated, the crystals form tophi, which can cause significant tissue damage. Pseudo gout is a condition which is caused by calcium crystals. When calcium crystals cause attacks of inflammation in tendons it is called 'calcific tendinitis'. The invention further provides compositions and methods for the treatment of this disorder as well.

Generally, as also disclosed above, there are many types of arthritis, it should be noted that the compositions, as well as methods, combined compositions and kits of the invention may be also applicable for treating in addition to all primary forms of arthritis indicated, also to all secondary forms of arthritis. These conditions may include lupus erythematosus, Henoch-Schönlein purpura, psoriatic arthritis, reactive arthritis, haemochromatosis, hepatitis, Wegener's granulomatosis (and many other vasculitis syndromes), Lyme disease, familial mediterranean fever, hyperimmunoglobulinemia D with recurrent fever, TNF receptor associated periodic syndrome and inflammatory bowel disease (including Crohn's Disease and ulcerative colitis).

Examples 14 and 15 clearly demonstrates a significant ameliorating effect of the humanized anti-peptide-6 antibodies using the TNBS-colitis animal model. Thus, in another specific embodiment, the pharmaceutical compositions, as well as methods, combined compositions and kits of the invention may be applicable for preventing, treating, ameliorating or inhibiting inflammatory bowel disease (IBD), specifically, ulcerative colitis and Crohn's disease.

According to a specific embodiment, treatment, prevention or improvement in colitis or in Crohn's disease may be reflected in the suppression of body weight loss and the inflammatory response associated with the disease and the improvement of the overall microscopic histological disease score. For example, treatment with the humanized antibodies of the invention may reduce microscopic disease score by at least 5%, at least 10%, at least 15%, at least 20%, at least 25%, at least 30%, at least 40%, at least 50% or even by at least 55 or 60% or even more, as compared to the microscopic disease score in an untreated control. Furthermore, in another embodiment, treatment with the humanized antibodies of the invention may reduce body weight loss by at least 5%, at least 10%, at least 15%, at least 20%, at least 25%, at least 30%, at least 40%, at least 50%, at least 60%, at least 70%, at least 71%, at least 72%, at least 73%, or even by 75% or even more, as compared to the body weight loss in an untreated control.

Inflammatory bowel diseases (IBD) are common gastrointestinal disorders, that can be perceived as being the result of a dysbalance between Th1-pro-inflammatory and Th2-anti-inflammatory subtypes of immune responses. IBD is a group of inflammatory conditions of the colon and small intestine. The major types of IBD are Crohn's disease and ulcerative colitis (UC). Other forms of IBD account for far fewer cases. These are Collagenous colitis, Lymphocytic colitis, Ischaemic colitis, Diversion colitis, Behçet's syndrome and Indeterminate colitis which is inability to make a definitive diagnosis distinguishing Crohn's disease from Ulcerative colitis.

The main difference between Crohn's disease and UC is the location and nature of the inflammatory changes. Crohn's can affect any part of the gastrointestinal tract, from mouth to anus (skip lesions), although a majority of the cases start in the terminal ileum. Ulcerative colitis, in contrast, is restricted to the colon and the rectum. Microscopically, ulcerative colitis is restricted to the mucosa (epithelial lining of the gut), while Crohn's disease affects the whole bowel wall. Finally, Crohn's disease and ulcerative colitis present with extra-intestinal manifestations (such as liver problems, arthritis, skin manifestations and eye problems) in different proportions. Crohn's disease and Ulcerative colitis share the same symptoms such as diarrhea, vomiting, weight loss, fever and abdominal pain.

A recent hypothesis posits that IBD may be caused by an overactive immune system attacking various tissues of the digestive tract because of the lack of traditional targets such as parasites and worms. The number of people being diagnosed with IBD has increased as the number of infections by parasites such as roundworm, hookworm and human whipworms, has fallen, and the condition is still rare in countries where parasitic infections are common.

There are several extra-intestinal manifestations that accompany IBD, for example: autoimmune phenomena; immune complexes have a role in target organ damage; and, immunosuppressive agents such as glucocorticoids, azathioprine, methotrexate and cyclosporin are used to alleviate the disease. Patients with IBD have antibodies against components of colon cells and several different bacterial antigens. These antigens gain access to the immune system as a consequence of epithelial damage. Abnormalities of T cell-mediated immunity, including coetaneous anergy and diminished responsiveness to T cell stimuli, have also been described in these patients. In addition, changes in mucosal cell mediated immunity were identified, including increased concentrations of mucosal IgG cells and changes in T cells subsets, suggesting antigen stimulation. Exposure of target antigens after infectious, immune, or toxic damage, leads to activation of mucosal immune cells resulting in cytokines that lead to mucosal inflammatory response. Secretion of pro-inflammatory cytokines such as IFNγ, contributes to an increase in mucosal permeability, and has been described in animal models of IBD.

Both CD4 and CD8 lymphocytes can be typed as either Th1 cells that produce IL-2 and IFNγ, or Th2 cells that produce IL-4, and IL-10. The way the immune system responds to foreign and self antigens, is the result of a balance between the two subtypes of responses. A Th1 type response is involved in the pathogenesis of several autoimmune and chronic inflammatory disorders such as IBD. Thus experimental colitis and IBD in humans can be perceived as a dysbalance between pro-inflammatory Th1-type and anti-inflammatory Th2-type cytokines. It has been recently shown, in both animals and humans, that anti-inflammatory cytokines such as IL10 can downregulate the pro-inflammatory effects of Th1-mediated cytokines, thereby alleviating immune-mediated disorders.

Usually, treatment of IBD is started by administering drugs with strong anti-inflammatory effects, such as prednisone. Once the inflammation is successfully controlled, the patient is usually switched to a more moderate drug to keep the disease in remission. If unsuccessful, a combination of immunosuppression drugs may be administered. The goal of treatment is toward achieving remission, after which the patient is usually switched to a weaker drug with fewer potential side effects. Every so often, an acute resurgence of the original symptoms may appear; this is known as a "flare-up". Depending on the circumstances, it may dissipate on its own or require medication. The time between flare-ups may be anywhere from weeks to years, and varies wildly between patients—a few have never experienced a flare-up. Often, steroids are used to control disease flares and were once acceptable as a maintenance drug. Biologicals such as TNF inhibitors have been in use for several years in Crohn's disease patients and recently in patients with ulcerative colitis. Severe cases may require surgery, such as bowel resection, strictureplasty or a temporary or permanent colostomy or ileostomy.

Crohn's disease is one type of inflammatory bowel disease (IBD). It is a chronic condition for which there is currently no cure. It is characterised by periods of improvement followed by episodes when symptoms flare up. It can affect any area of the digestive tract, also referred to as the gastrointestinal (GI) tract from the mouth to the anus, but it most commonly affects the lower part of the small intestine, called the ileum. The swelling extends deep into the lining of the affected organ. The swelling can cause pain and can make the intestines empty frequently, resulting in diarrhea. Crohn's disease can be categorized by the area which it affects. Ileocolic Crohn's disease, affects both the ileum (the last part of the small intestine that connects to the large intestine) and the large intestine, and accounts for fifty percent of cases. Crohn's ileitis, affecting the ileum only, accounts for thirty percent of cases, and Crohn's colitis, affecting the large intestine, accounts for the remaining twenty percent of cases of Crohn's involving the last part of the small intestine and the large intestine and may be particularly difficult to distinguish from ulcerative colitis. Gastroduodenal Crohn's disease causes inflammation in the stomach and first part of the small intestine, called the duodenum. Jejunoileitis causes spotty patches of inflammation in the top half of the small intestine, called the jejunum. Crohn's disease may also be called ileitis or enteritis.

Abdominal pain may be the initial symptom of Crohn's disease. It is often accompanied by diarrhea, Symptoms caused by intestinal stenosis are also common in Crohn's disease. Abdominal pain is often most severe in areas of the bowel with stenoses.

Crohn's disease, like many other chronic, inflammatory diseases, can cause a variety of systemic symptoms. Among children, growth failure is common. Many children are first diagnosed with Crohn's disease based on inability to maintain growth. In addition to systemic and gastrointestinal involvement, Crohn's disease can affect many other organ systems. Inflammation of the interior portion of the eye, known as uveitis, can cause eye pain, especially when exposed to light (photophobia). Inflammation may also involve the white part of the eye (sclera), a condition called episcleritis. Both episcleritis and uveitis can lead to loss of vision if untreated.

Crohn's disease is associated with a type of rheumatologic disease known as seronegative spondyloarthropathy. This group of diseases is characterized by inflammation of one or more joints (arthritis) or muscle insertions (enthesitis). The arthritis can affect larger joints such as the knee or shoulder or may exclusively involve the small joints of the hand and feet. The arthritis may also involve the spine, leading to ankylosing spondylitis if the entire spine is involved or simply sacroiliitis if only the lower spine is involved. The symptoms of arthritis include painful, warm, swollen, stiff joints and loss of joint mobility or function.

A colonoscopy is the best test for making the diagnosis of Crohn's disease as it allows direct visualization of the colon and the terminal ileum, identifying the pattern of disease involvement. Finding a patchy distribution of disease, with involvement of the colon or ileum but not the rectum, is suggestive of Crohn's disease.

Currently there is no cure for Crohn's disease and remission may not be possible or prolonged if achieved. Treatment for Crohn's disease is only when symptoms are active and involve first treating the acute problem, then maintaining remission.

Acute treatment uses medications to reduce inflammation (normally amino salicylate anti-inflammatory drugs and corticosteroids). When symptoms are in remission, treatment enters maintenance with a goal of avoiding the recurrence of symptoms. Prolonged use of corticosteroids has significant side-effects; as a result they are generally not used for long-term treatment. Alternatives include aminosalicylates alone, though only a minority are able to maintain the treatment, and many require immunosuppressive drugs.

Medications used to treat the symptoms of Crohn's disease include 5-aminosalicylic acid (5-ASA) formulations, prednisone, immunomodulators such as azathioprine, mercaptopurine, methotrexate, infliximab, adalimumab, certolizumab[ and natalizumab. Hydrocortisone is used in severe attacks of Crohn's disease. Since late 1990s, biological medications are available (see Infliximab). Crohn's cannot be cured by surgery, though it is used when partial or a full blockage of the intestine occurs.

The incidence of Crohn's disease has been ascertained from population studies in Norway and the United States and is similar at 6 to 7.1:100,000. Crohn's disease is more common in northern countries, and shows a higher preponderance in northern areas of the same country. The incidence of Crohn's disease is thought to be similar in Europe but lower in Asia and Africa. Crohn's disease has a bimodal distribution in incidence as a function of age: the disease tends to strike people in their teens and 20s, and people in their 50s through to their 70s.

It should be noted that the humanized antibodies of the invention are also applicable for the treatment or prevention of Crohn's disease, as described above, and of Ulcerative colitis, as described below.

Ulcerative Colitis (U.C.) is another chronic (long lasting) inflammation of the lining of the GI tract. UC is usually continuous from the rectum, with the rectum almost universally being involved and the disease confined to the colon (large bowel). The lining becomes inflamed and is characterized by open sores or ulcers. During active diseases, ulcers form where inflammation has killed the cells that usually line the colon, then bleed and produce pus. Inflammation in the colon also causes the colon to empty frequently, causing diarrhea mixed with blood, of gradual onset. Ulcerative colitis is an intermittent disease, with periods of exacerbated symptoms, and periods that are relatively symptom-free. Although the symptoms of ulcerative colitis can sometimes diminish on their own, the disease usually requires treatment to go into remission.

Ulcerative colitis occurs in 35-100 people for every 100,000 in the United States or less than 0.1% of the population. The disease is more prevalent in northern countries of the world, as well as in northern areas of individual countries or other regions.

The incidence of ulcerative colitis in North America is 10-12 new cases per 100,000 per year, with a peak incidence of ulcerative colitis occurring between the ages of 15 and 25. Prevalence is 1 per 1000. There is thought to be a bimodal distribution in age of onset, with a second peak in incidence occurring in the 6th decade of life. The disease affects females more than males.

The geographic distribution of ulcerative colitis and Crohn's disease is similar worldwide, with highest incidences in the United States, Canada, the United Kingdom, and Scandinavia. Higher incidences are seen in northern locations compared to southern locations in Europe and the United States.

As with Crohn's disease, the prevalence of ulcerative colitis is greater among Ashkenazi Jews and decreases progressively in other persons of Jewish descent, non-Jewish Caucasians, Africans, Hispanics, and Asians.

The clinical presentation of ulcerative colitis depends on the extent of the disease process. Patients usually present with diarrhea mixed with blood and mucus, of gradual onset. They also may have signs of weight loss, and blood on rectal examination. The disease is usually accompanied with different degrees of abdominal pain, from mild discomfort to severely painful cramps.

Ulcerative colitis is associated with a general inflammatory process that affects many parts of the body. Sometimes these associated extra-intestinal symptoms are the initial signs of the disease, such as painful, arthritic knees in a teenager. The presence of the disease cannot be confirmed, however, until the onset of intestinal manifestations.

About half of the people diagnosed with ulcerative colitis have mild symptoms. Others suffer frequent fevers, bloody diarrhea, nausea, and severe abdominal cramps. Ulcerative colitis may also cause problems such as arthritis (seronegative arthritis, ankylosing spondylitis, sacroiliitis), inflammation of the eye (iritis, uveitis, episcleritis), liver disease, and osteoporosis. These complications may be the result of inflammation triggered by the immune system because people with ulcerative colitis have abnormalities of the immune system.

Ulcerative colitis is normally continuous from the rectum up the colon. The disease is classified by the extent of involvement, depending on how far up the colon the disease extends:

In addition to the extent of involvement, UC patients may also be characterized by the severity of their disease.

Standard treatment for ulcerative colitis depends on extent of involvement and disease severity. The goal is to induce remission initially with medications, followed by the administration of maintenance medications to prevent a relapse of the disease. The concept of induction of remission and maintenance of remission is very important. The medications used to induce and maintain a remission somewhat overlap, but the treatments are different. Physicians first direct treatment to inducing a remission which involves relief of symptoms and mucosal healing of the lining of the colon and then longer term treatment to maintain the remission.

Drugs used include aminosalicylates (e.g. 5-amonosalicylic acid or 5-ASA), corticosteroids (e.g. prednisone), immunosuppressive drugs (e.g. methotrexate) and biological treatments (e.g. infliximab). Unlike Crohn's disease, ulcerative colitis can generally be cured by surgical removal of the large intestine.

Ulcerative colitis is not caused by emotional distress or sensitivity to certain foods or food products, but these factors may trigger symptoms in some people. The stress of living with ulcerative colitis may also contribute to a worsening of symptoms. While there are drugs available to induce and maintain remission from disease, these are only partially successful and about 25 to 40 percent of ulcerative colitis patients must eventually have their colons removed because of massive bleeding, severe illness, rupture of the colon, or risk of cancer.

The best test for diagnosis of ulcerative colitis remains endoscopy. A flexible sigmoidoscopy is usually sufficient to support the diagnosis. Biopsies of the mucosa are taken to definitively diagnose UC and differentiate it from Crohn's disease, which is managed differently clinically.

It should be noted that the humanized antibodies of the invention are also applicable for the treatment or prevention of IBD and all its subtypes, some of which were described in greater detail hereinabove.

As with IBD, including Crohn's disease and UC, psoriasis is also an inflammatory disorder affecting and affected by pro- and anti-inflammatory cytokine production. Although the exact causes and pathogenesis of psoriasis are unknown, overexpression of proinflammatory, type 1 (Th1) cytokines has been demonstrated in psoriasis and is believed to be of pathophysiological importance. Importantly, a relative deficiency in cutaneous IL-10 mRNA expression compared with other inflammatory dermatoses was demonstrated. Moreover, previous publications demonstrate that patients during established antipsoriatic therapy showed higher IL-10 mRNA expression of peripheral blood mononuclear cells than patients before therapy. This suggested that IL-10 may have antipsoriatic capacity. Indeed, subcutaneous administration of IL-10 produced immunosuppressive effects in patients (depressed monocytic HLA-DR expression, TNF-alpha and IL-12 secretion capacity, IL-12 plasma levels, and responsiveness to recall antigens) as well as a shift toward a type 2 (Th2) cytokine pattern (increasing proportion of IL-4, IL-5, and IL-10 producing T cells, selective increase in IgE serum levels) were observed. Thus, the importance of IL-10 for the treatment of psoriasis is clear. Therefore, according to one specific embodiment, the humanized antibodies of the invention may be used for preventing, treating, ameliorating or inhibiting psoriasis or any related conditions.

More particularly, psoriasis is a common skin condition that features patchy, raised, red areas of skin inflammation with scaling. Psoriasis often affects the tips of the elbows and knees, the scalp, the navel, and the area surrounding the genitals or anus. It occurs when the immune system sends out faulty signals that speed up the growth cycle of skin cells. The scaly patches commonly caused by psoriasis, called psoriatic plaques, are areas of inflammation and excessive skin production. Skin rapidly accumulates at these sites which gives it a silvery-white appearance. Plaques frequently occur on the skin of the elbows and knees, but can affect any area including the scalp, palms of hands and soles of feet, and genitals. In contrast to eczema, psoriasis is more likely to be found on the outer side of the joint. The disorder is a chronic recurring condition that varies in severity from minor localized patches to complete body coverage. Fingernails and toenails are frequently affected (psoriatic nail dystrophy) and can be seen as an isolated symptom. As mentioned in connection with arthritis, psoriasis can also cause inflammation of the joints, which is known as psoriatic arthritis. Ten to fifteen percent of people with psoriasis develop psoriatic arthritis. There are many treatments available, but because of its chronic recurrent nature psoriasis is a challenge to treat. The symptoms of psoriasis can manifest in a variety of forms. Variants include plaque, pustular, guttate and flexural psoriasis. Psoriasis may be classified into nonpustular and pustular types. It should be noted that the methods of the invention contemplate the treatment of Nonpustular as well as Pustular psoriasis.

More specifically, Nonpustular psoriasis includes Psoriasis vulgaris and Psoriatic erythroderma. Psoriasis vulgaris (also known as Chronic stationary psoriasis or Plaque-like psoriasis), is the most common form of psoriasis. It affects 80 to 90% of people with psoriasis. Plaque psoriasis typically appears as raised areas of inflamed skin covered with silvery white scaly skin. These areas are called plaques.

Psoriatic erythroderma (Erythrodermic psoriasis) involves the widespread inflammation and exfoliation of the skin over most of the body surface. It may be accompanied by severe itching, swelling and pain. It is often the result of an exacerbation of unstable plaque psoriasis, particularly following the abrupt withdrawal of systemic treatment. This form of psoriasis can be fatal, as the extreme inflammation and exfoliation disrupt the body's ability to regulate temperature and for the skin to perform barrier functions.

In yet another specific embodiment, the humanized antibodies of the invention, as well as compositions, methods and kits thereof, may be used for treating Pustular psoriasis. Pustular psoriasis appears as raised bumps that are filled with non-infectious pus (pustules). The skin under and surrounding the pustules became red and tender. Pustular psoriasis can be localized, commonly to the hands and feet (palmoplantar pustulosis), or generalized with widespread patches occurring randomly on any part of the body. Pustular psoriasis subtypes include Generalized pustular psoriasis (Pustular psoriasis of von Zumbusch), Pustulosis palmaris et plantaris (Persistent palmoplantar pustulosis, Pustular psoriasis of the Barber type, Pustular psoriasis of the extremities), Annular pustular psoriasis, Acrodermatitis continua and Impetigo herpetiformis.

It should be appreciated that the humanized antibodies of the invention, as well as compositions, methods and kits thereof may be also applicable for treating any additional types of psoriasis, for example, Drug-induced psoriasis, Inverse psoriasis, or flexural psoriasis, appears as smooth inflamed patches of skin. It occurs in skin folds, particularly around the genitals (between the thigh and groin), the armpits, under an overweight stomach (pannus), and under the breasts (inframammary fold). It is aggravated by friction and sweat, and is vulnerable to fungal infections.

Still further, the humanized antibodies may be used for treating Guttate psoriasis. This type pf psoriasis is characterized by numerous small, scaly, red or pink, teardrop-shaped lesions. These numerous spots of psoriasis appear over large areas of the body, primarily the trunk, but also the limbs, and scalp. Guttate psoriasis is often preceded by a streptococcal infection, typically streptococcal pharyngitis.

Nail psoriasis that may be also treated by the method of the invention produces a variety of changes in the appearance of finger and toe nails. These changes include discoloring under the nail plate, pitting of the nails, lines going across the nails, thickening of the skin under the nail, and the loosening (onycholysis) and crumbling of the nail.

As mentioned herein before, the humanized antibodies of the invention, as well as compositions, methods and kits thereof may be used for treating psoriatic arthritis. Psoriatic arthritis involves joint and connective tissue inflammation. Psoriatic arthritis can affect any joint but is most common in the joints of the fingers and toes. This can result in a sausage-shaped swelling of the fingers and toes known as dactylitis. Psoriatic arthritis can also affect the hips, knees and spine (spondylitis). About 10-15% of people who have psoriasis also have psoriatic arthritis.

In some embodiments, treatment of a subject suffering from psoriasis may improve the physiological state of the subject, for example, smoothing skin that was rough due to the disease. In preferred embodiments, topical application of humanized antibodies of the invention does not irritate the skin and does not promote inflammation.

It should be appreciated that other chronic or acute inflammatory-related skin pathologic conditions may be treated by the humanized antibodies of the invention, as well as compositions, methods and kits thereof. Such additional conditions include dermatitis, inflammatory skin injuries, inflammatory-related disturbances of skin pigmentation, for example, Vitiligo and eczemas.

More specifically, certain embodiments of the invention relates to the use of the humanized antibodies of the invention, as well as compositions, methods and kits thereof treating dermatitis. The term "dermatitis" refers to inflammation of the skin, in general. The different kinds usually have in common an allergic reaction to specific allergens. The term may be used to refer to eczema, which is also known as dermatitis eczema or eczematous dermatitis. A diagnosis of eczema often implies atopic dermatitis (childhood eczema), but without proper context, it means nothing more than a "rash", i.e. a transient skin inflammation. In some languages, "dermatitis" and eczema are synonyms, while in other languages "dermatitis" implies an acute condition and "eczema" a chronic one. The two conditions are often classified together.

According to another specific embodiment, the compositions, as well as methods, combined compositions and kits of the invention may be used for the treatment and/or amelioration of an autoimmune disorder, such as diabetes. Thus, according to one specific embodiment, the humanized antibodies of the invention may be used for preventing, treating, ameliorating or inhibiting diabetes type I.

Diabetes mellitus, is a syndrome characterized by disordered metabolism and inappropriately high blood sugar (hyperglycaemia) resulting from either low levels of the hormone insulin or from abnormal resistance to insulin's effects coupled with inadequate levels of insulin secretion to compensate. The characteristic symptoms are excessive urine production (polyuria), excessive thirst and increased fluid intake (polydipsia), and blurred vision; these symptoms are likely absent if the blood sugar is only mildly elevated.

There are three main forms of diabetes: type 1, type 2 and gestational diabetes (occurs during pregnancy). Type 1 diabetes mellitus is characterized by loss of the insulin-producing beta cells of the islets of Langerhans in the pancreas, leading to a deficiency of insulin. The main cause of this beta cell loss is a T-cell mediated autoimmune attack. There is no known preventative measure that can be taken against type 1 diabetes. Most affected people are otherwise healthy and of a healthy weight when onset occurs. Sensitivity and responsiveness to insulin are usually normal, especially in the early stages. Type 1 diabetes can affect children or adults and was traditionally termed "juvenile diabetes" as it represents a majority of cases of diabetes affecting children.

The principal treatment of type 1 diabetes, even from the earliest stages, is replacement of insulin combined with careful monitoring of blood glucose levels using blood testing monitors. Without insulin, diabetic ketoacidosis can develop and may result in coma or death. Emphasis is also placed on lifestyle adjustments (diet and exercise) though these cannot reverse the loss. Apart from the common subcutaneous injections, it is also possible to deliver insulin by a pump, which allows continuous infusion of insulin 24 hours a day at preset levels, and the ability to program doses (a bolus) of insulin as needed at meal times.

Type 1 treatment must be continued indefinitely. Treatment does not impair normal activities, if sufficient awareness, appropriate care, and discipline in testing and medication are taken.

The prevalence rate in the USA is 0.12% of the population or nearly 340,000 people. The incidence rate is about 30,000 annual cases, 0.01% of the population.

In yet another specific embodiment, the humanized antibodies of the invention may be used for preventing, treating, ameliorating or inhibiting diabetes type II. Diabetes mellitus type 2, or non-insulin-dependent diabetes mellitus (NIDDM) or adult-onset diabetes, is a metabolic disorder that is characterized by high blood glucose in the context of insulin resistance and relative insulin deficiency. As the condition progresses, medications may be needed. Long-term complications from high blood sugar include an increased risk of heart attacks, strokes, amputation, and kidney failure. There are many factors which can potentially give rise to or exacerbate type 2 diabetes. These include obesity, hypertension, elevated cholesterol (combined hyperlipidemia), and with the condition often termed metabolic syndrome (it is also known as Syndrome X, Reavan's syndrome, or CHAOS). Other causes include acromegaly, Cushing's syndrome, thyrotoxicosis, pheochromocytoma, chronic pancreatitis, cancer and drugs. Additional factors found to increase the risk of type 2 diabetes include aging, high-fat diets and a less active lifestyle.

Insulin resistance means that body cells do not respond appropriately when insulin is present. Unlike type 1 diabetes mellitus, insulin resistance is generally "post-receptor", meaning it is a problem with the cells that respond to insulin rather than a problem with the production of insulin. Severe complications can result from improperly managed type 2 diabetes, including renal failure, erectile dysfunction, blindness, slow healing wounds (including surgical incisions), and arterial disease, including coronary artery disease. The onset of type 2 has been most common in middle age and later life, although it is being more frequently seen in adolescents and young adults due to an increase in child obesity and inactivity. A type of diabetes called MODY is increasingly seen in adolescents, but this is classified as a diabetes due to a specific cause and not as type 2 diabetes.

There is growing evidence that there may be a link between inflammation and the pathogenesis of Type 2 diabetes. This evolving concept which suggests that insulin resistance and type 2 diabetes may have an immune component provides a new avenue to investigate immunotherapeutic approaches to both understand the pathogenesis of type 2 diabetes and to develop new treatments for the disease.

In yet another example for immune-related disorder, the invention further provides the use of the humanized antibodies of the invention, as well as compositions and kits thereof, in methods for preventing, treating, ameliorating or inhibiting Multiple sclerosis. More specifically, Multiple sclerosis (abbreviated MS, formerly known as disseminated sclerosis or encephalomyelitis disseminata) is a chronic, inflammatory, demyelinating disease that affects the central nervous system (CNS). Disease onset usually occurs in young adults, is more common in women, and has a prevalence that ranges between 2 and 150 per 100,000 depending on the country or specific population.

MS affects the neurons in the areas of the brain and spinal cord known as the white matter. These cells carry signals in between the grey matter areas, where the processing is done, and between these and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. The name multiple sclerosis refers to the scars (scleroses—better known as plaques or lesions) in the white matter. Loss of myelin in these lesions causes some of the symptoms, which vary widely depending upon which signals are interrupted. However, more advanced forms of imaging are now showing that much of the damage happens outside these regions. Almost any neurological symptom can accompany the disease.

MS takes several forms, with new symptoms occurring either in discrete episodes (relapsing forms) or slowly accumulating over time (progressive forms). Most people are first diagnosed with relapsing-remitting MS but develop secondary-progressive MS (SPMS) after a number of years. Between episodes or attacks, symptoms may go away completely, but permanent neurological problems often persist, especially as the disease advances.

Although much is known about the mechanisms involved in the disease process, the cause remains elusive. The theory with the most adherents is that it results from an autoimmune reaction. The disease does not have a cure, but several therapies have proven helpful. Treatments attempt to return function after an episode, prevent new attacks, and prevent disability. As with any treatment, medications have several adverse effects, and many therapies are still under investigation.

MS is typically characterized clinically by recurrent or chronically progressive neurologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease. EAE serves as a useful experimental model for investigating new therapeutic strategies in MS. Various immunosuppressive agents were found effective in prevention and treatment of EAE, including corticosteroids and copolymer 1. However, patients are so far treated either symptomatically or with immunosuppressive agents, and no satisfactory therapy for MS has as yet been established.

Thus, the invention includes compositions and methods of treating, delaying or preventing the onset of MS, comprising the administering the antibody of the invention to a subject in need thereof.

As shown by the following Examples, the anti-peptide-6 humanized antibodies of the invention clearly exhibit an anti-inflammatory effect. More specifically, FIGS. 14 and 15 show that exposure of human PBMCs to anti-peptide-6 humanized antibody of the invention (specifically, the VH2/VK3 variant and an $F(ab)_2$ fragment thereof) elicits sequential events resulting eventually in the up-regulation of the IL-10 gene expression. The increase of IL-10 secretion in the inflammatory site can divert the local cytokine profile from an inflammatory to an anti-inflammatory response and thus may explain the mechanism of protection against inflammation rendered by these antibodies.

Induction of IL-10 secretion may be a direct effect of the interaction of the antibodies with macrophage proteins and does not require the presence of any HSP antigen. The anti-peptide-6 humanized antibodies of the invention bind specifically to human macrophage membrane proteins, as illustrated in FIG. 12. Thus, the antibodies of the invention may be used as immunomodulators, modulating the Th1/Th2 cell balance towards an anti-inflammatory Th2 response. Therefore, the invention further provides a composition and method for increasing the expression and levels of IL-10 (Interleukin-10). According to this aspect, the composition of the invention comprises as an active ingredient an effective amount of at least one isolated and purified anti-peptide-6 humanized antibody directed against a peptide consisting of the amino acid sequence of SEQ ID. NO. 15. The composition of the invention may optionally comprise a pharmaceutically acceptable carrier, excipient or diluent.

According to one embodiment, wherein indicate "increasing" or "enhancing" the expression or the levels of an anti-inflammatory cytokine, for example, any one of IL-10, IL-4 and IL-6, specifically of IL-10, it is meant that such increase or enhancement may be an increase or elevation of between about 10% to 100% of the expression of such cytokines. The terms "increase", "augmentation" and "enhancement" as used herein relate to the act of becoming progressively greater in size, amount, number, or intensity. Particularly, an increase of 10%, 15%, 20%, 25%, 30%, 35%, 40%, 45%, 50%, 55%, 60%, 65%, 70%, 75%, 80%, 85%, 90%, 95% or 100% of the expression as compared to a suitable control. It should be further noted that increase or elevation may be also an increase of about 2 to 100 folds. Still further, it should be appreciated that the increase of the levels or expression of said IL-10 cytokine may be either in the transcription, translation or the stability of said cytokine. With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

As indicated above, the enhanced expression of IL-10 may modulate the Th1/Th2 balance towards the Th2 anti-inflammatory response. Therefore, the antibodies of the invention may be useful in conditions where modulation of the Th1/Th2 balance towards an anti-inflammatory reaction is desired. Thus, according to one embodiment, the compositions of the invention may be used for increasing the expression and levels of IL-10 in a subject in need thereof, thereby modulating the Th1/Th2 cell balance towards an anti-inflammatory Th2 response in the treated subject. According to one specific embodiment, such subject is a subject suffering of an immune-related disorder. For example, an immune-related disorder such as an autoimmune disease, (for example, arthritis, IBD, psoriasis, types-1 and 2 diabetes, multiple sclerosis (MS), lupus, Graves disease and thyroiditis), graft rejection pathology and graft versus host disease, and disorders induced by super antigens, such as toxic shock, septic shock and severe sepsis.

It should be further appreciated that in general, the composition as well as the methods, combined compositions and kits of the present invention may be used in preventing, treating, ameliorating or inhibiting any autoimmune disease such as for example, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM) and NIDDM, systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pemphigoid, dermatitis herpetiformis, inflammatory bowel disease, ulcerative colitis and Crohn's disease and fatty liver disease.

Pharmaceutical compositions comprising the humanized antibodies of the present invention are useful for parenteral administration, i.e., intraperitoneally (i.p.), subcutaneously (s.c.), intramuscularly (i.m.) and intravenously (i.v.), as well as for oral and topical application. The compositions for parenteral administration commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate. The concentration of the humanized antibodies in these formulations can vary widely, i.e., from less than about 0.01%, usually at least about 0.1% to as much as 5% by weight and will be selected primarily based on fluid volumes, and viscosities in accordance with the particular mode of administration selected.

More specifically, injectable compositions that include the anti-peptide-6 humanized antibody of the invention may be prepared in water, saline, isotonic saline, phosphate-buffered saline, citrate-buffered saline, and the like and may optionally be mixed with a nontoxic surfactant. Under ordinary conditions of storage and use, these preparations may contain a preservative to prevent the growth of microorganisms. Pharmaceutical dosage forms suitable for injection or infusion include sterile, aqueous solutions or dispersions or sterile powders comprising an active ingredient which powders are adapted for the extemporaneous preparation of sterile injectable or infusible solutions or dispersions. Preferably, the ultimate dosage form is a sterile fluid and stable under the conditions of manufacture and storage. A liquid carrier or vehicle of the solution, suspension or dispersion may be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. Isotonic agents such as sugars, buffers, or sodium chloride may be included. Prolonged absorption of the injectable compositions can be brought about by the inclusion in the composition of agents delaying absorption, for example, aluminum monosterate hydrogels and gelatin. Solubility enhancers may be added.

Sterile injectable compositions may be prepared by incorporating an anti-peptide-6 humanized antibody in the desired amount in the appropriate solvent with various other ingredients, e.g. as enumerated above, and followed by sterilization, as desired, by, for example filter sterilization. In the case of sterile powders for the preparation of sterile injectable solutions, methods of preparation include vacuum drying and freeze-drying techniques, which yield a powder of the active ingredient plus any additional desired ingredient present in a previously sterile-filtered solution. Any suitable sterilization process may be employees, such as filter sterilization, e.g. 0.22 micron filter or nanofiltration, gamma or electron beam sterilization.

In various embodiments, the final solution is adjusted to have a pH between about 4 and about 9, between about 5 and about 7, between about 5.5 and about 6.5, or about 6. The pH of the composition may be adjusted with a pharmacologically acceptable acid, base or buffer.

Still further, the compositions of the invention may be presented in unit dose forms containing a predetermined amount of each active ingredient per dose. Such a unit may be adapted to provide 0.1-100 mg/Kg of body weight of the humanized antibody of the invention. Specifically, either 0.1-10 mg/Kg, 5-15 mg/Kg, 10-30 mg/Kg, 25-50 mg/Kg 40-80 mg/Kg or 60-100 mg/Kg. More specifically, said effective dosage is about 0.01 to about 100 mg/Kg of humanized antibodies, about 0.1 to about 90 mg/Kg, about 0.3 to about 8 mg/Kg, about 0.4 to about 70 mg/Kg, about 0.5 to about 60 mg/Kg, about 0.7 to about 50 mg/Kg, about 0.8 to about 40 mg/Kg, about 0.9 to about 30 mg/Kg, about 1 to about 20 mg/Kg, specifically, about 1 to about 10 mg/Kg. Such doses can be provided in a single dose or as a number of discrete doses. The ultimate dose will of course depend on the condition being treated, the route of administration and the age, weight and condition of the patient and will be at the doctor's discretion.

As indicated above, in addition to the parenteral route, the compositions of the invention may be adapted for administration by any other appropriate route, for example by the oral (including buccal or sublingual), rectal, nasal, topical (including buccal, sublingual or transdermal) or vaginal route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets, powders or granules, solutions or suspensions in aqueous or non-aqueous liquids, edible foams or whips, or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time.

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either paraffin or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Specific embodiments contemplate skin inflammatory conditions, specifically, psoriasis treatment by topical administration of the affected skin areas of an ointment, cream, suspensions, paste, lotions, powders, solutions, oils, encapsulated gel, liposomes containing the humanized antibody of the invention, any nano-particles containing the antibody, or sprayable aerosol or vapors containing said antibody. Conventional pharmaceutical carriers, aqueous, powder or oily bases, thickeners and the like may be necessary or desirable. The term "topically applied" or "topically administered" means that the ointment, cream, emollient, balm, lotion, solution, salve, unguent, or any other pharmaceutical form is applied to some or all of that portion of the skin of the patient skin that is, or has been, affected by, or shows, or has shown, one or more symptoms of psoriasis.

In preferred embodiments, the administration of the humanized antibody of the invention for the treatment of skin disorders, specifically psoriasis, is by topical dressing. The term "dressing" means a covering for a wound or surgical site, typically composed of a cloth, fabric, synthetic membrane, gauze, or the like. It is usually a polymer-containing matrix covering an area of the skin. The dressing may or may not be in intimate contact with the skin. It can be, for example, a cloth or gauze, or it can be a polymer solution painted or sprayed on the skin, the polymer solidifying on the skin when the solvent dries off and/or when the polymer crosslinks. Dressings also include gels, typically cross-linked hydrogels, which are intended principally to cover and protect wounds, surgical sites, and the like.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurized aerosols, nebulizers or insufflators.

Pharmaceutical formulations adapted for vaginal administration may be presented as pessaries, tampons, creams, gels, pastes, foams or spray formulations.

Preferred unit dosage formulations are those containing a daily, biweekly, weekly, every few weeks or monthly dose or sub-dose, as herein above recited, or an appropriate fraction thereof, of an active ingredient. It should be indicated that there are also instances, especially in IBD, in which a large bolus dose is given initially and then the dose is reduced for continued treatment.

It should be understood that in addition to the ingredients particularly mentioned above, the formulations may also include other agents conventional in the art having regard to the type of formulation in question, for example those suitable for oral administration may include flavoring agents.

A further aspect of the invention provides a method for preventing, treating, ameliorating or inhibiting an immune-related disorder. The method of the invention comprises the step of administering to a subject in need thereof a therapeutically effective amount of at least one isolated and purified humanized antibody that specifically binds a polypeptide comprising SEQ ID NO: 15 or of a composition comprising the same. According to one embodiment, the humanized antibody used by the method of the invention comprises:

(a) a heavy chain variable region which comprises Cys at position H22, Ser at H23, Gly at H26, Phe at H27, Ser at H28, Leu at H29, Ser at H30, Thr at H31, Ser at H32, Asn at H33, Met at H34, Gly at H35, Val at H35A, Gly at H35B, Leu at H48, His at H50, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and optionally, at least one of Leu at H49, Tyr at H74, Ile at H11, Ser at H41 and Ser at H108; and (b) a light chain variable region which comprises Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Trp at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and optionally at least one of Met at L21, Ile at L10 and Ala at L80 (positions are determined according to the Rabat numbering system).

According to one embodiment, the method of the invention may use any of the humanized antibodies of the invention or any compositions comprising the same, as described by the invention. One particular embodiment relates to the use of at least one humanized antibody having a heavy chain variable region of SEQ ID NO. 21 and a light chain variable region of SEQ ID NO. 26 (VH2/VK3).

According to one embodiment, the method of the invention may be particularly applicable for preventing, treating, ameliorating or inhibiting immune-related disorders such as autoimmune or inflammatory disorders.

According to one specific embodiment the method of the invention is particularly applicable for treating an inflammatory arthritis.

According to another embodiment, the method of the invention may be used for the treatment of an inflammatory bowel disease (IBD).

According to another embodiment, the method of the invention may be used for the treatment of psoriasis.

In yet another embodiment, the method of the invention may be used for treating autoimmune disorders such as diabetes.

In yet another embodiment, the method of the invention may be used for the treatment of MS (multiple sclerosis).

As used herein, in the specification and in the claims section below, the term "treat" or treating and their derivatives includes substantially inhibiting, slowing or reversing the progression of a condition, substantially ameliorating clinical symptoms of a condition or substantially preventing the appearance of clinical symptoms of a condition.

As used herein, "disease", "disorder", "condition" and the like, as they relate to a subject's health, are used interchangeably and have meanings ascribed to each and all of such terms.

As used herein, "subject" means a mammal to which an agent, such as an antibody, is administered for the purposes of treatment or investigation. Mammals include mice, rats, cats, guinea pigs, hamsters, dogs, monkeys, chimpanzees, and humans.

The invention further encompasses the use of the antibodies of the invention for treating any condition related to the conditions descried above. It is understood that the interchangeably used terms "associated" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology.

For arthritis, such associated or related conditions may include, by way of example, all types of primary inflammatory arthritis, for example, Rheumatoid arthritis, Septic arthritis, Psoriatic arthritis, Reactive arthritis (ReA), Ankylosing spondylitis (previously known as Bechterew's disease, Bechterew syndrome), Juvenile idiopathic arthritis (JIA) and Gout (metabolic arthritis). In addition to all primary forms of arthritis indicated, the condition treated by the invention may include all secondary forms of arthritis, for example, lupus erythematosus, Henoch-Schönlein purpura, haemochromatosis, hepatitis, Wegener's granulomatosis (and many other vasculitis syndromes), Lyme disease, familial mediterranean fever, hyperimmunoglobulinemia D with recurrent fever, TNF receptor associated periodic syndrome and inflammatory bowel disease (including Crohn's Disease and ulcerative colitis).

For IBD, such associated or related conditions may include, by way of example, Crohn's disease, Ulcerative colitis, Collagenous colitis, Lymphocytic colitis, Ischaemic colitis, Diversion colitis, Behçet's syndrome and Indeterminate colitis.

For psoriasis, such associated or related conditions may include, by way of example, psoriatic arthritis, Pemphigus Vulgaris, Bullous Pemphigoid, Dermatomyositis, Cicatricial Pemphigoid, CREST Syndrome, Lupus, Discoid Lupus and Vitiligo.

For diabetes, such associated or related conditions may include, for example, eye related complications (cataract, glaucoma, retinopathy), neuropathy, nephropathy, cardiomyopathy, stroke, hypertension, peripheral arterial disease and sores.

A further aspect of the invention provides a method for increasing the expression and levels of IL-10 in a subject in need thereof, the method comprises the step of administering to said subject a therapeutically effective amount of at least one isolated and purified humanized antibody that specifically binds a polypeptide comprising SEQ ID NO: 15 or of a composition comprising the same. According to one embodiment, any of the humanized antibodies of the invention may be used for said method.

According to one embodiment, increasing the expression and levels of IL-10 leads to modulation of the Th1/Th2 cell balance towards an anti-inflammatory Th2 response in the treated subject that is suffering of an immune-related disorder.

It should be further noted that the invention provides the use of the humanized antibodies described herein, specifically, the VH2/VK3 variant, for preparing compositions for preventing, treating, ameliorating or inhibiting an immune-related disorder.

The present invention demonstrates the use of the novel humanized anti-peptide-6 antibodies as an immuno-modulatory agent applicable in the treatment of immune-related disorders. It should be also appreciated that the beneficial immuno-modulatory effect of said antibodies may be enhanced by combination thereof with other known anti-inflammatory agents. Thus, the invention further provides any combinations or mixtures of the antibodies of the invention with any therapeutic agent, specifically, an anti-inflammatory agent. Therefore, according to certain embodiments, the invention provides the use of a therapeutically effective amount of a combination of at least one isolated and purified humanized antibody or any antigen-binding fragment thereof and at least one anti-inflammatory agent selected from a group consisting of Methylprednisone (MPS), anti-TNF agents, etanercept (ENBREL®), infliximab (REMICADE®), adalimumab (HUMIRA®), certolizumab pegol (CIMZIA®), anti-IL-6 agents, tocilizumab (ACTEMRA®), anti-IL-1-receptor agents, kineret (ANAKINRA®), CTLA-4-Ig, abatacept (ORENCIA®), anti-CD20 agents, rituximab (MabThera; RITUXAN®), methotrexate, any corticosteroid derivatives and any other anti-inflammatory agent for treating, preventing, ameliorating, reducing or delaying an immune-related disorder. It should be noted that such additional anti-inflammatory agent may be an agent that induces an anti-inflammatory response through any other pathway than the mechanisms of the anti-peptide 6 antibodies which include a pathway that involves, induction of IL-10.

The present invention therefore particularly relates to additive and synergistic combinations of at least one isolated and purified humanized antibody or any antigen-binding fragment thereof and at least one anti-inflammatory agent selected from a group consisting of Methylprednisone (MPS), anti-TNF agents, etanercept (ENBREL®), infliximab (REMICADE®), adalimumab (HUMIRA®), certolizumab pegol (CIMZIA®), anti-IL-6 agents, tocilizumab (ACTEMRA®), anti-IL-1-receptor agents, kineret (ANAKINRA®), CTLA-4-Ig, abatacept (ORENCIA®), anti-CD20 agents, rituximab (MabThera; RITUXAN®), methotrexate, any corticosteroid derivatives, and any anti-inflammatory agent inducing any signaling pathway that is different than the anti-peptide 6pathway, whereby those additive and synergistic combinations are useful in treating subjects suffering from an immune-related disorder, for example, arthritis, IBD, psoriasis or diabetes. The synergistic and additive compositions of the invention may also be used for the treatment of subjects presenting with symptoms or signs of such disorders.

By synergic combination is meant that the effect of both isolated and purified humanized antibody or any antigen-binding fragment thereof and at least one anti-inflammatory agent selected from a group consisting of Methylprednisone (MPS), anti-TNF agents, etanercept (ENBREL®), infliximab (REMICADE®), adalimumab (HUMIRA®), certolizumab pegol (CIMZIA®), anti-IL-6 agents, tocilizumab (ACTEMRA®), anti-IL-1-receptor agents, kineret (ANAKINRA®), CTLA-4-Ig, abatacept (ORENCIA®), anti-CD20 agents, rituximab (MabThera; RITUXAN®), methotrexate, and any corticosteroid derivatives, or any other anti-inflammatory agent, is greater than the sum of the therapeutic effects of administration of any of these compounds separately, as a sole treatment. More specifically the additional anti-inflammatory agent may induce a pathway that is different than the pathways induced by anti-peptide 6 antibodies, for example, any pathway involved in IL-10 induction.

The combined compounds of the present invention are generally administered in the form of a pharmaceutical composition comprising both compounds of this invention together with a pharmaceutically acceptable carrier or diluent. However, according to some embodiments, both compounds may be administered separately. Thus, the compounds used by this invention can be administered either individually in a kit or together in any conventional oral or mucosal dosage form.

More particularly, since the present invention relates to the treatment of diseases and conditions with a combination of active ingredients which may be administered separately, the invention also relates as a further aspect, to combining separate pharmaceutical compositions in kit form. The kit includes at least two separate pharmaceutical compositions: (i) isolated and purified humanized antibody or any antigen-binding fragment thereof, particularly any of the humanized antibodies of the invention, optionally in a first dosage form (ii) at least one anti-inflammatory agent selected from a group consisting of Methylprednisone (MPS), anti-TNF agents, etanercept (ENBREL®), infliximab (REMICADE®), adalimumab (HUMIRA®), certolizumab pegol (CIMZIA®), anti-IL-6 agents, tocilizumab (ACTEMRA®), anti-IL-1-receptor agents, kineret (ANAKINRA®), CTLA-4-Ig, abatacept (ORENCIA®), anti-CD20 agents, rituximab (MabThera; RITUXAN®), methotrexate, any corticosteroid derivatives, and any anti-inflammatory agent inducing any other pathway that is different than the anti-peptide 6 pathway, optionally, in a second dosage form.

The kit of the invention may also further contain (iii) container means for containing said first and second dosage forms.

More specifically, the kit includes container means for containing both separate compositions, such as a divided bottle or a divided foil packet. However, the separate compositions may also be contained within a single, undivided container. Typically the kit includes directions for the administration of the separate components. The kit form is particularly advantageous when the separate components are preferably administered in different dosage forms (e.g., parenteral), are administered at different dosage intervals, or when titration of the individual components of the combination is desired by the prescribing physician.

Achieving a therapeutic effect is meant for example, where the kit is intended for the treatment of a specific disorder, the therapeutic effect may be for example slowing the progression of the treated condition.

It should be appreciated that both components of the kit, the isolated and purified humanized antibody of the invention, optionally, in the first dosage form and the at least one anti-inflammatory agent selected from a group consisting of Methylprednisone (MPS), anti-TNF agents, etanercept (ENBREL®), infliximab (REMICADE®), adalimumab (HUMIRA®), certolizumab pegol (CIMZIA®), anti-IL-6 agents, tocilizumab (ACTEMRA®), anti-IL-1-receptor agents, kineret (ANAKINRA®), CTLA-4-Ig, abatacept (ORENCIA®), anti-CD20 agents, rituximab (MabThera; RITUXAN®), methotrexate, any corticosteroid derivatives, and any anti-inflammatory agent inducing any other pathway that is different than the anti-peptide 6 pathway, optionally, in the second dosage form may be administered simultaneously.

Alternatively, said first compound or dosage form and said second compound or dosage form are administered sequentially in either order.

The compositions containing the present humanized antibodies or any combination, mixture or cocktail thereof, can be administered for prophylactic and/or therapeutic treatments. In therapeutic application, compositions are administered to a patient already affected by an immune-related disorder (e.g., arthritis, IBD, psoriasis, MS and diabetes) in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.01 to about 100 mg/Kg of humanized antibodies per dose, with dosages of from 0.1 to 50 mg and 1 to 10 mg per Kg of body weight being more commonly used. More specifically, said effective dosage is about 0.01 to about 100 mg/Kg of humanized antibodies, about 0.1 to about 90 mg/Kg, about 0.3 to about 8 mg/Kg, about 0.4 to about 70 mg/Kg, about 0.5 to about 60 mg/Kg, about 0.7 to about 50 mg/Kg, about 0.8 to about 40 mg/Kg, about 0.9 to about 30 mg/Kg, about 1 to about 20 mg/Kg, specifically, about 1 to about 10 mg/Kg. Single or multiple administrations on a daily, biweekly, weekly, every few weeks or monthly schedule can be carried out with dose levels and pattern being selected by the treating physician.

In prophylactic applications, compositions containing the humanized antibodies or any combination, mixture or cocktail thereof are administered to a patient who is at risk of developing the disease state to enhance the patient's resistance. Such an amount is defined to be a "prophylactically effective dose". In this use, the precise amounts again depend upon the patient's state of health and general level of immunity, but generally range from 0.1 to 100 mg per dose, especially 1 to 10 mg per Kg of body weight. More specifically, said effective dosage is about 0.01 to about 100 mg/Kg of humanized antibodies, about 0.1 to about 90 mg/Kg, about 0.3 to about 8 mg/Kg, about 0.4 to about 70 mg/Kg, about 0.5 to about 60 mg/Kg, about 0.7 to about 50 mg/Kg, about 0.8 to about 40 mg/Kg, about 0.9 to about 30 mg/Kg, about 1 to about 20 mg/Kg, specifically, about 1 to about 10 mg/Kg.

Single or multiple administrations of the compositions are administered depending on the dosage and frequency as required and tolerated by the patient. In any event, the composition should provide a sufficient quantity of the humanized antibodies of this invention to effectively treat the patient. Preferably, single administration is desired, where the dosage is administered once. However, in most cases the dosage is administered periodically until either a therapeutic is achieved and to maintain the therapeutic effect or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems.

Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly.

Polymers can be used for ion-controlled release of the humanized anti-peptide-6 antibody compositions of the present invention. Various degradable and nondegradable polymeric matrices for use in controlled drug delivery are known in the art.

In yet another embodiment, liposomes are used for controlled release as well as drug targeting of the lipid-capsulated drug.

A further aspect of the invention relates to host cell line transformed or transfected with an expression vector encoding a humanized antibody of the invention. In one particular embodiment, this expression vector encodes both, the variable heavy and the variable light chains.

In certain embodiments, such cell line express a humanized antibody having a heavy chain variable region comprising an amino acid sequence as denoted by SEQ ID NO: 21 and a light chain variable region comprising an amino acid sequence as denoted by SEQ ID NO: 26.

In one particular embodiment, the cell line of the invention is described in Examples 23-26, and deposited under the accession no. CNCM I-4356.

"Host cell" as used herein refers to cells which can be recombinantly transformed with vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which require the induced phenotype for survival.

"Cells", "host cells" or "recombinant cells" are terms used interchangeably herein. It is understood that such terms refer not only to the particular subject cells but to the progeny or potential progeny of such a cell. Because certain modification may occur in succeeding generation due to either mutation or environmental influences, such progeny may not, in fact, be identical to the parent cell, but are still included within the scope of the term as used herein.

As used herein, the term "transfection" means the introduction of a nucleic acid, e.g., an expression vector, into a recipient cells by nucleic acid-mediated gene transfer. "Transformation", as used herein, refers to a process in which a cell's genotype is changed as a result of the cellular uptake of exogenous DNA or RNA.

The invention further provides an expression vector for the expression of a humanized antibody having both a heavy chain variable region comprising an amino acid sequence as denoted by SEQ ID NO: 21 and a light chain variable region comprising an amino acid sequence as denoted by SEQ ID NO: 26.

In specific embodiments, the invention provides an expression vector for the expression of a humanized heavy chain variable region comprising an amino acid sequence as denoted by SEQ ID NO: 21. An example of such a vector is the pANTVhG1/4 vector shown in FIG. 2 and Example 2.

In other embodiments, the invention provides an expression vector for the expression of a humanized light chain variable region comprising an amino acid sequence as denoted by SEQ ID NO: 26. An example of such a vector is the vector pANTVK shown in FIG. 2 and Example 2.

Most preferably, the invention provides an expression vector for the expression of a humanized antibody having both a heavy chain variable region comprising an amino acid sequence as denoted by SEQ ID NO: 21 and a light chain variable region comprising an amino acid sequence as denoted by SEQ ID NO: 26. An example of such a vector is the pPRO14 vector shown in FIG. 26 and Example 22.

One specifically preferred expression vector may be the mammalian expression plasmid pPRO14 shown in FIG. 26. Other preferred expression vectors are the mammalian expression vectors pANTVK and pANTVhG1/4 shown in FIG. 2.

Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. This typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

A vector may additionally include appropriate restriction sites, antibiotic resistance or other markers for selection of vector-containing cells. Plasmids are the most commonly used form of vector but other forms of vectors which serve an equivalent function and which are, or become, known in the art are suitable for use herein. See, e.g., Pouwels et al., Cloning Vectors: a Laboratory Manual (1985 and supplements), Elsevier, N.Y.; and Rodriquez, et al. (eds.) Vectors: a Survey of Molecular Cloning Vectors and their Uses, Buttersworth, Boston, Mass. (1988), which are incorporated herein by reference.

It should be noted that the invention further encompasses the chimeric anti-peptide-6 antibodies as encoded by SEQ ID NO. 9, 10 and 11. These antibodies have a heavy chain variable region of SEQ ID NO. 1 and a light chain variable region of SEQ ID NO. 2. It should be noted that these antibodies carry a mouse variable region and a human constant region and are also referred to as the reference or parent antibodies. According to certain embodiments, the mouse anti-peptide-6 antibody, the chimeric or humanized antibodies of the invention comprise heavy and light chain variable regions as described herein, with the proviso that the antibody is not identical to a murine monoclonal antibody designated as MF9 in U.S. Pat. No. 7,488,476.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted.

Thus, according to another aspect, the present invention provides a chimeric murine monoclonal antibody that specifically binds a polypeptide comprising SEQ ID NO: 15, wherein said antibody comprises a human immunoglobulin constant region and a murine immunoglobulin variable region, said variable region comprising a light chain variable region having the amino acid sequence as denoted by SEQ ID NO. 2 and a heavy chain variable region having the amino acid sequence as denoted by SEQ ID NO. 1.

According to some embodiments, the invention provides a composition comprising as an active ingredient an effective amount of at least one isolated and purified chimeric monoclonal antibody according to the invention that specifically binds a polypeptide comprising SEQ ID NO: 15.

According to more specific embodiments, the invention provides a pharmaceutical composition for the treatment, prophylaxis amelioration or delay of onset of an immune-related disorder, wherein said composition comprising as an active ingredient a therapeutically effective amount of at least one isolated and purified chimeric monoclonal antibody according to the invention that specifically binds a polypeptide comprising SEQ ID NO: 15.

The invention also contemplates a method for the treatment, prophylaxis amelioration or delay of onset of an immune-related disorder comprising the step of administering to a subject in need thereof a therapeutically effective amount of at least one isolated and purified chimeric monoclonal antibody according to the invention that specifically binds a polypeptide comprising SEQ ID NO: 15.

According to other embodiments, the invention provides a combined composition comprising at least one isolated and purified chimeric monoclonal antibody according to the invention that specifically binds a polypeptide comprising SEQ ID NO: 15, and at least one anti-inflammatory agent selected from a group consisting of Methylprednisone (MPS), anti-TNF agents, etanercept (ENBREL®), infliximab (REMICADE®), adalimumab (HUMIRA®), certolizumab pegol (CIMZIA®), anti-IL-6 agents, tocilizumab (ACTEMRA®), anti-IL-1-receptor agents, kineret (ANAKINRA®), CTLA-4-Ig, abatacept (ORENCIA®), anti-CD20 agents, rituximab (MabThera; RITUXAN®), methotrexate, any corticosteroid derivatives and any anti-inflammatory agent inducing any signaling pathway, specifically a pathway that is different than the pathways induced by anti-peptide 6, for example, any pathway involved in IL-10 induction.

According to particular embodiments, the invention considers the use of a therapeutically effective amount of at least one isolated and purified chimeric monoclonal antibody according to the invention that specifically binds a polypeptide comprising SEQ ID NO: 15, in the preparation of a composition for the treatment, prophylaxis, onset delay or amelioration of an immune-related disorder.

Still further, the invention provides the use of the chimeric antibody described herein in kits, as well as for diagnostic application.

The inventors previously demonstrated that serum anti-peptide-6 antibodies titer was significantly lower in rheumatoid arthritis patients in comparison with healthy subjects. Thus, the inventors contemplate the use of serum anti-peptide-6 as a marker for rheumatoid arthritis, or, indeed, inflammatory disorders in general.

Therefore, in a further aspect, the present invention provides diagnostic kits and methods for the detection and monitoring of an immune disorder, in a mammalian subject, specifically, immune-related disorders including those that involve a decrease in anti-inflammatory cytokine expression, particularly, IL-10 expression. Such immune-related disorders include arthritis, IBD (e.g., Crohn's disease and ulcerative colitis), psoriasis, diabetes, and MS. More specifically, the diagnostic methods and kits provided by the invention use as a marker for immune-related disorders, the level of anti-peptide-6 antibodies in the tested biologic sample. Reduced levels of anti-peptide-6 antibodies in the tested sample as compared to the levels in a healthy control, indicates that the sample is of a subject suffering from an immune-related disorder. It should be appreciated that the diagnostic kits and methods of the invention further provide a tool for a "tailor-made" or personalized therapy, by identifying subjects suffering from a specific inflammatory disease that are likely to be benefit from treatment with the humanized anti-peptide-6 antibodies.

It is appreciated that the diagnostic methods and kits provided by the invention constitute a competitive antibody binding assay, wherein the amount of the anti-peptide-6 antibodies comprised in a sample of interest, specifically, a serum sample, is determined by incubation of said sample with a known amount of isolated and purified peptide-6, followed by incubation of the same peptide-6 with a known amount of the humanized anti-peptide-6 antibody of the invention, optionally, labeled with a detectable moiety or label. Thus, the amount of anti-peptide-6 antibody in said sample of interest is proportional to the decrease in peptide-6-bound labeled anti-peptide-6 antibody.

According to one embodiment, the invention provides a diagnostic method for the detection and monitoring of an immune disorder that is likely to be responsive to treatment with the humanized anti-peptide-6 antibodies, in a mammalian subject, comprising the steps of: (a) contacting a tested sample with a predetermined amount of an isolated peptide-6 (SEQ ID NO. 15), under suitable conditions allowing the binding of said peptide to anti-peptide-6 antibodies; (b) adding to the sample-peptide-6 mixture of (a) a predetermined amount of the humanized anti-peptide-6 antibody of the invention, optionally, labeled with a detectable label. It should be appreciated that steps (a) and (b) can be done either sequentially or at the same time; (c) determining the binding of the humanized anti-peptide-6 antibody to peptide-6 in the sample, by suitable means; Since binding of the anti-peptide-6 antibody in the sample competes with the binding of the humanized anti-peptide-6 antibody of the invention to peptide-6, displacement of the humanized-antipeptide-6 antibody by the anti-peptide-6 antibody in the sample, is reflected by reduction in peptide-6-humanized antibody binding; (d) evaluating the amount of the anti-peptide-6 antibody in the tested sample by extrapolation from a standard curve established by displacement of serial dilutions of peptide-6 and the labeled humanized antibody of the invention, by serial dilutions of anti-peptide-6 antibody. Reduced amounts of anti-peptide-6 antibody in the tested sample, indicates that the sample is of a subject suffering from an immune-related disorder that is likely to benefit from treatment with humanized anti-peptide-6 antibodies.

According to one specific embodiment, the sample is incubated with a predetermined amount of isolated peptide-6, attached to a solid support, followed by addition of predetermined amount of the humanized anti-peptide-6 antibody of the invention, labeled with a detectable label.

The term "sample" in the present specification and claims is meant to include biological samples. Biological samples may be obtained from mammal, specifically, a human subject, include fluid, solid (e.g., stool) or tissue. The term "sample" may also include body fluids such as serum, urine, blood, milk, cerebrospinal fluid, rinse fluid obtained from wash of body cavities, phlegm, pus. Some samples that are a priori not liquid are contacted with a liquid buffers which are then used according to the diagnostic method of the invention.

Biological samples may be obtained from all of the various families of domestic animals, as well as feral or wild animals, including, but not limited to, such animals as ungulates, bear, fish, lagamorphs, rodents, etc. Preferably, the sample is liquid, specifically, a body fluid sample, most preferably, a serum sample and of mammalian origin, specifically, human.

The invention further provides a kit for the detection and monitoring of an immune disorder in a mammalian subject. The kit of the invention may further provide information regarding the potential responsiveness of the examined patient to respond to treatment using the anti-peptide-6 antibodies of the invention. The kit of the invention may comprise: (a) means for obtaining a biological sample from the tested subject; (b) a humanized anti-peptide-6 antibody labeled with a detectable moiety; (c) an isolated peptide-6, optionally attached to a solid support; (d) means for detecting the amount of an immuno-complex formed between the labeled humanized anti-peptide-6 antibody and peptide-6 attached to the solid support; (e) standard curve established by displacement of serial dilutions of peptide-6 and the labeled humanized antibody of the invention, by serial dilution of an unlabelled anti-peptide-6 antibody (f) instructions for carrying out the detection of the presence and quantity of anti-peptide-6 antibodies in said sample, preferably, by the method of the invention described herein-above.

It is understood that said solid support that may be suitable for use in the kits of the present invention is typically substantially insoluble in liquid phases. Solid supports of the current invention are not limited to a specific type of support. Rather, a large number of supports are available and are known to one of ordinary skill in the art. Thus, useful solid supports include solid matrixes, such as aerogels and hydrogels, resins, beads, biochips (including thin film coated biochips), microfluidic chip, a silicon chip, preferably, multi-well plates (also referred to as microtitre plates or microplates).

It should be noted that for diagnostic application described herein, the humanized antibodies of the invention may be conjugated to a detectable label. One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholine-esterase. The detection can be accomplished by colorimetric methods, which employ a chromogenic substrate for the enzyme. Detection may also be accomplished by visual comparison of the extent of enzymatic reaction of a substrate in comparison with similarly prepared standards.

Detection may be accomplished by using any of a variety of other immunoassays. For example, by radioactive labeling of the antibodies of the invention or antibody fragments, it is possible to detect the levels of anti-peptide-6 antibodies in the sample through the use of a radioimmunoassay (RIA). The radioactive isotope can be detected by such means as the use of a $\gamma$ counter or a scintillation counter or by autoradiography.

Alternatively, it is also possible to label an antibody in accordance with the present invention with a fluorescent compound, fluorescence emitting metals, a chemiluminescent compound or a bioluminescent compound.

It is appreciated that the diagnostic and method of the invention both optionally make use of suitable buffers and solutions for the interaction of the antibodies of the invention and antibodies comprised in a tested sample with peptide-6 and for the competitive binding assay of the two antibodies. The buffers are also useful for the dissolution of solid and semi-solid samples prior to the sample analysis according to the method of the invention.

The competitive binding of the antibodies of the invention and antibodies present in a sample of interest according to the diagnostic kits and methods of the invention usually require the maintenance of specific pH and osmolarity conditions. Presence or absence of some detergents and solvents may also alter the bindings efficiency. The pH is typically maintained at a relatively neutral level, such as from about 6 to about 9, and in some embodiments, about 7. Osmolarity is usually adjusted by the addition of salts, such as, for example sodium chloride, potassium chloride, magnesium chloride and other salts. Some non-limiting examples of detergents and solvents that may be used for adjustment of binding conditions include Tween-20, Triton X100, PEG, DMSO, Nonidet P-40 and others. Some non-limiting examples of biologically compatible buffers that may be used to maintain the desired pH and osmolarity include borate buffers, phosphate-buffered saline (PBS), 2-(N-morpholino) ethane sulfonic acid ("MES"), tris-hydroxymethylaminomethane ("Tris"), citrate buffers, and so forth.

All scientific and technical terms used herein have meanings commonly used in the art unless otherwise specified. The definitions provided herein are to facilitate understanding of certain terms used frequently herein and are not meant to limit the scope of the present disclosure.

The invention will be described in more detail on basis of the following Examples, which are illustrative only and do not in any way limit the invention. Many modifications and variations of the present invention are possible in light of the present teachings. It is therefore understood, that within the scope of the appended claims, the invention may be practiced otherwise than specifically described.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., Molecular cloning: A laboratory manual, Cold Springs Harbor Laboratory, New-York (1989, 1992), and in Ausubel et al., Current Protocols in Molecular Biology, John Wiley and Sons, Baltimore, Md. (1988).

Standard organic synthesis protocols known in the art not specifically described herein are generally followed essentially as in Organic syntheses: Vol. 1-79, editors vary, J. Wiley, New York, (1941-2003); Gewert et al., Organic synthesis workbook, Wiley-VCH, Weinheim (2000); Smith & March, Advanced Organic Chemistry, Wiley-Interscience; 5th edition (2001).

Standard medicinal chemistry methods known in the art not specifically described herein are generally followed essentially as in the series "Comprehensive Medicinal Chemistry", by various authors and editors, published by Pergamon Press.

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Vanderkerken K The 5T2MM murine model of multiple myeloma: maintenance and analysis. [Methods Mol. Med. 113:191-205 (2005); Epstein J. The SCID-hu myeloma model. Methods Mol. Med. 113:183-90 (2005)].

Antibodies

- Mouse anti-peptide-6 antibody is a mouse monoclonal antibody developed from peptide-6-immunized Balb/C mice by the hybridoma technique and is of the IgM isotype.
- Chimeric anti-peptide-6 IgG1 mouse antibodies were developed by Antitope Ltd. using the chimerization technique as described by Example 1. The resulting chimeric antibodies are composed of the mouse variable region of the mouse antibody (denoted by SEQ ID NO. 1 and 2 and FIGS. 1A, 1B) and the human constant region of the IgG1 isotype.
- Humanized anti-peptide-6 antibodies based on the mouse reference antibody were produced by Antitope Ltd. using the Composite Human Antibody™ technique (described in WO 2006/082406), as described by Example 2.

FITC labeled humanized antibodies were used for the FACS analysis.

In some embodiments the term Proximab may be used to describe monoclonal antibodies against the peptide-6 epitope of the MT HSP65.

- Anti-CD14-PE (Sigma)
- Anti-CD14-APC (Miltenyi Biotech)
- HRP labeled mouse anti-human kappa light chains (Sigma, Cat. No. A7164)
- goat anti-mouse IgM peroxidase (Sigma Catalogue No. A8786)
- goat anti-human IgG peroxidase (Sigma Catalogue No. A7164)

Cell Lines

- CHO dhfr-(ECACC Cat. No. 94060607, Lot No. 05G020)
- THP-1 (ATCC Number TIB-202) monocyte cells
- RAW murine macrophages
- NSO cells (ECACC 85 110503, Porton, UK)

Restriction Enzymes

- BssH II (New England Biolabs Cat. No. R0199)
- BamH I (New England Biolabs Cat. No. R0136)
- Mlu I (New England Biolabs Cat. No. R0198)
- Hind III (New England Biolabs Cat. No. R0140)
- SspI (New England Biolabs Cat. No. R0132)

Culture Medium and Supplements

- CD DG44 (Invitrogen, Cat. No. 12610-010)
- Glutamax (Invitrogen, Cat. No. 35050))
- DMEM (Invitrogen, Cat. No. 41966)
- Dialyzed FBS (Invitrogen, Cat No. 26400
- H/T (Invitrogen, Cat. No. 11067)
- CD-OptiCHO (Invitrogen, Cat. No. 12681-029)
- FBS (Ultra low IgG Cat No. 16250-078 Invitrogen, Paisley UK)
- Penicillin/Streptomycin (Invitrogen, Paisley UK)
- DMSO (Sigma, Cat No. D2650)
- Methotrexate (Sigma, Cat No. A6770)

Reagents and Kits

- Lipofectamine 2000 (Invitrogen, Cat. No. 11668027)
- TMB substrate (Invitrogen Cat. No. 00-2023) or (Sigma Catalogue No. T0440)
- Minerva Biolabs Venor® GeM Mycoplasma Detection Kit (Cat. No. 11-1050)
- Protein A sepharose column (GE Healthcare Catalogue No. 110034-93)
- Fc capture/kappa chain detection ELISA (Sigma Catalogue No. I6260 and A7164) against a human IgG1/kappa or IgG4/kappa standard (Sigma Catalogue No. I5154 and I4631)

Equipment

- Binder CB150 incubator
- Dynex Technologies MRX TC II plate reader
- Vi-CELL™ XR counter (Beckman Coulter)
- 6 well tissue culture plates (Corning, Cat. No. 3516)
- MaxiSorp 96 well flat bottom microtitre plate (Fisher, Cat. No. DIS-971-030J)
- Erlenmeyer flasks (Corning, Cat. No. 431407)

Animals

- For the Adjuvant-Induced Arthritis model, six to eight week old female inbred Lewis rats (Harlan Laboratories, Israel) were injected intradermally at the base of the tail with 1 mg of *Mycobacterium Tuberculosis* (MT) H37Ra (Difco, Detroit, Mich.) in CFA (Difco
- For the Collagen-Induced Arthritis model, Nine week old male DBA/1 mice (Harlan Laboratories, Israel) were used. Mice were injected s.c. at the base of the tail with 200 μg collagen type II emulsified in CFA (Difco). Three weeks later mice were boosted s.c. with the same concentration of collagen II.
- For the TNBS colitis model, Balb/C mice were sensitized with 160 μL of the haptenizing agent TNBS (Sigma-Aldrich, St. Louis, Mo.) at a concentration of 2.5% in 50% ethanol by skin painting.
- Sprague-Dawley (SD) male rats, purchased from Harlan-Israel facilities, treated with streptozotocin (70 mg/kg) for use as diabetes type I model.
- 8-week-old female C57BL/6 mice by injecting s.c. into the left para-lumbar region 125 μg of myelin oligodendrocyte glycoprotein 35-55 peptide (MOG35-55) emulsified in complete Freund's adjuvant (CFA) containing 5 mg/ml heat-killed *Mycobacterium tuberculosis* for use as an MS model.

Cloning of Cap1

Cap1 was PCR amplified from THP-1 cDNA with primers Cap1bamF (GCGTAGTC GGA TCC ATG GCT GAC ATG CAA AAT CTG G, SEQ ID NO. 99) and caplxhoyeshstopR (GCGTAGTC CTC GAG TTA TCC AGC AAT TTC TGT CAC TGT GGT GAC C, SEQ ID NO. 100). The resulting ≈1400 bp PCR product was inserted into PGEMT vector (Promega) resulting in Cap1 with stop codon in PGEMT. (Sequencing results show perfect sequence).

Next, Cap1 was cut out of the pGEMT vector with BamHI and XhoI. The 1400 bp band was ligated to a modified Pet22b vector (Novagen) cut with same, resulting in Cap1, flanked by 6×HIS at the N terminus and a stop codon at the end of the gene.

Generation of Mouse Anti-Peptide-6-Producing Hybridomas

Six-weeks-old female Balb/c mice or Lewis rats were injected subcutaneously with 100 μg peptide-6 (GPKGRNVVLEKKWGAP, as denoted by SEQ ID NO. 15) suspended in complete Freund's adjuvant (CFA). Animals were injected 2 more times with the peptide in incomplete Freund's adjuvant (IFA) at 3 weeks intervals. Sera were collected for measurement of anti-peptide-6 antibody levels by ELISA and animals with the highest levels were treated with 2 consecutive intraperitoneal injections of 50 μg peptide in PBS. On the following day spleens were fused with the BALB/c Ig-nonsecreting myeloma NSO. The presence of antibodies specifically recognizing peptide-6 (SEQ ID NO. 15) was detected in the supernatants by specific ELISA, and positive clones were expanded.

Anti-peptide-6 antibodies were purified from the supernatants of hybridoma cells. Purification was performed by thioadsorption followed by protein G chromatography (Adar Biotech, Israel). The purity of antibodies was confirmed by SDS-PAGE.

Preparation of $F(ab)_2$ Fragment of Humanized Anti-Peptide-6 Antibody $F(ab)_2$ fragments of the humanized VH2/VK3 anti-peptide-6 antibody were generated using an $F(ab)_2$ preparation kit based on pepsin digestion (Pierce; according to the manufacturers' instructions). $F(ab)_2$ fragments were labeled with FITC using Dylight™ Antibody Labeling Kit (Pierce; according to the manufacturers' instructions).

Preparation of Human Peripheral Blood Mononuclear Cells (PBMC)

Human venous blood was collected from a healthy donor and layered on a Ficol gradient to separate and enrich the white blood cell fraction. After centrifugation (1800 RPM for 30 minutes), the mononuclear band was collected, transferred into a new tube, washed with 20 ml phosphate buffered saline (PBS) and centrifuged at 1100 RPM for 10 minutes. Cells were plated on 24-well cell culture plates, at a concentration of $1.5\times10^6$ cells/well in 1 ml RPMI supplemented with 2 mM glutamine, 100 μg/ml streptomycin, 100 U/ml penicillin (all reagents from Biological Industries, Israel) and 10% human serum (Sigma).

Fluorescence Activated Cell Sorting (FACS) Analysis $10^6$ PBMC cells were placed in eppendorff tubes ($10^6$ cells/100 μl of 1% BSA and 1% goat serum (Sigma) in PBS). Cells were then incubated for 1 hr at 4° C. with anti-CD14 antibodies alone or together with humanized whole or $F(ab)_2$ anti-peptide-6 antibodies. The cells were then washed with PBS and staining was determined by a LSRII Flow Cytometer (BD). Data was analyzed using the FCS express 3 program (De novo).

ELISA—Binding of Variant Composite Antibodies to Peptide-6

Immulon MaxiSorp, 96 well flat bottom microtitre plates (Fisher Cat. No. DIS-971-030J) were pretreated with 5% glutaraldehyde in PBS (100 μl/well) in the dark, overnight at room temperature, and then coated with peptide-6 (SEQ ID NO. 15) at 10 μg/ml in PBS, overnight at 4° C. Plates were washed with PBS/0.05% Tween 20 and then blocked for 1 hour with 2% BSA/PBS. Antibodies were diluted in 2% BSA/PBS to a starting concentration of 100 μg/ml. Doubling dilutions were made down the plate and the plates were then incubated for 1 hour at room temperature.

Each ELISA plate included the chimeric anti-peptide-6 antibody as a positive control. Plates were washed and 100 μl goat anti-human IgG kappa peroxidase conjugate (Sigma Cat. No. A7164) diluted 1:1000 in PBS/0.05% Tween 20 was added to each well. After 1 hour incubation at room temperature, plates were washed and the assay developed by the addition of 100 μl/well TMB substrate (Sigma Cat No. T0440). The reaction was stopped by the addition of 50 μl/well 3M HCL. Absorbance was read at 450 nm (Dynex MRX TCII plate reader) and plotted against antibody concentration.

ELISA—Evaluation of Cytokine Levels

Evaluation of cytokine levels in cell culture or in the serum of animals was carried out utilizing specific kits from R&D SYSTEMS, Minneapolis Minn. USA (according to the manufacturer's instructions).

Induction and Clinical Assessment of Adjuvant-Induced Arthritis

Six to eight week old female inbred Lewis rats (Harlan Laboratories, Israel) were injected intradermally at the base of the tail with 1 mg of *Mycobacterium tuberculosis* (MT) H37Ra (Difco, Detroit, Mich.) in CFA (Difco). Severity of arthritis (arthritis index) was assessed every other day by a blinded observer as follows: 0, no arthritis; 1, redness of the joint; 2, redness and swelling of the joint. The ankle and tarsal-metatarsal joints of each paw were scored. A maximum score of 16 can be obtained.

Histopathology Assessment in Adjuvant-Induced Arthritis

Rats were euthanized and hind legs were removed and fixed in formalin. Joints were stained with stained with haematoxylin and eosin (H&E) and evaluated by a specialized veterinary pathologist Induction and Clinical Assessment of Collagen-Induced Arthritis Nine week old male DBA/1 mice (Harlan Laboratories, Israel) were injected s.c. at the base of the tail with 200 μg collagen type II emulsified in CFA (Difco). Three weeks later mice were boosted s.c. with the same concentration of collagen II. The severity of arthritis was assessed daily by measuring feet diameter of hind and fore paws by caliper by a blinded observer. As controls, the inventors measured 4 mice of about the same age that were not injected with collagen. The mean of the healthy mice served as a "cut-off" measurement. Starting from day 5 after the boost injection, every mouse with a score value above the average of the healthy mice (in one paw or more) was assigned to one of the treatment groups.

Induction and Clinical Assessment of Hapten-Mediated (TNBS) Colitis

Balb/C mice were sensitized with 160 μL of the haptenizing agent TNBS (Sigma-Aldrich, St. Louis, Mo.) at a concentration of 2.5% in 50% ethanol by skin painting. A week later, 120 μl of 1% TNBS in 50% ethanol was administered intrarectally via a 3.5-French catheter. Mice were sacrificed 3 days after intrarectal TNBS administration. Animals were weighed at the time of sensitization, intrarectal administration and every day following such until sacrifice. Clinical assessment was carried out by evaluating weight loss and histopathology of the colon tissue post mortem.

Histopathology Assessment in TNBS Colitis

Tissues were fixed in phosphate buffered saline containing 4% formalin and embedded in paraffin. Sections (5 μm) were stained with haematoxylin and eosin. The degree of inflammation was assessed by a blinded pathologist using the following scoring system from 0-4: 0, no signs of inflammation; 1, low level of leucocyte infiltration; 2, moderate level of leucocyte infiltration; 3, high level of leucocyte infiltration, high vascular density, thickening of bowel wall; 4, transmural infiltrations, loss of goblet cells, high vascular density, strong bowel wall thickening, edema.

Pharmacokinetic Analysis of Serum Humanized Anti-Peptide-6 after s.c. and i.p. Administration Eighteen male DBA/1 mice (7-8 weeks old) were divided into two groups of nine mice each. The first group was treated with 500 μg VH2/VK3 i.p and the second group was treated with 500 μg VH2/VK3 s.c. both on day 0. Each group was divided to three subgroups of 3 mice each, with all mice in each subgroup being bled from the eye on the same days following antibody administration. Subgroup 1 was bled on days 0, 3 and 8, subgroup 2 on days 1, 4 and 10 and subgroup 3 on days 2 and 11. At the end of the experiment, mice were sacrificed, bled and organs (heart, spleen, kidney, lung and liver) were harvested and incubated in 4% formalin for 24 hours and then removed to 80% Ethanol (which is optimal for immunofluorescence slide preparations). Sera were collected and kept at −20° C. for the determination of IL-10 and VH2/VK3 content.

EAE model for MS—EAE is induced in 8-week-old female C57BL/6 mice by injecting s.c. into the left para-lumbar region 125 μg of myelin oligodendrocyte glycoprotein 35-55 peptide (MOG35-55) emulsified in complete Freund's adjuvant (CFA) containing 5 mg/ml heat-killed *Mycobacterium tuberculosis*. Immediately thereafter, and, again, at 48 h, the mice are inoculated i.p. with 0.5 ml of pertussis toxin (400 ng). 7 days later the mice are further challenged with an additional injection of MOG35-55 peptide in CFA injected into the right para-lumbar region. Mice are treated with the humanized anti-peptide-6 antibody of the invention, Rituximab or vehicle (PBS) as indicated EAE clinical score is evaluated as follows 0—without clinical disease;
1—tail weakness;
2—hind limb weakness sufficient to impair righting;
3—one limb plagic;
4—paraplegia with forelimb weakness;
5—quadriplegia;
6—death.

Example 1

Generation of Chimeric Anti-Peptide-6 Antibodies

Chimeric antibodies in which the heavy and light chain variable region (VH and VL) sequences are derived from the mouse anti-peptide-6 monoclonal antibody were constructed as a first step in generating anti-peptide-6 humanized antibodies. The heavy and light chain variable region (VH and VL) sequences of the mouse antibodies have been determined and chimeric anti-peptide-6 antibodies have been produced comprising the mouse variable regions and human IgG1 or IgG4/kappa constant regions.

Briefly, mouse cells were successfully revived from the frozen vial and mRNA was extracted from the hybridoma cells using mRNA extraction kit according to the manufacturer's instructions (Promega Catalogue No. Z5400). RT-PCR was performed using degenerate primer pools for murine signal sequences with a single constant region primer. Heavy chain variable region mRNA was amplified using a set of six degenerate primer pools (5' primers: MuIgV$_H$5'-A to F, and 3' primers: MuIgMV$_H$3'-1 and MuIgGV$_H$3'-2, as shown by Table 1) and light chain variable region mRNA was amplified using a set of eight degenerate primer pools (5' primers: MuIGκV$_L$5'-A to κG, and MuIGλV$_L$5'-A and 3' primers: MuIgκV$_L$3'-1 and MuIgλV$_L$3'-1, as shown by Table 1). 50 μl of Reaction mixture contained 36.25 μl PCR Grade water, 5 μl 10× NovaTaq buffer, 5.25 μl dNTPs (final concentration of 0.2 mM), 2.50 primers (10 pmol/μl) and 1 μl (1.25 U) NovaTaq DNA Polymerase (Cat. No. 7103-3). Reaction conditions were 30-40 cycles of denaturation for 1 minute at 94° C., annealing for 1 minute at 50° C., extension for 2 minutes at 72° C. and final extension for 6 minutes at 72° C. Amplification products were obtained with heavy chain and κ light chain primer pools but not from the λ primer pool. Therefore, the light chain is from the κ cluster in each case. It should be noted that for cloning purpose, VH region genes were amplified by PCR using primers that were designed to engineer in a 5' MIuI and a 3' HindIII restriction enzyme site. VL regions were amplified using primers that were designed to engineer in BssHII and BamHI restriction enzyme sites.

TABLE 1

Primers used for chimeric antibodies cloning

| SEQ ID No. | Sequence | Length | Name-Pool |
|---|---|---|---|
| 60 | ATGRASTTSKGGYTMARCTKGRTTT | 25 | MuIgVH5'-A |
| 61 | ATGRAATGSASCTGGGTYWTYCTCTT | 26 | MuIgVH5'-B |
| 62 | ATGGACTCCAGGCTCAATTTAGTTTTCCT | 29 | MuIgVH5'-C |
| 63 | ATGGCTGTCYTRGBGCTGYTCYTCTG | 26 | MuIgVH5'-C |
| 64 | ATGGVTTGGSTGTGGAMCTTGCYATTCCT | 29 | MuIgVH5'-C |
| 65 | ATGAAATGCAGCTGGRTYATSTTCTT | 26 | MuIgVH5'-D |
| 66 | ATGGRCAGRCTTACWTYYTCATTCCT | 26 | MuIgVH5'-D |
| 67 | ATGATGGTGTTAAGTCTTCTGTACCT | 26 | MuIgVH5'-D |
| 68 | ATGGGATGGAGCTRTATCATSYTCTT | 26 | MuIgVH5'-E |
| 69 | ATGAAGWTGTGGBTRAACTGGRT | 23 | MuIgVH5'-E |
| 70 | ATGGRATGGASCKKIRTCTTTMTCT | 25 | MuIgVH5'-E |
| 71 | ATGAACTTYGGGYTSAGMTTGRTTT | 25 | MuIgVH5'-F |
| 72 | ATGTACTTGGGACTGAGCTGTGTAT | 25 | MuIgVH5'-F |
| 73 | ATGAGAGTGCTGATTCTTTTGTG | 23 | MuIgVH5'-F |
| 74 | ATGGATTTTGGGCTGATTTTTTTTATTG | 28 | MuIgVH5'-F |
| 75 | ACGAGGGGGAAGACATTTGGGAA | 23 | MuIgMVH3'-1 |
| 76 | CCAGGGRCCARKGGATARACIGRTGG | 26 | MuIgGVH3'-2 |
| 77 | ATGRAGWCACAKWCYCAGGTCTTT | 24 | MuIgkVL5'-A |
| 78 | ATGGAGACAGACACACTCCTGCTAT | 25 | MuIgkVL5'-B |
| 79 | ATGGAGWCAGACACACTSCTGYTATGGGT | 29 | MuIgkVL5'-C |

TABLE 1-continued

| SEQ ID No. | Sequence | Length | Name-Pool |
|---|---|---|---|
| | Primers used for chimeric antibodies cloning | | |
| 80 | ATGAGGRCCCCTGCTCAGWTTYTTGGIWTCTT | 32 | MuIgkVL5'-D |
| 81 | ATGGGCWTCAAGATGRAGTCACAKWYYCWGG | 31 | MuIgkVL5'-D |
| 82 | ATGAGTGTGCYCACTCAGGTCCTGGSGTT | 29 | MuIgkVL5'-E |
| 83 | ATGTGGGGAYCGKTTTYAMMCTTTTCAATTG | 31 | MuIgkVL5'-E |
| 84 | ATGGAAGCCCCAGCTCAGCTTCTCTTCC | 28 | MuIgkVL5'-E |
| 85 | ATGAGIMMKTCIMTTCAITTCYTGGG | 26 | MuIgkVL5'-F |
| 86 | ATGAKGTHCYCIGCTCAGYTYCTIRG | 26 | MuIgkVL5'-F |
| 87 | ATGGTRTCCWCASCTCAGTTCCTTG | 25 | MuIgkVL5'-F |
| 88 | ATGTATATATGTTTGTTGTCTATTTCT | 27 | MuIgkVL5'-F |
| 89 | ATGAAGTTGCCTGTTAGGCTGTTGGTGCT | 29 | MuIgkVL5'-G |
| 90 | ATGGATTTWCARGTGCAGATTWTCAGCTT | 29 | MuIgkVL5'-G |
| 91 | ATGGTYCTYATVTCCTTGCTGTTCTGG | 27 | MuIgkVL5'-G |
| 92 | ATGGTYCTYATVTTRCTGCTGCTATGG | 27 | MuIgkVL5'-G |
| 93 | ACTGGATGGTGGGAAGATGGA | 21 | MuIgkVL3'-1 |
| 94 | ATGGCCTGGAYTYCWCTYWTMYTCT | 25 | MuIgλVL5'-A |
| 95 | AGCTCYTCWGWGGAIGGYGGRAA | 23 | MuIgλVL3'-1 |

Amplification products were cloned into pSTBlue-1 Perfectly Blunt Cloning Kit (TB183, Cat. No. 70191-3) or Single dA Tailing Kit (TB059, Cat. No. 69282-3) and pSTBlue AccepTor Vector Cloning Kit (TB248, Cat. No. 70595-3) and sequenced. The resultant amino acid sequences of the mouse VH (SEQ ID NO. 1) and VL (SEQ ID NO. 2, are shown in FIG. 1A-1B. Brief analysis of the sequences presented by Table 2, indicates that none of the variable region sequences are unusual.

TABLE 2

| | Antibody Sequence analysis Chimeric mouse-human | |
|---|---|---|
| | H Chain | L Chain |
| CDR 1 Length | 7aa | 12aa |
| CDR 2 Length | 16aa | 7aa |
| CDR 3 Length | 15aa | 9aa |
| Closest Human Germline[b] | IGHV2-5 *01 (70%) | IGKV3D-20 *01 (66%) |
| Closest Human FR1[b] | IGHV2-70 *06 (72%) | IGKV1D-17 *01 (68%) |
| Closest Human FR2[b] | IGHV4-59 *10 (85%) | IGKV11-55 *01 (80%) |
| Closest Human FR3[b] | IGHV2-70 *13 (72%) | IGK6D-55 *01 (81%) |
| Closest Human J[b] | J4*01 (80%) | J2 (83%) |

[a]CDR definitions and sequence numbering according to Kabat
[b]Germline ID(s) indicated followed by % homology Expression of Chimeric Antibody The mouse variable regions were subsequently transferred to an expression vector system for both IgG1 and IgG4 heavy chains. More specifically, VH and VL region PCR products were cloned into the vectors pANTVhG1/4 and pANTVκ, respectively (FIG. 2), at the MIuI/HindIII and BssHII/BamHI sites, respectively. Both pANTVhG1/4 and pANTVK are pAT153-based plasmids containing a human Ig expression cassette. The heavy chain cassette in pANTVhG1/4 consists of a human genomic IgG1 constant region gene driven by an hCMV promoter, with a downstream human IgG4 polyA region. pANTVhG1/4 also contains a hamster dhfr gene driven by the SV40 promoter with a downstream SV40 polyA region.

The light chain cassette of pANTVκ includes the genomic human kappa constant region driven by an hCMV promoter with a downstream light chain polyA region. Cloning sites between a human Ig leader sequence and the constant regions allow the insertion of the variable region genes.

NSO cells (ECACC 85 110503, Porton, UK) were co-transfected with these two plasmids via electroporation and selection was carried out in DMEM (Invitrogen, Paisley UK)+5% FBS (Ultra low IgG Cat No. 16250-078 Invitrogen, Paisley UK)+Penicillin/Streptomycin (Invitrogen, Paisley UK)+100 nM Methotrexate (Sigma, Poole UK). A number of methotrexate resistant colonies were identified and cell lines positive for IgG expression were expanded. In addition, CHO-K1 cells were transiently transfected via a lipid based delivery system. Seventy two hours after transfection, cell media was harvested for antibody purification. Chimeric mouse antibodies were purified from cell culture supernatants on a Protein A sepharose column (GE Healthcare Catalogue No. 110034-93) and quantified using an Fc capture/kappa chain detection ELISA (Sigma Catalogue No. I6260 and A7164) against a human IgG1/kappa or IgG4/kappa standard (Sigma Catalogue No. I5154 and I4631) as appropriate. Full vector nucleic acid sequences of the chimeric mouse-human Vκ, VH IgG4 and VH IgG1 are denoted by SEQ ID NO. 9, 10 and 11, respectively.

Binding of the Chimeric Antibody to Peptide-6

The binding of chimeric mouse IgG1 antibodies to peptide-6 (SEQ ID NO. 15) relative to the reference mouse monoclonal antibodies was assessed by ELISA. Antibodies were diluted in 2% BSA/PBS to a starting concentration of 300 μg/ml (30 μg/well) and then double diluted across the plate. These antibody dilutions were incubated for 1 hour at room temperature on Nunc Immuno MaxiSorp 96 well flat bottom microtitre plates (Fisher Cat No. DIS-971-030J) pre-coated with 10 μg/ml (100 μl/well) peptide-6. The appropriate secondary antibodies were added at 100 μl/well: goat anti-mouse IgM peroxidase, or goat anti-human IgG peroxidase. After a further one hour of incubation at room temperature the assay was developed by the addition of 100 μl/well TMB substrate (Sigma Catalogue No. T0440). The reaction was stopped with the addition of 500/well 3M HCl.

Absorbance was read at 450 nm (Dynex MRX TCII) and plotted against antibody concentration. As shown by FIG. 3, the chimeric mouse binding curve did not plateau at the highest concentrations and therefore, an accurate $ED_{50}$ value has not been determined. However, a comparison with the binding of the mouse monoclonal reference antibody (FIG. 3A) indicated that the chimeric mouse antibody (FIG. 3B) binds with greater efficiency than the reference antibody. Furthermore, there appears to have been no reduction in binding efficiency as a result of the conversion from pentameric IgM to monomeric IgG.

Example 2

Generation of Composite Human Antibody Variants of the Mouse Anti-Peptide-6 Antibody Anti-peptide-6 Composite Human Antibodies were next generated for the mouse monoclonal antibodies. Generally, segments of human variable region (V region) sequence were sourced from unrelated human antibody sequence databases. Each selected sequence segment (as well as the junctions between segments) were tested for the potential to bind to MHC class II, and all final Composite Human Antibody sequence variants were designed to avoid T cell epitopes. V region genes of the Composite Human Antibody were generated using synthetic oligonucleotides encoding combinations of the human sequence segments. These were then cloned into vectors containing human constant regions, and antibodies were produced and tested for binding to target antigens by competition ELISA.

Design of Composite Human Antibody Variable Region Sequences

Composite human VH and VL sequences were designed by comparison of mouse sequences and fragments of different naturally occurring human VH and VL sequences and selection of such human fragments to build the composite human sequences. More specifically, structural models of the mouse monoclonal antibody V regions were produced using Swiss PDB and analyzed in order to identify important "constraining" amino acids in the mouse V regions that were likely to be involved in the binding of the antibody to the antigen. The choice of human VH and VL sequence fragments thus was constrained for the presence of certain amino acids at corresponding positions in the reference mouse antibody which were considered to be potentially involved in antibody binding. Residues contained within the CDRs (using both Rabat and Chothia definitions), together with a number of FR (Framework) residues, were considered to be relevant. More specifically, for VH, the constraining amino acids are: Cys at position H22, Ser at H23, Gly at H26, Phe at H27, Ser at H28, Leu at H29, Ser at H30, Thr at H31, Ser at H32, Asn at H33, Met at H34, Gly at H35, Val at H35A, Gly at H35B, Leu at H48, His at H50, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and optionally, at least one of Leu at H49, Tyr at H74, Ile at H11, Ser at H41 and Ser at H108. For VK, the constraining amino acids are: Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Trp at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and optionally at least one of Met at L21, He at L10 and Ala at L80 (Kabat numbering). Both the VH and VK sequences of the reference mouse antibody contain a number of typical human FR residue motifs close to the CDRs, whereas the CDR 1 and 2 motifs of both chains were found to be comparable to many murine antibodies. Generally, from the above analysis, it was considered that composite human sequences for the humanized antibody could be created with wide latitude of alternatives outside of CDRs but with only a narrow menu of possible alternative residues within the CDR sequences. Preliminary analysis indicated that corresponding sequence segments from several human antibodies could be combined to create CDRs similar or identical to those in the mouse sequences. For regions outside of and flanking the CDRs, a wide selection of human sequence segments were identified as possible components of the novel Composite Human Antibody variable regions.

Epitope Avoidance and Design of Variants

Based upon the above analysis, a large preliminary set of sequence segments that could be used to create the anti-peptide-6 mouse-based Composite Human Antibody variants were selected and analyzed using iTope™ technology (described in PCT/GB2007/000736) for analysis of peptide binding to human MHC class II alleles, and using the TCED™ (T Cell Epitope Database, Antitope Ltd.) database of known antibody sequence-related T cell epitopes. Sequence segments where significant non-human MHC class II binding peptides were identified, or scored significant hits against the TCED™ were discarded. This resulted in a reduced set of segments, and combinations of these were again analyzed, as above, to ensure that the junctions between segments did not contain potential T cell epitopes. Selected segments as presented by Table 3 were then combined to produce heavy and light chain variable region sequences for synthesis, as also illustrated by FIG. 4.

TABLE 3

Sequence segments used in the assembly of the Composite Human sequences

| SEQ. ID No. | Amino Acid Sequence | Reference No. |
|---|---|---|
| VH1: | | |
| 12 | QVTLKESGPAI | DBVHANT51981 |
| 13 | VKPTQTLTLTCSFSGFSLSTS | ABK81616 |
| 14 | NMGVGWIRQP | DBVHANT30390 |
| 16 | WIRQPSGKGLEW | AAB35009 |
| 17 | GKGLEWLL | CAC39364 |
| 18 | HILWNDSK | DBVHANT35766 |
| 19 | YYNPALKSR | AAY26951 |
| 34 | RLTISKDT | IGHV2-70 |

TABLE 3-continued

Sequence segments used in the assembly of the Composite Human sequences

| SEQ. ID No. | Amino Acid Sequence | Reference No. |
|---|---|---|
| 35 | TYKNQVVLTMTNMDPVDTAT | ABI50684 |
| 36 | YYCARMGGYY | AAY33304 |
| 37 | GYYGNYGY | DBVHANT21614 |
| 38 | YAMDYWGQGT | 3B9V_A |
| 39 | WGQGTSVTVSS | AAB01769 |
| VH2: | | |
| 40 | QVTLKESGPALVKPTQTLTLTC | IGHV2-70 |
| 13 | VKPTQTLTLTCSFSGFSLSTS | ABK81616 |
| 14 | NMGVGWIRQP | DBVHANT30390 |
| 41 | W1RQPAGKGLEW | IGHV4-61 |
| 17 | GKGLEWLL | CAC39364 |
| 18 | HILWNDSK | DBVHANT35766 |
| 19 | YYNPALKSR | AAY26951 |
| 34 | RLTISKDT | IGHV2-70 |
| 35 | TYKNQVVLTMTNMDPVDTAT | ABI50684 |
| 36 | YYCARMGGYY | AAY33304 |
| 37 | GYYGNYGY | DBVHANT21614 |
| 42 | YAMDYWGQGTLVTVSS | 3B9V_A |
| VH3: | | |
| 40 | QVTLKESGPALVKPTQTLTLTC | IGHV2-70 |
| 13 | VKPTQTLTLTCSFSGFSLSTS | ABK81616 |
| 14 | NMGVGWIRQP | DBVHANT30390 |
| 41 | WIRQPAGKGLEW | IGHV4-61 |
| 17 | GKGLEWLL | CAC39364 |
| 18 | HILWNDSK | DBVHANT35766 |
| 19 | YYNPALKSR | AAY26951 |
| 43 | RLTISKDTSKNQVVLTMTNMDPVDTAT | IGHV2-70 |
| 36 | YYCARMGGYY | AAY33304 |
| 42 | YAMDYWGQGTLVTVSS | 3B9V_A |
| 96 | YGNYGY | |
| VH4: | | |
| 40 | QVTLKESGPALVKPTQTLTLTC | IGHV2-70 |
| 13 | VKPTQTLTLTCSFSGFSLSTS | ABK81616 |
| 14 | NMGVGWIRQP | DBVHANT30390 |
| 41 | WIRQPAGKGLEW | IGHV4-61 |
| 44 | GKGLEWLA | P01815 |
| 18 | HILWNDSK | DBVHANT35766 |

TABLE 3-continued

Sequence segments used in the assembly of the Composite Human sequences

| SEQ. ID No. | Amino Acid Sequence | Reference No. |
|---|---|---|
| 19 | YYNPALKSR | AAY26951 |
| 43 | RLTISKDTSKNQVVLTMTNMDPVDTAT | IGHV2-70 |
| 36 | YYCARMGGYY | AAY33304 |
| 42 | YAMDYWGQGTLVTVSS | 3B9V_A |
| 96 | YGNYGY | |
| VH1: | | |
| 45 | QIVLTQSPA | DBVKANT75847 |
| 46 | AILSLSPGERAT | ABG38354 |
| 47 | GERATMSCTAS | DBVKANT63518 |
| 48 | SSVSSSYL | DBVKANT55521 |
| 49 | YLHWYQQKPGKAPKL | AAO86903 |
| 50 | PKLWIYS | DBVKANT39443 |
| 51 | IYSTSNL | AAF86914 |
| 52 | LASGVPSRFSGSGSGT | ABB13606 |
| 53 | DYTLTISSLQ | IGKV1-NL1 |
| 54 | QAEDFATYYCHQ | AAK26827 |
| 55 | EDFATYYCHQYHR | DBVKANT12007 |
| 56 | SPPTFGQGTKLEIK | AAZ09112 |
| VK2: | | |
| 45 | QIVLTQSPA | DBVKANT75847 |
| 57 | ATLSLSPGERAT | ABA71381 |
| 47 | GERATMSCTAS | DBVKANT63518 |
| 48 | SSVSSSYL | DBVKANT55521 |
| 49 | YLHWYQQKPGKAPKL | AAO86903 |
| 50 | PKLWIYS | DBVKANT39443 |
| 51 | IYSTSNL | AAF86914 |
| 52 | LASGVPSRFSGSGSGT | ABB13606 |
| 58 | DYTLTISSLQPEDFATYYC | IGKV1-NL1 |
| 59 | PEDFATYYCHQYHR | DBVKANT12007 |
| 56 | SPPTFGQGTKLEIK | AAZ09112 |
| VK3: | | |
| 45 | QIVLTQSPA | DBVKANT75847 |
| 97 | ATLSLSPGERATLSCTAS | ABA71381 |
| 48 | SSVSSSYL | DBVKANT55521 |
| 49 | YLHWYQQKPGKAPKL | AAO86903 |
| 50 | PKLWIYS | DBVKANT39443 |
| 51 | IYSTSNL | AAF86914 |
| 52 | LASGVPSRFSGSGSGT | ABB13606 |

TABLE 3-continued

Sequence segments used in the assembly of the Composite Human sequences

| SEQ. ID No. | Amino Acid Sequence | Reference No. |
|---|---|---|
| 58 | DYTLTISSLQPEDFATYYC | IGKV1-NL1 |
| 59 | PEDFATYYCHQYHR | DBVKANT12007 |
| 56 | SPPTFGQGTKLEIK | AAZ09112 |

Construction of Composite Human Antibody™ Variants

Initial variant 1 Composite Human Antibody™ VH and VK region genes were synthesized using a series of overlapping oligonucleotides that were annealed, ligated and PCR amplified to give full length synthetic V regions. Subsequent Composite Human Antibody sequence variants were constructed using long overlapping oligonucleotides and PCR, using the initial variant 1 as the template. Flanking nucleotide sequences were also added at both ends of the genes in order to include restriction enzyme sites for cloning. The VH genes incorporated additional short 5' and 3' sequences containing MIuI and HindIII restriction sites respectively. The MIuI site is located in the signal sequence and the HindIII site is located in the first intron immediately downstream of the VH gene splice donor site. The VK genes incorporated an additional short 5' sequence containing a BssHII restriction site and an extended 3' sequence incorporating a BamHI restriction site. The BssHII site is located in the signal sequence and the BamHI site is located in the intron 32 nucleotides downstream of the VK gene splice donor site. The flanking sequences are shown in FIG. 5 and vector diagrams in FIG. 2. Four heavy chains and three light chains were constructed. FIG. 6 presents the amino acid sequence as well as the encoding nucleic acid sequences of these variants [heavy chain variable regions VH1-4, as denoted by SEQ ID NO. 20, 21, 22 and 23 (amino acid sequence), and 27, 28, 29, and 30, respectively (nucleic acid sequence), light chain variable regions VK1-3, as denoted by SEQ ID NO. 24, 25, 26 (amino acid sequence), and 31, 32, 33 (nucleic acid sequence), respectively.

The synthesized genes were cloned into a T/A cloning vector for sequence confirmation and propagation. Purified VH gene vector DNA was digested with MIuI and HindIII and purified VK gene vector DNA was digested with BssHII and BamHI, and the resultant fragments were separated on an agarose gel. The variant gene bands were excised from the gel, purified and ligated to similarly digested and purified expression vector DNA. After transformation into *E. coli* XL1-blue, colonies were PCR screened for the presence of an insert. Positive colonies were selected, grown and vector DNA purified and sequenced to confirm the identity of the inserted genes. VH and VK confirmed DNA preparations were prepared for transfection into NSO cells by mixing a total of 30 μg DNA at a molar ratio of 1:2 and linearising by digestion with restriction enzyme SspI. The digested DNA was ethanol precipitated and resuspended in 50 μl PBS pH 7.4.

Expression and Purification of Variant Antibodies

All combinations of composite heavy (VH1-4) and light chains (Vk1-3) (i.e. a total of 12 pairings) were stably transfected into NSO cells via electroporation and selected using 200 nM methotrexate (Sigma Cat. No. M8407-500MG). Methotrexate resistant colonies for each construct were tested for IgG expression levels and the best expressing lines were selected and frozen under liquid nitrogen.

IgG1 Variants were purified from cell culture supernatants on a Protein A Sepharose column (GE Healthcare Cat. No. 110034-93) and quantified by $OD_{280nm}$ using an extinction coefficient, $Ec_{(0.1\%)}$, based on the predicted amino acid sequence as shown by Table 4. Greater than 2 mg of each antibody was purified and analyzed by SDS PAGE. Bands corresponding to the predicted sizes of the heavy and light chains were observed with no evidence of any contamination (not shown).

TABLE 4

$Ec_{(0.1\%)}$ values for antibody variants

| Variant | $Ec_{(0.1\%)}$ |
|---|---|
| Mouse Chimera | 1.62 |
| Humanized AbVariants: | 1.62 |
| VH1-VK1 | |
| VH1-VK2 | |
| VH1-VK3 | |
| VH2-VK1 | |
| VH2-VK2 | |
| VH2-VK3 | |
| Humanized Ab Variants: | 1.60 |
| VH3-VK1 | |
| VH3-VK2 | |
| VH3-VK3 | |
| VH4-VK1 | |
| VH4-VK2 | |
| VH4-VK3 | |

Binding of the Variant Antibodies to Peptide-6

The binding of each of the humanized IgG1 variants to peptide-6 relative to the chimeric mouse-human antibody was assessed by ELISA as indicated in Experimental procedures. As shown by FIG. 7, all the antibody variants bound to peptide-6 at least as well as chimeric mouse-human antibody, and some appeared to bind considerably better. As shown by the figure, binding of the chimeric antibody and the humanized variants could not be quantified by calculation of $ED_{50}$ values since, in most cases, the plateau of the curve was not reached and, for some antibodies, the 50% maximum signal value was not obtained.

Nevertheless, a distinction between the variants was made upon apparent binding. The inventors have noted that variants containing VH1 gave consistently high background binding and therefore may not be considered as preferable variants. Taking into consideration both binding (FIG. 7) and sequence data, VH2/VK1, VH2/VK2, VH2/VK3 and VH3/VK2 are considered to be the four lead candidates. Of these, VH2/VK2 and VH2/VK3 were clearly the best binders, with VH2/VK3 giving marginally the best binding in subsequent experiments when directly compared to VH2/VK2 on the same plate (data not shown).

In summary, as shown by the present invention, composite Human Antibodies specific for peptide-6 have been constructed from amino acid sequence segments derived entirely from unrelated human antibody variable regions. All CDR and framework regions in the Composite Human Antibody variants comprised more than one unrelated human sequence segment (sourced from the human sequence databases), and all Composite Human Antibodies were designed specifically to avoid T cell epitopes. Four lineage variants were selected and some were demonstrated to have increased binding compared to the chimeric reference antibody.

Example 3

The Chimeric Monoclonal Anti-Peptide-6 IgG Antibody Induces the Secretion of IL-10 from Human PBMC Having shown that the chimeric mouse-human anti-peptide-6 IgG antibody binds to peptide-6 (FIG. 3) and induces IL-10 secretion in PBMC (FIG. 8), the inventors further analyzed the in-vitro dose-dependency of IL-10 secretion. Human PBMC were collected from a healthy donor and incubated with varying doses of the chimeric mouse-human anti-peptide-6 antibody for 48 hours. Untreated cells served as a control. The supernatant was collected and assayed with an IL-10 ELISA detection kit (R&D systems). As shown in FIG. 8, there is a significant increase in IL-10 secreted from the cells treated with the chimeric anti-peptide-6 antibody in comparison to untreated cells, and furthermore an initial dose response effect is shown (20 and 50 μg/ml).

Example 4

The Chimeric Monoclonal Anti-Peptide-6 IgG Antibodies Suppress Established Adjuvant-Induced Arthritis (AA)

The inventors next examined the in vivo effects of the chimeric mouse-human anti-peptide-6 IgG antibodies in an experimental model of established arthritis. Fifty Lewis rats were immunized on day 0 with MT in CFA to induce arthritis, and arthritis severity was measured via clinical scoring. Out of fifty rats injected with MT, forty three developed arthritis. On day 16, the animals with highest arthritis scores were combined into 5 groups (4 groups of 6 rats and 1 group of 7 rats) of which the mean disease severity ranged between 6.16 and 6.7.

Upon the peak of disease, rats were treated with the following: a. Mouse anti-peptide-6 antibody (IgM); b. Chimeric mouse-human anti-peptide-6 antibody (Chimeric Mouse-Human, SEQ ID NO. 1 and 2). Control rats were treated with saline and Rituximab (a chimeric antibody targeting a molecule not present in rats, F. Hoffmann-La Roche Ltd). The antibodies were administered intraperitoneally (i.p.) at a dose of 5 mg/kg on days 17 (just before reaching the peak of disease) and 21.

At the end of the experiment, the rats were sacrificed, and the hind paws of a control-treated and a chimeric mouse-human anti-peptide-6 treated rat were removed for pathology analysis.

As can be seen in FIG. 9, both the mouse IgM and the chimeric mouse-human IgG1 anti-peptide-6 antibodies significantly decreased the severity of AA. The control chimeric Rituximab had no effect on AA, thus an effect exerted via the human Fc fragment of the antibodies may be ruled out.

Furthermore, FIG. 10 depicts the pathology findings of joints from rats treated with the chimeric mouse-human anti-peptide-6 antibody compared to rats treated with the control antibody Rituximab. While joints from rats treated with the chimeric anti-peptide-6 antibody have normal structures (FIG. 10B), joints from Rituximab-treated rats show marked fibrosis and formation of reactive periosteal bone (FIG. 10A). Reactive bone is forming lobules surrounding by fibrous connective tissue forming a solid fibro-osseous mass.

Example 5

The Chimeric Anti-Peptide-6 Antibody Suppresses Established Adjuvant-Induced Arthritis Similar To ENBREL® and Methylprednisone (PPS), With Indications of A Synergistic Effect With MPS The immunomodulatory effect of the anti-peptide-6 antibodies is the basis for their therapeutic potential. It should be therefore appreciated that these anti-peptide-6 antibodies may be used as a sole treatment or in combination with other anti-inflammatory agents. The inventors thus evaluated the effects of the chimeric anti-peptide-6 antibody with/without anti-inflammatory agents such as etanercept ENBREL® or Methylprednisone (MPS) on AA in Lewis rats.

Lewis rats were immunized with MT/CFA on day 0. On day 16 rats were divided into 6 groups of 6 rats each. On day 17 rats were treated as follows: group 1. PBS (i.p.), group 2. Chimeric mouse-human anti-peptide-6 antibody (i.p. 5 mg/kg), group 3. ENBREL® (Subcutaneously (s.c.) (0.5 mg/kg), group 4. Methylprednisolone (MPS) (s.c. 5 mg/kg), group 5. Chimeric mouse-human anti-peptide-6 antibody (i.p. 5 mg/kg) and ENBREL® (s.c. 0.5 mg/kg) and group 6. Chimeric mouse-human anti-peptide-6 antibody (i.p. 5 mg/kg) and MPS (s.c. 5 mg/kg).

As can be seen in FIG. 11, all of the treatments were effective in suppressing the severity of arthritis. The chimeric mouse-human anti-peptide-6 antibody was effective similarly to either MPS or ENBREL® when administered alone. Furthermore, when the chimeric anti-peptide-6 antibody is administered along with high doses of MPS, a higher level of disease suppression is achieved, thereby suggesting a potential synergistic effect of combination of both.

Example 6

The Humanized Anti-Peptide-6 Antibody Binds to Human Macrophages (CD14+ Cells)

Having shown that the humanized anti-peptide-6 antibody variants described in Example 2 bind significantly to peptide-6 (FIG. 7), the inventors further analyzed the effects of the most effective variant (VH2/VK3) in binding to human macrophage cells. Human PBMC ($10^6$) were collected from a healthy donor and were stained with an anti-CD14 antibody (APC conjugated) alone or double stained with the humanized VH2/VK3 anti-peptide-6 antibody (FITC conjugated; 10 μg). The cells were then analyzed by FACS for the binding of the antibodies. The CD14 marker is present on macrophage cells, and therefore staining of CD14 positive cells is indicative of staining to human macrophages.

The results presented in the density plots of FIGS. 12A and 12B, show that the humanized VH2/VK3 anti-peptide-6 antibody binds to most of the CD14 positive cells (macrophages constituting ~10% of the isolated cell population, lower right quadrant of FIG. 12A). These results are similar to binding of the original mouse monoclonal antibody (IgM) to human macrophages (data not shown). The results in the histogram plots of FIG. 12C, depict the percent of cells out of the CD14+ population that were stained with FITC (without the anti-peptide-6 antibody—black, with the anti-peptide-6 antibody—white), showing that the humanized anti-peptide-6 antibody bind a large percent of the CD14+ population.

Example 7

The Humanized Anti-Peptide-6 Antibody Binds Adenylyl Cyclase-Associated Protein 1 (CAP1)

In a previous patent application IL2010/000231 (not published yet), the inventors have shown that the anti-peptide-6 antibody recognizes hydrophilic membrane protein on the surface of macrophages. Mass-spectrometric analysis identified this target protein as adenylyl cyclase-associated protein 1 (CAP1). These results were reinforced by the retention of an anti-CAP1-recognized protein on an anti-peptide-6 affinity column (but not on a control Rituximab column).

To verify that the humanized anti-peptide-6 variant antibody recognizes CAP1 like the chimeric anti-peptide-6 antibody, the inventors performed a Western blot analysis using the humanized VH2/VK3 variant. Human CAP1 fused to His tag at the N-terminus was cloned and expressed in *E. Coli* BL21. The protein was enriched from supernatant of bacterial lysate by affinity chromatography on a Ni-sepharose column. The eluate was used for SDS-PAGE, followed by Western blot analysis along with a control, a non-relevant His tagged protein (His CREB). Three similar blots were prepared and used for detection with the following antibodies: commercial mouse anti human CAP1, commercial mouse anti His and humanized anti-peptide-6 antibodies of the invention. As can be seen in FIG. 13, humanized VH2/VK3 recognized the His-tagged CAP1 protein specifically, providing a further indication that this specific variant retains the ability of binding and potentially signaling through CAP1.

Example 8

The Humanized VH2/VK3 Variant Anti-Peptide-6 Antibody Significantly Induces the Secretion of IL-10 from Human PBMC Given that the VH2/VK3 variant (comprising the heavy chain variable region of SEQ ID NO. 21 and the light chain variable region of SEQ ID NO. 26) was most effective in binding to peptide-6 (FIG. 7) and showed as well significant binding to human macrophages (FIG. 12), the inventors next analyzed the activity of this antibody in the in vitro biologic assay of IL-10 secretion. The inventors further analyzed the IL-10 secretion of an additional humanized anti-peptide-6 antibody variant that was effective in binding to peptide-6 (VH2/VK1). Human PBMC were collected from a healthy donor and incubated with 200 μg of either the humanized anti-peptide-6 variant VH2/VK1 or VH2/VK3 for 48 hours. Untreated cells served as a control. The supernatant was collected and assayed with an IL-10 ELISA detection kit (R&D systems).

As clearly shown in FIG. 14, there is a significant increase in IL-10 secreted from the cells treated with the humanized VH2/VK3 anti-peptide-6 antibody in comparison to the humanized VH2/VK1 anti-peptide-6 antibody variant or untreated cells. The results seen with the VH2/VK3 variant are similar to previous findings shown with the chimeric anti-peptide-6 antibody (FIG. 8). The current results indicate that this biological activity of the anti-peptide-6 antibody was retained by the VH2/VK3 variant, but not by the VH2/VK1 variant.

Example 2 (FIG. 7) demonstrated the peptide-6 binding kinetics of different VH and VK humanized antibody variants. In their next experiment, the inventors sought to assess the correlation between the antibody variants peptide-6 binding affinities and IL-10 induction. The inventors used peptide-6 coated ELISA plates (as in Example 2) to assess peptide-6 affinities for VH3/VK2, VH2/VK3, VH2/VK1 and VH2/VK2, and collected supernatants from PBMC cultures incubated with either 33 or 100 μg/ml of each of the antibody variants to determine IL-10 induction. FIG. 15A shows that, generally, 100 μg/ml antibody induced higher IL-10 expression than did 33 μg/ml, and that the VH2/VK3 variant induced higher IL-10 expression than the other variants. FIG. 15B illustrates the peptide-6 binding affinities of the different variants, showing the highest affinity was also displayed by VH2/VK3. However, surprisingly, in the case of other variants, peptide-6 binding and IL-10 induction did not exactly correlate.

As exhibiting the best IL-10 induction, the VH2/VK3 was selected as the lead antibody for further in vivo experimentation.

Example 9

The $F(ab)_2$ Fragment of the Humanized VH2/VK3 Anti Peptide-6 Antibody Binds to Human Macrophages (CD14+ Cells) and Induces the Secretion of IL-10 from Human PBMC In order to confirm the effects shown with the VH2/VK3 antibody are not mediated via the Fc portion of the antibody, the inventors prepared $F(ab)_2$ fragment of the VH2/VK3 anti-peptide-6 antibody and evaluated the effects on binding to human macrophages and induction of secretion of IL-10.

Human PBMC ($10^6$) were collected from a healthy donor and were stained with an anti-CD14 antibody (PE conjugated) alone or double stained with the $F(ab)_2$ fragment of the humanized VH2/VK3 anti-peptide-6 antibody (FITC conjugated; 10 μg). The cells were then analyzed by FACS for the binding of the antibodies. In a separate experiment, human PBMC were collected from a healthy donor and incubated with 150 μg of the $F(ab)_2$ fragment of the humanized anti-peptide-6 VH2/VK3 antibody for 48 hours. Untreated cells served as a control. The supernatant was collected and assayed with an IL-10 ELISA detection kit (R&D systems).

The results presented in the density plots of FIGS. 16A and 16B, show that the $F(ab)_2$ fragment of the humanized VH2/VK3 anti-peptide-6 antibody binds to CD14 positive cells (macrophages constituting ~11% of the donor's isolated cell population, lower right quadrant of FIG. 16A). These results are similar to binding of the whole VH2/VK3 anti-peptide-6 antibody to human macrophages (FIG. 12B). The results in the histogram plots of FIG. 16C depict the percent of cells out of the CD14+ population that were stained with FITC (without the $F(ab)_2$ fragment of the anti-peptide-6 antibody—black, with the $F(ab)_2$ fragment of the anti-peptide-6 antibody—white), showing that the $F(ab)_2$ fragment of the humanized anti-peptide-6 antibody binds to a large percent of the CD14+ population.

As shown in FIG. 17, there is a significant increase in IL-10 secreted from the cells treated with the $F(ab)_2$ fragment of the humanized VH2/VK3 anti-peptide-6 antibody in comparison to untreated cells. These results are similar to the above results depicting the increase in IL-10 secretion with the whole VH2/VK3 anti-peptide-6 antibody (FIG. 14). These findings clearly indicate and confirm that the functional characteristics of the VH2/VK3 anti-peptide-6 antibody are related to the antigen-binding regions of the $F(ab)_2$ portion of the molecule.

Example 10

The Humanized VH2/VK3 Anti-Peptide-6 Antibody Suppresses Established Adjuvant-Induced Arthritis The inventors next examined the in vivo effects of the humanized VH2/VK3 anti-peptide-6 antibody in an experimental model of established arthritis. Lewis rats were immunized with MT/CFA on day 0 to induce arthritis, and arthritis severity was measured via clinical scoring. On day 14 rats were divided into three groups. On day 15, towards the peak of the disease, rats were treated as follows: group 1. PBS (i.p.); group 2; Humanized VH2/VK3 (i.p. 2.5 mg/kg); and group 3. Chimeric mouse-human anti-peptide-6 antibody (i.p. 5 mg/kg).

As can be seen in FIG. 18, the humanized VH2/VK3 anti-peptide-6 antibody was effective in significantly suppressing the severity of established AA, similar to the chimeric mouse-human anti-peptide-6 antibody, and in comparison to PBS treated animals.

Example 11

The Humanized VH2/VK3 Anti-Peptide-6 Antibody Induces the Secretion of IL-10 in the Serum of Rats with Established Adjuvant-Induced Arthritis The inventors furthermore evaluated the in vivo effects of the humanized anti-peptide-6 antibody on the induction of IL-10 secretion in the serum of animals having established arthritis. Lewis rats were immunized with MT/CFA on day 0. Rats were treated on days 11 and 15 with humanized VH2/VK3 (IP 1 mg/kg), or with PBS for comparison. Severity of arthritis was evaluated by clinical scoring, and animals were sacrificed on day 19 and serum levels of various cytokines were measured by ELISA (R&D systems). Serum of healthy untreated animals served as a control.

As can be seen in FIG. 19, there is a clear induction of IL-10 levels in adjuvant-induced arthritic animals treated with the humanized VH2/VK3. These findings correlate with reduction in severity of arthritis upon treatment with the humanized VH2/VK3 (FIG. 18).

Furthermore, there is a reduction following VH2/VK3 administration in the levels of other cytokines that are elevated in arthritic animals, such as IL-6 and IFN-γ, whereas other cytokine levels remain negligible in all groups, such as IL-4, IL-17, IL-1 and TNFα

Example 12

The Humanized VH2/VK3 Anti-Peptide-6 Antibody Suppresses Collagen-Induced Arthritis The inventors next examined the in vivo effects of the humanized VH2/VK3 anti-peptide-6 antibody in an additional experimental model of arthritis, the Collagen-Induced Arthritis (CIA) model in mice. Male DBA/1 mice were immunized on day 0 with collagen type II emulsified in CFA to induce arthritis, and a boost dose given on day 21.85% of the mice developed CIA within 2.5 weeks after the boost injection. Upon clinical signs of disease, the mice were treated with a single dose of either the humanized VH2/VK3 anti-peptide-6 antibody (i.p. 200 μg) or tris buffered saline (TBS).

As can be seen in FIG. 20, the humanized VH2/VK3 anti-peptide-6 antibody was effective in significantly suppressing the severity of established CIA, in comparison to the TBS control treatment.

Example 13

The Humanized Anti-Peptide-6 Antibody Induces IL-10 Secretion from Rheumatoid Arthritis Patients' PBMC In pursuance of Example 8, where the humanized anti-peptide-6 antibody was shown to induce IL-10 expression in healthy donor PBMC, and of Example 11 showing that treatment with the humanized antibody induces higher IL-10 levels in the serum of AA rats serum, the inventors assessed the efficacy of the VH2/VK3 variant in the induction of IL-10 in PBMC collected from rheumatoid arthritis (RA) patients. PBMC were collected from two RA patients and incubated for 48 hours with or without 200 μg of the humanized anti-peptide-6 antibody (VH2/VK3). Supernatants were then assayed for secreted IL-10 content. As clearly seen in FIG. 21, the VH2/VK3 variant induced a robust increase in the amount of IL-10 secreted by treated PBMC Example 14

The Humanized VH2/VK3 Anti-Peptide-6 Antibody Ameliorates TNBS Colitis, an Animal Model of Inflammatory Bowel Disease (IBD)

Based on the unique anti-inflammatory mechanism of the anti-peptide-6 antibodies, the inventors evaluated the effects of the humanized VH2/VK3 anti-peptide-6 antibody in an additional experimental model of an autoimmune inflammatory disease. The model depicted herein is the TNBS Colitis model, an animal model of IBD.

Twenty Balb/C mice were sensitized via TNBS skin-painting (designated day −7), followed by intrarectal administration of TNBS a week later (designated day 0). The humanized VH2/VK3 antibody (200 μg) was administered at three time points (−6, −2, +1) via i.p. injection to treated animals which were compared with untreated control animals. All the animals were weighed at the time of sensitization, intrarectal administration and every day following such. The animals were sacrificed three days following intrarectal administration (designated +3) following significant weight loss (>5%) in the control group and the colon tissue was removed and sent for histopathological analysis.

As can be seen in FIGS. 22 and 23, the humanized VH2/VK3 antibody was effective in suppressing the weight loss and inflammatory response associated with the disease. This can be seen based on the overall microscopic disease score per group (*p<0.05 compared to control mice) and a representative histologic picture (magnification ×100). Minimal inflammatory response is seen in the colon of the VH2/VK3 treated mice vs significant inflammation seen in the colon of the control mice.

Example 15

The Humanized VH2/VK3 Anti-Peptide-6 Antibody Ameliorates the Severity of TNBS Colitis Compared to Control Antibodies The inventors have shown in Example 14 that the VH2/VK3 variant ameliorates the detrimental effects exerted by the haptenizing agent TNBS in the mouse IBD model. To reinforce these results, the inventors performed a similar experiment, comparing the effects of the Humanized VH2/VK3 anti-Peptide-6 antibody with Rituximab a negative control mAb and PBS (the vehicle).

Balb/C mice were sensitized via TNBS skin-painting (Day −7), followed by intrarectal administration of TNBS a week later (designated as day 0). The VH2/VK3 variant (8 mg/kg), Rituximab (8 mg/kg) or PBS, were administered following sensitization and on day 1 following intrarectal induction. The mice were weighed at the time of sensitization, intrarectal administration and every day following such. The animals were sacrificed 3 days following intrarectal administration (Day 3) following significant weight loss in the control groups.

FIG. 24 clearly shows that the humanized anti-peptide-6 VH2/VK3 variant was effective in suppressing the weight loss, minimizing TNBS-induced weight loss to 3.5%, compared with 15% weight loss in the PBS treated animals and 14% in the Rituximab animals.

Example 16

The Humanized VH2/VK3 Anti-Peptide-6 Antibody for the Treatment of Diabetes Using a Diabetic Mouse Model Encouraged by the beneficial effect of the antibody of the invention on an inflammatory condition demonstrated using the Arthritis and IBD models, the inventors next examine the potential beneficial effect of the humanized anti-peptide-6 antibody on another immune-related disorder, using a mouse diabetes models. Thus, the possible use of the VH2/VK3 variant in prophylaxis and/or amelioration of diabetes is next examined using the NOD mouse as a model for diabetes.

The inventors examine the effect of the humanized VH2/VK3 anti-peptide-6 antibody using NOD mice by administering via i.v. to NOD mice (n=8 per group) 8 mg/kg of the humanized VH2/VK3 anti-peptide-6 antibody on weeks 8 and 12. Control mice receive PBS. Mice are monitored every other week for blood glucose levels and weight.

Example 17

The Humanized VH2/VK3 Anti-Peptide-6 Antibody for the Treatment of Psoriasis

The trials are performed among a sample of 20 patients, 10 men and 10 women, aged 17 to 71. Every form of psoriasis is represented: plaque psoriasis, scalp psoriasis, guttate psoriasis, erythrodermic psoriasis and reversed psoriasis.

The treatment consists of an i.v. injection of 5 mg/Kg body weight of the VH2/VK3 variant once every two weeks for one month (3 administrations).

None of the usual treatments for psoriasis are used during this study, in a way that the results obtained can only be attributed to the VH2/VK3 variant.

The effect of topical application of the humanized anti-peptide-6 antibody is further examined. Therefore, either 500 μl of placebo (PBS) or 500 μl (10 mg/ml) of the VH2/VK3 variant are placed on waterproof occlusion bandages. Subsequently, the occlusion bandages are placed on the left elbow (VH2/VK3 variant) and the right elbow (PBS) on a patient suffering from psoriasis, said patient having large, visible psoriatic plaques at both elbows at the time when treatment is initiated.

The occlusion bandages are renewed daily. When bandages are renewed, remains of old administered substance are removed and toxicology is estimated, before placing a fresh occlusion bandage with fresh anti-peptide-6 VH2/VK3 variant or PBS. The condition of the elbows and knee is documented by digital photography with automatic time stamp on all pictures.

The treatment is administered for 4 days and smoothening of the treated psoriatic plaques as well as healing with normal looking skin being monitored.

Example 18

The Humanized VH2/VK3 Anti-Peptide-6 Antibody in the Treatment and Prevention of Experimental Autoimmune Encephalomyelitis (EAE) in Mice To further investigate the effect of the humanized VH2/VK3 anti-peptide-6 antibody on immune-related disorders, the EAE as a model for Multiple Sclerosis (MS) is next used. EAE is induced in 8-week-old female C57BL/6 mice by injecting myelin oligodendrocyte glycoprotein 35-55 peptide (MOG35-55) in the first and seventh days of the experiment. Mice are further inoculated with pertussis toxin in the first and second day of experiment as indicated in Experimental Procedures. Four groups of mice (containing ten mice each) are evaluated for clinical score as detailed in Experimental Procedures. The first group (A), examining the potential preventive and protective effect of the humanized anti-peptide-6 antibody, receives weekly treatment with the VH2/VK3 variant (200 μg) initiated three days prior to MOG injection and terminated on day 37, and followed by treatment with vehicle from day 37 to day 52. Mice of the second group (B) are treated weekly with the VH2/VK3 variant (200 μg) starting on the seventh day following MOG injection, throughout the end of the experiment at day fifty two. The third group (C), receives weekly treatment with the VH2/VK3 variant (200 μg) initiated on the first day throughout the end of the experiment at day fifty two. The control group (D) is treated with vehicle (PBS) the first day throughout the end of the experiment at day fifty two. The mice are clinically scored according to the criteria set forth in the Experimental Procedures.

Example 19

The Humanized VH2/VK3 Anti-Peptide-6 Antibody does not have any Significant Pathological Effects at Increased Doses The inventors next evaluated the safety of administration of increasing doses of the humanized VH2/VK3 anti-peptide-6 antibody in animals. Ten male Balb/C mice (7 week old), divided into 5 groups of 2 mice each, were treated once i.p. with increasing doses of the mouse anti-peptide-6 IgM antibody or the humanized VH2/VK3 antibody (in two separate experiments) as follows:

| | |
|---|---|
| Mouse 1 and 2 | saline (control) |
| Mouse 3 and 4 | 5 mg/kg body weight (BW) |
| Mouse 5 and 6 | 10 mg/kg BW |
| Mouse 7 and 8 | 20 mg/kg BW |
| Mouse 9 and 10 | 40 mg/kg BW |

Mice were observed every other day for changes in body weight, behavior as well as any other abnormal signs. After 2 weeks, mice were sacrificed and the heart, liver, lung, spleen and kidney were removed for pathology analysis.

The results were as follows:

1. Behavioral Surveillance

Mice were observed every other day. Their behavior was normal, and there were no changes in their appearance including their fur, skin and eyes. No changes were found in their food consumption and their weight increased with time.

2. Pathology Findings

There were no significant pathological findings even at the highest dose of 40 mg/kg, thereby providing initial data as to the safety of administration of an anti-peptide-6 antibody, specifically humanized VH2/VK3.

Example 20

Pharmacokinetic Profile of the Humanized VH2/VK3 Anti-Peptide-6 Antibody

An important application of the present invention is the treatment of patients using the antibody of the invention. For this purpose, the antibody half-life in vivo must be profiled. The inventors thus determined the levels of injected humanized Ab (the VH2/VK3 variant) remaining in the blood of mice over time. One group of 7-8 week-old DBA/1 mice was treated with 500 μg VH2/VK3 intraperitoneally (i.p.) on day 0 and a second group was treated with 500 μg VH2/VK3 subcutaneously (s.c.) on day 0. The two groups were further divided to three groups each, wherein each group was bled retro-orbitally on different days post-injection i.e. subgroup 1: days 0, 3 and 8, subgroup 2: days 1, 4 and 10 and subgroup 3; days 2 and 11. Sera were collected and kept at −20 C for the determination of VH2/VK3. FIG. 25 shows the VH2/VK3 serum content during an 11-day period, indicating that the serum half-life for both i.p. and s.c. administration is approximately 10 days.

Example 21

Construction of PRO01 VH2/VK3 Expression Vector

In order to use the humanized VH2/VK3 anti-peptide-6 antibody to treat patients, a large quantity of the antibody would be needed, and so, to improve antibody production yield, a bicistronic expression plasmid incorporating both the light and heavy antibody chains was produced.

The heavy chain vector pANTVhG1 was modified by the insertion of a short linker upstream of the CMV promoter of the heavy chain expression cassette, which contained restriction enzyme sites compatible with those at either end of the light chain expression cassette (Spe I and Pci I). The light chain expression cassette was then excised from the light chain expression vector pANTVK and transferred to the modified heavy chain expression vector to create the dual expression vector pANT18. This expression vector also contains a pMB1 origin of replication for propagation in prokaryotic cells and β-lactamase (ApR) gene for prokaryotic selection.

The dual expression vector pANT18 (as described above) and the PRO01 light chain variant VK3 were digested with the restriction enzymes BssH II and BamH I. The digested fragments were gel purified and ligated together. This new plasmid, along with the PRO01 heavy chain variant VH2, were digested with the restriction enzymes Mlu I and Hind III and the digested fragments gel purified and ligated together to form the PRO01 dual expression vector pPRO14 shown in FIG. 26.

Example 22

Transfection of PRO01 VH2/VK3 Expression Vector, Initial Cell Line Selection and Adaptation to Suspension Culture in Chemically Defined Medium The plasmid pPRO14, which has a single SspI recognition site located in the beta-lactamase gene, was linearized using this restriction enzyme. Linearized plasmid DNA was transfected into CHO dhfr-cells taken from a Master Cell Bank that had been tested and certified as free from bacteria, fungi, mycoplasma and adventitious agents, in keeping with applicable regulations (performed by ECACC, Health Protection Agency, Porton Down, UK). Cell cultures were maintained in chemically defined medium (CD DG44) supplemented with 40 ml/L Glutamax in a shaking incubator (Kuhner Climo-shaker ISF1-X) set at 100 rpm in baffled Erlenmeyer flasks at 8% $CO_2$ and 37° C. 48 hours prior to transfection, cells were plated out into 6 well tissue culture plates in DMEM medium supplemented with 1% Dialyzed FBS, Glutamax and H/T. Plasmid DNA was introduced by lipid-mediated transfection using Lipofectamine 2000. At 24 hours post-transfection, cells were diluted into 100 ml DMEM+1% FBS+Glutamax, added at 10 ml/L (H/T supplement was omitted) and dispensed into 96 well, flat bottom, tissue culture plates at 100 µl/well. Cells were then incubated in a humidified atmosphere at 8% $CO_2$ and 37° C. (Binder CB150). After a further 24 hours, DMEM medium was removed and replaced with 100 µl/well CD-OptiCHO supplemented with 40 ml/l Glutamax. Plates were returned to the incubator and scanned regularly using the Genetix, Clone Select Imager to track the growth of cells in each well. Fresh selection medium was added at regular intervals during the incubation time to ensure that nutrient levels remained constant.

After several weeks, a large number of wells were identified that contained actively growing colonies of cells. Supernatants from these wells were sampled and assayed for human IgG titres using a human IgG1 Fc capture/Kappa light chain detection ELISA. Based on the results from this assay, a total of 46 of the colonies were transferred into 24 well plates containing 0.5 ml/well of CD OptiCHO medium supplemented with 40 ml/L of Glutamax. When cells in the wells were nearly confluent, supernatant from each of these 46 wells was sampled and assayed for IgG titre. Based on these results, the 29 best expressing cell lines were selected for expansion into T-25 flasks. These cell lines were again grown to near confluence, at which point supernatants were sampled and assayed for IgG titre as above. Based on these results, the 20 best expressing cell lines were expanded into T-75 flasks. Cell culture supernatants from confluent T-75 flasks were sampled and IgG titres quantified as above. The results of all these assays are shown in Table 5. Comparison of the expression levels between the 20 cell lines allowed the identification of the twelve best expressing cell lines (bold/italic in Table 5), as those to carry forward for further analysis and development.

TABLE 5

| Human IgG1 Titres from initial cell lines IgG titres (µg/ml) | | | | |
|---|---|---|---|---|
| Cell line ID | 96-well plate | 24-well plate | T25 flask | T75 flask |
| PRO01-A-14-501 | 0.42 | 0.12 | — | — |
| PRO01-A-14-502 | 0.20 | 0.13 | — | — |
| PRO01-A-14-503 | 0.25 | 0.17 | — | — |
| PRO01-A-14-504 | 0.19 | 0.15 | — | — |
| PRO01-A-14-505 | 0.36 | 0.12 | 0.11 | — |
| PRO01-A-14-506 | 0.28 | 0.16 | 0.28 | — |
| PRO01-A-14-507 | 0.06 | 0.04 | — | — |
| PRO01-A-14-508 | 0.64 | 0.58 | 1.56 | 1.28 |
| PRO01-A-14509 | 0.13 | 0.08 | — | — |
| PR 01-A-14-510 | 1.30 | 1.40 | 1.20 | 1.23 |
| PRO01-A-14-511 | 0.35 | 0.17 | 0.27 | — |
| PRO01-A-14-512 | 0.58 | 0.27 | 0.24 | — |
| PRO01-A-14-513 | 0.70 | 0.15 | — | — |
| ***PRO01-A-14-514*** | ***0.50*** | ***0.64*** | ***1.31*** | ***1.89*** |
| PRO01-A-14-515 | 0.81 | 0.62 | 0.47 | — |
| PRO01-A-14-516 | 1.20 | 0.66 | 0.49 | — |
| PRO01-A-14-517 | 0.44 | 0.12 | — | — |
| ***PRO01-A-14-518*** | ***1.71*** | ***1.18*** | ***0.84*** | ***3.75*** |
| PRO01-A-14-519 | 0.63 | 0.37 | 0.33 | — |
| PRO01-A-14-520 | 1.07 | 0.25 | — | — |
| ***PRO01-A-14-521*** | ***0.93*** | ***0.73*** | ***1.29*** | ***1.51*** |
| PRO01-A-14-522 | 1.05 | 0.52 | 0.84 | 0.64 |
| ***PRO01-A-14-523*** | ***0.83*** | ***0.82*** | ***0.78*** | ***1.26*** |
| ***PRO01-A-14-524*** | ***1.70*** | ***0.89*** | ***1.54*** | ***2.80*** |
| PRO01-A-14-525 | 0.77 | 0.52 | — | — |
| PRO01-A-14-526 | 1.69 | 0.77 | 3.25 | 1.16 |
| PRO01-A-14-527 | 1.16 | 0.85 | 0.58 | 0.93 |
| PRO01-A-14-528 | 1.22 | 0.93 | 0.44 | — |
| PRO01-A-14-529 | 0.79 | 0.62 | 0.98 | 0.71 |
| PRO01-A-14-530 | 0.41 | 0.19 | — | — |
| ***PRO01-A-14-531*** | ***1.38*** | ***0.85*** | ***5.70*** | ***3.74*** |
| PRO01-A-14-532 | 0.48 | 0.19 | — | — |
| PRO01-A-14-533 | 0.77 | 0.64 | 1.01 | 0.37 |
| PRO01-A-14-534 | 0.86 | 1.16 | 0.64 | 0.36 |
| PRO01-A-14-535 | 0.66 | 0.54 | 1.22 | 1.01 |
| PRO01-A-14-536 | 0.97 | 0.44 | 0.93 | — |
| ***PRO01-A-14-537*** | ***1.18*** | ***1.92*** | ***4.21*** | ***1.35*** |
| ***PRO01-A-14-538*** | ***1.27*** | ***1.00*** | ***8.48*** | ***1.99*** |
| ***PRO01-A-14-539*** | ***0.80*** | ***0.69*** | ***2.44*** | ***1.33*** |
| ***PRO01-A-14-540*** | ***0.68*** | ***1.67*** | ***2.64*** | ***1.46*** |
| PRO01-A-14-541 | 0.86 | 0.65 | 0.88 | — |
| ***PRO01-A-14-542*** | ***1.27*** | ***1.23*** | ***0.90*** | ***1.30*** |
| ***PRO01-A-14-543*** | ***1.29*** | ***1.24*** | ***2.00*** | ***1.37*** |
| PRO01-A-14-544 | 1.32 | 0.15 | — | — |
| PRO01-A-14-545 | 1.17 | 0.79 | — | — |
| PRO01-A-14-546 | 0.88 | 0.40 | — | — |

Colonies selected for the first round of gene amplification are emphasized in bold/italic.

Specific production rate (SPR) analysis was performed on each of these twelve cell lines and specific productivity was expressed in pg/cell/day. The results are shown in Table 6.

TABLE 6

| Specific production rate analysis | | | | | | |
|---|---|---|---|---|---|---|
| Cell line ID | Harvest titre (Th) μg/ml | Initial titre (Ti) μg/ml | Viable cell count at harvest (Vh) ×10^6 cells/ml | Initial cell count (Vi) ×10^6 cells/ml | Elapsed time between Ti and Th days | Specific production rates (SPR) pg/cell/day |
| PRO01-A-14-514 | 1.84 | 0 | 0.21 | 0.1 | 3 | 4.0 |
| PRO01-A-14-518 | 0.52 | 0 | 0.12 | 0.1 | 3 | 1.6 |
| PRO01-A-14-521 | 0.51 | 0 | 0.18 | 0.1 | 3 | 1.2 |
| PRO01-A-14-523 | 0.77 | 0 | 0.20 | 0.1 | 3 | 1.7 |
| PRO01-A-14-524 | 2.29 | 0 | 0.22 | 0.1 | 3 | 4.8 |
| PRO01-A-14-531 | 3.32 | 0 | 0.20 | 0.1 | 3 | 7.4 |
| PRO01-A-14-537 | 3.58 | 0 | 0.58 | 0.1 | 3 | 3.5 |
| PRO01-A-14-538 | 2.42 | 0 | 0.22 | 0.1 | 3 | 5.0 |
| PRO01-A-14-539 | 1.13 | 0 | 0.16 | 0.1 | 3 | 2.9 |
| PRO01-A-14-540 | 0.71 | 0 | 0.35 | 0.1 | 3 | 1.1 |
| PRO01-A-14-542 | 1.32 | 0 | 0.19 | 0.1 | 3 | 2.3 |
| PRO01-A-14-543 | 1.05 | 0 | 0.19 | 0.1 | 3 | 2.4 |

Specific production rates (SPR) on the twelve initial best cell lines. SPR was calculated as (pg/cell/day) = ((Th − Ti)/((Vh + Vi)/2))/time, where: Th = harvest titre (μg), Ti = initial titre (μg) = 0, Vh = Viable cell count at harvest (×10^6 cells), Vi = Initial cell count (×10^6 cells) and Time = elapsed time (days) between Ti and Th.

The twelve cell lines selected shown in Table 6 were progressed into a first round of gene amplification. The gene amplification process occurs as the result of selective pressure under increasing concentration of methotrexate (MTX). For the first round of gene amplification, cultures from T75 flasks were seeded into 12 well plates, with each well containing increasing concentrations of MTX. Medium in each well was changed weekly until cells were confluent. After two weeks, supernatant from each culture with increasing levels of MTX (0.05-50.0 μM) were sampled and assayed for IgG titre. The results for each of the twelve cell lines are shown in Table 7. These results demonstrated that in some instances an increase in antibody titre was observed at certain levels of MTX, compared to the well where MTX was omitted (well A1). Selected wells for each cell line were progressed to assess the SPR.

SPR analysis was performed and productivity was expressed in pg/cell/day. Comparisons were made between cultures growing in the differing MTX concentrations for all cell lines and the results are shown in Table 7.

TABLE 7

| MTX gene amplification | | | | | | | |
|---|---|---|---|---|---|---|---|
| Cell line ID | MTX concentration (μM) | Harvest titre (Th) μg/ml | Initial titre (Ti) μg/ml | Viable cell count at harvest (Vh) ×10^6 cells/ml | Initial cell count (Vi) ×10^6 cells/ml | Elapsed time between Ti and Th days | Specific production rates (SPR) pg/cell/day |
| PRO01-B-14-514-3.13 | 3.13 | 1.79 | 0 | 0.18 | 0.1 | 3 | 4.3 |
| PRO01-B-14-514-6.25 | 6.25 | 1.53 | 0 | 0.19 | 0.1 | 3 | 3.5 |
| PRO01-B-14-514-12.5 | 12.5 | 1.64 | 0 | 0.18 | 0.1 | 3 | 3.9 |
| PRO01-B-14-514-25 | 25 | 1.82 | 0 | 0.13 | 0.1 | 3 | 5.3 |
| PRO01-B-14-518-3.13 | 3.13 | 1.18 | 0 | 0.23 | 0.1 | 3 | 2.4 |
| ***PRO01- B-14-518-6.25*** | ***6.25*** | ***1.46*** | ***0*** | ***0.25*** | ***0.1*** | ***3*** | ***2.8*** |
| PRO01-B-14-518-12.5 | 12.5 | 0.79 | 0 | 0.22 | 0.1 | 3 | 1.6 |
| PRO01-B-14-518-25 | 25 | 0.83 | 0 | 0.21 | 0.1 | 3 | 1.8 |
| PRO01-B-14-521-3.13 | 3.13 | 0.69 | 0 | 0.27 | 0.1 | 3 | 1.2 |
| PRO01-B-14-521-6.25 | 6.25 | 0.67 | 0 | 0.24 | 0.1 | 3 | 1.3 |
| PRO01-B-14-521-12.5 | 12.5 | 0.92 | 0 | 0.26 | 0.1 | 3 | 1.7 |
| PRO01-B-14-521-25 | 25 | 0.62 | 0 | 0.19 | 0.1 | 3 | 1.4 |
| PRO01-B-14-521-50 | 50 | 0.76 | 0 | 0.29 | 0.1 | 3 | 1.3 |
| PRO01-B-14-523-6.25 | 6.25 | 0.87 | 0 | 0.33 | 0.1 | 3 | 1.3 |
| PRO01-B-14-523-12.5 | 12.5 | 1.17 | 0 | 0.40 | 0.1 | 3 | 1.6 |
| PRO01-B-14-523-25 | 25 | 1.04 | 0 | 0.35 | 0.1 | 3 | 1.5 |
| PRO01-B-14-523-50 | 50 | 1.50 | 0 | 0.34 | 0.1 | 3 | 2.3 |
| PRO01-B-14-524-0.4 | 0.4 | 0.85 | 0 | 0.35 | 0.1 | 3 | 1.3 |
| ***PRO01- B-14-524-0.8*** | ***0.8*** | ***11.08*** | ***0*** | ***0.36*** | ***0.1*** | ***3*** | ***16.1*** |
| PRO01-B-14-524-1.56 | 1.56 | 2.13 | 0 | 0.42 | 0.1 | 3 | 2.7 |
| PRO01-B-14-524-3.13 | 3.13 | 2.20 | 0 | 0.40 | 0.1 | 3 | 2.9 |
| PRO01-B-14-531-0.4 | 0.4 | 2.98 | 0 | 0.24 | 0.1 | 3 | 5.8 |
| PRO01-B-14-531-0.8 | 0.8 | 3.73 | 0 | 0.26 | 0.1 | 3 | 6.9 |
| PRO01-B-14-531-1.56 | 1.56 | 3.68 | 0 | 0.25 | 0.1 | 3 | 7.0 |
| PRO01-B-14-531-3.13 | 3.13 | 2.46 | 0 | 0.20 | 0.1 | 3 | 5.5 |
| PRO01-B-14-537-1.56 | 1.56 | 2.75 | 0 | 0.45 | 0.1 | 3 | 3.3 |
| PRO01-B-14-537-3.13 | 3.13 | 2.87 | 0 | 0.40 | 0.1 | 3 | 3.8 |
| PRO01-B-14-537-6.25 | 6.25 | 2.35 | 0 | 0.45 | 0.1 | 3 | 2.8 |
| PRO01-B-14-537-12.5 | 12.5 | 1.82 | 0 | 0.38 | 0.1 | 3 | 2.5 |
| PRO01-B-14-537-25 | 25 | 1.81 | 0 | 0.34 | 0.1 | 3 | 2.7 |
| PRO01-B-14-537-50 | 50 | 1.78 | 0 | 0.21 | 0.1 | 3 | 3.8 |

TABLE 7-continued

MTX gene amplification

| Cell line ID | MTX concentration (μM) | Harvest titre (Th) μg/ml | Initial titre (Ti) μg/ml | Viable cell count at harvest (Vh) ×10$^6$ cells/ml | Initial cell count (Vi) ×10$^6$ cells/ml | Elapsed time between Ti and Th days | Specific production rates (SPR) pg/cell/day |
|---|---|---|---|---|---|---|---|
| PRO01-B-14-538-1.56 | 1.56 | 4.16 | 0 | 0.32 | 0.1 | 3 | 6.6 |
| PRO01-B-14-538-3.13 | 3.13 | 2.77 | 0 | 0.34 | 0.1 | 3 | 4.2 |
| PRO01-B-14-538-6.25 | 6.25 | 1.46 | 0 | 0.20 | 0.1 | 3 | 3.2 |
| ***PRO01-B-14-538-12.5*** | ***12.5*** | ***3.91*** | ***0*** | ***0.20*** | ***0.1*** | ***3*** | ***8.7*** |
| PRO01-B-14-538-25 | 25 | 2.06 | 0 | 0.17 | 0.1 | 3 | 5.1 |
| PRO01-B-14-538-50 | 50 | 1.28 | 0 | 0.15 | 0.1 | 3 | 3.4 |
| PRO01-B-14-539-6.25 | 6.25 | 1.47 | 0 | 0.26 | 0.1 | 3 | 2.7 |
| PRO01-B-14-539-12.5 | 12.5 | 1.68 | 0 | 0.25 | 0.1 | 3 | 3.2 |
| ***PRO01-B-14-540-0.2*** | ***0.2*** | ***1.05*** | ***0*** | ***0.21*** | ***0.1*** | ***3*** | ***3.0*** |
| PRO01-B-14-540-6.25 | 6.25 | 0.87 | 0 | 0.21 | 0.1 | 3 | 1.9 |
| PRO01-B-14-540-12.5 | 12.5 | 0.81 | 0 | 0.18 | 0.1 | 3 | 1.9 |
| PRO01-B-14-540-25 | 25 | 1.02 | 0 | 0.21 | 0.1 | 3 | 2.2 |
| PRO01-B-14-540-50 | 50 | 1.28 | 0 | 0.3 | 0.1 | 3 | 2.1 |
| PRO01-B-14-542-0.4 | 0.4 | 0.85 | 0 | 0.21 | 0.1 | 3 | 1.8 |
| PRO01-B-14-542-0.8 | 0.8 | 0.88 | 0 | 0.22 | 0.1 | 3 | 1.8 |
| PRO01-B-14-542-1.56 | 1.56 | 0.47 | 0 | 0.11 | 0.1 | 3 | 1.5 |
| PRO01-B-14-542-3.13 | 3.13 | 0.48 | 0 | 0.1 | 0.1 | 3 | 1.6 |
| PRO01-B-14-543-3.13 | 3.13 | 0.85 | 0 | 0.16 | 0.1 | 3 | 2.2 |
| PRO01-B-14-543-6.25 | 6.25 | 1.00 | 0 | 0.14 | 0.1 | 3 | 2.8 |
| PRO01-B-14-543-12.5 | 12.5 | 0.75 | 0 | 0.14 | 0.1 | 3 | 2.1 |
| PRO01-B-14-543-25 | 25 | 0.75 | 0 | 0.14 | 0.1 | 3 | 2.1 |

The twelve cell lines displaying optimal SPR (see Table 6) were seeded in 12-well format and incubated with the indicated range of MTX. Supernatant was sampled for antibody titre every two weeks. SPR was analyzed to detect gene amplification under MTX selective pressure.

Table 7 shows that there was a clear increase in productivity for a number of the cultures subjected to increasing MTX concentrations. In particular, cell line PRO01-B-14-524-0.8 containing 0.8 μM MTX showed nearly a fourfold increase in specific productivity. Cultures highlighted in bold/italic in Table 7 were selected to go into a second round of gene amplification.

A second round of gene amplification in the presence of MTX was performed. Every week, medium was changed in each well of the 12-well plate until cells were confluent. After two to four weeks, supernatant from each culture with increasing levels of MTX was sampled and assayed for IgG titre. The results for each of the cell lines are shown in Table 8. Initial titre data from 12 well plates indicated that no amplification occurred in the majority of wells; however fourteen wells were subjected to an assessment of SPR (Table 8). Results from this SPR analysis demonstrated that further gene amplification had not occurred in the increased MTX concentrations used. At this stage, cells from the second round of amplification were frozen down and stored in vapour phase liquid nitrogen.

TABLE 8

Repeated MTX gene amplification

| Cell line ID | Harvest titre (Th) μg/ml | Initial titre (Ti) μg/ml | Cell count at harvest (Vh) ×10$^6$ cells/ml | Initial cell count (Vi) ×10$^6$ cells/ml | Elapsed time between Ti and Th days | Specific production rates (SPR) pg/cell/day |
|---|---|---|---|---|---|---|
| PRO01-C-14-518-(6.25) 75 | 0.48 | 0 | 0.30 | 0.1 | 3 | 0.8 |
| PRO01-C-14-518-(6.25) 125 | 0.84 | 0 | 0.26 | 0.1 | 3 | 1.6 |
| PRO01-C-14-518-(6.25) | 0.92 | 0 | 0.34 | 0.1 | 3 | 1.4 |
| PRO01-C-14-524-(0.8) 1.6 | 11.40 | 0 | 0.67 | 0.1 | 3 | 7.4 |
| PRO01-C-14-524-(0.8) 3.2 | 4.73 | 0 | 0.34 | 0.1 | 3 | 7.2 |
| PRO01-C-14-524-(0.8) 4.8 | 7.68 | 0 | 0.48 | 0.1 | 3 | 8.8 |
| PRO01-C-14-524-(0.8) 12.8 | 4.45 | 0 | 0.28 | 0.1 | 3 | 7.8 |
| PRO01-C-14-524-(0.8) 16 | 4.90 | 0 | 0.39 | 0.1 | 3 | 6.7 |
| PRO01-C-14-538-(12.5) 150 | 1.69 | 0 | 0.22 | 0.1 | 3 | 3.5 |
| PRO01-C-14-538-(12.5) 175 | 2.01 | 0 | 0.25 | 0.1 | 3 | 3.8 |
| PRO01-C-14-538-(12.5) 200 | 1.59 | 0 | 0.24 | 0.1 | 3 | 3.1 |
| PRO01-C-14-538-(12.5) 250 | 1.72 | 0 | 0.23 | 0.1 | 3 | 3.5 |
| PRO01-C-14-540-(25) 150 | 0.80 | 0 | 0.19 | 0.1 | 3 | 1.8 |
| PRO01-C-14-540-(25) 300 | 0.75 | 0 | 0.18 | 0.1 | 3 | 1.8 |

Specific production rates (SPR) after the second round of amplification. SPRs were calculated as described for Table 6.

Due to the lack of increased hIgG expression after a second round of gene amplification, the best expressing cell line from the first round, PRO01-B-14-524-0.8, was selected to progress into limited dilution cloning in the absence of MTX. After one day incubation, plates were examined using a Genetix Clone Select Imager. Pictures of each plate were taken twice a week for two weeks there after. Plates were scored to identify single colonies. This was carried out independently by two researchers and colonies scored as single by both researchers were expanded. As a result, 84 wells were deemed to contain clonal cell lines derived from a single cell. All eighty four wells were sampled and assayed for hIgG1 titre. Based on these results, the best fifty seven clones were expanded into 24 well plates. Expansion was progressed through 6 well plates, T-25 flasks and T-75 flasks in the absence of MTX. At each stage, prior to expansion, cell supernatants were assayed for hIgG1 titre. Due to low IgG titres, a number of clones were dropped at each stage so that a total of 38 remained by the time the clones had been expanded into T-75 flasks. Each of the 38 selected clones were then subjected to SPR analysis. Results of this analysis can be seen in Table 9.

Based on these results, thirteen clonal cell lines were identified as having the highest productivities PRO01-D-14-524-AG, PRO01-D-14-524-AJ PRO01-D-14-524-AO PRO01-D-14-524-AR PRO01-D-14-524-AW PRO01-D-14-524-AZ PRO01-D-14-524-BE PRO01-D-14-524-BH PRO01-D-14-524-BI PRO01-D-14-524-BJ PRO01-D-14-524-BN PRO01-D-14-524-CA and PRO01-D-14-524-CD. These clones were then expanded and a small stock frozen down and stored in vapour phase liquid nitrogen. These cell lines were adapted to suspension culture.

TABLE 9

Limited dilution cloning and SPR analysis

| Cell line ID | Harvest titre (Th) μg/ml | Initial titre (Ti) μg/ml | Viable cell count at harvest (Vh) ×10^6 cells/ml | Initial cell count (Vi) ×10^6 cells/ml | Elapsed time between Ti and Th Days | Specific production rates (SPR) pg/cell/day |
|---|---|---|---|---|---|---|
| PRO01-D-14-524-AA | 2.46 | 0 | 0.39 | 0.1 | 3 | 3.3 |
| PRO01-D-14-524-AB | 2.40 | 0 | 0.57 | 0.1 | 3 | 2.4 |
| PRO01-D-14-524-AC | 2.54 | 0 | 0.59 | 0.1 | 3 | 2.5 |
| PRO01-D-14-524-AD | 2.58 | 0 | 0.51 | 0.1 | 3 | 2.8 |
| PRO01-D-14-524-AE | 5.68 | 0 | 0.54 | 0.1 | 3 | 5.9 |
| PRO01-D-14-524-AF | 2.73 | 0 | 0.62 | 0.1 | 3 | 2.5 |
| ***PRO01-D-14-524-AG*** | ***7.81*** | ***0*** | ***0.29*** | ***0.1*** | ***3*** | ***13.4*** |
| PRO01-D-14-524-AH | 2.10 | 0 | 0.25 | 0.1 | 3 | 4.0 |
| ***PRO01-D-14-524-AJ*** | ***14.62*** | ***0*** | ***0.61*** | ***0.1*** | ***3*** | ***13.7*** |
| PRO01-D-14-524-AK | 8.34 | 0 | 0.43 | 0.1 | 3 | 10.5 |
| PRO01-D-14-524-AL | 4.31 | 0 | 0.49 | 0.1 | 3 | 4.9 |
| PRO01-D-14-524-AM | 3.17 | 0 | 0.52 | 0.1 | 3 | 3.4 |
| PRO01-D-14-524-AN | 2.47 | 0 | 0.19 | 0.1 | 3 | 5.7 |
| ***PRO01-D-14-524-AO*** | ***18.95*** | ***0*** | ***0.70*** | ***0.1*** | ***3*** | ***15.8*** |
| PRO01-D-14-524-AP | 6.48 | 0 | 0.54 | 0.1 | 3 | 6.8 |
| PRO01-D-14-524-AQ | 6.45 | 0 | 0.59 | 0.1 | 3 | 6.2 |
| ***PRO01-D-14-524-AR*** | ***12.29*** | ***0*** | ***0.53*** | ***0.1*** | ***3*** | ***15.5*** |
| PRO01-D-14-524-AV | 4.96 | 0 | 0.63 | 0.1 | 3 | 4.5 |
| ***PRO01-D-14-524-AW*** | ***10.54*** | ***0*** | ***0.45*** | ***0.1*** | ***3*** | ***12.8*** |
| ***PRO01-D-14-524-AZ*** | ***11.15*** | ***0*** | ***0.54*** | ***0.1*** | ***3*** | ***11.6*** |
| PRO01-D-14-524-BC | 7.45 | 0 | 0.70 | 0.1 | 3 | 6.2 |
| PRO01-D-14-524-BD | 4.98 | 0 | 0.44 | 0.1 | 3 | 6.1 |
| ***PRO01-D-14-524-BE*** | ***13.21*** | ***0*** | ***0.37*** | ***0.1*** | ***3*** | ***18.7*** |
| PRO01-D-14-524-BG | 9.24 | 0 | 0.38 | 0.1 | 3 | 12.8 |
| ***PRO01-D-14-524-BH*** | ***19.72*** | ***0*** | ***0.44*** | ***0.1*** | ***3*** | ***24.3*** |
| ***PRO01-D-14-524-BI*** | ***18.85*** | ***0*** | ***0.36*** | ***0.1*** | ***3*** | ***27.3*** |
| ***PRO01-D-14-524-BJ*** | ***17.67*** | ***0*** | ***0.39*** | ***0.1*** | ***3*** | ***24.0*** |
| PRO01-D-14-524-BK | 6.45 | 0 | 0.46 | 0.1 | 3 | 7.7 |
| PRO01-D-14-524-BM | 13.33 | 0 | 0.56 | 0.1 | 3 | 13.5 |
| ***PRO01-D-14-524-BN*** | ***15.95*** | ***0*** | ***0.37*** | ***0.1*** | ***3*** | ***22.6*** |
| PRO01-D-14-524-BO | 8.45 | 0 | 0.46 | 0.1 | 3 | 10.1 |
| PRO01-D-14-524-BP | 8.46 | 0 | 0.53 | 0.1 | 3 | 9.0 |
| PRO01-D-14-524-BR | 9.08 | 0 | 0.23 | 0.1 | 3 | 18.3 |
| PRO01-D-14-524-BX | 12.15 | 0 | 0.44 | 0.1 | 3 | 15.1 |
| PRO01-D-14-524-BZ | 11.27 | 0 | 0.38 | 0.1 | 3 | 15.7 |
| ***PRO01-D-14-524-CA*** | ***11.36*** | ***0*** | ***0.25*** | ***0.1*** | ***3*** | ***21.6*** |
| PRO01-D-14-524-CC | 6.80 | 0 | 0.39 | 0.1 | 3 | 9.3 |
| ***PRO01-D-14-524-BP*** | ***16.07*** | ***0*** | ***0.30*** | ***0.1*** | ***3*** | ***26.8*** |

Specific production rates (SPR) of clonal cell lines after dilution cloning. Cell lines highlighted in bold/italic were selected to go into suspension adaptation. SPRs were calculated as described for Table 6.

The above cultures were adapted to suspension culture in a chemically defined medium (CD OptiCHO supplemented with 40 ml per litre glutamax). Cultures of actively dividing cells growing in T175 tissue culture flasks as semi-adherent cultures were dissociated from plastic by gentle tapping. Suspensions were counted and $2\times10^7$ cells were seeded into 250 mL baffled Erlenmeyer flasks containing 65 mL CD OptiCHO growth medium. The flasks were then topped up with 5 mL of conditioned medium, reserved from the T-flask culture. Cultures were placed on a humidified shaking platform (Kuhner Climo-shaker ISF1-X) set at 100 rpm in 8% $CO_2$ at 37° C. Every 2-3 days, the viable cell density of the culture was determined using a Vi-CELL™ XR counter. When cell densities had doubled, cells were passaged by splitting 1:1 into fresh medium. After the second passage a duplicate flask was seeded and used to freeze down a small cell stock of 2 vials ($1\times10^7$ cells/vial). Cells underwent further passages and were considered adapted to suspension culture once the cell density doubled every 2-3 days and the cell viability could be maintained at approximately 95%. After adaptation of each cell line to suspension culture in chemically defined growth medium, a cell stock was cryopreserved ($1\times10^7$ cells/vial) in liquid nitrogen.

Example 23

Determination of Growth Characteristics, Specific Production Rates and Stability in Suspension Cultures SPR for suspension culture adapted cell lines in a chemically defined medium was determined. Briefly, $3\times10^7$ cells from a healthy culture were used to seed a 250 ml baffled Erlenmeyer flask in a total volume of 70 ml chemically defined medium. Cell counts and samples for IgG titre were taken daily over a 2 week period and IgG titres were quantified by ELISA. Results from cell counts and IgG ELISA were plotted against time, and SPR and cell doubling times were calculated as follows:

$$\text{Cell Doubling Time}=(\text{Time}\times24)/(\text{Log}_2(V_h/V_i))$$

$$\text{SPR (pg/cell/day)}=((T_h-T_i)/((V_h+V_i)/2))/\text{time}$$

Where:

$T_h$=harvest titre μg/mL $T_i$=initial titre μg/mL $V_h$=Harvest Viable cell count at ($\times10^6$ cells/mL)

$V_i$=Initial Viable cell count ($\times10^6$ cells/mL)

Time=elapsed time (days) between $T_i$ and $T_h$

SPR was calculated over 3 day intervals. The peak values obtained from this assessment are shown in Table 10, together with the estimated doubling times, maximum cell densities and peak IgG titres for each of the 12 suspension adapted clones. On the basis of these values, four clones were selected as lead candidates: PRO01-SF-14-524-AJ, PRO01-SF-14-524-AO, PRO01-SF-14-524-AZ and PRO01-SF-14-524-BE. These four lines were maintained in a continuous culture and a further sample was taken for SPRs to give a 10 generation stability profile. The productivity curves for both studies are shown in FIGS. 27 to 30 and the results are summarised in Table 11.

TABLE 10

SPR analysis of suspension cultures

| Cell line ID | Maximum cell density ($\times10^6$/mL) | Cell doubling time (hrs) | Peak SPR (pg/cell/day) | Peak titre (mg/L) |
|---|---|---|---|---|
| PRO01-SF-14-524-AG | 1.02 | 50 | 24.2 | 113 |
| PRO01-SF-14-524-AJ | 1.86 | 33 | 22.3 | 155 |
| PRO01-SF-14-524-AO | 1.25 | 45 | 37.4 | 199 |
| PRO01-SF-14-524-AR | 1.31 | 62 | 22.9 | 156 |
| PRO01-SF-14-524-AW | 1.64 | 44 | 11.9 | 88 |
| PRO01-SF-14-524-AZ | 1.30 | 42 | 31.3 | 199 |
| PRO01-SF-14-524-BE | 1.37 | 35 | 28.3 | 170 |
| PRO01-SF-14-524-BH | 0.85 | 59 | 32.6 | 152 |
| PRO01-SF-14-524-BI | 1.15 | 53 | 24.2 | 163 |
| PRO01-SF-14-524-BJ | 1.01 | 70 | 15.7 | 90 |

TABLE 10-continued

SPR analysis of suspension cultures

| Cell line ID | Maximum cell density ($\times10^6$/mL) | Cell doubling time (hrs) | Peak SPR (pg/cell/day) | Peak titre (mg/L) |
|---|---|---|---|---|
| PRO01-SF-14-524-CA | 1.51 | 38 | 7.6 | 40 |
| PRO01-SF-14-524-CD | 1.82 | 23 | 20.6 | 132 |

Growth and productivity characteristics for suspension adapted cell lines.

TABLE 11

Growth and productivity characteristics for lead suspension adapted cell lines over two SPR studies

| Cell line ID | SPR | Maximum cell density ($\times10^6$/mL) | Cell doubling time (hrs) | Peak SPR (pg/cell/day) | Peak titre (mg/L) |
|---|---|---|---|---|---|
| PRO01-SF-14-524-AJ | #1 | 1.86 | 33 | 22.3 | 155 |
| PRO01-SF-14-524-AJ | #2 | 1.79 | 29 | 24.3 | 116 |
| PRO01-SF-14-524-AO | #1 | 1.25 | 45 | 37.4 | 199 |
| PRO01-SF-14-524-AO | #2 | 1.67 | 32 | 27.0 | 183 |
| PRO01-SF-14-524-AZ | #1 | 1.30 | 42 | 31.3 | 199 |
| PRO01-SF-14-524-AZ | #2 | 1.68 | 38 | 34.4 | 185 |
| PRO01-SF-14-524-BE | #1 | 1.37 | 35 | 28.3 | 170 |
| PRO01-SF-14-524-BE | #2 | 1.40 | 39 | 28.4 | 120 |

For all four cell lines, total time in culture decreased from 9 days to 8 days before the study was stopped. This is reflected in the fact that the cell doubling times decreased between the two studies, indicating that not all of the cell lines were fully adapted to shake flask culture. For the cell line PRO0'-SF-14-524-AO, the specific production rate of the culture decreased between the two studies, although it still remained high. For the other three cell lines, PRO01-SF-14-524-AJ, PRO01-SF-14-524-AZ and PRO01-SF-14-524-BE, specific productivity remained very similar between the two studies indicating that over ten generations productivity per cell is stable.

The four lead cell lines were expanded and a seed cell bank prepared. Briefly, cells were expanded to 300 mL total volume and were harvested when cell density exceeded $0.85\times10^6$ cells/mL and viability was >90% cells. The cells were harvested by centrifugation and resuspended in an appropriate volume of freezing medium to yield a cell suspension at $1\times10^7$ cells/mL. This was dispensed in 1 ml aliquots into 2 ml sterile cryotubes. Vials were frozen down at a controlled rate of 1° C./min down to −80° C. The cell bank was then transferred to vapour phase liquid nitrogen for longer term storage. An inventory of frozen stocks of the lead cell lines is shown in Table 12.

TABLE 12

| Inventory of PRO01 lead cell line frozen stocks | | |
|---|---|---|
| Cell line ID | No. of frozen vials | Date frozen |
| PRO01-SF-14-524-AJ | 36 | 27th Apr. 2010 |
| PRO01-SF-14-524-AO | 21 | 28th Apr. 2010 |
| PRO01-SF-14-524-AZ | 23 | 7th May 2010 |
| PRO01-SF-14-524-BE | 22 | 11th May 2010 |

Thaw testing was performed for each cell line adapted to suspension cultures in chemically defined Opti-CHO medium. One vial from each cell bank was removed from liquid nitrogen storage and thawed into 70 mL chemically defined growth medium. Cell density and viability were monitored daily for five days post thaw. A summary of the data is shown in Table 13. This data demonstrates that the seed stock cell bank is viable and growing cultures can be recovered from liquid nitrogen storage.

TABLE 13

| Cell density and viability of cultures five days after thawing frozen cells | | |
|---|---|---|
| Cell line ID | Cells/mL Day 5 | Viability (%) Day 5 |
| PRO01-SF-14-524-AJ | $0.8 \times 10^6$ | 93.4 |
| PRO01-SF-14-524-AO | $0.77 \times 10^6$ | 94.3 |
| PRO01-SF-14-524-AZ | $0.44 \times 10^6$ | 84.6 |
| PRO01-SF-14-524-BE | $0.72 \times 10^6$ | 94.0 |

Example 24

Cell-Line Produced Antibody Binding to Target Antigen

The binding of antibody secreted by the lead cell lines (after adaptation to chemically defined medium) to Peptide-6 was confirmed by ELISA. Briefly, antibody was purified from cell culture supernatants using a protein A affinity column. Purified antibody was then formulated in 10 mM Sodium Acetate buffer, pH 5.5 and stored at +4° C. Glutaraldehyde treated Nunc MaxiSorp 96 well flat bottom microtitre plate were coated with 10 μg/ml solution of Peptide-6 in PBS at 100 μl/well, at 4° C. overnight. A dilution series of each antibody from 400 μg/ml to 6.25 μg/ml was prepared and 100 μl/well was added to the coated plates and incubated for 1 hour at room temperature. The antibody binding was determined by incubating for 1 hour at room temperature with 100 μl/well of a 1/1000 dilution of HRP labelled mouse anti-human kappa light chains, followed by detection with 100 μl/well TMB substrate. After stopping the reaction with 50 μl/well 3M HCl, absorbance at 450 nm was measured. FIG. 31 shows that each of the antibodies from the supernatants of the lead cell lines binds to Peptide-6 with similar binding curves and similar to the chimeric and humanized antibodies produced from NSO cells.

Example 25

Mycoplasma and Sterility Testing for Antibody Producing Cell-Lines

Culture supernatants from the cell-banked material were tested in-house for mycoplasma using a Minerva Biolabs Venor® GeM Mycoplasma Detection Kit. This kit uses PCR to detect 16S RNA from 79 species of mycoplasma with a detection limit of 3 mycoplasma per sample. A positive control of 191 bp is included with each sample that demonstrates that the reactions have worked and samples positive for mycoplasma yield a band of 265-278 bp. Agarose gels of PCR reactions for cell lines PRO01-D-14-524-AJ, PRO01-D-14-524-AO, PRO01-D-14-524-AZ and PRO01-D-14-524-BE showed no evidence of a mycoplasma specific band.

The PRO01-D-14-524-AJ cell line was deposited according to Budapest Treaty registration and accession number CNCM I-4356. Deposit of cells has been performed in accordance with the provisions of the Budapest treaty.

The invention claimed is:

1. A humanized antibody or any antigen-binding fragment thereof that specifically binds a polypeptide comprising SEQ ID NO: 15, the humanized antibody comprising:

a) a heavy chain variable region which comprising an amino Acid sequence which is at least about 70% identical to SEQ ID NO. 1, said heavy chain variable region comprising Cys at position H22, Ser at H23, Gly at H26, Phe at H27, Ser at H28, Leu at H29, Ser at H30, Thr at H31, Ser at H32, Asn at H33, Met at H34, Gly at H35, Val at H35A, Gly at H35B, Leu at H48, His at H50, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and, optionally, at least one of Leu at H49, Tyr at H74, Ile at H11, Ser at H41 and Ser at H108; and b) a light chain variable region which comprising an amino Acid sequence which is at least about 70% identical to SEQ ID NO. 2, said light chain variable region comprising Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Trp at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and optionally at least one of Met at L21, Ile at L10 and Ala at L80;

wherein the positions are determined according to the Kabat numbering system.

2. The humanized antibody according to claim 1, wherein said heavy chain variable region comprises an amino acid sequence which is at least about 70% identical to SEQ ID NO. 1, said heavy chain variable region comprising a substitution in at least one position selected from the group consisting of H10, H11, H12, H13, H15, H19, H41, H49, H74, H75, H79, H81, H82, H82A, H82C, H84, H85 and H108, and wherein said light chain variable region comprises an amino acid sequence which is at least about 70% identical to SEQ ID NO. 2, said light chain variable region comprising a substitution in at least one position selected from the group consisting of L10, L11, L13, L15, L19, L21, L22, L42, L43, L60, L70, L72, L78, L79, L80, L83 and L100, wherein the positions are determined according to the Kabat numbering system.

3. A humanized antibody according to claim 2 that specifically binds a polypeptide comprising SEQ ID NO: 15, the humanized antibody comprising:

a) a heavy chain variable region as shown in SEQ ID NO: 1, except that H10 is Ala, H11 is Ile or Leu, H12 is Val, H13 is Lys, H15 is Thr, H19 is Thr, H41 is Ser or Ala, H49 is Leu or Ala, H74 is Tyr or Ser, H75 is Lys, H79 is Val, H81 is Thr, H82 is Met, H82A is Thr, H82C is Met, H84 is Pro, H85 is Val and H108 is Ser or Leu; and b) a light chain variable region as shown in SEQ ID NO: 2, except that L10 is Ile or Thr, L11 is Leu, L13 is Leu, L15 is Pro, L19 is Ala, L21 is Met or Leu, L22 is Ser, L42 is Lys, L43 is Ala, L60 is Ser, L70 is Asp, L72 is Thr, L78 is Leu, L79 is Gln, L80 is Ala or Pro, L83 is Phe and L100 is Gln;

wherein the positions are determined according to the Kabat numbering system.

4. The humanized antibody according to claim 2, wherein said antibody comprises:

a) a heavy chain variable region comprising an amino acid sequence that is at least about 60% identical to any one of SEQ ID NO. 21, 22, 23 and 20, wherein said heavy chain variable region comprises a substitution in at least one position selected from the group consisting of H10, H11, H12, H13, H15, H19, H41, H49, H74, H75, H79, H81, H82, H82A, H82C, H84, H85 and H108; and b) a light chain variable region comprising an amino acid sequence that is at least about 60% identical to any one of SEQ ID NO. 26, 24 and 25, wherein said light chain variable region comprises a substitution in at least one position selected from the group consisting of L10, L11, L13, L15, L19, L21, L22, L42, L43, L60, L70, L72, L78, L79, L80, L83 and L100;

wherein the positions are determined according to the Kabat numbering system.

5. The humanized antibody according to claim 4, wherein the heavy chain variable region is selected from the group consisting of SEQ ID NO: 21, SEQ ID NO: 22, SEQ ID NO: 23 and SEQ ID NO: 20, and wherein the light chain variable region is selected from the group consisting of SEQ ID NO: 26, SEQ ID NO: 24 and SEQ ID NO: 25.

6. The humanized antibody according to claim 5, wherein the heavy chain variable region is SEQ ID NO: 21 and the light chain variable region is selected from the group consisting of SEQ ID NO: 26, SEQ ID NO: 24, and SEQ ID NO: 25.

7. The humanized antibody according to claim 6, wherein the heavy chain variable region is SEQ ID NO: 21 and the light chain variable region is SEQ ID NO: 26.

8. The humanized antibody according to claim 6, wherein the heavy chain variable region is SEQ ID NO: 21 and the light chain variable region is SEQ ID NO: 25.

9. The humanized antibody according to claim 6, wherein the heavy chain variable region is SEQ ID NO: 21 and the light chain variable region is SEQ ID NO: 24.

10. The humanized antibody according to claim 5, wherein the heavy chain variable region is SEQ ID NO: 22 and the light chain variable region is selected from the group consisting of SEQ ID NO: 24, SEQ ID NO: 25, and SEQ ID NO: 26.

11. The humanized antibody according to claim 10, wherein the heavy chain variable region is SEQ ID NO: 22 and the light chain variable region is SEQ ID NO: 25.

12. A chimeric monoclonal antibody that specifically binds a polypeptide comprising SEQ ID NO: 15, wherein said antibody comprises a human immunoglobulin constant region and a murine immunoglobulin variable region, said variable region comprising a light chain variable region having the amino acid sequence as denoted by SEQ ID NO. 2 and a heavy chain variable region having the amino acid sequence as denoted by SEQ ID NO. 1.

13. A composition comprising a pharmaceutically acceptable carrier, excipient or diluent, and, as an active ingredient, an effective amount of at least one humanized antibody or antigen-binding fragment thereof that specifically binds a polypeptide comprising SEQ ID NO: 15, the humanized antibody comprising:

a) a heavy chain variable region comprising an amino acid sequence which is at least about 70% identical to SEQ ID NO. 1, said heavy chain variable region comprising Cys at position H22, Ser at H23, Gly at H26, Phe at H27, Ser at H28, Leu at H29, Ser at H30, Thr at H31, Ser at H32, Asn at H33, Met at H34, Gly at H35, Val at H35A, Gly at H35B, Leu at H48, His at HSO, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and, optionally, at least one of Leu at H49, Tyr at H74, Ile at H11, Ser at H41 and Ser at H108; and b) a light chain variable region comprising an amino acid sequence which is at least about 70% identical to SEQ ID NO. 2, said light chain variable region comprising Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Trp at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and, optionally, at least one of Met at L21, Ile at L10 and Ala at L80;

wherein the positions are determined according to the Kabat numbering system.

14. A pharmaceutical composition for the treatment or amelioration of an immune-related disorder, wherein said disorder is an inflammatory bowel disease (IBD) or arthritis, and wherein said composition comprises a pharmaceutically acceptable carrier, excipient or diluent, and, as an active ingredient, a therapeutically effective amount of at least one humanized antibody or antigen-binding fragment thereof according to claim 1.

15. A combined composition comprising at least one anti-inflammatory agent and at least one humanized antibody or antigen-binding fragment thereof according to claim 1, wherein said anti-inflammatory agent is selected from the group consisting of Methylprednisone (MPS), anti-TNF agents, etanercept, Infliximab, Adalimumab, certolizumab pegol, anti-IL-6 agents, tocilizumab, anti-IL-1-receptor agents, kineret, CTLA-4-Ig, abatacept, anti-CD20 agents, rituximab, methotrexate, and any corticosteroid derivatives.

16. A kit for achieving a therapeutic effect in a subject suffering from an immune-related disorder, said disorder being an inflammatory bowel disease (IBD) or arthritis, said kit comprising:

(i) at least one humanized antibody or antigen-binding fragment thereof according to claim 1, and a pharmaceutically acceptable carrier or diluent, optionally, in a first unit dosage form;

(ii) at least one anti-inflammatory agent, and a pharmaceutically acceptable carrier or diluent, optionally, in a second unit dosage form; and (iii) container means for containing said first and second dosage forms, wherein said anti-inflammatory agent is selected from the group consisting of Methylprednisone (MPS), anti-TNF agents, etanercept, Infliximab, Adalimumab, certolizumab pegol, anti-IL-6 agents, tocilizumab, anti-IL-1-receptor agents, kineret, CTLA-4-Ig, abatacept, anti-CD20 agents, rituximab, methotrexate, and any corticosteroid derivatives.

17. A method for the treatment or amelioration of an immune-related disorder, wherein said disorder is an inflammatory bowel disease (IBD) or arthritis, said method comprising the step of administering to a subject in need thereof a therapeutically effective amount of at least one humanized antibody or antigen-binding fragment thereof that specifically binds a polypeptide comprising SEQ ID NO: 15, or of a composition comprising the same, wherein said humanized antibody comprises:

a) a heavy chain variable region comprising an amino acid sequence which is at least about 70% identical to SEQ ID NO. 1, said heavy chain variable region comprising Cys at position H22, Ser at H23, Gly at H26, Phe at H27, Ser at H28, Leu at H29, Ser at H30, Thr at H31, Ser at H32, Asn at H33, Met at H34, Gly at H35, Val at H35A, Gly at H35B, Leu at H48, His at HSO, Ile at H51, Leu at H52, Trp at H53, Asn at H54, Asp at H55, Ser at H56, Lys at H57, Tyr at H58, Tyr at H59, Asn at H60, Pro at H61, Ala at H62, Leu at H63, Lys at H64, Ser at H65, Cys at H92, Met at H95, Gly at H96, Gly at H97, Tyr at H98, Tyr at H99, Gly at H100, Asn at H100A, Tyr at H100B, Gly at H100C, Tyr at H100D, Tyr at H100E, Ala at H100F, Met at H100G, Asp at H101 and Tyr at H102, and, optionally, at least one of Leu at H49, Tyr at H74, Ile at H11, Ser at H41 and Ser at H108; and b) a light chain variable region comprising an amino acid sequence which is at least about 70% identical to SEQ ID NO. 2, said light chain variable region comprising Gln at position L1, Cys at L23, Thr at L24, Ala at L25, Ser at L26, Ser at L27, Ser at L27A, Val at L28, Ser at L29, Ser at L30, Ser at L31, Tyr at L32, Leu at L33, His at L34, Trp at L47, Ser at L50, Thr at L51, Ser at L52, Asn at L53, Leu at L54, Ala at L55, Ser at L56, Tyr at L71, Cys at L88, His at L89, Gln at L90, Tyr at L91, His at L92, Arg at L93, Ser at L94, Pro at L95, Pro at L96 and Thr at L97 and, optionally, at least one of Met at L21, Ile at L10 and Ala at L80;

wherein the positions are determined according to the Kabat numbering system.

18. The method according to claim 17, wherein said immune-related disorder is an inflammatory arthritis or an inflammatory bowel disease (IBD).

19. A method for increasing the expression and levels of IL-10 in a subject in need thereof, said method comprising the step of administering to said subject a therapeutically effective amount of at least one humanized antibody or antigen-binding fragment thereof according to claim 1, or of a composition comprising the same.

20. A host cell line transformed or transfected with an expression vector encoding a humanized antibody or antigen-binding fragment thereof according to claim 1.

21. The host cell line according to claim 20, wherein said cell line expresses a humanized antibody having a heavy chain variable region comprising the amino acid sequence of SEQ ID NO: 21 and a light chain variable region comprising an the amino acid sequence of SEQ ID NO: 26.

* * * * *

UNITED STATES PATENT AND TRADEMARK OFFICE

CERTIFICATE OF CORRECTION

PATENT NO. : 8,680,241 B2
APPLICATION NO. : 13/392548
DATED : March 25, 2014
INVENTOR(S) : Yakov Naparstek It is certified that error appears in the above-identified patent and that said Letters Patent is hereby corrected as shown below:

In the Claims

Claim 1, column 149, line 49, delete “which”

Claim 1, column 149, line 59, delete “and optionally” and insert --and, optionally,--

Claim 13, column 151, line 52, delete “HSO” and insert --H50--

Claim 17, column 152, line 61, delete “HSO” and insert --H50--

Claim 21, column 154, line 17, delete “an”

Signed and Sealed this
Ninth Day of June, 2015

Michelle K. Lee

Michelle K. Lee
*Director of the United States Patent and Trademark Office*

SEQUENCE LISTING

```
<160> NUMBER OF SEQ ID NOS: 101

<210> SEQ ID NO 1
<211> LENGTH: 125
<212> TYPE: PRT
<213> ORGANISM: Mus musculus

<400> SEQUENCE: 1

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asn Met Gly Val Gly Trp Ile Arg Gln Pro Ser Gly Lys Gly Leu Glu
        35                  40                  45

Trp Leu Leu His Ile Leu Trp Asn Asp Ser Lys Tyr Tyr Asn Pro Ala
    50                  55                  60

Leu Lys Ser Arg Leu Thr Ile Ser Lys Asp Thr Tyr Asn Asn Gln Val
65                  70                  75                  80

Phe Leu Lys Ile Ala Asn Val Asp Thr Ala Asp Thr Ala Thr Tyr Tyr
                85                  90                  95

Cys Ala Arg Met Gly Gly Tyr Tyr Gly Asn Tyr Gly Tyr Tyr Ala Met
            100                 105                 110
```

```
Asp Tyr Trp Gly Gln Gly Thr Ser Val Thr Val Ser Ser
        115                 120                 125


<210> SEQ ID NO 2
<211> LENGTH: 108
<212> TYPE: PRT
<213> ORGANISM: Mus musculus

<400> SEQUENCE: 2

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Ser Gly Thr Lys Leu Glu Ile Lys
            100                 105


<210> SEQ ID NO 3
<211> LENGTH: 375
<212> TYPE: DNA
<213> ORGANISM: Mus musculus

<400> SEQUENCE: 3

caggttactc tgaaagagtc tggccctggg atattgcagc cctcccagac cctcagtctg      60

acttgttctt tctctgggtt ttcactgagc acttctaata tgggtgtagg ctggattcgt     120

cagccttcag ggaagggtct ggagtggctg ttacacattt tgtggaatga tagtaagtac     180

tataacccag ccctgaagag ccggctcaca atctccaagg atacctacaa caaccaggta     240

ttcctcaaga tcgccaatgt ggacactgca gatactgcca catactactg tgctcgaatg     300

gggggctact atggtaacta tgggtactat gctatggact actggggtca aggaacctca     360

gtcaccgtct cctca                                                      375


<210> SEQ ID NO 4
<211> LENGTH: 324
<212> TYPE: DNA
<213> ORGANISM: Mus musculus

<400> SEQUENCE: 4

caaattgttc tcacccagtc tccagcaatc atgtctgcat ctctagggga acgggtcacc      60

atgacctgca ctgccagctc aagtgtaagt tccagttact tgcactggta ccagcagaag     120

ccaggatcct cccccaaact ctggatttat agcacatcca acctggcttc tggagtccca     180

gctcgcttca gtggcagtgg gtctgggacc tcttactctc tcacaatcag cagcatggag     240

gctgaagatg ctgccactta ttactgccac cagtatcatc gttccccacc cacgttcggc     300

tcggggacaa agttggaaat aaaa                                            324


<210> SEQ ID NO 5
<211> LENGTH: 21
<212> TYPE: DNA
<213> ORGANISM: Artificial Sequence
```

<220> FEATURE:
<223> OTHER INFORMATION: VH 5' Flanking nucleic acid sequence

<400> SEQUENCE: 5
gttgctacgc gtgtccactc c 21

<210> SEQ ID NO 6
<211> LENGTH: 15
<212> TYPE: DNA
<213> ORGANISM: Artificial Sequence
<220> FEATURE:
<223> OTHER INFORMATION: VH 3' Flanking nucleic acid sequence

<400> SEQUENCE: 6
ggtaagcttt ctggg 15

<210> SEQ ID NO 7
<211> LENGTH: 16
<212> TYPE: DNA
<213> ORGANISM: Artificial Sequence
<220> FEATURE:
<223> OTHER INFORMATION: VK 5' Flanking nucleic acid sequence

<400> SEQUENCE: 7
cccaggcgcg cgatgt 16

<210> SEQ ID NO 8
<211> LENGTH: 45
<212> TYPE: DNA
<213> ORGANISM: Artificial Sequence
<220> FEATURE:
<223> OTHER INFORMATION: VK 3' Flanking nucleic acid sequence

<400> SEQUENCE: 8
cgtgagtaga atttaaactt tgcttcctca gttggatccc gcaat 45

<210> SEQ ID NO 9
<211> LENGTH: 4449
<212> TYPE: DNA
<213> ORGANISM: Artificial Sequence
<220> FEATURE:
<223> OTHER INFORMATION: VK Chimera Full Vector nucleic acid Sequence

<400> SEQUENCE: 9
actagttatt aatagtaatc aattacgggg tcattagttc atagcccata tatggagttc 60
cgcgttacat aacttacggt aaatggcccg cctggctgac cgcccaacga cccccgccca 120
ttgacgtcaa taatgacgta tgttcccata gtaacgccaa tagggacttt ccattgacgt 180
caatgggtgg agtatttacg gtaaactgcc cacttggcag tacatcaagt gtatcatatg 240
ccaagtacgc cccctattga cgtcaatgac ggtaaatggc ccgcctggca ttatgcccag 300
tacatgacct tatgggactt tcctacttgg cagtacatct acgtattagt catcgctatt 360
accatggtga tgcggttttg gcagtacatc aatgggcgtg gatagcggtt tgactcacgg 420
ggatttccaa gtctccaccc cattgacgtc aatgggagtt tgttttggca ccaaaatcaa 480
cgggactttc caaaatgtcg taacaactcc gccccattga cgcaaatggg cggtaggcgt 540
gtacggtggg aggtctatat aagcagagct cgtttagtga accgtcagat ctggcacgag 600
ggtctcctca ggttgccgcc accatgaggg tccccgctca gctcctgggg ctcctgctgc 660
tctggctccc aggcgcgcga tgtcaaattg ttctcaccca gtctccagca atcatgtctg 720
catctctagg ggaacgggtc accatgacct gcactgccag ctcaagtgta agttccagtt 780
acttgcactg gtaccagcag aagccaggct cctcccccaa actctggatt tatagcacat 840

```
ccaacctggc ttctggagtc ccagctcgct tcagtggcag tgggtctggg acctcttact    900

ctctcacaat cagcagcatg gaggctgaag atgctgccac ttattactgc caccagtatc    960

atcgttcccc acccacgttc ggctcgggga caaagttgga aataaaacgt gagtagaatt   1020

taaactttgc ttcctcagtt ggatcccgca attctaaact ctgagggggt cggatgacgt   1080

ggccattctt tgcctaaagc attgagttta ctgcaaggtc agaaaagcat gcaaagccct   1140

cagaatggct gcaaagagct ccaacaaaac aatttagaac tttattaagg aatagggga    1200

agctaggaag aaactcaaaa catcaagatt ttaaatacgc ttcttggtct ccttgctata   1260

attatctggg ataagcatgc tgttttctgt ctgtccctaa catgccctgt gattatccgc   1320

aaacaacaca cccaagggca gaactttgtt acttaaacac catcctgttt gcttctttcc   1380

tcaggaactg tggctgcacc atctgtcttc atcttcccgc catctgatga gcagttgaaa   1440

tctggaactg cctctgttgt gtgcctgctg aataacttct atcccagaga ggccaaagta   1500

cagtggaagg tggataacgc cctccaatcg ggtaactccc aggagagtgt cacagagcag   1560

gacagcaagg acagcaccta cagcctcagc agcaccctga cgctgagcaa agcagactac   1620

gagaaacaca aagtctacgc ctgcgaagtc acccatcagg gcctgagctc gcccgtcaca   1680

aagagcttca acaggggaga gtgttagagg gagaagtgcc cccacctgct cctcagttcc   1740

agcctgaccc cctcccatcc tttggcctct gacccttttt ccacagggga cctacccta    1800

ttgcggtcct ccagctcatc tttcacctca cccccctcct cctccttggc tttaattatg   1860

ctaatgttgg aggagaatga ataaataaag tgaatctttg cacctgtggt ttctctcttt   1920

cctcaattta ataattatta tctgttgttt accaactact caatttctct tataagggac   1980

taaatatgta gtcatcctaa ggcgcataac catttataaa aatcatcctt cattctattt   2040

taccctatca tcctctgcaa gacagtcctc cctcaaaccc acaagccttc tgtcctcaca   2100

gtcccctggg ccatggtagg agagacttgc ttccttgttt tcccctcctc agcaagccct   2160

catagtcctt tttaagggtg acaggtctta cggtcatata tcctttgatt caattccctg   2220

ggaatcaacc aaggcaaatt tttcaaaaga agaaacctgc tataaagaga atcattcatt   2280

gcaacatgat ataaaataac aacacaataa aagcaattaa ataaacaaac aatagggaaa   2340

tgtttaagtt catcatggta cttagactta atggaatgtc atgccttatt tacattttta   2400

aacaggtact gagggactcc tgtctgccaa gggccgtatt gagtactttc cacaacctaa   2460

tttaatccac actatactgt gagattaaaa acattcatta aaatgttgca aaggttctat   2520

aaagctgaga gacaaatata ttctataact cagcaatccc actacatgtg agcaaaaggc   2580

cagcaaaagg ccaggaaccg taaaaaggcc gcgttgctgg cgtttttcca taggctccgc   2640

ccccctgacg agcatcacaa aaatcgacgc tcaagtcaga ggtggcgaaa cccgacagga   2700

ctataaagat accaggcgtt tccccctgga agctccctcg tgcgctctcc tgttccgacc   2760

ctgccgctta ccggatacct gtccgccttt ctcccttcgg gaagcgtggc gctttctcat   2820

agctcacgct gtaggtatct cagttcggtg taggtcgttc gctccaagct gggctgtgtg   2880

cacgaacccc ccgttcagcc cgaccgctgc gccttatccg gtaactatcg tcttgagtcc   2940

aacccggtaa gacacgactt atcgccactg gcagcagcca ctggtaacag gattagcaga   3000

gcgaggtatg taggcggtgc tacagagttc ttgaagtggt ggcctaacta cggctacact   3060

agaaggacag tatttggtat ctgcgctctg ctgaagccag ttaccttcgg aaaaagagtt   3120

ggtagctctt gatccggcaa acaaaccacc gctggtagcg gtggtttttt tgtttgcaag   3180

cagcagatta cgcgcagaaa aaaaggatct caagaagatc ctttgatctt ttctacgggg   3240
```

tctgacgctc agtggaacga aaactcacgt taagggattt tggtcatgag attatcaaaa 3300
aggatcttca cctagatcct tttaaattaa aaatgaagtt ttaaatcaat ctaaagtata 3360
tatgagtaaa cttggtctga cagttaccaa tgcttaatca gtgaggcacc tatctcagcg 3420
atctgtctat ttcgttcatc catagttgcc tgactccccg tcgtgtagat aactacgata 3480
cgggagggct taccatctgg ccccagtgct gcaatgatac cgcgagaccc acgctcaccg 3540
gctccagatt tatcagcaat aaaccagcca gccggaaggg ccgagcgcag aagtggtcct 3600
gcaactttat ccgcctccat ccagtctatt aattgttgcc gggaagctag agtaagtagt 3660
tcgccagtta atagtttgcg caacgttgtt gccattgcta caggcatcgt ggtgtcacgc 3720
tcgtcgtttg gtatggcttc attcagctcc ggttcccaac gatcaaggcg agttacatga 3780
tcccccatgt tgtgcaaaaa agcggttagc tccttcggtc ctccgatcgt tgtcagaagt 3840
aagttggccg cagtgttatc actcatggtt atggcagcac tgcataattc tcttactgtc 3900
atgccatccg taagatgctt ttctgtgact ggtgagtact caaccaagtc attctgagaa 3960
tagtgtatgc ggcgaccgag ttgctcttgc ccggcgtcaa tacgggataa taccgcgcca 4020
catagcagaa ctttaaaagt gctcatcatt ggaaaacgtt cttcggggcg aaaactctca 4080
aggatcttac cgctgttgag atccagttcg atgtaaccca ctcgtgcacc caactgatct 4140
tcagcatctt ttactttcac cagcgtttct gggtgagcaa aaacaggaag gcaaaatgcc 4200
gcaaaaaagg gaataagggc gacacggaaa tgttgaatac tcatactctt cctttttcaa 4260
tattattgaa gcatttatca gggttattgt ctcatgagcg gatacatatt tgaatgtatt 4320
tagaaaaata aacaaatagg ggttccgcgc acatttcccc gaaaagtgcc acctgacgtc 4380
taagaaacca ttattatcat gacattaacc tataaaaata ggcgtatcac gaggccctat 4440
tgattattg 4449

<210> SEQ ID NO 10
<211> LENGTH: 6399
<212> TYPE: DNA
<213> ORGANISM: Artificial Sequence
<220> FEATURE:
<223> OTHER INFORMATION: IgG1 VH Chimera Full Vector nucleic acid sequence

<400> SEQUENCE: 10
actagtgatc catcacatgt tgcatgcagg ctagttatta atagtaatca attacggggt 60
cattagttca tagcccatat atggagttcc gcgttacata acttacggta aatggcccgc 120
ctggctgacc gcccaacgac ccccgcccat tgacgtcaat aatgacgtat gttcccatag 180
taacgccaat agggactttc cattgacgtc aatgggtgga gtatttacgg taaactgccc 240
acttggcagt acatcaagtg tatcatatgc caagtacgcc ccctattgac gtcaatgacg 300
gtaaatggcc cgcctggcat tatgcccagt acatgacctt atgggacttt cctacttggc 360
agtacatcta cgtattagtc atcgctatta ccatggtgat gcggttttgg cagtacatca 420
atgggcgtgg atagcggttt gactcacggg gatttccaag tctccacccc attgacgtca 480
atgggagttt gttttggcac caaaatcaac gggactttcc aaaatgtcgt aacaactccg 540
ccccattgac gcaaatgggc ggtaggcgtg tacggtggga ggtctatata agcagagctc 600
gtttagtgaa ccgtcagatc tggcacgagg ctggactcac aagtctttct cttcagtgac 660
aaacacagaa atagagccgc caccatgggt tggagcctca tcttgctctt ccttgtcgct 720
gttgctacgc gtgtccactc ccaggttact ctgaaagagt ctggccctgg gatattgcag 780

-continued

```
ccctcccaga ccctcagtct gacttgttct ttctctgggt tttcactgag cacttctaat    840
atgggtgtag gctggattcg tcagccttca gggaagggtc tggagtggct gttacacatt    900
ttgtggaatg atagtaagta ctataaccca gccctgaaga gccggctcac aatctccaag    960
gatacctaca acaaccaggt attcctcaag atcgccaatg tggacactgc agatactgcc   1020
acatactact gtgctcgaat ggggggctac tatggtaact atgggtacta tgctatggac   1080
tactggggtc aaggaacctc agtcaccgtc tcctcaggta agctttctgg ggcaggccgg   1140
gcctgacctt ggctttgggg caggggtgg gctaaggtga cgcaggtggc gccagccagg    1200
cgcacaccca atgcccgtga gcccagacac tggacgctga acctcgcgga cagttaagaa   1260
cccaggggcc tctgcgccct gggcccagct ctgtcccaca ccgcggtcac atggcaccac   1320
ctctcttgca gcctccacca agggcccatc ggtcttcccc ctggcaccct cctccaagag   1380
cacctctggg ggcacagcag ccctgggctg cctggtcaag gactacttcc ccgaaccggt   1440
gacggtgtcg tggaactcag gcgccctgac cagcggcgtg cacaccttcc cggctgtcct   1500
acagtcctca ggactctact ccctcagcag cgtggtgacc gtgccctcca gcagcttggg   1560
cacccagacc tacatctgca acgtgaatca caagcccagc aacaccaagg tggacaagag   1620
agttggtgag aggccagcac agggagggag ggtgtctgct ggaagccagg ctcagcgctc   1680
ctgcctggac gcatcccggc tatgcagccc cagtccaggg cagcaaggca ggccccgtct   1740
gcctcttcac ccggaggcct ctgcccgccc cactcatgct cagggagagg gtcttctggc   1800
tttttcccca ggctctgggc aggcacaggc taggtgcccc taacccaggc cctgcacaca   1860
aaggggcagg tgctgggctc agacctgcca agagccatat ccgggaggac cctgcccctg   1920
acctaagccc accccaaagg ccaaactctc cactccctca gctcggacac cttctctcct   1980
cccagattcc agtaactccc aatcttctct ctgcagagcc caaatcttgt gacaaaactc   2040
acacatgccc accgtgccca ggtaagccag cccaggcctc gccctccagc tcaaggcggg   2100
acaggtgccc tagagtagcc tgcatccagg gacaggcccc agccgggtgc tgacacgtcc   2160
acctccatct cttcctcagc acctgaactc ctggggggac cgtcagtctt cctcttcccc   2220
ccaaaaccca aggacaccct catgatctcc cggacccctg aggtcacatg cgtggtggtg   2280
gacgtgagcc acgaagaccc tgaggtcaag ttcaactggt acgtggacgg cgtggaggtg   2340
cataatgcca agacaaagcc gcgggaggag cagtacaaca gcacgtaccg tgtggtcagc   2400
gtcctcaccg tcctgcacca ggactggctg aatggcaagg agtacaagtg caaggtctcc   2460
aacaaagccc tcccagcccc catcgagaaa accatctcca aagccaaagg tgggacccgt   2520
ggggtgcgag ggccacatgg acagaggccg gctcggccca ccctctgccc tgagagtgac   2580
cgctgtacca acctctgtcc ctacagggca gccccgagaa ccacaggtgt acaccctgcc   2640
cccatcccgg gaagagatga ccaagaacca ggtcagcctg acctgcctgg tcaaaggctt   2700
ctatcccagc gacatcgccg tggagtggga gagcaatggg cagccggaga acaactacaa   2760
gaccacgcct cccgtgctgg actccgacgg ctccttcttc ctctacagca agctcaccgt   2820
ggacaagagc aggtggcagc aggggaacgt cttctcatgc tccgtgatgc atgaggctct   2880
gcacaaccac tacacacaga agagcctctc cctgtctccg ggtaaatgag tgccacggcc   2940
ggcaagcccc cgctccccag gctctcgggg tcgcgcgagg atgcttggca cgtaccccgt   3000
gtacatactt cccaggcacc cagcatggaa ataaagcacc cagcgcttcc ctgggcccct   3060
gcgagactgt gatggttctt tccacgggtc aggccgagtc tgaggcctga gtggcatgag   3120
ggaggcagag tgggtcccac tgtccccaca ctggcccagg ctgtgcaggt gtgcctgggc   3180
```

```
cgcctagggt ggggctcagc caggggctgc cctcggcagg gtgggggatt tgccagcgtg   3240
gccctccctc cagcagacat gcatgtgagc aaaaggccag caaaaggcca ggaaccgtaa   3300
aaaggccgcg ttgctggcgt ttttccatag gctccgcccc cctgacgagc atcacaaaaa   3360
tcgacgctca agtcagaggt ggcgaaaccc gacaggacta taaagatacc aggcgtttcc   3420
ccctggaagc tccctcgtgc gctctcctgt tccgaccctg ccgcttaccg gatacctgtc   3480
cgcctttctc ccttcgggaa gcgtggcgct ttctcatagc tcacgctgta ggtatctcag   3540
ttcggtgtag gtcgttcgct ccaagctggg ctgtgtgcac gaaccccccg ttcagcccga   3600
ccgctgcgcc ttatccggta actatcgtct tgagtccaac ccggtaagac acgacttatc   3660
gccactggca gcagccactg gtaacaggat tagcagagcg aggtatgtag gcggtgctac   3720
agagttcttg aagtggtggc ctaactacgg ctacactaga aggacagtat ttggtatctg   3780
cgctctgctg aagccagtta ccttcggaaa aagagttggt agctcttgat ccggcaaaca   3840
aaccaccgct ggtagcggtg gtttttttgt ttgcaagcag cagattacgc gcagaaaaaa   3900
aggatctcaa gaagatcctt tgatcttttc tacggggtct gacgctcagt ggaacgaaaa   3960
ctcacgttaa gggattttgg tcatgagatt atcaaaaagg atcttcacct agatcctttt   4020
aaattaaaaa tgaagtttta aatcaatcta aagtatatat gagtaaactt ggtctgacag   4080
ttaccaatgc ttaatcagtg aggcacctat ctcagcgatc tgtctatttc gttcatccat   4140
agttgcctga ctccccgtcg tgtagataac tacgatacgg gagggcttac catctggccc   4200
cagtgctgca atgataccgc gagacccacg ctcaccggct ccagatttat cagcaataaa   4260
ccagccagcc ggaagggccg agcgcagaag tggtcctgca actttatccg cctccatcca   4320
gtctattaat tgttgccggg aagctagagt aagtagttcg ccagttaata gtttgcgcaa   4380
cgttgttgcc attgctacag gcatcgtggt gtcacgctcg tcgtttggta tggcttcatt   4440
cagctccggt tcccaacgat caaggcgagt tacatgatcc cccatgttgt gcaaaaaagc   4500
ggttagctcc ttcggtcctc cgatcgttgt cagaagtaag ttggccgcag tgttatcact   4560
catggttatg gcagcactgc ataattctct tactgtcatg ccatccgtaa gatgcttttc   4620
tgtgactggt gagtactcaa ccaagtcatt ctgagaatag tgtatgcggc gaccgagttg   4680
ctcttgcccg gcgtcaatac gggataatac cgcgccacat agcagaactt taaaagtgct   4740
catcattgga aaacgttctt cggggcgaaa actctcaagg atcttaccgc tgttgagatc   4800
cagttcgatg taacccactc gtgcacccaa ctgatcttca gcatctttta ctttcaccag   4860
cgtttctggg tgagcaaaaa caggaaggca aaatgccgca aaaaagggaa taagggcgac   4920
acggaaatgt tgaatactca tactcttcct ttttcaatat tattgaagca tttatcaggg   4980
ttattgtctc atgagcggat acatatttga atgtatttag aaaaataaac aaataggggt   5040
tccgcgcaca tttccccgaa aagtgccacc tgacgtctaa gaaaccatta ttatcatgac   5100
attaacctat aaaaataggc gtatcacgag gccctattga ttattgacta gctagtgtgg   5160
aatgtgtgtc agttagggtg tggaaagtcc ccaggctccc cagcaggcag aagtatgcaa   5220
agcatgcatc tcaattagtc agcaaccagg tgtggaaagt ccccaggctc cccagcaggc   5280
agaagtatgc aaagcatgca tctcaattag tcagcaacca tagtcccgcc cctaactccg   5340
cccatcccgc ccctaactcc gcccagttcc gcccattctc cgccccatgg ctgactaatt   5400
ttttttattt atgcagaggc cgaggccgcc tcggcctctg agctattcca gaagtagtga   5460
ggaggctttt ttggaggcct aggcttttgc aaaaagctag cttggtgccc tcatggttcg   5520
accattgaac tgcatcgtcg ccgtgtccca aaatatgggg attggcaaga acggagaccg   5580
```

```
accctggcct ccgctcagga acgagttcaa gtacttccaa agaatgacca caacctcttc   5640

agtggaaggt aaacagaatc tggtgattat gggtaggaaa acctggttct ccattcctga   5700

gaagaatcga cctttaaagg acagaattaa tatagttctc agtagagaac tcaaagaacc   5760

accacgagga gctcattttc ttgccaaaag tttggatgat gccttaagac ttattgaaca   5820

accggaattg gcaagtaaag tagacatggt ttggatagtc ggaggcagtt ctgtttacca   5880

ggaagccatg aatcaaccag gccacctcag actctttgtg acaaggatca tgcaggaatt   5940

tgaaagtgac acgtttttcc cagaaattga tttggggaaa tataaacttc tcccagaata   6000

cccaggcgtc ctctctgagg tccaggagga aaaaggcatc aagtataagt ttgaagtcta   6060

cgagaagaaa gactaacagg aagatgcttt caagttctct gctcccctcc taaagctatg   6120

catttttata agaccatggg acttttgctg gctttagatc ataatcagcc ataccacatt   6180

tgtagaggtt ttacttgctt taaaaaacct cccacacctc cccctgaacc tgaaacataa   6240

aatgaatgca attgttgttg ttaacttgtt tattgcagct tctaatggtt acaaataaag   6300

caatagcatc acaaatttca caaataaagc atttttttca ctgcattcta gttgtggttt   6360

gtccaaactc atcaatgtat cttatcatgt ctggatcgg                          6399
```

<210> SEQ ID NO 11
<211> LENGTH: 6358
<212> TYPE: DNA
<213> ORGANISM: Artificial Sequence
<220> FEATURE:
<223> OTHER INFORMATION: IgG4 VH Chimera Full Vector nucleic acid Sequence

<400> SEQUENCE: 11

```
actagttatt aatagtaatc aattacgggg tcattagttc atagcccata tatggagttc     60

cgcgttacat aacttacggt aaatggcccg cctggctgac cgcccaacga cccccgccca    120

ttgacgtcaa taatgacgta tgttcccata gtaacgccaa tagggacttt ccattgacgt    180

caatgggtgg agtatttacg gtaaactgcc cacttggcag tacatcaagt gtatcatatg    240

ccaagtacgc cccctattga cgtcaatgac ggtaaatggc ccgcctggca ttatgcccag    300

tacatgacct tatgggactt tcctacttgg cagtacatct acgtattagt catcgctatt    360

accatggtga tgcggttttg gcagtacatc aatgggcgtg gatagcggtt tgactcacgg    420

ggatttccaa gtctccaccc cattgacgtc aatgggagtt tgttttggca ccaaaatcaa    480

cgggactttc caaaatgtcg taacaactcc gccccattga cgcaaatggg cggtaggcgt    540

gtacggtggg aggtctatat aagcagagct cgtttagtga accgtcagat ctggcacgag    600

gctggactca caagtctttc tcttcagtga caaacacaga aatagagccg ccaccatggg    660

ttggagcctc atcttgctct tccttgtcgc tgttgctacg cgtgtccact cccaggttac    720

tctgaaagag tctggccctg ggatattgca gccctcccag accctcagtc tgacttgttc    780

tttctctggg ttttcactga gcacttctaa tatgggtgta ggctggattc gtcagccttc    840

agggaagggt ctggagtggc tgttacacat tttgtggaat gatagtaagt actataaccc    900

agccctgaag agccggctca caatctccaa ggatacctac aacaaccagg tattcctcaa    960

gatcgccaat gtggacactg cagatactgc cacatactac tgtgctcgaa tggggggcta   1020

ctatggtaac tatgggtact atgctatgga ctactggggt caaggaacct cagtcaccgt   1080

ctcctcaggt aagctttctg gggcaggccg ggcctgactt tggctggggg cagggagggg   1140

gctaaggtga cgcaggtggc gccagccagg tgcacaccca atgcccatga gcccagacac   1200

tggaccctgc atggaccatc gcggatagac aagaaccgag ggcctctgc gccctgggcc    1260
```

-continued

```
cagctctgtc ccacaccgcg gtcacatggc accacctctc ttgcagcttc caccaagggc   1320
ccatccgtct tcccccctggc gccctgctcc aggagcacct ccgagagcac agccgccctg   1380
ggctgcctgg tcaaggacta cttccccgaa ccggtgacgg tgtcgtggaa ctcaggcgcc   1440
ctgaccagcg gcgtgcacac cttcccggct gtcctacagt cctcaggact ctactccctc   1500
agcagcgtgg tgaccgtgcc ctccagcagc ttgggcacga agacctacac ctgcaatgta   1560
gatcacaagc ccagcaacac caaggtggac aagagagttg gtgagaggcc agcacaggga   1620
gggagggtgt ctgctggaag ccaggctcag ccctcctgcc tggacgcacc ccggctgtgc   1680
agccccagcc cagggcagca aggcaggccc catctgtctc ctcacctgga ggcctctgac   1740
caccccactc atgctcaggg agagggtctt ctggattttt ccaccaggct ccgggcagcc   1800
acaggctgga tgcccctacc ccaggccctg cgcatacagg ggcaggtgct gcgctcagac   1860
ctgccaagag ccatatccgg gaggaccctg cccctgacct aagcccaccc caaaggccaa   1920
actctccact ccctcagctc agacaccttc tctcctccca gatctgagta actcccaatc   1980
ttctctctgc agagtccaaa tatggtcccc catgcccatc atgcccaggt aagccaaccc   2040
aggcctcgcc ctccagctca aggcgggaca ggtgccctag agtagcctgc atccagggac   2100
aggccccagc cgggtgctga cgcatccacc tccatctctt cctcagcacc tgagttcctg   2160
gggggaccat cagtcttcct gttcccccca aaacccaagg acactctcat gatctcccgg   2220
acccctgagg tcacgtgcgt ggtggtggac gtgagccagg aagaccccga ggtccagttc   2280
aactggtacg tggatggcgt ggaggtgcat aatgccaaga caaagccgcg ggaggagcag   2340
ttcaacagca cgtaccgtgt ggtcagcgtc ctcaccgtcc tgcaccagga ctggctgaac   2400
ggcaaggagt acaagtgcaa ggtctccaac aaaggcctcc cgtcctccat cgagaaaacc   2460
atctccaaag ccaaaggtgg gacccacggg gtgcgagggc cacatggaca gaggtcagct   2520
cggcccaccc tctgccctgg gagtgaccgc tgtgccaacc tctgtcccta cagggcagcc   2580
ccgagagcca caggtgtaca ccctgccccc atcccaggag gagatgacca agaaccaggt   2640
cagcctgacc tgcctggtca aaggcttcta ccccagcgac atcgccgtgg agtgggagag   2700
caatgggcag ccggagaaca actacaagac cacgcctccc gtgctggact ccgacggctc   2760
cttcttcctc tacagcaggc taaccgtgga caagagcagg tggcaggagg ggaatgtctt   2820
ctcatgctcc gtgatgcatg aggctctgca caaccactac acacagaaga gcctctccct   2880
gtctctgggt aaatgagtgc cagggccggc aagcccccgc tccccgggct ctcggggtcg   2940
cgcgaggatg cttggcacgt accccgtcta catacttccc aggcacccag catggaaata   3000
aagcacccac cactgccctg ggcccctgtg agactgtgat ggttctttcc acgggtcagg   3060
ccgagtctga ggcctgagtg acatgaggga ggcagagcgg gtcccactgt ccccacactg   3120
gcccaggctg tgcaggtgtg cctgggccac ctagggtggg gctcagccag ggctgccct   3180
cggcagggtg ggggatttgc cagcgtggcc ctccctccag cagacatgtg agcaaaaggc   3240
cagcaaaagg ccaggaaccg taaaaaggcc gcgttgctgg cgtttttcca taggctccgc   3300
ccccctgacg agcatcacaa aaatcgacgc tcaagtcaga ggtggcgaaa cccgacagga   3360
ctataaagat accaggcgtt tccccctgga agctccctcg tgcgctctcc tgttccgacc   3420
ctgccgctta ccggatacct gtccgccttt ctcccttcgg gaagcgtggc gctttctcat   3480
agctcacgct gtaggtatct cagttcggtg taggtcgttc gctccaagct gggctgtgtg   3540
cacgaacccc ccgttcagcc cgaccgctgc gccttatccg gtaactatcg tcttgagtcc   3600
aacccggtaa gacacgactt atcgccactg gcagcagcca ctggtaacag gattagcaga   3660
```

```
gcgaggtatg taggcggtgc tacagagttc ttgaagtggt ggcctaacta cggctacact   3720
agaaggacag tatttggtat ctgcgctctg ctgaagccag ttaccttcgg aaaaagagtt   3780
ggtagctctt gatccggcaa acaaaccacc gctggtagcg gtggtttttt tgtttgcaag   3840
cagcagatta cgcgcagaaa aaaaggatct caagaagatc ctttgatctt ttctacgggg   3900
tctgacgctc agtggaacga aaactcacgt taagggattt tggtcatgag attatcaaaa   3960
aggatcttca cctagatcct tttaaattaa aaatgaagtt ttaaatcaat ctaaagtata   4020
tatgagtaaa cttggtctga cagttaccaa tgcttaatca gtgaggcacc tatctcagcg   4080
atctgtctat ttcgttcatc catagttgcc tgactccccg tcgtgtagat aactacgata   4140
cgggagggct taccatctgg ccccagtgct gcaatgatac cgcgagaccc acgctcaccg   4200
gctccagatt tatcagcaat aaaccagcca gccggaaggg ccgagcgcag aagtggtcct   4260
gcaactttat ccgcctccat ccagtctatt aattgttgcc gggaagctag agtaagtagt   4320
tcgccagtta atagtttgcg caacgttgtt gccattgcta caggcatcgt ggtgtcacgc   4380
tcgtcgtttg gtatggcttc attcagctcc ggttcccaac gatcaaggcg agttacatga   4440
tcccccatgt tgtgcaaaaa agcggttagc tccttcggtc ctccgatcgt tgtcagaagt   4500
aagttggccg cagtgttatc actcatggtt atggcagcac tgcataattc tcttactgtc   4560
atgccatccg taagatgctt ttctgtgact ggtgagtact caaccaagtc attctgagaa   4620
tagtgtatgc ggcgaccgag ttgctcttgc ccggcgtcaa tacgggataa taccgcgcca   4680
catagcagaa ctttaaaagt gctcatcatt ggaaaacgtt cttcggggcg aaaactctca   4740
aggatcttac cgctgttgag atccagttcg atgtaaccca ctcgtgcacc caactgatct   4800
tcagcatctt ttactttcac cagcgtttct gggtgagcaa aaacaggaag gcaaaatgcc   4860
gcaaaaaagg gaataagggc gacacggaaa tgttgaatac tcatactctt cctttttcaa   4920
tattattgaa gcatttatca gggttattgt ctcatgagcg gatacatatt tgaatgtatt   4980
tagaaaaata aacaaatagg ggttccgcgc acatttcccc gaaaagtgcc acctgacgtc   5040
taagaaacca ttattatcat gacattaacc tataaaaata ggcgtatcac gaggccctat   5100
tgattattga ctagtgtgga atgtgtgtca gttagggtgt ggaaagtccc caggctcccc   5160
agcaggcaga agtatgcaaa gcatgcatct caattagtca gcaaccaggt gtggaaagtc   5220
cccaggctcc ccagcaggca gaagtatgca aagcatgcat ctcaattagt cagcaaccat   5280
agtcccgccc ctaactccgc ccatcccgcc cctaactccg cccagttccg cccattctcc   5340
gccccatggc tgactaattt tttttattta tgcagaggcc gaggccgcct cggcctctga   5400
gctattccag aagtagtgag gaggcttttt tggaggccta ggcttttgca aaaagctagc   5460
ttggtgccct catggttcga ccattgaact gcatcgtcgc cgtgtcccaa aatatgggga   5520
ttggcaagaa cggagaccga ccctggcctc cgctcaggaa cgagttcaag tacttccaaa   5580
gaatgaccac aacctcttca gtggaaggta aacagaatct ggtgattatg ggtaggaaaa   5640
cctggttctc cattcctgag aagaatcgac ctttaaagga cagaattaat atagttctca   5700
gtagagaact caaagaacca ccacgaggag ctcattttct tgccaaaagt ttggatgatg   5760
ccttaagact tattgaacaa ccggaattgg caagtaaagt agacatggtt tggatagtcg   5820
gaggcagttc tgtttaccag gaagccatga atcaaccagg ccacctcaga ctctttgtga   5880
caaggatcat gcaggaattt gaaagtgaca cgtttttccc agaaattgat ttggggaaat   5940
ataaacttct cccagaatac ccaggcgtcc tctctgaggt ccaggaggaa aaaggcatca   6000
agtataagtt tgaagtctac gagaagaaag actaacagga agatgctttc aagttctctg   6060
```

```
ctcccctcct aaagctatgc atttttataa gaccatggga cttttgctgg ctttagatca   6120

taatcagcca taccacattt gtagaggttt tacttgcttt aaaaaacctc ccacacctcc   6180

ccctgaacct gaaacataaa atgaatgcaa ttgttgttgt taacttgttt attgcagctt   6240

ctaatggtta caaataaagc aatagcatca caaatttcac aaataaagca tttttttcac   6300

tgcattctag ttgtggtttg tccaaactca tcaatgtatc ttatcatgtc tggatcgg     6358


<210> SEQ ID NO 12
<211> LENGTH: 11
<212> TYPE: PRT
<213> ORGANISM: Artificial Sequence
<220> FEATURE:
<223> OTHER INFORMATION: Amino acid sequence of a segment

<400> SEQUENCE: 12

Gln Val Thr Leu Lys Glu Ser Gly Pro Ala Ile
1               5                   10


<210> SEQ ID NO 13
<211> LENGTH: 21
<212> TYPE: PRT
<213> ORGANISM: Artificial Sequence
<220> FEATURE:
<223> OTHER INFORMATION: Amino acid sequence of a segment

<400> SEQUENCE: 13

Val Lys Pro Thr Gln Thr Leu Thr Leu Thr Cys Ser Phe Ser Gly Phe
1               5                   10                  15

Ser Leu Ser Thr Ser
            20


<210> SEQ ID NO 14
<211> LENGTH: 10
<212> TYPE: PRT
<213> ORGANISM: Artificial Sequence
<220> FEATURE:
<223> OTHER INFORMATION: Amino acid sequence of a segment

<400> SEQUENCE: 14

Asn Met Gly Val Gly Trp Ile Arg Gln Pro
1               5                   10


<210> SEQ ID NO 15
<211> LENGTH: 16
<212> TYPE: PRT
<213> ORGANISM: Artificial Sequence
<220> FEATURE:
<223> OTHER INFORMATION: Amino acid sequence of peptide-6

<400> SEQUENCE: 15

Gly Pro Lys Gly Arg Asn Val Val Leu Glu Lys Lys Trp Gly Ala Pro
1               5                   10                  15


<210> SEQ ID NO 16
<211> LENGTH: 12
<212> TYPE: PRT
<213> ORGANISM: Artificial Sequence
<220> FEATURE:
<223> OTHER INFORMATION: Amino acid sequence of a segment

<400> SEQUENCE: 16

Trp Ile Arg Gln Pro Ser Gly Lys Gly Leu Glu Trp
1               5                   10
```

<210> SEQ ID NO 17
<211> LENGTH: 8
<212> TYPE: PRT
<213> ORGANISM: Artificial Sequence
<220> FEATURE:
<223> OTHER INFORMATION: Amino acid sequence of a segment

<400> SEQUENCE: 17

```
Gly Lys Gly Leu Glu Trp Leu Leu
1               5
```

<210> SEQ ID NO 18
<211> LENGTH: 8
<212> TYPE: PRT
<213> ORGANISM: Artificial Sequence
<220> FEATURE:
<223> OTHER INFORMATION: Amino acid sequence of a segment

<400> SEQUENCE: 18

```
His Ile Leu Trp Asn Asp Ser Lys
1               5
```

<210> SEQ ID NO 19
<211> LENGTH: 9
<212> TYPE: PRT
<213> ORGANISM: Artificial Sequence
<220> FEATURE:
<223> OTHER INFORMATION: Amino acid sequence of a segment

<400> SEQUENCE: 19

```
Tyr Tyr Asn Pro Ala Leu Lys Ser Arg
1               5
```

<210> SEQ ID NO 20
<211> LENGTH: 125
<212> TYPE: PRT
<213> ORGANISM: Artificial Sequence
<220> FEATURE:
<223> OTHER INFORMATION: VH1 amino acid sequence

<400> SEQUENCE: 20

```
Gln Val Thr Leu Lys Glu Ser Gly Pro Ala Ile Val Lys Pro Thr Gln
1               5                   10                  15

Thr Leu Thr Leu Thr Cys Ser Phe Ser Gly Phe Ser Leu Ser Thr Ser
            20                  25                  30

Asn Met Gly Val Gly Trp Ile Arg Gln Pro Ser Gly Lys Gly Leu Glu
        35                  40                  45

Trp Leu Leu His Ile Leu Trp Asn Asp Ser Lys Tyr Tyr Asn Pro Ala
    50                  55                  60

Leu Lys Ser Arg Leu Thr Ile Ser Lys Asp Thr Tyr Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Gly Gly Tyr Tyr Gly Asn Tyr Gly Tyr Tyr Ala Met
            100                 105                 110

Asp Tyr Trp Gly Gln Gly Thr Ser Val Thr Val Ser Ser
        115                 120                 125
```

<210> SEQ ID NO 21
<211> LENGTH: 125
<212> TYPE: PRT
<213> ORGANISM: Artificial Sequence
<220> FEATURE:
<223> OTHER INFORMATION: VH2 amino acid sequence

<400> SEQUENCE: 21

```
Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Asn Met Gly Val Gly Trp Ile Arg Gln Pro Ala Gly Lys Gly Leu Glu
        35                  40                  45

Trp Leu Leu His Ile Leu Trp Asn Asp Ser Lys Tyr Tyr Asn Pro Ala
    50                  55                  60

Leu Lys Ser Arg Leu Thr Ile Ser Lys Asp Thr Tyr Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Gly Gly Tyr Tyr Gly Asn Tyr Gly Tyr Tyr Ala Met
            100                 105                 110

Asp Tyr Trp Gly Gln Gly Thr Leu Val Thr Val Ser Ser
        115                 120                 125
```

<210> SEQ ID NO 22
<211> LENGTH: 125
<212> TYPE: PRT
<213> ORGANISM: Artificial Sequence
<220> FEATURE:
<223> OTHER INFORMATION: VH3 amino acid sequence

<400> SEQUENCE: 22

```
Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Asn Met Gly Val Gly Trp Ile Arg Gln Pro Ala Gly Lys Gly Leu Glu
        35                  40                  45

Trp Leu Leu His Ile Leu Trp Asn Asp Ser Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Gly Gly Tyr Tyr Gly Asn Tyr Gly Tyr Tyr Ala Met
            100                 105                 110

Asp Tyr Trp Gly Gln Gly Thr Leu Val Thr Val Ser Ser
        115                 120                 125
```

<210> SEQ ID NO 23
<211> LENGTH: 125
<212> TYPE: PRT
<213> ORGANISM: Artificial Sequence
<220> FEATURE:
<223> OTHER INFORMATION: VH4 amino acid sequence

<400> SEQUENCE: 23

```
Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Asn Met Gly Val Gly Trp Ile Arg Gln Pro Ala Gly Lys Gly Leu Glu
        35                  40                  45

Trp Leu Ala His Ile Leu Trp Asn Asp Ser Lys Tyr Tyr Asn Pro Ala
```

```
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Gly Gly Tyr Tyr Gly Asn Tyr Gly Tyr Tyr Ala Met
            100                 105                 110

Asp Tyr Trp Gly Gln Gly Thr Leu Val Thr Val Ser Ser
        115                 120                 125


<210> SEQ ID NO 24
<211> LENGTH: 108
<212> TYPE: PRT
<213> ORGANISM: Artificial Sequence
<220> FEATURE:
<223> OTHER INFORMATION: VK1 amino acid sequence

<400> SEQUENCE: 24

Gln Ile Val Leu Thr Gln Ser Pro Ala Ile Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Ala Glu Asp Phe Ala Thr Tyr Tyr Cys His Gln Tyr His Arg Ser Pro
                85                  90                  95

Pro Thr Phe Gly Gln Gly Thr Lys Leu Glu Ile Lys
            100                 105


<210> SEQ ID NO 25
<211> LENGTH: 108
<212> TYPE: PRT
<213> ORGANISM: Artificial Sequence
<220> FEATURE:
<223> OTHER INFORMATION: VK2 amino acid sequence

<400> SEQUENCE: 25

Gln Ile Val Leu Thr Gln Ser Pro Ala Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Pro Thr Phe Gly Gln Gly Thr Lys Leu Glu Ile Lys
            100                 105


<210> SEQ ID NO 26
<211> LENGTH: 108
<212> TYPE: PRT
```

<213> ORGANISM: Artificial Sequence
<220> FEATURE:
<223> OTHER INFORMATION: VK3 amino acid sequence

<400> SEQUENCE: 26

```
Gln Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Leu His Trp Tyr Gln Gln Lys Pro Gly Lys Ala Pro Lys Leu Trp
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Pro Thr Phe Gly Gln Gly Thr Lys Leu Glu Ile Lys
            100                 105
```

<210> SEQ ID NO 27
<211> LENGTH: 375
<212> TYPE: DNA
<213> ORGANISM: Artificial Sequence
<220> FEATURE:
<223> OTHER INFORMATION: VH1 nucleic acid sequence

<400> SEQUENCE: 27

```
caggttactc tgaaagagtc tggccctgcc atagtgaagc ccacccagac cctcaccctg     60

acttgttctt tctctgggtt ttcactgagc acttctaata tgggtgtagg ctggattcgt    120

cagccttcag ggaagggtct ggagtggctg ttacacattt tgtggaatga tagtaagtac    180

tataacccag ccctgaagag ccggctcaca atctccaagg atacctacaa gaaccaggta    240

gtgctcacca tgaccaatat ggaccctgtg gatactgcca catactactg tgctcgaatg    300

gggggctact atggtaacta tgggtactat gctatggact actggggtca aggaacctca    360

gtcaccgtct cctca                                                     375
```

<210> SEQ ID NO 28
<211> LENGTH: 375
<212> TYPE: DNA
<213> ORGANISM: Artificial Sequence
<220> FEATURE:
<223> OTHER INFORMATION: VH2 nucleic acid sequence

<400> SEQUENCE: 28

```
caggttactc tgaaagagtc tggccctgcc ctggtgaagc ccacccagac cctcaccctg     60

acttgttctt tctctgggtt ttcactgagc acttctaata tgggtgtagg ctggattcgt    120

cagcctgccg ggaagggtct ggagtggctg ttacacattt tgtggaatga tagtaagtac    180

tataacccag ccctgaagag ccggctcaca atctccaagg atacctacaa gaaccaggta    240

gtgctcacca tgaccaatat ggaccctgtg gatactgcca catactactg tgctcgaatg    300

gggggctact atggtaacta tgggtactat gctatggact actggggtca aggaaccctg    360

gtcaccgtct cctca                                                     375
```

<210> SEQ ID NO 29
<211> LENGTH: 375
<212> TYPE: DNA
<213> ORGANISM: Artificial Sequence
<220> FEATURE:
<223> OTHER INFORMATION: VH3 nucleic acid sequence

<400> SEQUENCE: 29

```
caggttactc tgaaagagtc tggccctgcc ctggtgaagc ccacccagac cctcaccctg     60

acttgttctt tctctgggtt ttcactgagc acttctaata tgggtgtagg ctggattcgt    120

cagcctgccg ggaagggtct ggagtggctg ttacacattt tgtggaatga tagtaagtac    180

tataacccag ccctgaagag ccggctcaca atctccaagg atacctccaa gaaccaggta    240

gtgctcacca tgaccaatat ggaccctgtg gatactgcca catactactg tgctcgaatg    300

gggggctact atggtaacta tgggtactat gctatggact actggggtca aggaaccctg    360

gtcaccgtct cctca                                                     375
```

<210> SEQ ID NO 30
<211> LENGTH: 375
<212> TYPE: DNA
<213> ORGANISM: Artificial Sequence
<220> FEATURE:
<223> OTHER INFORMATION: VH4 nucleic acid sequence

<400> SEQUENCE: 30

```
caggttactc tgaaagagtc tggccctgcc ctggtgaagc ccacccagac cctcaccctg     60

acttgttctt tctctgggtt ttcactgagc acttctaata tgggtgtagg ctggattcgt    120

cagcctgccg ggaagggtct ggagtggctg gcccacattt tgtggaatga tagtaagtac    180

tataacccag ccctgaagag ccggctcaca atctccaagg atacctccaa gaaccaggta    240

gtgctcacca tgaccaatat ggaccctgtg gatactgcca catactactg tgctcgaatg    300

gggggctact atggtaacta tgggtactat gctatggact actggggtca aggaaccctg    360

gtcaccgtct cctca                                                     375
```

<210> SEQ ID NO 31
<211> LENGTH: 324
<212> TYPE: DNA
<213> ORGANISM: Artificial Sequence
<220> FEATURE:
<223> OTHER INFORMATION: VK1 nucleic acid sequence

<400> SEQUENCE: 31

```
caaattgttc tcacccagtc tccagcaatc ctgtctctgt ctccagggga acgggccacc     60

atgagctgca ctgccagctc aagtgtaagt tccagttact tgcactggta ccagcagaag    120

ccaggaaagg cccccaaact ctggatttat agcacatcca acctggcttc tggagtccca    180

tctcgcttca gtggcagtgg gtctgggacc gattacaccc tcacaatcag cagcctgcag    240

gctgaagatt tcgccactta ttactgccac cagtatcatc gttccccacc cacgttcggc    300

caggggacaa agttggaaat aaaa                                           324
```

<210> SEQ ID NO 32
<211> LENGTH: 324
<212> TYPE: DNA
<213> ORGANISM: Artificial Sequence
<220> FEATURE:
<223> OTHER INFORMATION: VK2 nucleic acid sequence

<400> SEQUENCE: 32

```
caaattgttc tcacccagtc tccagcaacc ctgtctctgt ctccagggga acgggccacc     60

atgagctgca ctgccagctc aagtgtaagt tccagttact tgcactggta ccagcagaag    120

ccaggaaagg cccccaaact ctggatttat agcacatcca acctggcttc tggagtccca    180
```

```
tctcgcttca gtggcagtgg gtctgggacc gattacaccc tcacaatcag cagcctgcag    240

cctgaagatt tcgccactta ttactgccac cagtatcatc gttccccacc cacgttcggc    300

caggggacaa agttggaaat aaaa                                           324
```

<210> SEQ ID NO 33
<211> LENGTH: 324
<212> TYPE: DNA
<213> ORGANISM: Artificial
<220> FEATURE:
<223> OTHER INFORMATION: VK3 nucleic acid sequence

<400> SEQUENCE: 33

```
caaattgttc tcacccagtc tccagcaacc ctgtctctgt ctccagggga acgggccacc     60

ctgagctgca ctgccagctc aagtgtaagt tccagttact tgcactggta ccagcagaag    120

ccaggaaagg cccccaaact ctggatttat agcacatcca acctggcttc tggagtccca    180

tctcgcttca gtggcagtgg gtctgggacc gattacaccc tcacaatcag cagcctgcag    240

cctgaagatt tcgccactta ttactgccac cagtatcatc gttccccacc cacgttcggc    300

caggggacaa agttggaaat aaaa                                           324
```

<210> SEQ ID NO 34
<211> LENGTH: 8
<212> TYPE: PRT
<213> ORGANISM: Artificial
<220> FEATURE:
<223> OTHER INFORMATION: Amino acid sequence of a segment

<400> SEQUENCE: 34

```
Arg Leu Thr Ile Ser Lys Asp Thr
1               5
```

<210> SEQ ID NO 35
<211> LENGTH: 20
<212> TYPE: PRT
<213> ORGANISM: Artificial
<220> FEATURE:
<223> OTHER INFORMATION: amino acid sequence of a segment

<400> SEQUENCE: 35

```
Thr Tyr Lys Asn Gln Val Val Leu Thr Met Thr Asn Met Asp Pro Val
1               5                   10                  15

Asp Thr Ala Thr
            20
```

<210> SEQ ID NO 36
<211> LENGTH: 10
<212> TYPE: PRT
<213> ORGANISM: Artificial
<220> FEATURE:
<223> OTHER INFORMATION: amino acid sequence of a segment

<400> SEQUENCE: 36

```
Tyr Tyr Cys Ala Arg Met Gly Gly Tyr Tyr
1               5                   10
```

<210> SEQ ID NO 37
<211> LENGTH: 8
<212> TYPE: PRT
<213> ORGANISM: Artificial
<220> FEATURE:
<223> OTHER INFORMATION: amino acid sequence of a segment

<400> SEQUENCE: 37

Gly Tyr Tyr Gly Asn Tyr Gly Tyr
1 5

<210> SEQ ID NO 38
<211> LENGTH: 10
<212> TYPE: PRT
<213> ORGANISM: Artificial
<220> FEATURE:
<223> OTHER INFORMATION: Amino acid sequence of a segment

<400> SEQUENCE: 38

Tyr Ala Met Asp Tyr Trp Gly Gln Gly Thr
1 5 10

<210> SEQ ID NO 39
<211> LENGTH: 11
<212> TYPE: PRT
<213> ORGANISM: Artificial
<220> FEATURE:
<223> OTHER INFORMATION: Amino acid sequence of a segment

<400> SEQUENCE: 39

Trp Gly Gln Gly Thr Ser Val Thr Val Ser Ser
1 5 10

<210> SEQ ID NO 40
<211> LENGTH: 22
<212> TYPE: PRT
<213> ORGANISM: Artificial
<220> FEATURE:
<223> OTHER INFORMATION: Amino acid sequence of a segment

<400> SEQUENCE: 40

Gln Val Thr Leu Lys Glu Ser Gly Pro Ala Leu Val Lys Pro Thr Gln
1 5 10 15

Thr Leu Thr Leu Thr Cys
20

<210> SEQ ID NO 41
<211> LENGTH: 12
<212> TYPE: PRT
<213> ORGANISM: Artificial
<220> FEATURE:
<223> OTHER INFORMATION: Amino acid sequence of a segment

<400> SEQUENCE: 41

Trp Ile Arg Gln Pro Ala Gly Lys Gly Leu Glu Trp
1 5 10

<210> SEQ ID NO 42
<211> LENGTH: 16
<212> TYPE: PRT
<213> ORGANISM: Artificial
<220> FEATURE:
<223> OTHER INFORMATION: Amino acid sequence of a segment

<400> SEQUENCE: 42

Tyr Ala Met Asp Tyr Trp Gly Gln Gly Thr Leu Val Thr Val Ser Ser
1 5 10 15

<210> SEQ ID NO 43
<211> LENGTH: 27
<212> TYPE: PRT
<213> ORGANISM: Artificial
<220> FEATURE:
<223> OTHER INFORMATION: Amino acid sequence of a segment

<400> SEQUENCE: 43

```
Arg Leu Thr Ile Ser Lys Asp Thr Ser Lys Asn Gln Val Val Leu Thr
1               5                   10                  15

Met Thr Asn Met Asp Pro Val Asp Thr Ala Thr
            20                  25
```

<210> SEQ ID NO 44
<211> LENGTH: 8
<212> TYPE: PRT
<213> ORGANISM: Artificial
<220> FEATURE:
<223> OTHER INFORMATION: Amino acid sequence of a segment

<400> SEQUENCE: 44

```
Gly Lys Gly Leu Glu Trp Leu Ala
1               5
```

<210> SEQ ID NO 45
<211> LENGTH: 9
<212> TYPE: PRT
<213> ORGANISM: Artificial
<220> FEATURE:
<223> OTHER INFORMATION: Amino acid sequence of a segment

<400> SEQUENCE: 45

```
Gln Ile Val Leu Thr Gln Ser Pro Ala
1               5
```

<210> SEQ ID NO 46
<211> LENGTH: 12
<212> TYPE: PRT
<213> ORGANISM: Artificial
<220> FEATURE:
<223> OTHER INFORMATION: Amino acid sequence of a segment

<400> SEQUENCE: 46

```
Ala Ile Leu Ser Leu Ser Pro Gly Glu Arg Ala Thr
1               5                   10
```

<210> SEQ ID NO 47
<211> LENGTH: 11
<212> TYPE: PRT
<213> ORGANISM: Artificial
<220> FEATURE:
<223> OTHER INFORMATION: Amino acid sequence of a segment

<400> SEQUENCE: 47

```
Gly Glu Arg Ala Thr Met Ser Cys Thr Ala Ser
1               5                   10
```

<210> SEQ ID NO 48
<211> LENGTH: 8
<212> TYPE: PRT
<213> ORGANISM: Artificial
<220> FEATURE:
<223> OTHER INFORMATION: Amino acid sequence of a segment

<400> SEQUENCE: 48

```
Ser Ser Val Ser Ser Ser Tyr Leu
1               5
```

<210> SEQ ID NO 49
<211> LENGTH: 15
<212> TYPE: PRT
<213> ORGANISM: Artificial
<220> FEATURE:
<223> OTHER INFORMATION: Amino acid sequence of a segment

<400> SEQUENCE: 49

Tyr Leu His Trp Tyr Gln Gln Lys Pro Gly Lys Ala Pro Lys Leu
1 5 10 15

<210> SEQ ID NO 50
<211> LENGTH: 7
<212> TYPE: PRT
<213> ORGANISM: Artificial
<220> FEATURE:
<223> OTHER INFORMATION: Amino acid sequence of a segment

<400> SEQUENCE: 50

Pro Lys Leu Trp Ile Tyr Ser
1 5

<210> SEQ ID NO 51
<211> LENGTH: 7
<212> TYPE: PRT
<213> ORGANISM: Artificial
<220> FEATURE:
<223> OTHER INFORMATION: Amino acid sequence of a segment

<400> SEQUENCE: 51

Ile Tyr Ser Thr Ser Asn Leu
1 5

<210> SEQ ID NO 52
<211> LENGTH: 16
<212> TYPE: PRT
<213> ORGANISM: Artificial
<220> FEATURE:
<223> OTHER INFORMATION: Amino acid sequence of a segment

<400> SEQUENCE: 52

Leu Ala Ser Gly Val Pro Ser Arg Phe Ser Gly Ser Gly Ser Gly Thr
1 5 10 15

<210> SEQ ID NO 53
<211> LENGTH: 10
<212> TYPE: PRT
<213> ORGANISM: Artificial Sequence
<220> FEATURE:
<223> OTHER INFORMATION: Amino acid sequence of a segment

<400> SEQUENCE: 53

Asp Tyr Thr Leu Thr Ile Ser Ser Leu Gln
1 5 10

<210> SEQ ID NO 54
<211> LENGTH: 12
<212> TYPE: PRT
<213> ORGANISM: Artificial Sequence
<220> FEATURE:
<223> OTHER INFORMATION: Amino acid sequence of a segment

<400> SEQUENCE: 54

Gln Ala Glu Asp Phe Ala Thr Tyr Tyr Cys His Gln
1 5 10

<210> SEQ ID NO 55
<211> LENGTH: 13
<212> TYPE: PRT
<213> ORGANISM: Artificial Sequence
<220> FEATURE:
<223> OTHER INFORMATION: Amino acid sequence of a segment

<400> SEQUENCE: 55

```
Glu Asp Phe Ala Thr Tyr Tyr Cys His Gln Tyr His Arg
1               5                   10


<210> SEQ ID NO 56
<211> LENGTH: 14
<212> TYPE: PRT
<213> ORGANISM: Artificial Sequence
<220> FEATURE:
<223> OTHER INFORMATION: Amino acid sequence of a segment

<400> SEQUENCE: 56

Ser Pro Pro Thr Phe Gly Gln Gly Thr Lys Leu Glu Ile Lys
1               5                   10


<210> SEQ ID NO 57
<211> LENGTH: 12
<212> TYPE: PRT
<213> ORGANISM: Artificial Sequence
<220> FEATURE:
<223> OTHER INFORMATION: Amino acid sequence of a segment

<400> SEQUENCE: 57

Ala Thr Leu Ser Leu Ser Pro Gly Glu Arg Ala Thr
1               5                   10


<210> SEQ ID NO 58
<211> LENGTH: 19
<212> TYPE: PRT
<213> ORGANISM: Artificial Sequence
<220> FEATURE:
<223> OTHER INFORMATION: Amino acid sequence of a segment

<400> SEQUENCE: 58

Asp Tyr Thr Leu Thr Ile Ser Ser Leu Gln Pro Glu Asp Phe Ala Thr
1               5                   10                  15

Tyr Tyr Cys


<210> SEQ ID NO 59
<211> LENGTH: 14
<212> TYPE: PRT
<213> ORGANISM: Artificial Sequence
<220> FEATURE:
<223> OTHER INFORMATION: Amino acid sequence of a segment

<400> SEQUENCE: 59

Pro Glu Asp Phe Ala Thr Tyr Tyr Cys His Gln Tyr His Arg
1               5                   10


<210> SEQ ID NO 60
<211> LENGTH: 25
<212> TYPE: DNA
<213> ORGANISM: Artificial Sequence
<220> FEATURE:
<223> OTHER INFORMATION: Nucleic acid sequence of a primer used for
      chimeric antibodies cloning

<400> SEQUENCE: 60

atgrasttsk ggytmarctk grttt                                         25


<210> SEQ ID NO 61
<211> LENGTH: 26
<212> TYPE: DNA
<213> ORGANISM: Artificial Sequence
<220> FEATURE:
<223> OTHER INFORMATION: Nucleic acid sequence of a primer used for
      chimeric antibodies cloning
```

<400> SEQUENCE: 61
atgraatgsa sctgggtywt yctctt 26

<210> SEQ ID NO 62
<211> LENGTH: 29
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 62
atggactcca ggctcaattt agttttcct 29

<210> SEQ ID NO 63
<211> LENGTH: 26
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 63
atggctgtcy trgbgctgyt cytctg 26

<210> SEQ ID NO 64
<211> LENGTH: 29
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 64
atggvttggs tgtggamctt gcyattcct 29

<210> SEQ ID NO 65
<211> LENGTH: 26
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 65
atgaaatgca gctggrtyat sttctt 26

<210> SEQ ID NO 66
<211> LENGTH: 26
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 66
atggrcagrc ttacwtyytc attcct 26

<210> SEQ ID NO 67
<211> LENGTH: 26
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 67
atgatggtgt taagtcttct gtacct 26

<210> SEQ ID NO 68
<211> LENGTH: 26
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 68
atgggatgga gctrtatcat sytctt 26

<210> SEQ ID NO 69
<211> LENGTH: 23
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 69
atgaagwtgt ggbtraactg grt 23

<210> SEQ ID NO 70
<211> LENGTH: 25
<212> TYPE: DNA
<213> ORGANISM: Artificial Sequence
<220> FEATURE:
<223> OTHER INFORMATION: Nucleic acid sequence of a primer used for chimeric antibodies cloning
<220> FEATURE:
<221> NAME/KEY: misc_feature
<222> LOCATION: (15)..(15)
<223> OTHER INFORMATION: Inosine

<400> SEQUENCE: 70
atggratgga sckknrtctt tmtct 25

<210> SEQ ID NO 71
<211> LENGTH: 25
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 71
atgaacttyg ggytsagmtt grttt 25

<210> SEQ ID NO 72
<211> LENGTH: 25
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 72
atgtacttgg gactgagctg tgtat 25

<210> SEQ ID NO 73
<211> LENGTH: 23
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 73
atgagagtgc tgattctttt gtg 23

<210> SEQ ID NO 74
<211> LENGTH: 28
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 74
atggattttg ggctgatttt ttttattg 28

<210> SEQ ID NO 75
<211> LENGTH: 23
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 75 acgagggga agacatttgg gaa 23

<210> SEQ ID NO 76
<211> LENGTH: 26
<212> TYPE: DNA
<213> ORGANISM: Artificial Sequence
<220> FEATURE:
<223> OTHER INFORMATION: Nucleic acid sequence of a primer used for chimeric antibodies cloning
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(23)
<223> OTHER INFORMATION: Inosine

<400> SEQUENCE: 76
ccagggrcca rkggatarac ngrtgg 26

<210> SEQ ID NO 77
<211> LENGTH: 24
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 77
atgragwcac akwcycaggt cttt 24

<210> SEQ ID NO 78
<211> LENGTH: 25
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 78
atggagacag acacactcct gctat 25

<210> SEQ ID NO 79
<211> LENGTH: 29

<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 79
atggagwcag acacactsct gytatgggt 29

<210> SEQ ID NO 80
<211> LENGTH: 32
<212> TYPE: DNA
<213> ORGANISM: Artificial Sequence
<220> FEATURE:
<223> OTHER INFORMATION: Nucleic acid sequence of a primer used for chimeric antibodies cloning
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (29)..(29)
<223> OTHER INFORMATION: Inosine

<400> SEQUENCE: 80
atgaggrccc ctgctcagwt tyttggnwtc tt 32

<210> SEQ ID NO 81
<211> LENGTH: 31
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 81
atgggcwtca agatgragtc acakwyycwg g 31

<210> SEQ ID NO 82
<211> LENGTH: 29
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 82
atgagtgtgc ycactcaggt cctggsgtt 29

<210> SEQ ID NO 83
<211> LENGTH: 31
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 83
atgtggggay cgktttyamm cttttcaatt g 31

<210> SEQ ID NO 84
<211> LENGTH: 28
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 84
atggaagccc cagctcagct tctcttcc 28

<210> SEQ ID NO 85
<211> LENGTH: 26
<212> TYPE: DNA
<213> ORGANISM: Artificial Sequence
<220> FEATURE:
<223> OTHER INFORMATION: Nucleic acid sequence of a primer used for chimeric antibodies cloning
<220> FEATURE:
<221> NAME/KEY: misc_feature
<222> LOCATION: (6)..(6)
<223> OTHER INFORMATION: Inosine
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: Inosine
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (19)..(19)
<223> OTHER INFORMATION: Inosine

<400> SEQUENCE: 85
atgagnmmkt cnmttcantt cytggg 26

<210> SEQ ID NO 86
<211> LENGTH: 26
<212> TYPE: DNA
<213> ORGANISM: Artificial Sequence
<220> FEATURE:
<223> OTHER INFORMATION: Nucleic acid sequence of a primer used for chimeric antibodies cloning
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (13)..(13)
<223> OTHER INFORMATION: Inosine
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)
<223> OTHER INFORMATION: Inosine

<400> SEQUENCE: 86
atgakgthcy cngctcagyt yctnrg 26

<210> SEQ ID NO 87
<211> LENGTH: 25
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 87
atggtrtccw casctcagtt ccttg 25

<210> SEQ ID NO 88

<211> LENGTH: 27
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 88
atgtatatat gtttgttgtc tatttct 27

<210> SEQ ID NO 89
<211> LENGTH: 29
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 89
atgaagttgc ctgttaggct gttggtgct 29

<210> SEQ ID NO 90
<211> LENGTH: 29
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 90
atggatttwc argtgcagat twtcagctt 29

<210> SEQ ID NO 91
<211> LENGTH: 27
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 91
atggtyctya tvtccttgct gttctgg 27

<210> SEQ ID NO 92
<211> LENGTH: 27
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 92
atggtyctya tvttrctgct gctatgg 27

<210> SEQ ID NO 93
<211> LENGTH: 21
<212> TYPE: DNA
<213> ORGANISM: Artificial Sequence
<220> FEATURE:
<223> OTHER INFORMATION: Nucleic acid sequence of a primer used for chimeric antibodies cloning

<400> SEQUENCE: 93
actggatggt gggaagatgg a 21

<210> SEQ ID NO 94
<211> LENGTH: 25
<212> TYPE: DNA

<213> ORGANISM: Artificial Sequence
<220> FEATURE:
<223> OTHER INFORMATION: Nucleic acid sequence of a primer used for chimeric antibodies cloning

<400> SEQUENCE: 94
atggcctgga ytycwctywt mytct 25

<210> SEQ ID NO 95
<211> LENGTH: 23
<212> TYPE: DNA
<213> ORGANISM: Artificial Sequence
<220> FEATURE:
<223> OTHER INFORMATION: Nucleic acid sequence of a primer used for chimeric antibodies cloning
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)

<400> SEQUENCE: 95
agctcytcwg wgganggygg raa 23

<210> SEQ ID NO 96
<211> LENGTH: 6
<212> TYPE: PRT
<213> ORGANISM: Artificial
<220> FEATURE:
<223> OTHER INFORMATION: amino acid sequence of a segment

<400> SEQUENCE: 96

Tyr Gly Asn Tyr Gly Tyr
1 5

<210> SEQ ID NO 97
<211> LENGTH: 18
<212> TYPE: PRT
<213> ORGANISM: Artificial
<220> FEATURE:
<223> OTHER INFORMATION: amino acid sequence of a segment

<400> SEQUENCE: 97

Ala Thr Leu Ser Leu Ser Pro Gly Glu Arg Ala Thr Leu Ser Cys Thr
1 5 10 15

Ala Ser

<210> SEQ ID NO 98
<211> LENGTH: 22
<212> TYPE: PRT
<213> ORGANISM: Artificial
<220> FEATURE:
<223> OTHER INFORMATION: Sequence combining peptide 6 and peptide 7

<400> SEQUENCE: 98

Gly Pro Lys Gly Arg Asn Val Val Leu Glu Lys Lys Trp Gly Ala Pro
1 5 10 15

Thr Ile Thr Asn Asp Gly
20

<210> SEQ ID NO 99
<211> LENGTH: 36
<212> TYPE: DNA
<213> ORGANISM: Artificial
<220> FEATURE:
<223> OTHER INFORMATION: Cap1bamF

```
<400> SEQUENCE: 99

gcgtagtcgg atccatggct gacatgcaaa atctgg                           36


<210> SEQ ID NO 100
<211> LENGTH: 45
<212> TYPE: DNA
<213> ORGANISM: Artificial
<220> FEATURE:
<223> OTHER INFORMATION: cap1xhoyeshstopR

<400> SEQUENCE: 100

gcgtagtcct cgagttatcc agcaatttct gtcactgtgg tgacc                 45


<210> SEQ ID NO 101
<211> LENGTH: 16
<212> TYPE: PRT
<213> ORGANISM: Artificial
<220> FEATURE:
<223> OTHER INFORMATION: Peptide 7

<400> SEQUENCE: 101

Val Val Leu Glu Lys Lys Trp Gly Ala Pro Thr Ile Thr Asn Asp Gly
1               5                   10                  15
```